(12) United States Patent
Xu et al.

(10) Patent No.: US 10,100,016 B2
(45) Date of Patent: Oct. 16, 2018

(54) CONDENSED RING DERIVATIVE, AND PREPARATION METHOD, INTERMEDIATE, PHARMACEUTICAL COMPOSITION AND USE THEREOF

(71) Applicant: SHANGHAI YINGLI PHARMACEUTICAL CO., LTD., Shanghai (CN)

(72) Inventors: Zusheng Xu, Shanghai (CN); Nong Zhang, Shanghai (CN); Qingrui Sun, Shanghai (CN); Tianzhi Wu, Shanghai (CN)

(73) Assignee: SHANGHAI YINGLI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/985,848

(22) Filed: May 22, 2018

(65) Prior Publication Data
US 2018/0265476 A1    Sep. 20, 2018

Related U.S. Application Data

(62) Division of application No. 15/559,181, filed as application No. PCT/CN2016/073043 on Feb. 1, 2016.

(30) Foreign Application Priority Data

Mar. 24, 2015  (CN) .......................... 2015 1 0131828

(51) Int. Cl.
| | | |
|---|---|---|
| *C07D 217/14* | (2006.01) | |
| *C07D 231/56* | (2006.01) | |
| *C07D 237/30* | (2006.01) | |
| *C07D 333/60* | (2006.01) | |
| *C07D 495/04* | (2006.01) | |
| *C07D 471/04* | (2006.01) | |
| *C07D 239/78* | (2006.01) | |
| *C07D 405/04* | (2006.01) | |
| *C07B 59/00* | (2006.01) | |

(52) U.S. Cl.
CPC .......... *C07D 217/14* (2013.01); *C07B 59/002* (2013.01); *C07D 231/56* (2013.01); *C07D 237/30* (2013.01); *C07D 239/78* (2013.01); *C07D 333/60* (2013.01); *C07D 405/04* (2013.01); *C07D 471/04* (2013.01); *C07D 495/04* (2013.01); *C07B 2200/05* (2013.01)

(58) Field of Classification Search
CPC .. C07D 217/14; C07D 231/56; C07D 237/30; C07D 239/78; C07D 333/60; C07D 405/04; C07D 471/04; C07D 495/04; C07B 59/002; C07B 2200/05
USPC ........................................................ 514/248
See application file for complete search history.

(56) References Cited

U.S. PATENT DOCUMENTS

| | | |
|---|---|---|
| 3,558,655 A | 1/1971 | Kaltenbronn |
| 4,224,330 A | 9/1980 | Henrick et al. |
| 2009/0082367 A1 | 3/2009 | Yoshimura et al. |
| 2012/0142727 A1 | 6/2012 | Kinoyama et al. |
| 2013/0115190 A1 | 5/2013 | Hiebert et al. |
| 2014/0005221 A1 | 1/2014 | Nagai et al. |
| 2014/0005224 A1 | 1/2014 | Hillebrand et al. |

FOREIGN PATENT DOCUMENTS

| | | |
|---|---|---|
| CA | 2880178 A1 | 1/2014 |
| CN | 101400660 A | 4/2009 |
| CN | 102482220 A | 5/2012 |
| CN | 106008340 A | 10/2016 |
| EP | 2762476 A | 8/2014 |
| JP | H10120680 A | 5/1998 |
| JP | 2006528967 A | 12/2006 |
| JP | 2009525275 A | 7/2009 |
| JP | 2011520809 A | 7/2011 |
| JP | 2013526615 A | 6/2013 |
| WO | 0121598 A | 3/2001 |
| WO | 2004103997 A1 | 12/2004 |
| WO | 2007089557 A2 | 8/2007 |
| WO | 2009137404 A1 | 11/2009 |
| WO | 2011150156 A2 | 12/2011 |
| WO | 2014079787 A1 | 5/2014 |
| WO | 2014177596 A1 | 11/2014 |
| WO | 2015027222 A2 | 2/2015 |

OTHER PUBLICATIONS

PCT International Search Report dated Apr. 26, 2016 in International Patent Application No. PCT/CN2016/073043.
Taiwan Office Action dated Jan. 25, 2017 in Taiwan Patent Application No. TW105109178.
Rejection decision dated Jul. 10, 2017 in Taiwan Patent Application No. TW105109178.
Puig et al. CurrOpin Rheumatol, 2008, 20, 187-191 (Abstract).
Edwards et al. Cleve Clin J Med, 2008, 75(Suppl 5), pp. 13-16.
Hediger et al. Physiology 2005, 20(2), pp. 125-133.
Extended European Search Report dated Dec. 21, 2017 in European Patent Application No. 16767632.9.
Kundu et al., "cyclopenta[f]isoquinoline derivatives designed to bind specifically to native deoxyribonucleic acid. 1. Synthesis of 3-ethoxy-8-methyl-7(5)H-cyclopentar[f]isoquinoline", Journal of Medicinal Chemistry, vol. 18, No. 4, 1975, pp. 395-399.
Machine translation of JP10120680A, 2018.
Stratford et al., "Alkylation of Styrylacetic Acid Systems Using Lithium Diisopropylamide-Hexamethylphosphoramide. Effect of Temperature Variation", J. Org. Chem., vol. 44, No. 9, Dec. 31, 1979, p. 1571.

(Continued)

*Primary Examiner* — Kristin A Vajda
(74) *Attorney, Agent, or Firm* — Dilworth IP, LLC

(57) ABSTRACT

Disclosed are a condensed ring derivative, and a preparation method, an intermediate, a pharmaceutical composition and a use thereof. The condensed ring derivative of the present invention has a significant inhibitive effect on URAT1, which can effectively alleviate or treat hyperuricemia and other related diseases.

16 Claims, No Drawings

(56) References Cited

OTHER PUBLICATIONS

First Office Action dated Feb. 20, 2018 in Japanese Patent Application No. JP 2017-550129.
First Office Action dated Feb. 22, 2018 in Canadian Patent Application No. 2,980,484.
First Office Action dated Mar. 13, 2018 in New Zealand Patent Application No. 735044.
First Office Action dated Mar. 21, 2018 in Australian Patent Application No. 2016236669.
Notification to Make Divisional Application dated Jan. 4, 2018 in Chinese Patent Application 201610071297.X.
First Office Action dated Apr. 17, 2018 in Russian Patent Application No. 2017134044/04.
First Office Action dated Apr. 24, 2018 in Chinese Patent Application No. 201610071297.X.
First Office Action dated Apr. 11, 2018 in Israeli Patent Application No. 254098.
"4-chloro-thieno[2,3-c]pyridine-2-acetic acid", Aurora Fine Chemicals, Entered in STN Dec. 27, 2013.
CAS Registry # 1514761-58-0 "4-amino-thieno[2,3-c]pyridine-2-acetic acid" Aurora Fine Chemicals, Entered in STN Jan. 9, 2014.
"Decarboxylation reaction of β-benzothiophene carboxylic acid catalyzed by H3O", Computers and Applied Chemistry, vol. 30, No. 9, Sep. 28, 2013, pp. 1021-1027.
Othman et al., "Intramolecular cyclization of amido acids into pyrrolidinothieno (or [1]benzothieno)[3]azepinediones", Journal of Heterocyclic Chemistry, Jan.-Feb. 1997, 34(1), pp. 225-231.

CONDENSED RING DERIVATIVE, AND PREPARATION METHOD, INTERMEDIATE, PHARMACEUTICAL COMPOSITION AND USE THEREOF

CROSS-REFERENCE TO RELATED APPLICATIONS

This application is a divisional application of U.S. application Ser. No. 15/559,181 filed on Sep. 18, 2017, which is a 35 U.S.C. § 371 U.S. national phase patent application of International Application PCT/CN2016/073043 filed on Feb. 1, 2016, which claims priority to Chinese Patent Application CN201510131828.5 filed on Mar. 24, 2015, the contents of which are incorporated herein by reference in their entireties.

FIELD OF INVENTION

The present invention relates to a condensed ring derivative, and preparation method, intermediate, pharmaceutical composition and use thereof.

BACKGROUND OF THE INVENTION

Hyperuricemia (HUA) is related to many diseases such as gout, hypertension, diabetes, hypertriglyceridemia, metabolic syndrome, coronary heart disease and renal damage etc. (Puig J G, et al. *Curr Opin Rheumatol,* 2008, 20, 187-191; Edwards N L, et al. *Cleve Clin J Med,* 2008, 75 (Suppl 5), 13-16), which has been a metabolic disease threatening human's health, and was recognized as one of the twenty stubborn and chronic diseases in the $21^{st}$ century by the United Nations.

Uric acid is the final product metabolized from the purine in vivo, which goes through glomerular filtration mainly in its origin form, and reabsorption, re-secretion by renal tubule, finally excreted with urine, and very few of them can enter enteric cavity through the secreting of the mesenteric cells. (Hediger M A, et al. *Physiology* 2005, 20(2), 125-133). 51 section of the proximal convoluted tubule is the position where the uric acid is reabsorbed, and 98%-100% filtered uric acid enters the epithelium through urate transporter 1 (URAT1) upon the brush border membrane of the tubular epithelial cells. Inhibiting the activity of the URAT1 can reduce the reabsorption of the uric acid, which allows the uric acid excreted with urine thereby lowering the level of the uric acid in the blood and relieving or treating hyperuricemia and various related diseases.

DESCRIPTION OF THE INVENTION

The technical problem to be solved in the present invention is to provide a condensed ring derivative totally different from the prior art, and preparation method, intermediate, pharmaceutical composition and use thereof. The condensed ring derivative of the present invention has obvious inhibitory activity against URAT1, which can effectively relieve or treat hyperuricemia and various related diseases.

The present invention provides a condensed ring derivative having a structure of formula I, a tautomer, a mesomer, a racemate, an enantiomer, a diastereoisomer, or a pharmaceutically acceptable salt, a metabolite, a metabolic precursor or a pro-drug thereof,

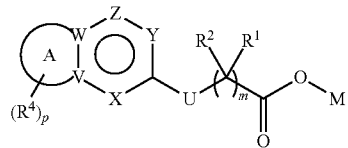

Wherein ring A is an aryl (preferably a $C_{6-10}$ aryl, more preferably a phenyl (e.g.

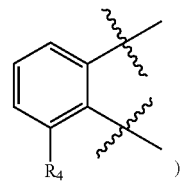

)

or a heteroaryl (preferably a $C_{2-5}$ heteroaryl having 1-3 heteroatoms selected from N or S, more preferably pyridinyl (e.g.

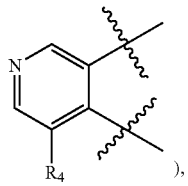

), imidazolyl (e.g.

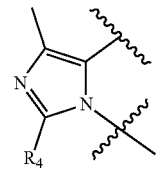

or

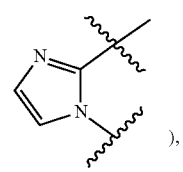 [SMILES: *c1nccn1*]

), pyrazolyl (e.g.

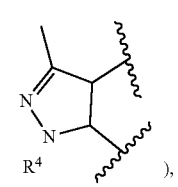

), triazolyl (e.g.

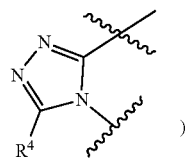
)

or pyridazinyl (e.g.

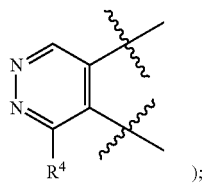
);

M is a hydrogen, a deuterium or a pharmaceutically acceptable cation (preferably a sodium ion, a potassium ion or a calcium ion);

U is a chemical bond (preferably a single bond or a double bond),

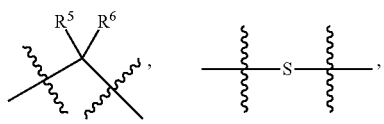

V and W are independently C or N, provided that V and W are not N simultaneously;

X is

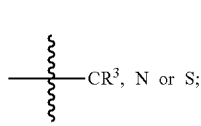

Y is a chemical bond (preferably a single bond or a double bond),

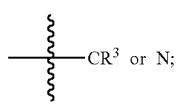

Z is

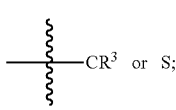

$R^1$ and $R^2$ are independently H, D, a halogen (preferably F, Cl, Br or I, more preferably F), an alkyl (preferably a $C_{1-4}$ alkyl), CN, an alkoxy (preferably a $C_{1-4}$ alkoxy), a cycloalkyl (preferably a $C_{3-6}$ cycloalkyl), an alkenyl (preferably a $C_{2-4}$ alkenyl), a alkynyl (preferably a $C_{2-4}$ alkynyl) or a heterocycloalkyl (preferably a $C_{2-10}$ heterocycloalkyl having 1-2 heteroatoms selected from O, S or N; the $C_{2-10}$ heterocycloalkyl is preferably a $C_{2-5}$ heterocycloalkyl); or, $R^1$, $R^2$ together with the carbon atom attached form a cycloalkyl (preferably a $C_{3-6}$ cycloalkyl, more preferably cyclobutyl) or a heterocyclic group (preferably a $C_{2-5}$ heterocyclic group having 1-2 heteroatoms selected from O or S); the alkyl, the alkoxy, the cycloalkyl, the alkenyl, the alkynyl, the heterocycloalkyl, the cycloalkyl formed by $R^1$, $R^2$ and the carbon atom attached, or the heteroalkyl formed by $R^1$, $R^2$ and the carbon atom attached can further be substituted by a substituent selected from the group consisting of D (e.g.

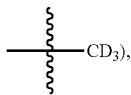

a halogen (e.g. F, Cl, Br or I, preferably Cl), CN, an alkyl (preferably a $C_{1-4}$ alkyl), an alkoxy (preferably a $C_{1-4}$ alkoxy), a cycloalkyl (preferably a $C_{3-6}$ cycloalkyl), an alkenyl (preferably a $C_{2-4}$ alkenyl), an alkynyl (preferably a $C_{2-4}$ alkynyl), a heterocycloalkyl (preferably a $C_{2-10}$ heterocycloalkyl having 1-2 heteroatoms selected from O, S or N; the $C_{2-10}$ heterocycloalkyl is preferably a $C_{2-5}$ heterocycloalkyl) or an aryl (preferably a $C_{6-10}$ aryl);

$R^3$ is H, D, a halogen (preferably F, Cl, Br or I, more preferably F), an alkyl (preferably a $C_{1-4}$ alkyl), an alkoxy (preferably a $C_{1-4}$ alkoxy), an aryl (preferably a $C_{6-10}$ aryl, more preferably a phenyl), a heteroaryl (preferably a $C_{2-5}$ heteroaryl having 1-3 heteroatoms selected from N, O or S; the $C_{2-10}$ heterocycloalkyl is preferably a $C_{2-5}$ heterocycloalkyl) or an amino

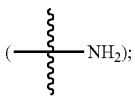

wherein the alkyl, the alkoxy, the aryl, the heteroaryl, the heterocycloalkyl or the amino can be further substituted by a substituent selected from the group consisting of D, a halogen (e.g. F, Cl, Br or I, preferably Cl), CN (e.g.

an alkyl (preferably a $C_{1-4}$ alkyl), an aryl (preferably a $C_{6-10}$ aryl, more preferably phenyl), an aryl substituted by halogen(s) (preferably 2,6-dichlorophenyl), a benzyl, a benzyl substituted by halogen(s) on the benzene ring (preferably 2,6-dichlorobenzyl), a benzoyl or a benzoyl substituted by a halogen on the benzene ring (preferably 2,6-dichlorobenzoyl); when the number of the substituents is more than one, the substituents are the same or different;

$R^4$ is H, D, a halogen (e.g. F, Cl, Br or I, preferably F or Cl), CN, $NH_2$, OH, an alkyl (preferably a $C_{1-4}$ alkyl), an alkoxy (preferably a $C_{1-4}$ alkoxy), a cycloalkyl (preferably a $C_{3-6}$ cycloalkyl), an alkenyl (preferably a $C_{2-4}$ alkenyl), an alkynyl (preferably a $C_{2-4}$ alkynyl), a heterocycloalkyl (preferably a $C_{2-10}$ heterocycloalkyl having 1-3 heteroatoms selected from N, S or O; the $C_{2-10}$ heterocycloalkyl is preferably a $C_{2-5}$ heterocycloalkyl), an aryl (preferably a $C_{6-10}$ aryl, more preferably a phenyl or a naphthyl) or a heteroaryl (preferably a $C_{2-10}$ heteroaryl having 1-2 heteroatoms selected from O, more preferably

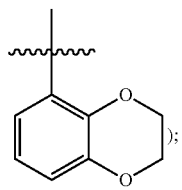 [SMILES: *c1cccc2c1OCCO2]

wherein the $NH_2$, the OH, the alkyl, the alkoxy, the cycloalkyl, the alkenyl, the alkynyl, the heterocycloalkyl, the aryl or the heteroaryl can further be substituted by a substituent selected from the group consisting of D, a halogen (e.g. F, Cl, Br or I, preferably F or Cl), CN, an alkyl (preferably a $C_{1-4}$ alkyl), an alkoxy (preferably a $C_{1-4}$ alkoxy), a cycloalkyl (preferably a $C_{3-6}$ cycloalkyl), an alkenyl (preferably a $C_{2-4}$ alkenyl), an alkynyl (preferably a $C_{2-4}$ alkynyl), a heterocycloalkyl (preferably a $C_{2-10}$ heterocycloalkyl having 1-2 heteroatoms selected from O, S or N; the $C_{2-10}$ heterocycloalkyl is preferably a $C_{2-5}$ heterocycloalkyl), an aryl (preferably a $C_{6-10}$ aryl), an aryl substituted by a halogen and/or CN (e.g.

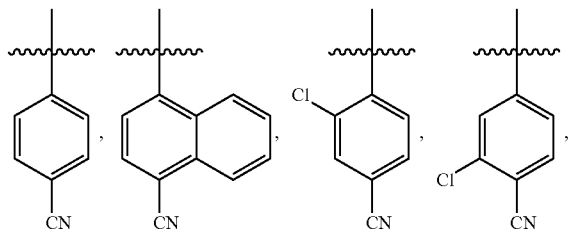

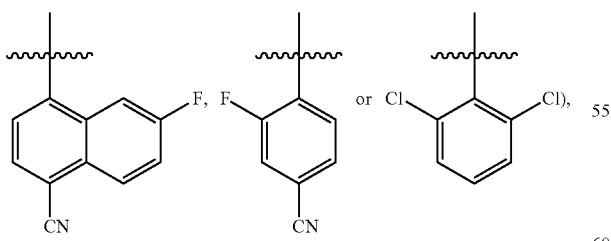

a heteroaryl (preferably a $C_{2-10}$ heteroaryl having 1-2 heteroatoms selected from O) or a heteroaryl substituted by CN (e.g.

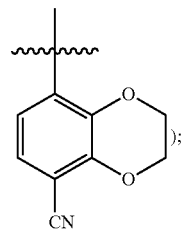 [SMILES: *c1ccc(C#N)c2c1OCCO2]

each of $R^5$ and $R^6$ is independently H, D, OH, a halogen (e.g. F, Cl, Br or I, preferably F), an alkyl (preferably a $C_{1-4}$ alkyl), CN, an alkoxy (preferably a $C_{1-4}$ alkoxy), a cycloalkyl (preferably a $C_{3-6}$ cycloalkyl), an alkenyl (preferably a $C_{2-4}$ alkenyl), an alkynyl (preferably a $C_{2-4}$ alkynyl) or a heterocycloalkyl (preferably a $C_{2-10}$ heterocycloalkyl having 1-2 heteroatoms selected from O, S or N; the $C_{2-10}$ heterocycloalkyl is preferably a $C_{2-5}$ heterocycloalkyl); or $R^5$, $R^6$ together with the carbon atom attached form a cycloalkyl (preferably a $C_{3-6}$ cycloalkyl) or a heterocyclic group (preferably a $C_{2-5}$ heterocyclic group having 1-2 heteroatoms selected from O or S); the alkyl, the alkoxy, the cycloalkyl, the alkenyl, the alkynyl, the heterocycloalkyl, the cycloalkyl formed by $R^5$, $R^6$ together with the carbon atom attached or the heteroalkyl formed by $R^5$, $R^6$ together with the carbon atom attached can further be substituted by a substituent selected from the group consisting of D, a halogen (e.g. F, Cl, Br or I, preferably Cl), CN, an alkyl (preferably a $C_{1-4}$ alkyl), an alkoxy (preferably a $C_{1-4}$ alkoxy), a cycloalkyl (preferably a $C_{3-6}$ cycloalkyl), an alkenyl (preferably a $C_{2-4}$ alkenyl), an alkynyl (preferably a $C_{2-4}$ alkynyl), a heterocycloalkyl (preferably a $C_{2-10}$ heterocycloalkyl having 1-2 heteroatoms selected from O, S or N; the $C_{2-10}$ heterocycloalkyl is preferably a $C_{2-5}$ heterocycloalkyl) or an aryl (preferably a $C_{6-10}$ aryl); $R^7$ is H or an alkyl (preferably a $C_{1-4}$ alkyl);

n is 0, 1 or 2;

p is 1, 2, 3 or 4.

Each of the letter and the substituent in the condensed ring derivative having a structure of formula I is preferably as follows:

M is H or a pharmaceutically acceptable cation;

each of $R^1$ and $R^2$ is H, a halogen (e.g. F, Cl, Br or I, preferably F) or an alkyl (preferably a $C_{1-4}$ alkyl); or IV, $R^2$ together with the carbon atom attached form a cycloalkyl (preferably a $C_{3-6}$ cycloalkyl, more preferably a cyclobutyl);

$R^3$ is H, a halogen (preferably F, Cl, Br or I, more preferably F), an alkyl (preferably a $C_{1-4}$ alkyl) or an aryl (preferably a $C_{6-10}$ aryl, more preferably a phenyl, wherein the $C_{6-10}$ aryl can be further substituted by one or more than one CN(s), e.g.

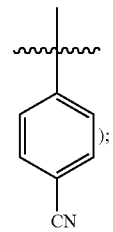

$R^4$ is H, a halogen (preferably F, Cl, Br or I, more preferably F), an alkyl (preferably a $C_{1-4}$ alkyl, wherein the $C_{1-4}$ alkyl can be further substituted by an aryl substituted by halogen(s), e.g.

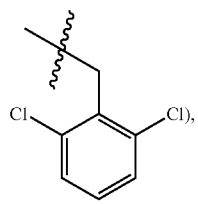

an aryl (preferably a $C_{6-10}$ aryl, more preferably a phenyl or a naphthyl, wherein the $C_{6-10}$ aryl can be further substituted by one or more than one CN(s) and/or halogen(s) (preferably F, Cl, Br or I, more preferably F or Cl), e.g. 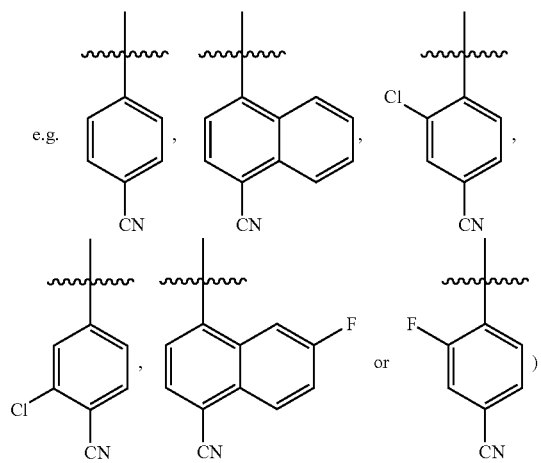

or a heteroaryl (preferably a $C_{2-10}$ heteroaryl having 1-2 heteroatoms selected from O, more preferably

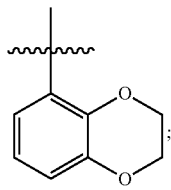 [SMILES: *c1cccc2c1OCCO2]

wherein the $C_{2-10}$ heteroaryl can be further substituted by one or more than one CN(s), e.g.

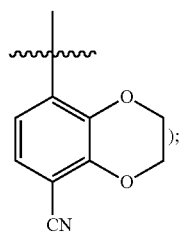 [SMILES: *c1ccc(C#N)c2c1OCCO2]

each of $R^5$ and $R^6$ is independently H, a halogen (e.g. F, Cl, Br or I, preferably F), an alkyl (preferably a $C_{1-4}$ alkyl) or OH;
p is 1.

The condensed ring derivative I in the present invention, is more preferably a compound having a structure of formula II,

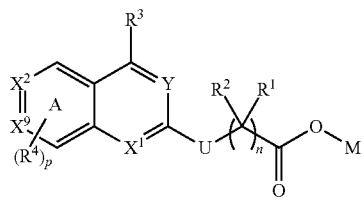

wherein each of $X^1$ and $X^2$ is independently CH or N; $X^9$ is CH or N; Y is CH or N; $R^1$, $R^2$, $R^3$, $R^4$, U, M, n and p are defined as above.

The condensed ring derivative I in the present invention, is more preferably a compound having a structure of formula III,

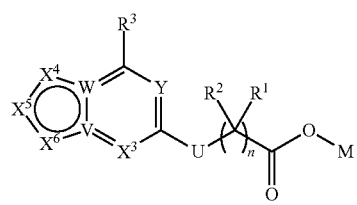

wherein $X^3$ is

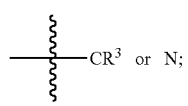

$X^4$ is

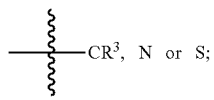

$X^5$ is

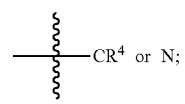

$X^6$ is

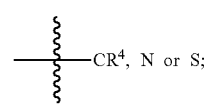

Y is CH or N; $R^1$, $R^2$, $R^3$, $R^4$, W, V, U, M and n are defined as above.

The condensed ring derivative I in the present invention, is more preferably a compound having a structure of formula IV,

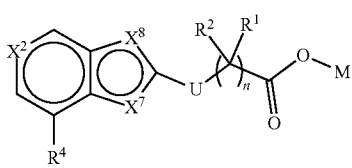

IV wherein $X^2$ is CH or N; each of $X^7$ and $X^8$ is independently CH or S; $R^1$, $R^2$, $R^4$, U, M and n are defined as above.

The compound having a structure of formula II in the present invention preferably has a structure of formula II-1,

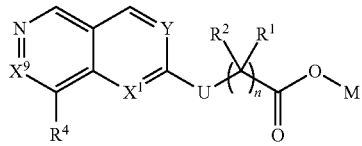

II-1 wherein $X^1$, $X^9$, Y, $R^1$, $R^2$, $R^4$, U, M and n are defined as above.

In a preferred embodiment of the present invention, in the compound having a structure of formula II-1, $X^1$ and Y are C; $X^9$ is C or N;

each of $R^1$ and $R^2$ is independently H or an alkyl (preferably a $C_{1-4}$ alkyl); or $R^1$, $R^2$ together with the carbon atom attached form a cycloalkyl (preferably a $C_{3-6}$ cycloalkyl, more preferably a cyclobutyl);

M is H;

$R^4$ is an aryl (preferably a $C_{6-10}$ aryl, more preferably a phenyl or a naphthyl, wherein the $C_{6-10}$ aryl can be further substituted by one or more than one CN(s) and/or halogen(s) (preferably F, Cl, Br or I, more preferably F or Cl), e.g.

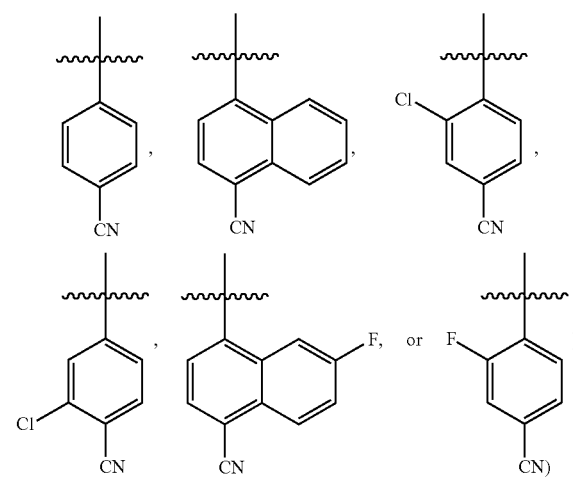

or a heteroaryl (preferably a $C_{2-10}$ heteroaryl having 1-2 heteroatoms selected from O, wherein the $C_{2-10}$ heteroatom can be further substituted by one or more than one CN(s), e.g.

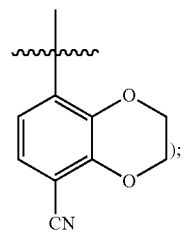

U is

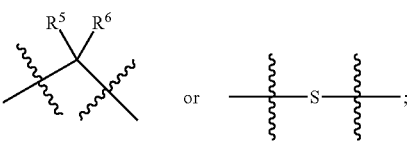

each of $R^5$ and $R^6$ is independently H or an alkyl (preferably a $C_{1-4}$ alkyl);

n is 1.

Preferably, in the compound having a structure of formula II-1, where U is

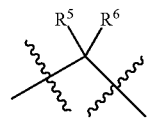

and both of $R^5$ and $R^6$ are hydrogen, $R^1$ and $R^2$ are not H at the same time;

where $X^9$ is N, U is

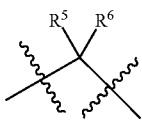

.

The compound having a structure of formula III in the present invention preferably has a structure of formula III-1,

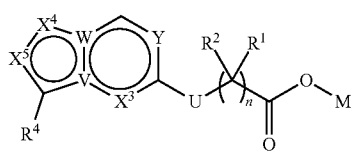

III-1 wherein $X^3$, $X^4$, $X^5$, Y, $R^1$, $R^2$, $R^3$, $R^4$, W, V, U, M and n are defined as above.

The compound having a structure of formula IV in the present invention preferably has a structure of formula IV-1,

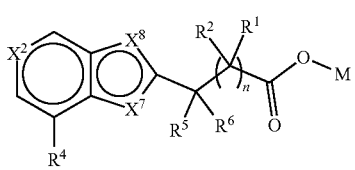

IV-1 wherein $X^2$, $X^7$, $X^8$, $R^1$, $R^2$, $R^4$, $R^5$, $R^6$, M and n are defined as above.

In a preferred embodiment of the present invention, in the compound having a structure of formula IV-1, $X^2$ is N;

each of $X^7$ and $X^8$ is independently CH or S;

each of $R^1$ and $R^2$ is independently H or an alkyl (preferably a $C_{1-4}$ alkyl);

R4 is an aryl (preferably a $C_{6-10}$ aryl, more preferably a phenyl or a naphthyl, wherein the $C_{6-10}$ aryl can be further substituted by one or more than one CN(s) and/or halogen(s) (preferably F, Cl, Br or I, more preferably F or Cl), e.g.

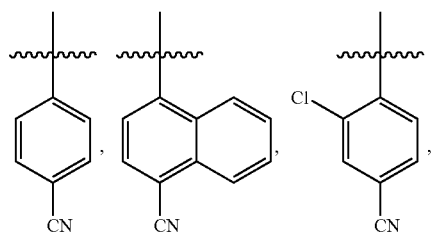

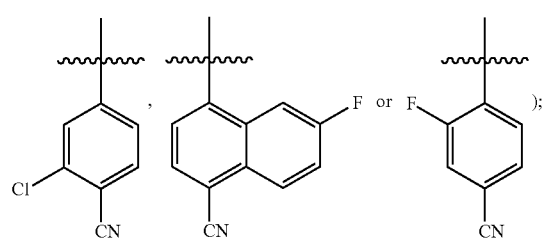

each of $R^5$ and $R^6$ is independently H or an alkyl (preferably a $C_{1-4}$ alkyl);

n is 0 or 1.

Preferably, $X^2$ is N; $X^7$ is CH; $X^8$ is S.

Preferably, in the compound having a structure of formula IV-1, M is H.

Preferably, in the compound having a structure of formula IV-1, where $R^1$ and/or $R^2$ is an alkyl, $R^5$ and $R^6$ are H; where $R^5$ and/or $R^6$ is an alkyl, $R^1$ and $R^2$ are H.

Preferably, in the compound having a structure of formula IV-1, where $X^7$ is S, $X^8$ is CH, $R^1$ and $R^2$ are alkyl, and $R^5$ and $R^6$ are H, $R^4$ is a phenyl.

The condensed ring derivative having a structure of formula I in the present invention is preferably selected from the compound consisting of

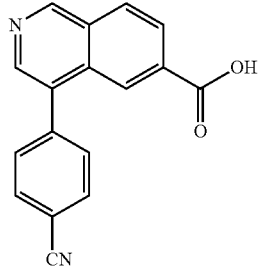

1

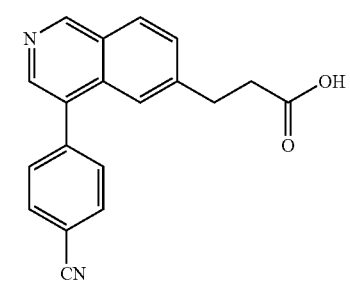

2

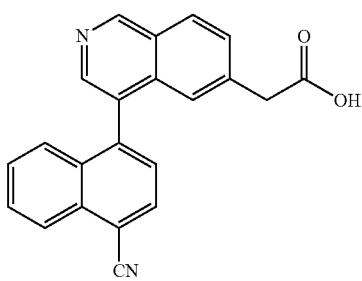

3

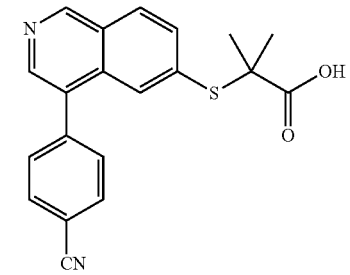

4

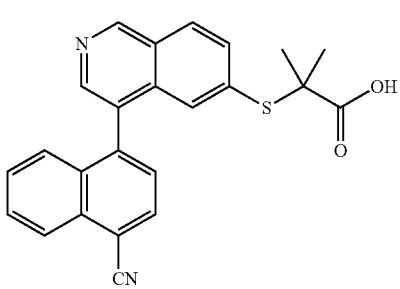

5

6
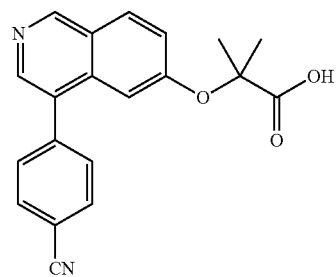
7
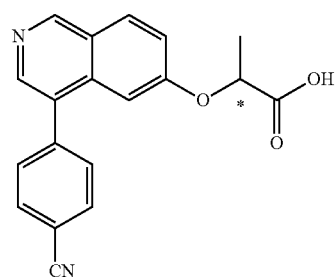
8
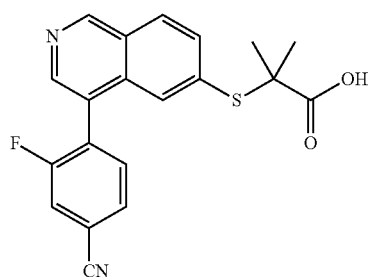
9
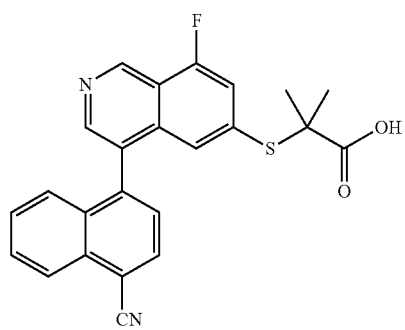
10
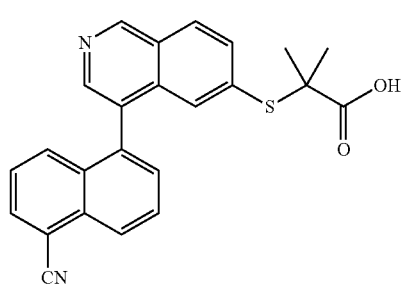
11
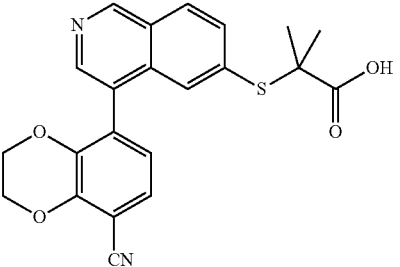
12
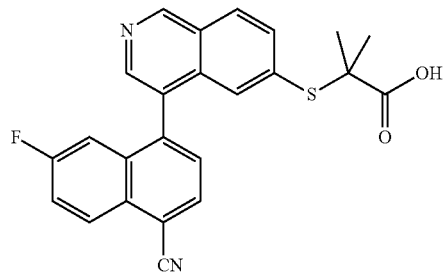
13
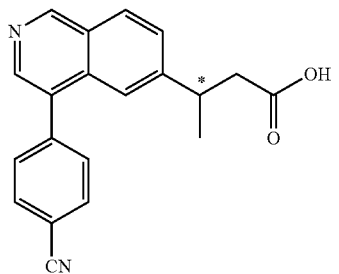
14
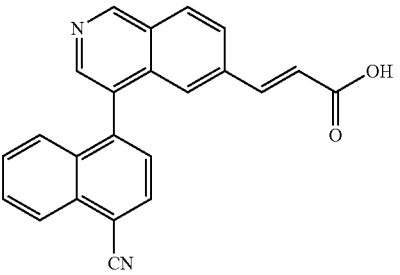
15
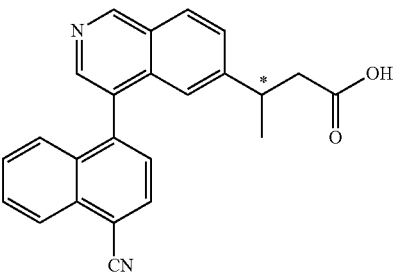

-continued
15
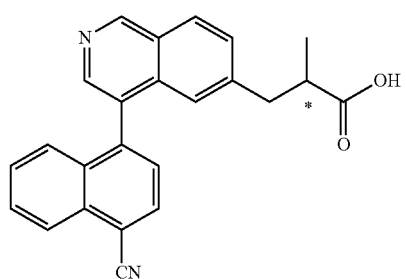
16
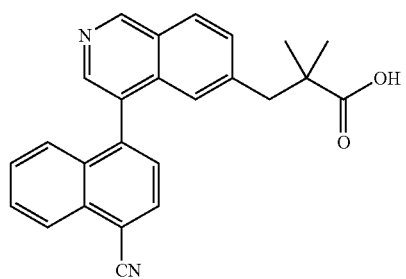
17
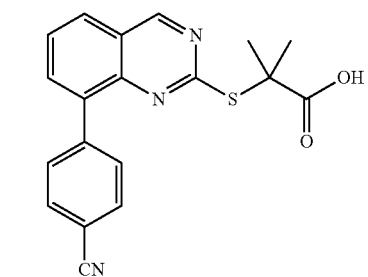
18
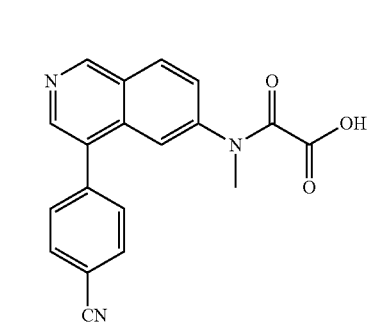
19
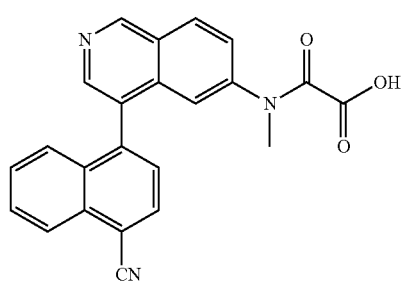
20
-continued
21
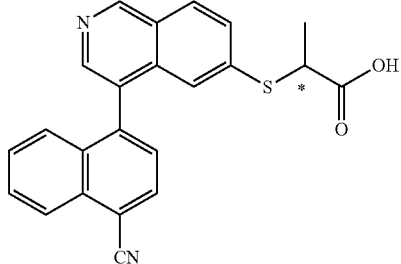
22
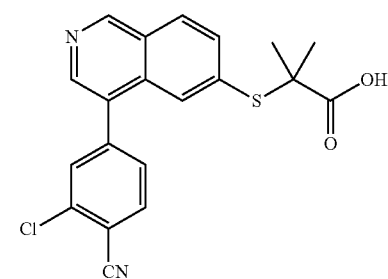
23
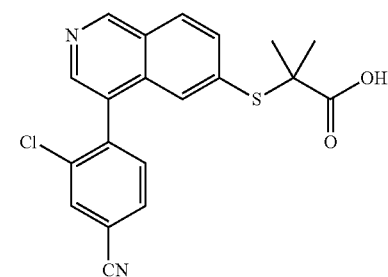
24
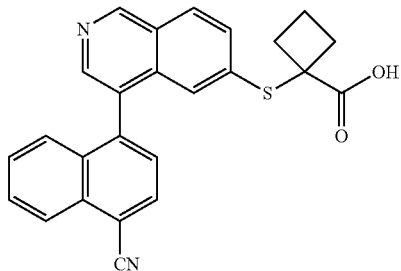
25
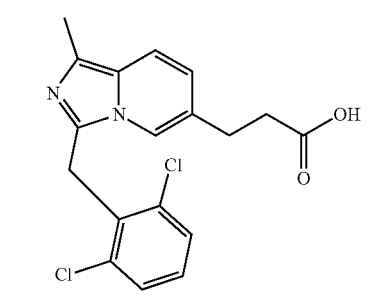

26 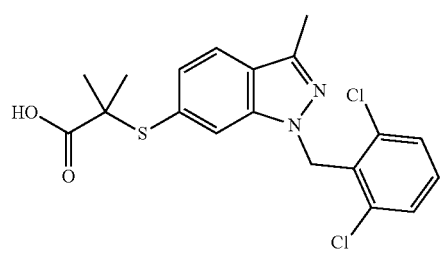
27 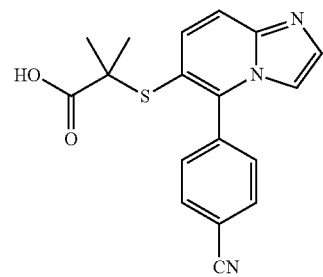
28 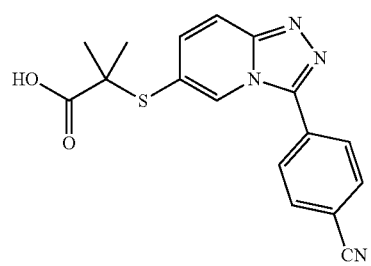
29 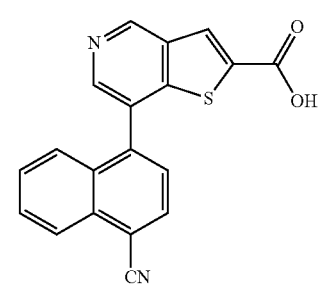
30 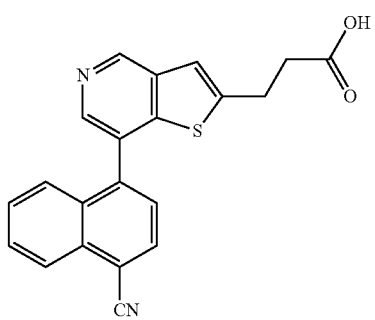
31 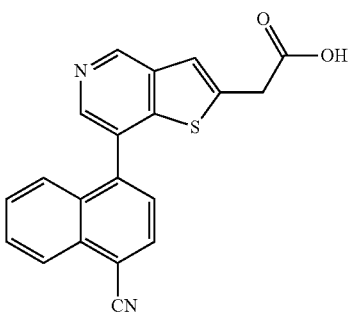
32 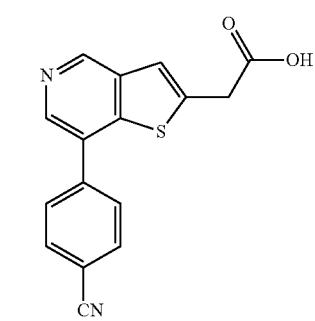
33 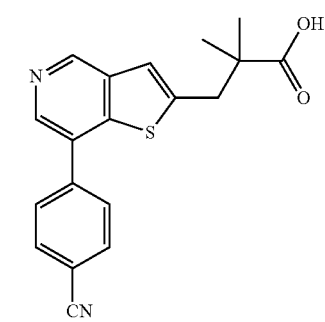
34 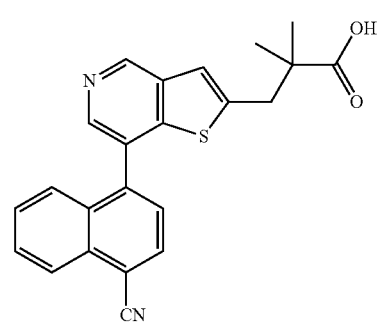
35 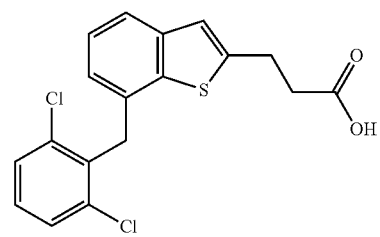

36
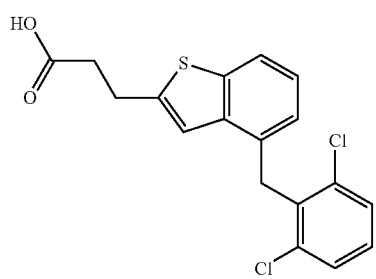
37
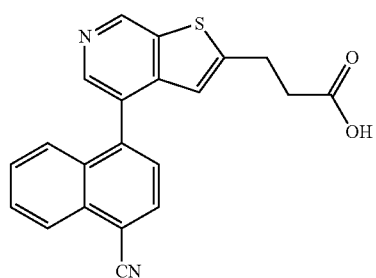
38
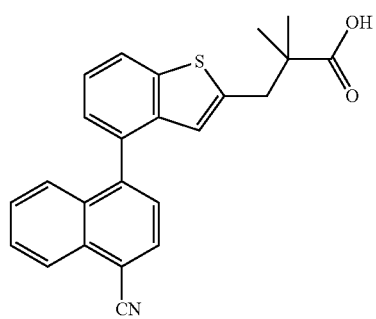
39
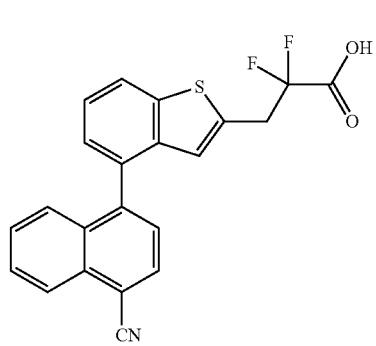
40
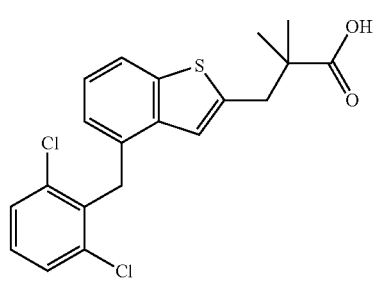
41
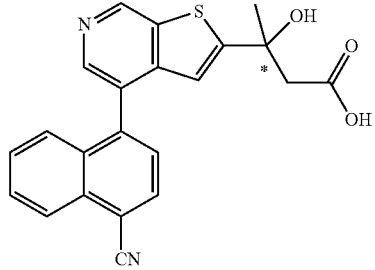
42
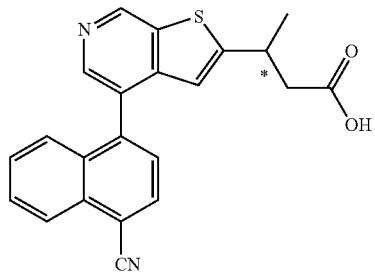
44
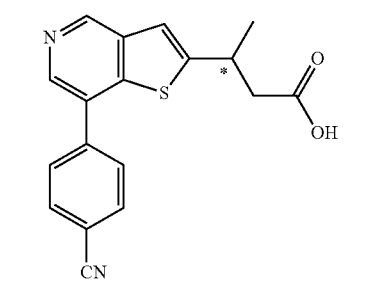
45
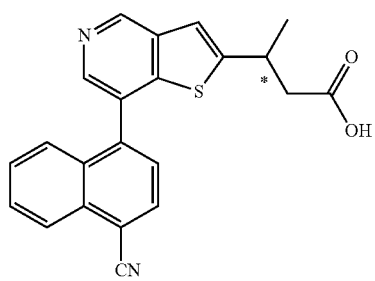
46
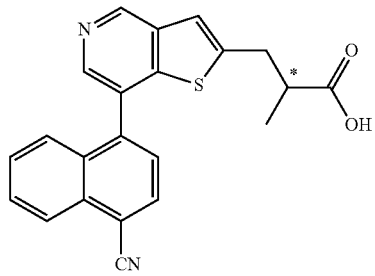

-continued

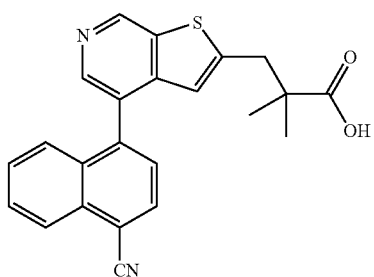
47

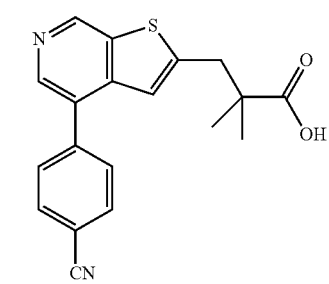
48

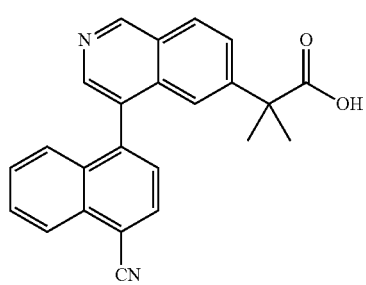
49

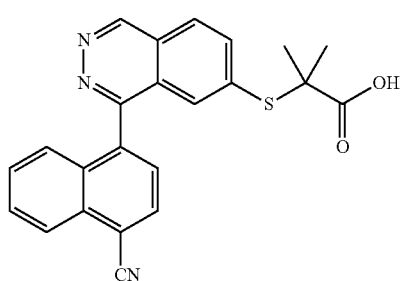
50

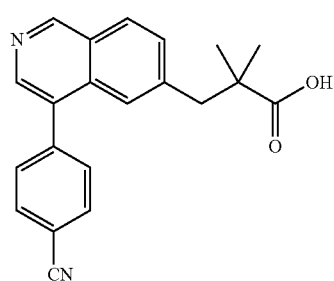
51

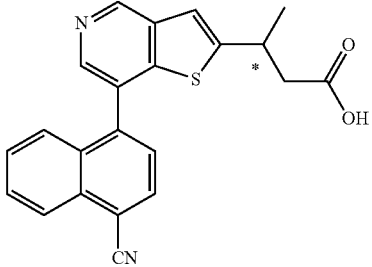
52

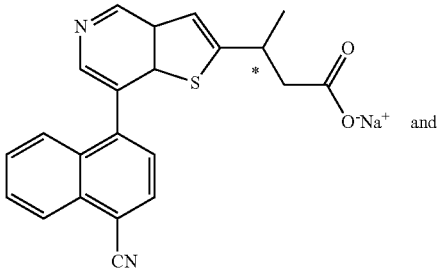
53

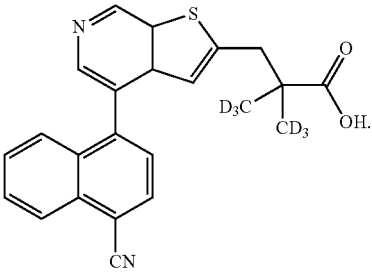
54

In the above compounds, the carbon marked with * is a chiral carbon or a non-chiral carbon; where it is a chiral carbon, it has S configuration or R configuration, where it is a non-chiral carbon, it is racemic.

The present invention also provides a process for preparing the condensed ring derivative having a structure of formula I, the tautomer, the mesomer, the racemate, the enantiomer, the diastereoisomer, or the pharmaceutically acceptable salt, the metabolite, the metabolic precursor or the pro-drug thereof, which can be synthesized according to the method known in the art with commercially available raw materials. In the present invention, the process for preparing the condensed ring derivative having a structure of formula I preferably comprises that in a solvent, in the presence of a base, carrying out a hydrolysis reaction on the compound having a structure of formula I-a to give the compound having a structure of formula I;

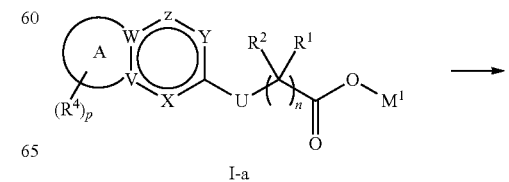

I-a

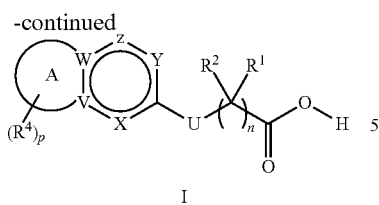

in formula I-a and I, ring A, IV, $R^2$, $R^4$, W, V, Z, Y, X, U, n and p are defined as above, in the compound having a structure of formula I-a, $M^1$ is an alkyl (preferably a $C_{1-4}$ alkyl). The method and condition of the hydrolysis reaction are common method and condition in the art, therefore, in the hydrolysis reaction, the solvent used and the amount thereof, the base used and the amount thereof, the temperature and time of the hydrolysis reaction, and the post treatment after the hydrolysis reaction can all be selected according to the common processes and conditions in the art. For example, the solvent can be a mixed solution of alcohols (e.g. methanol), ethers (e.g. THF) and water, or a mixed solution of alcohols (e.g. methanol) and water. The base can be alkalis hydroxide (e.g. LiOH and/or NaOH). Where a base is used, the base can be in the form of its aqueous solution (the molar concentration of the base aqueous solution can be 1 mol/L). The hydrolysis reaction can be carried out at room temperature. The process of the hydrolysis reaction can be monitored by the common method in the art (e.g. TLC, GC, HPLC or NMR etc.). The post treatment can comprise that mixing the reaction solution obtained after the hydrolysis reaction with the hydrochloric acid aqueous solution (e.g. 2 mol/L hydrochloric acid aqueous solution) and water (solid precipitated), filtering, washing the filtrate cake with water, drying under reduced pressure.

When M is a pharmaceutically acceptable cation, the compound having a structure of formula (I) wherein M is H can be neutralized by a hydroxide containing a pharmaceutically acceptable cation (e.g. sodium hydroxide). The conditions used in the process of a neutralizing reaction are common conditions used in the neutralizing reaction in the organic synthesis field.

The compound having a structure of formula I can be prepared according to the following process, comprising where U is

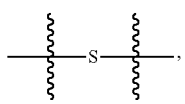

the compound having a structure of formula I can be prepared according to route I, which comprises

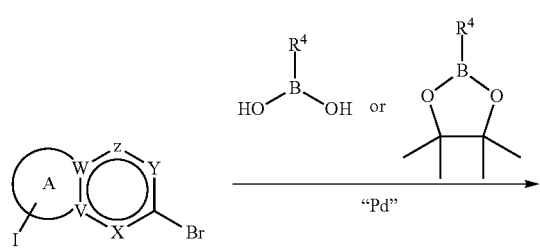

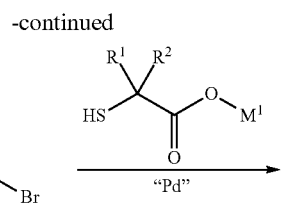

where U is

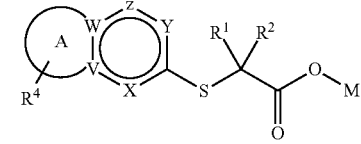

$R^6$ is H and n is 1, the compound having a structure of formula I can be prepared according to route II, which comprises

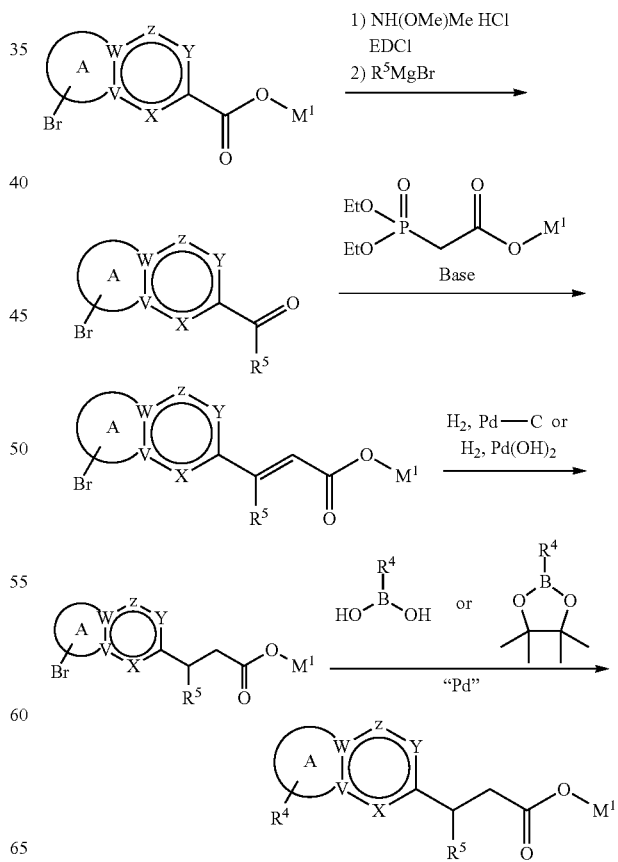

where U is

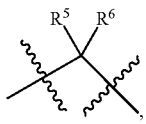

both $R^5$ and $R^6$ are H and n is 1, the compound having a structure of formula I can be prepared according to route III, which comprises

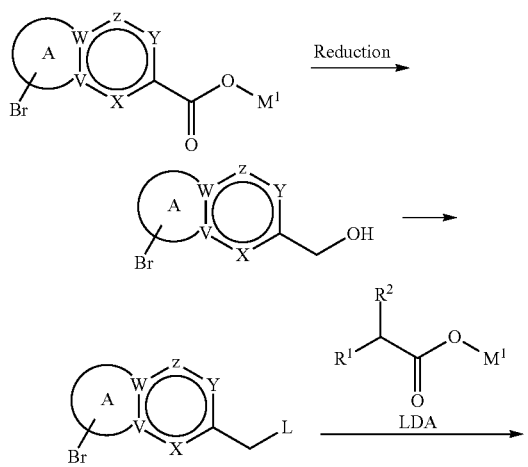

L = Cl, Br, I, OMs, OTs, OTf

In the above three routes, each letter or group involved is defined as above. Meanwhile, the conditions and steps used in the chemical reactions involved in the above three routes can refer to the common conditions and steps used in the art, and the compound obtained according to the above process can further be modified in the peripheral region, thereby obtaining other target compound of the present invention.

The present invention also provides a compound having a structure of formula I-a:

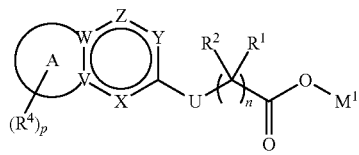

I-a wherein, ring A, $R^1$, $R^2$, $R^4$, W, V, Z, Y, X, U, n and p are defined as above; $M^1$ is an alkyl (preferably a $C_{1-4}$ alkyl).

The intermediate having a structure of formula I-a, further preferably has a structure of formula II-a:

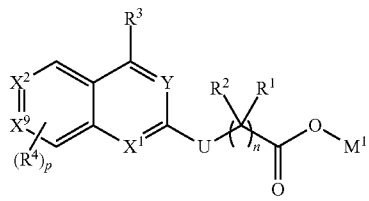

II-a wherein, $X^1$ and $X^2$ are independently CH or N; $X^9$ is CH or N; Y is CH or N; $R^1$, $R^2$, $R^3$, $R^4$, U, $M^1$, n and p are defined as above.

In the present invention, the intermediate having a structure of formula I-a, preferably has a structure of formula III-a:

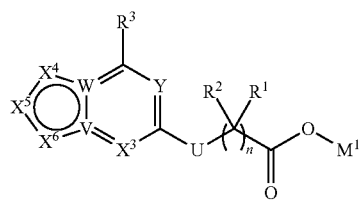

III-a wherein, $X^3$ is

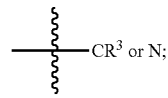

$CR^3$ or N;

$X^4$ is

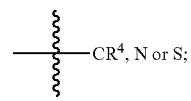

$CR^4$, N or S;

$X^5$ is

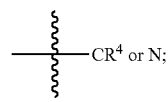

$CR^4$ or N;

$X^6$ is

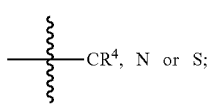

$CR^4$, N or S;

Y is CH or N; IV, $R^2$, $R^3$, $R^4$, W, V, U, $M^1$ and n are defined as above.

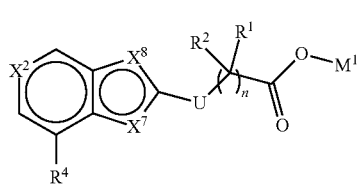

IV-a wherein, $X^2$ is CH or N; $X^7$ and $X^8$ are independently CH or S; $R^1$, $R^2$, $R^4$, U, $M^1$ and n are defined as above.

In the present invention, the compound having a structure of formula II-a, preferably has a structure of formula II-a-1:

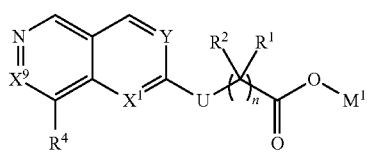

II-a-1 wherein, $X^1$, $X^9$, Y, $R^1$, $R^2$, $R^4$, U, $M^1$ and n are defined as above.

In the present invention, the compound having a structure of formula III-a, preferably has a structure of formula III-a-1:

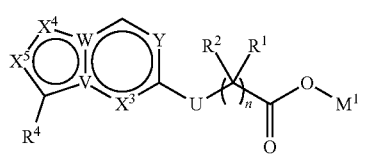

III-a-1 wherein, $X^3$, $X^4$, $X^5$, Y, IV, $R^2$, $R^4$, W, V, U, $M^1$ and n are defined as above.

In the present invention, the compound having a structure of formula IV-a, preferably has a structure of formula IV-a-1:

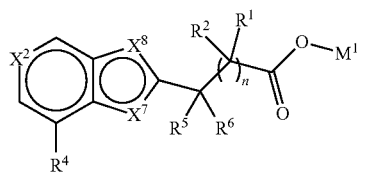

IV-a-1 wherein, $X^2$, $X^7$, $X^8$, $R^1$, $R^2$, $R^4$, $R^5$, $R^6$, $M^1$ and n are defined as above.

The intermediate having a structure of formula I-a, preferably is selected from the compound consisting of

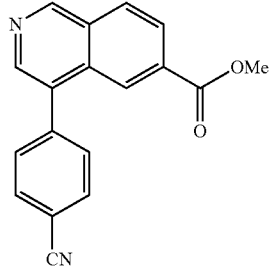

1-a

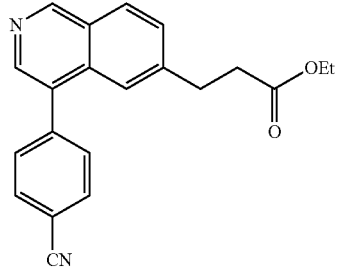

2-a

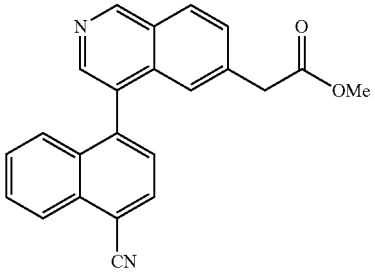

3-a

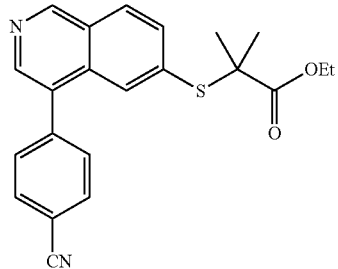

4-a

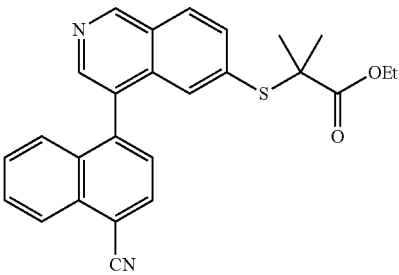

5-a 6-a
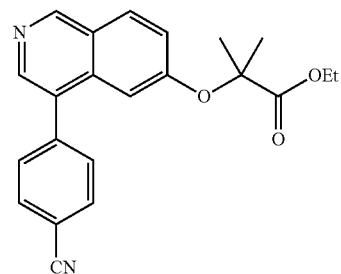
11-a
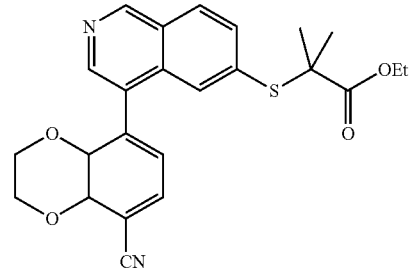
7-a
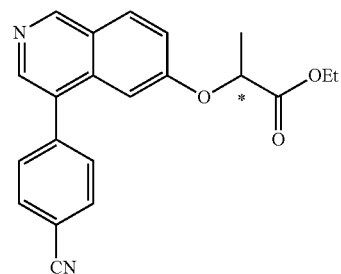
12-a
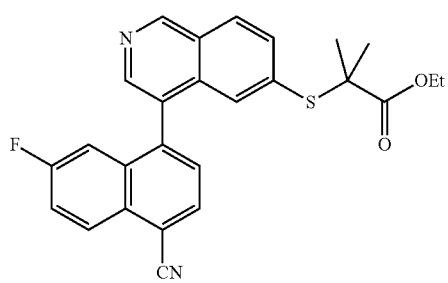
8-a
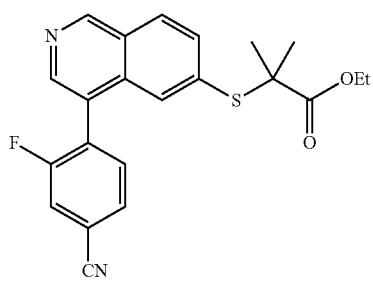
13-a
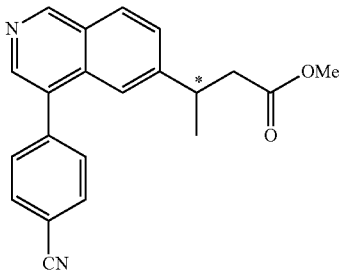
9-a
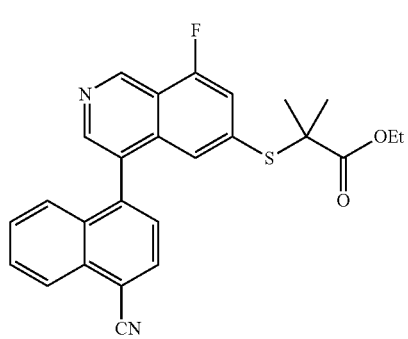
14-a
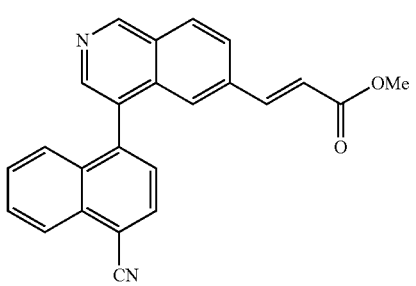
10-a
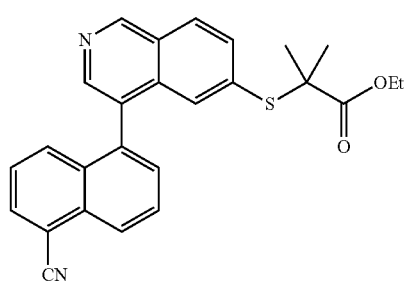
15-a
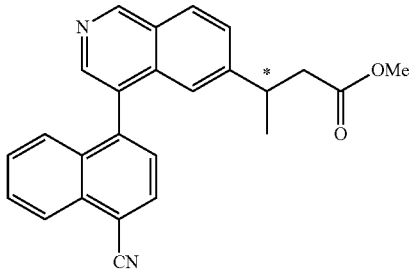

16-a
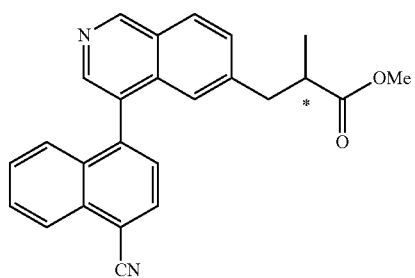
17-a
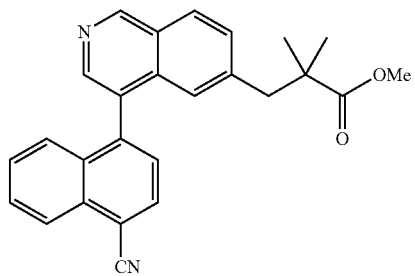
18-a
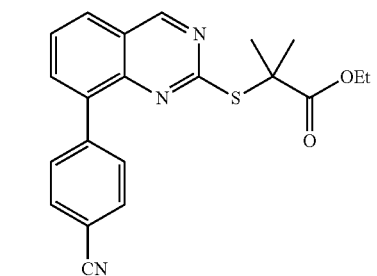
19-a
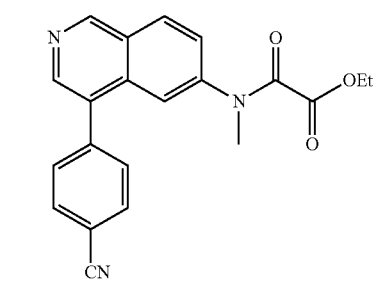
21-a
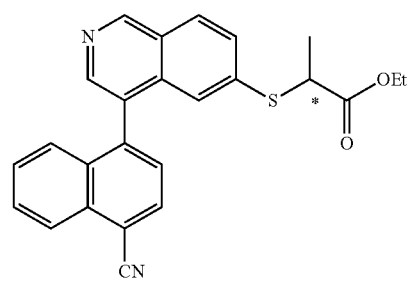
22-a
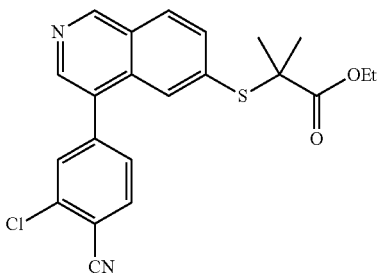
23-a
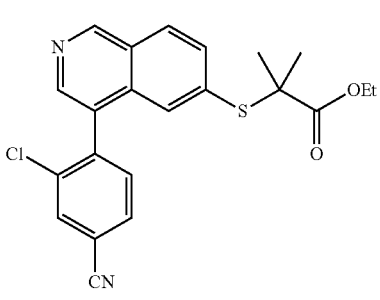
24-a
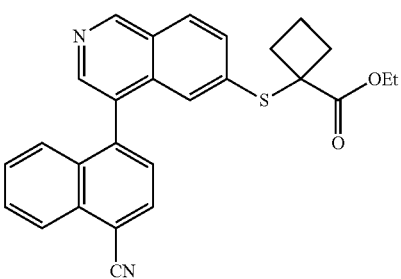
25-a
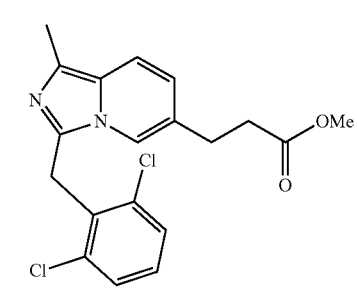
26-a
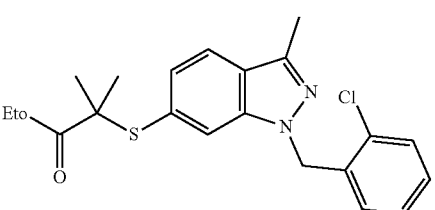
27-a
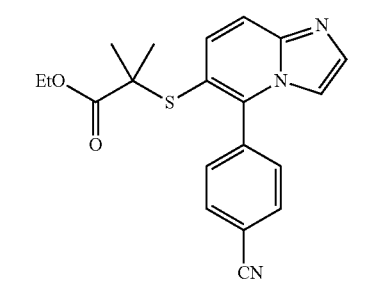

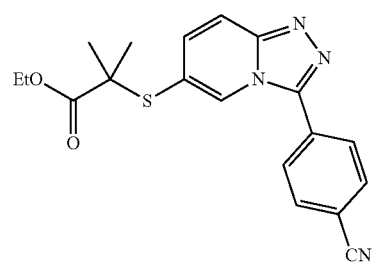
28-a
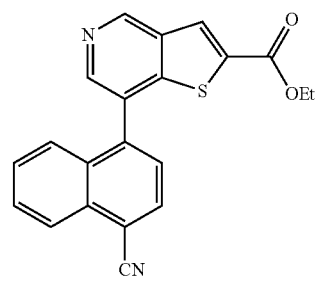
29-a
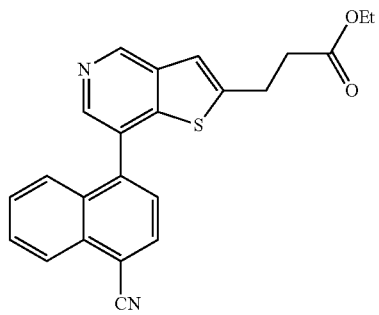
30-a
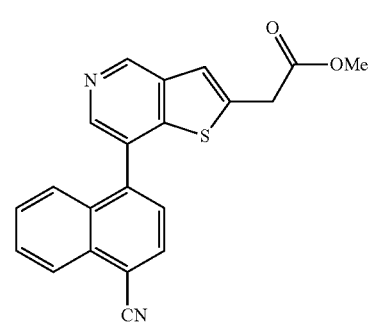
31-a
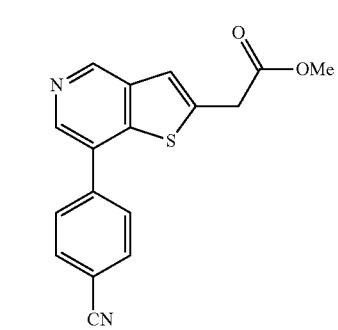
32-a
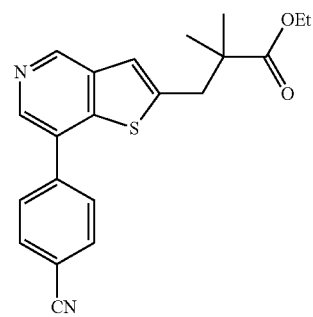
33-a
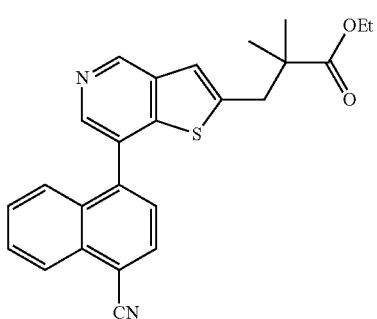
34-a
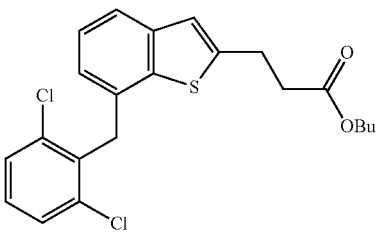
35-a
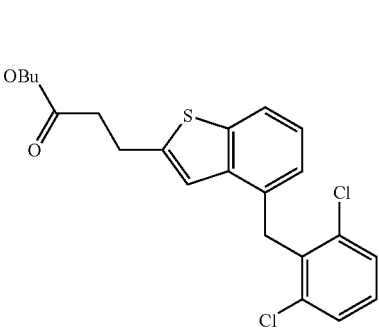
36-a
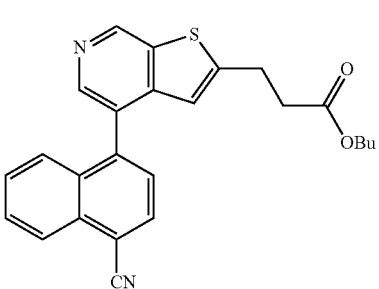
37-a

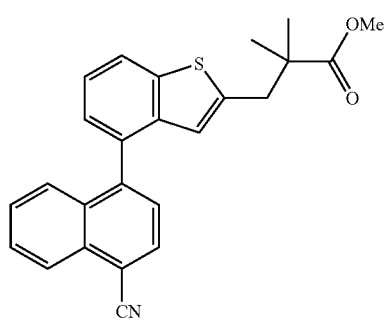
38-a
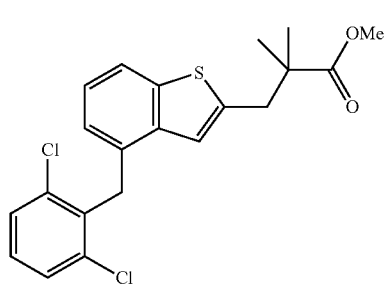
40-a
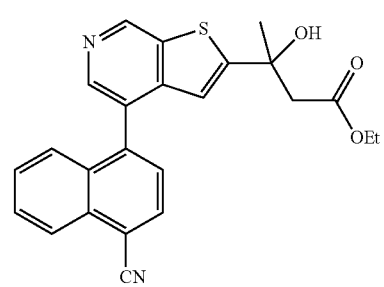
41-a
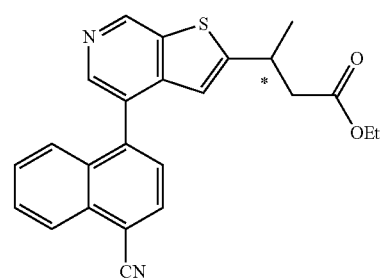
42-a
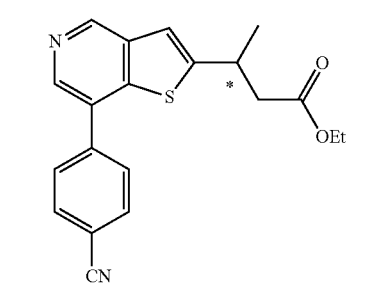
44-a
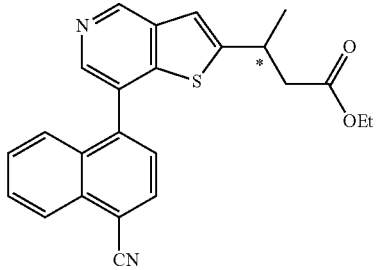
45-a
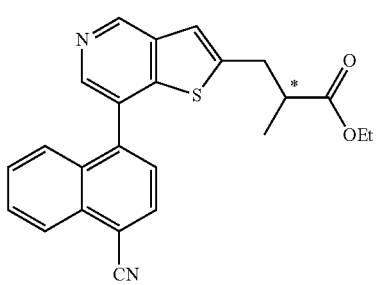
46-a
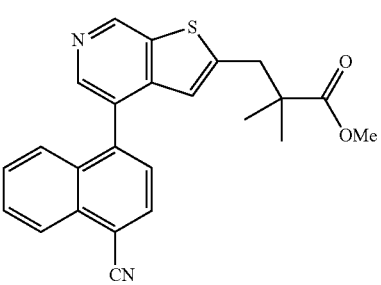
47-a
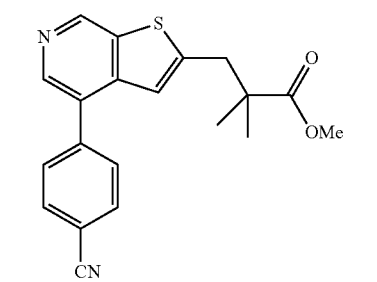
48-a
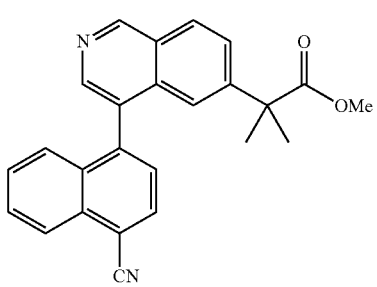
49-a

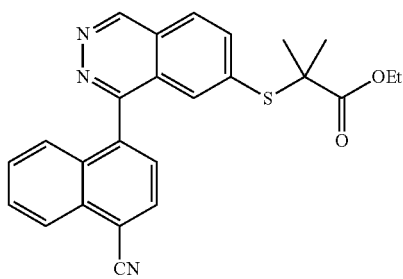

50-a

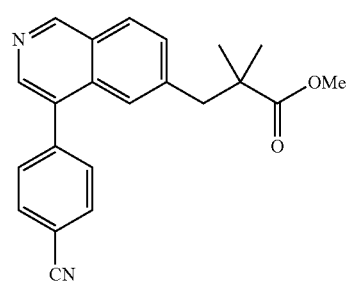

51-a

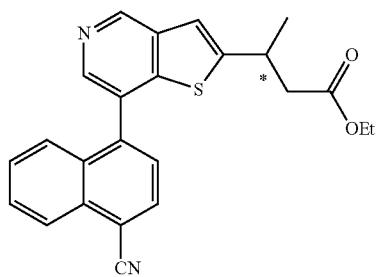

52-a

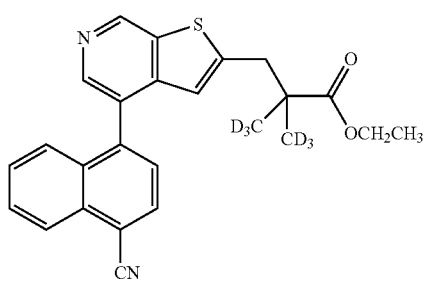

54-a

In above compounds, the carbon marked with * is a chiral carbon or a non-chiral carbon; where it is a chiral carbon, it has S configuration or R configuration, where it is a non-chiral carbon, it is racemic.

The present invention also provides one of enantiomers contained in the racemic compound 7-a, which is given by separating the racemic compound 7-a by an enantiomeric chromatographic column:

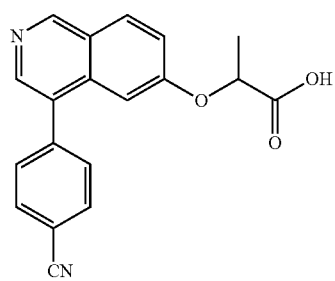

7-a racemate wherein the chromatograph is preferably Gilson 281, the preparative column is preferably r, r-Whelk-O1 (20×250 mm, 5 μm), the mobile phase is preferably Hexane:EtOH:DEA=70:30:0.1 (v/v/v); when the retaining time is 9.0 min, one enantiomer 7A-a is given; when the retaining time is 11.0 min, the other enantiomer 7B-a is given.

The present invention also provides one of enantiomers contained in the racemate 7:

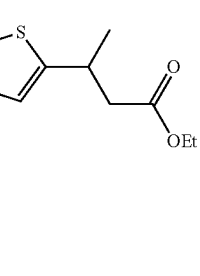

7 racemate wherein the process for preparing one enantiomer preferably comprises that in an organic solvent, in the presence of a base, carrying out a hydrolysis reaction on the enantiomer 7A-a; the process for preparing the other enantiomer preferably comprises that in an organic solvent, in the presence of a base, carrying out a hydrolysis reaction on the enantiomer 7B-a.

The present invention also provides one of the enantiomers contained in the racemate 42-a, which is given by separating the racemate 42-a by an enantiomeric chromatographic column:

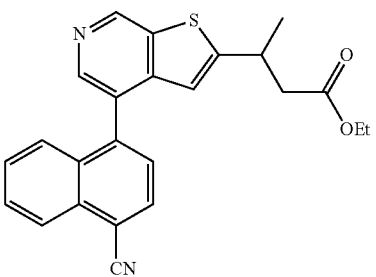

42-a racemate wherein the chromatograph is preferably SFC-80 (Thar, Waters), the preparative column is preferably AD 30×250 mm, 5 μm (Decial), the mobile phase is preferably n-Hexane-0.1% DEA:EtOH-0.1% DEA=80:20 (v/v); when the retaining time is 18.0 min, one enantiomer 43A-a is given; when the retaining time is 20.0 min, the other enantiomer 43B-a is given.

The present invention also provides one of the enantiomers contained in the racemate 42:

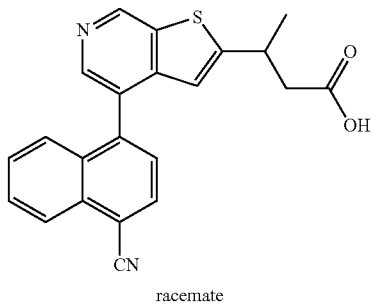

42 racemate wherein the process for preparing one enantiomer preferably comprises that in an organic solvent, in the presence of a base, carrying out a hydrolysis reaction on the enantiomer 43A-a; the process for preparing the other enantiomer preferably comprises that in an organic solvent, in the presence of a base, carrying out a hydrolysis reaction on the antimer 43B-a.

The present invention also provides one of the enantiomers contained in the racemate 44-a, which is given by separating the racemate 44-a by an enantiomeric chromatographic column:

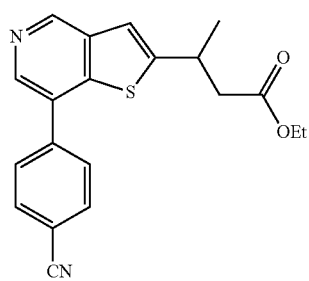

44-a racemate wherein the chromatograph is preferably Gilson 281, the preparative column is preferably r, r-Whelk-O1 (20×250 mm, 5 μm), the mobile phase is preferably n-Hexane:EtOH:DEA=70:30:0.1 (v/v/v); when the retaining time is 6.0 min, one enantiomer 44A-a is given; when the retaining time is 7.0 min, the other enantiomer 44B-a is given.

The present invention provides one of the enantiomers contained in the racemate 44:

44 racemate wherein the process for preparing one enantiomer preferably comprises that in an organic solvent, in the presence of a base, carrying out a hydrolysis reaction on the antimer 44A-a; the process for preparing the other enantiomer preferably comprises that in an organic solvent, in the presence of a base, carrying out a hydrolysis reaction on the antimer 44B-a.

The present invention provides one of the enantiomers contained in the racemate 45-a, which is given by separating the racemate 45-a by an enantiomeric chromatographic column:

45-a racemate wherein the chromatograph is preferably SFC-80 (Thar, Waters), the preparative column is preferably AD 30×250 mm, 5 μm (Decial), the mobile phase is preferably $CO_2$:(Methanol-0.1% $NH_4OH$)=65:35 (v/v); when the retaining time is 8.5 min, one enantiomer 45A-a is given; when the retaining time is 10.5 min, the other enantiomer 45B-a is given.

The present invention provides one of the enantiomers contained in the racemate 45:

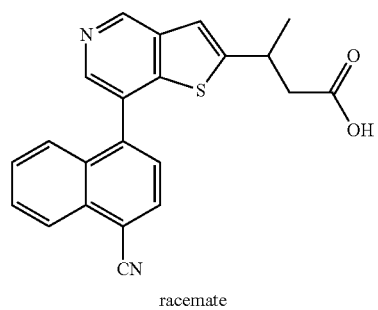

45 racemate wherein the process for preparing one enantiomer preferably comprises that in an organic solvent, in the presence of a base, carrying out a hydrolysis reaction on the antimer 45A-a; the process for preparing the other enantiomer preferably comprises that in an organic solvent, in the presence of a base, carrying out a hydrolysis reaction on the enantiomer 45B-a.

The present invention provides one of the enantiomers contained in the racemate 46-a, which is given by separating the racemate 46-a by an enantiomeric chromatographic column:

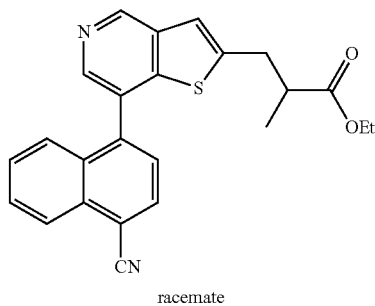

46-a racemate wherein the chromatograph is preferably Gilson 281, the preparative column is preferably r, r-Whelk-O1 (20×250 mm, 5 μm), the mobile phase is preferably Hexane:EtOH: DEA=80:20:0.1 (v/v/v); when the retaining time is 14.0 min, one enantiomer 46A-a is given; when the retaining time is 18.0 min, the other antimer 46B-a is given.

The present invention provides one of the enantiomers contained in the racemate 46:

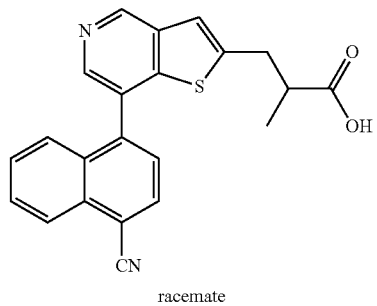

46 racemate wherein the process for preparing one enantiomer preferably comprises that in an organic solvent, in the presence of a base, carrying out a hydrolysis reaction on the enantiomer 46A-a; the process for preparing the other enantiomer preferably comprises that in an organic solvent, in the presence of a base, carrying out a hydrolysis reaction on the enantiomer 46B-a.

The present invention also provides one of the enantiomers included in the racemate 53, the process for preparing one enantiomer preferably comprises, in water, neutralizing the enantiomer 45A by NaOH.

The present invention also provides a use of the condensed ring derivative having a structure of formula I, the tautomer, the mesomer, the racemate, the enantiomer, the diastereoisomer, or the pharmaceutically acceptable salt, the metabolite, the metabolic precursor or the pro-drug thereof in manufacturing a medicament for preventing and/or treating hyperuricemia or its related diseases. The hyperuricemia related diseases generally include gout, hypertension, diabetes, hypertriglyceridemia, metabolic syndrome, coronary heart disease and renal damage and so on.

The present invention also provides a pharmaceutical composition, which comprises therapeutically effective amount of the condensed ring derivative having a structure of formula I, the tautomer, the mesomer, the racemate, the enantiomer, the diastereoisomer, or the pharmaceutically acceptable salt, the metabolite, the metabolic precursor or the pro-drug thereof, and one or more than one pharmaceutically acceptable carrier and/or diluter.

In the present invention, the pharmaceutical composition can be in the form of an oral administration, as well as a sterile injectable aqueous solution, which can be prepared according to any known process for preparing pharmaceutical composition in the art.

The pharmaceutical composition can be used alone, as well as in combination with other medicament having activity on lowering uric acid. The medicament having activity on lowering uric acid is selected from the group consisting of uric acid transporter 1 inhibitor, Xanthine oxidase inhibitor, Xanthine oxidoreductase and Xanthine dehydrogenase inhibitor, preferably Allopurinol and/or Febuxostat.

The present invention also provides a method for preventing and/or treating hyperuricemia or its related diseases, the method comprises administrating proactively effective amount and/or therapeutically effective amount of the condensed ring derivative having a structure of formula I, the tautomer, the mesomer, the racemate, the enantiomer, the diastereoisomer, or the pharmaceutically acceptable salt, the metabolite, the metabolic precursor or the pro-drug thereof to the subject, or administrating proactively effective amount and/or therapeutically effective amount of the pharmaceutical composition of the present invention to the subject.

Unless otherwise specified, the terms involved in the description and the claims of the present invention have following definitions:

"Alkyl" used herein (including used alone and contained in other groups) refers to a saturated linear and branched aliphatic hydrocarbyl containing 1-20 carbon atoms, preferably containing 1-10 carbon atoms, more preferably containing 1-8 carbon atoms, such as methyl, ethyl, n-propyl, iso-propyl, n-butyl, tert-butyl, iso-butyl, pentyl, hexyl, heptyl, octyl, nonyl, decyl, 4,4-dimethylpentyl, 2,2,4-trimethylpentyl, undecyl, dodecyl, and isomers thereof; as well as the alkyl containing 1-4 substituents (with no further substitutions) selected from the group consisting of D, a halogen (preferably F, Br, Cl or I), an alkyl, an alkoxy, an aryl, an aryloxy, an aryl or diaryl substituted by an aryl, an aralkyl, an aralkoxy, an alkenyl, an alkynyl, a cycloalkyl, a cycloalkenyl, a cycloalkyl alkyl, a cycloalkyl alkoxy, an optionally substituted amino, a hydroxyl, a hydroxyl alkyl, an acyl, an aldehyde group, a heteroaryl, a heteroaryloxy, a heterocycloalkyl, a heterocycloalkoxy, an aryl heteroaryl, an arylalkoxycarbonyl, a heteroarylalkyl, a heteroarylalkoxy, an aryloxyalkyl, an aryloxyaryl, an alkylamino, an amido, an arylcarbonylamino, a nitro, a nitrile group, a sulphydryl, a haloalkyl, a trihaloalkyl and/or an alkylthio. In the present invention, "$C_{x1}$-$C_{y1}$" alkyl (x1 and y1 are integers) having indicated number of carbon atoms, such as "$C_{1-4}$ alkyl", has the same definition of the "alkyl" described in this paragraph, except for the number of carbon atoms.

"Alkylidene" used herein (including used alone and contained in other groups) refers to a sub-saturated linear and branched aliphatic hydrocarbyl containing 1-20 carbon atoms, preferably containing 1-10 carbon atoms, more preferably containing 1-8 carbon atoms, such as methylene, ethylidene, propylidene, iso-propylidene, n-butylidene, tert-butylidene, iso-butylidene, pentylidene, hexylidene, heptylidene, octylidene, nonylidene, decylidene, bis(4,4-dimethylpentyl), bis(2,2,4-trimethylpentyl), undecylidene, dodecylidene, and the isomers thereof; including the alkylidene containing 1-4 substituents (without further substituents) selected from the group consisting of D, a halogen (preferably F, Br, Cl or I), an alkyl, an alkoxy, an aryl, an aryloxy, an aryl or diaryl substituted by an aryl, an aralkyl, an aralkoxy, an alkenyl, an alkynyl, an cycloalkyl, an cycloalkenyl, an cycloalkylalkyl, an cycloalkylalkoxy, an optionally substituted amino, an hydroxyl, an hydroxyalkyl, an acyl, an aldehyde group, an heteroaryl, an heteroaryloxy, an heterocycloalkyl, an heterocycloalkoxy, an arylheteroaryl, an arylalkoxycarbonyl, an heteroarylalkyl, an heteroarylalkoxy, an aryloxyalkyl, an aryloxyaryl, an alkylamino, an amido, an arylcarbonylamino, a nitro, a nitrile group, a sulphydryl, a haloalkyl, a trihaloalkyl and/or an alkylthio; one or more than one substituents together with the alkylidene can form a ring, thereby forming a fused ring or a spiro ring.

The term "aliphatic ring" or "cycloalkyl" (including used alone and contained in other groups) includes saturated or partially unsaturated (containing 1 or 2 double bonds) cyclic hydrocarbon group containing 1-3 rings, including monocycloalkyl, bicycloalkyl and tricycloalkyl which contains 3-20 carbon atoms which can form a ring, preferably contains 3-10 carbon atoms, e.g. cyclopropyl, cyclobutyl, cyclopentyl, cyclohexyl, cycloheptyl, cyclooctyl, cyclodecyl and cyclododecyl, cyclohexenyl; the cycloalkyl can be substituted by any of 1-4 substituents (without further substitutions) selected from the group consisting of D, a halogen, an alkyl, an alkoxy, a hydroxyl, an aryl, an aryloxy, an aralkyl, a cycloalkyl, an alkylamino, an amido, an oxo, an acyl, an arylcarbonylamino, an amino, a nitro, a nitrile group, a sulphydryl and/or an alkylthio and/or any alkyl group.

The term "alkoxy" refers to a cyclic or non-cyclic alkyl having indicated number of carbon atoms linked by an oxygen bridge. Therefore, "alkoxy" includes the definitions of the alkyl and the cycloalkyl.

The term "alkenyl" refers to a linear, branched or cyclic non-aryl hydrocarbyl having indicated carbon atoms and at least one carbon-carbon double bond. Preferably, it has one carbon-carbon double bond and can exist up to four non-aryl carbon-carbon double bonds. Therefore, "$C_{2-12}$ alkenyl" refers to an alkenyl having 2-12 carbon atoms. "$C_{2-6}$ alkenyl" refers to an alkenyl having 2-6 carbon atoms, including vinyl, propenyl, butenyl, 2-methyl butenyl and cyclohexenyl. The linear, branched and cyclic part of the alkenyl can contain a double bond, and if it is a substituted alkenyl, the alkenyl can be substituted (but the substituent with no further substitution).

The term "alkynyl" refers to a linear, branched or cyclic hydrocarbyl having indicated carbon atoms and at least one carbon-carbon triple bond. It can have up to three carbon-carbon triple bonds. Therefore, "$C_{2-12}$ alkynyl" refers to an alkynyl having 2-12 carbon atoms. "$C_{2-6}$ alkynyl" refers to an alkynyl having 2-6 carbon atoms, including ethynyl, propynyl, butynyl and 3-methyl butynyl etc.

The term "aryl" used herein refers to any stable monocyclic or bicyclic carbon rings which can have up to 7 atoms in each ring, and at least one of the rings is an aromatic ring. The typical aryl unit includes phenyl, naphthyl, tetrahydronaphthyl, 2, 3-dihydroindenyl, biphenyl, phenanthryl, anthryl or acenaphthyl. It can be understood that where the aryl is a bicyclic group and one of the ring is a non-aromatic ring, the linkage is through the aromatic ring. The aryl also includes any of 1-4 substituents (without further substitutions) selected from the group consisting of D, a halogen (F, Br Cl or I), an alkyl, an alkoxy, an aryl, an aryloxy, an aryl or diaryl substituted by an aryl, an aralkyl, an aralkoxy, an alkenyl, an alkynyl, a cycloalkyl, a cycloalkenyl, a cycloalkylalkyl, a cycloalkylalkoxy, an optionally substituted amino, a hydroxyl, a hydroxyalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a nitrile group, a sulphydryl, a haloalkyl, a trihaloalkyl and/or an alkylthio.

The term "halogen" refers to F, Cl, Br, I or At.

The term "hydroxyl" refers to

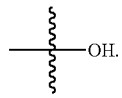

The term "amino" refers to

The term "cyano" refers to

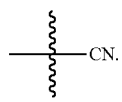

The term "carboxyl" refers to

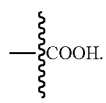

The term "sulfonyl" refers to

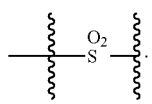

The term "acyl" refers to

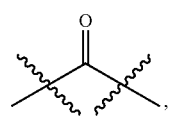 [SMILES: *C(*)=O]

a univalence group derived from an organic or inorganic oxygenic acid cleaving a hydroxyl off.

The term "haloalkyl" refers to an alkyl substituted by halogen at any position. Therefore, "haloalkyl" includes the definitions of the halogen and the alkyl.

The term "haloalkoxy" refers to an alkoxy substituted by halogen at any position. Therefore, "haloalkoxy" includes the definitions of the halogen and the alkoxy.

The term "aryloxy" refers to an aryl having indicated number of carbon atoms linked by an oxygen bridge. Therefore, "aryloxy" includes the definition of the aryl.

The term "aromatic hetero group" or "heteroaryl" used herein refers to a stable monocycle or bicycle which can have up to 7 atoms in each ring, and at least one of the rings is an aromatic ring containing 1-4 heteroatoms selected from O, N and S. The heteroaryl defined herein includes but not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolyl, oxazolyl, isoxazolyl, indolyl, pyrazinyl, pyridazinyl, pyridyl, pyrimidyl, pyrryl, tetrahydroquinoline. As defined in the heterocyclo, "heteroaryl" can also be understood including the N-Oxide derivative of any N-containing heteroaryl. Where the heteroaryl is a bicyclic group and one of the rings is a non-aromatic ring or without any heteroatom, it can be understood, the linkage is through the aryl or the ring containing the heteroatom. The heteroaryl can be substituted by any of 1-4 substituents selected from the group consisting of D, a halogen, an alkyl, an alkoxy, a hydroxyl, an aryl, an aryloxy, an aralkyl, a cycloalkyl, an alkylamino, an acylamino, an acyl, an arylcarbonylamino, an amino, a nitro, a nitrile group, a sulphydryl and/or an alkylthio and/or any of alkyl group.

The term "heterocyclo" or "heterocyclic group" used herein refers to a 5-10 membered aromatic or non-aromatic heterocycle having 1-4 heteroatoms selected from O, N and S, including bicyclic group. Therefore, "heterocyclic group" includes the aryl and the dihydro- or tetrahydro-analogues thereof. The embodiments of the "heterocyclic group" include but not limited to benzimidazolyl, benzofuranyl, benzofurazinyl, benzopyrazolyl, benzotriazolyl, benzothienyl, benzoxazolyl, carbazyl, carbazolyl, cinnolinyl, furanyl, imidazolyl, indolinyl, indolyl, indazolyl, isobenzofuranyl, pseudoindolyl, isoquinolyl, isothiazolyl, isoxazolyl, naphthalene pyrimidinyl, oxadiazolyl, oxazolyl, oxazoline, isoxazoline, oxycyclobutyl, pyranyl, pyrazinyl, pyrazolyl, pyridazinyl, pyridopyridyl, pyridazinyl, pyridyl, pyrimidyl, pyrryl, quinazolyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyrryl, dihydroquinolyl, dihydrotetrazolyl, dihydrothiadiazolyl, dihydrothiazolyl, dihydrothienyl, dihydrotriazolyl, dihydro-azetidinyl, methylenedioxybenzoyl, tetrahydrofuranyl, tetrahydrothienyl and N-Oxide thereof. The heterocyclo (without further substitution) can link with other groups by its carbon atom or heteroatom.

The term "cycloheteroaliphatic" or "heterocycloalkyl" used herein alone or contained in other groups refers to a saturated or partially unsaturated 4-12 membered ring having 1-4 heteroatoms (e.g. N, O and/or S). The heterocycloalkyl can contain 1-4 substituents (without further substitution), such as an alkyl, a halogen, an oxo and/or any of alkyl list above. Besides, any heterocycloalkyl can fuse to a cycloalkyl, an aryl, a heteroaryl or a heterocycloalkyl. The heterocycloalkyl can link to other groups through its carbon atom or heteroatom.

The term "aromatic ring" used herein refers to any stable monocyclic or bicyclic carbon rings which can have up to 7 atoms in each ring and at least one of the ring is an aromatic ring. The embodiments of the aromatic unit include phenyl, naphthyl, tetrahydronaphthyl, 2, 3-dihydroindenyl, biphenyl, phenanthryl, anthryl or acenaphthyl. It can be understood that when the aryl is a bicyclic group and one of the ring is a non-aromatic ring, the linkage is through "aromatic ring". The aromatic ring includes any of 1-4 substituents (without further substitution) selected from the group consisting of D, a halogen (F, Br, Cl or I), an alkyl, an alkoxy, an aryl, an aryloxy, an aryl or biaryl substituted with an aryl, an aralkyl, an aralkoxy, an alkenyl, an alkynyl, a cycloalkyl, a cycloalkenyl, a cycloalkylalkyl, a cycloalkylalkoxy, an amino, a hydroxyl, a hydroxyalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a nitrile group, a sulphydryl, a haloalkyl, a trihaloalkyl and/or an alkylthio.

The term "heteroaryl" or "aromatic heterocyclo" used herein refers to a stable monocyclic or bicyclic group which can have up to 7 atoms in each ring and at least one of the ring is an aromatic ring having 1-4 heteroatoms selected from O, N and S. In this definition, the heteroaryl includes but not limited to acridine, carbazole, cinnoline, carboline, quinoxaline, imidazole, pyrazole, pyrrole, indole, indoline, benzotriazole, benzimidazole, furan, thiophen, isothiazole, benzothiophene, dihydrobenzothiophene, benzofuran, isobenzofuran, benzoxazole, benzofuraxan, benzopyrazole, quinoline, isoindoline, isoquinoline, oxazole, oxadiazole, isoxazole, indole, pyrazine, pyridopyridine, tetrazolopyridine, pyridazine, pyridine, naphthalene pyrimidine, pyrimidine, pyrrole, tetrazole, thiadiazole, thiazole, thiophene, triazole, quinazoline, tetrahydroquinoline, dihydrobenzimidazole, dihydrobenzofuran, dihydrobenzoxazole, dihydroquinoline. As defined in the definition of heterocycle, "heteroaryl" is also understood to include N-Oxide derivatives of any N-containing heteroaryl. Where the heteroaryl is a bicyclic group and one of the ring is a non-aromatic ring or without any heteroatom, it can be understood that the linkage is through the aryl or the heteroatom contained in the ring. The heteroaryl can be substituted by any of 1-4 substituents (without further substitutions) selected from the group consisting of D, a halogen, an alkyl, an alkoxy, a hydroxyl, an aryl, an aryloxy, an aralkyl, a cycloalkyl, an alkylamino, an acylamino, an acyl, an arylcarbonylamino, an amino, a nitro, a nitrile group, a sulphydryl and/or an alkylthio and/or any alkyl defined in the present invention.

"Proactively effective amount and/or therapeutically effective amount" refers to an amount of the compound administered to a subject sufficient to prevent and/or treat the diseases involved in the present invention. Though the proactively effective amount and/or therapeutically effective amount of the compound depends on the compound, the condition and its severity, and the age of the subject to be treated, it can be determined by the person skilled in the art according to the common method.

As used in the present invention, when the specific salt, pharmaceutical composition, composition, excipient are mentioned to be "pharmaceutically acceptable", it means that the salt, pharmaceutical composition, composition, excipient are generally non-toxic, safe and suitable to be administered to the subject; the subject is preferably a mammal, more preferably human.

The term "pharmaceutically acceptable salt" as used herein refers to a pharmaceutically acceptable organic or inorganic salt of the compound of the present invention. Typical embodiments are include but not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methylsulfonate, ethylsulfonate, benzene sulfonate, tosilate, embonate (i.e. 1-1-methylene-bis(2-hydroxyl-3-naphthoate)).

As used herein, unless otherwise specified, the term "prodrug" refers to a derivative of a compound containing biological reactive functional groups, which can be cleaved from the compound or react in other ways to provide the compound under biological condition (in vivo or in vitro). Generally, the prodrug does not have activity, or have less activity than the compound itself, this makes the compound exhibit effects until the biological reactive functional group cleaved from the compound. The biological reactive functional group can hydrolyze or oxidize under biological condition to provide the compound. For example, the prodrug can include biologically hydrolysable groups. The biologically hydrolysable groups include but not limited to biologically hydrolysable phosphate, biologically hydrolysable ester, biologically hydrolysable amide, biologically hydrolysable carbonate, biologically hydrolysable carbamate and biologically hydrolysable uride.

The compound of the present invention can contain one or more than one asymmetric centers ("stereoisomers"). As used herein, the term "stereoisomers" refers to Cis- and Trans-isomer, R- and S-antimer and diastereomer. These stereoisomers can be prepared by asymmetric synthesis or chiral separation (e.g. isolating, crystallizing, TLC, column chromatography, gas chromatography, HPLC). These stereoisomers can also derive from the diastereomer obtained from reacting a mixture of the enantiomers or racemate with a proper chiral compound, followed by crystallizing or conducting any other proper common method.

As used herein, the term "subject" refers to any animal to be administered or have been administered with the compound or the pharmaceutical composition according to the embodiment of the present invention, preferably a mammal, most preferably human. As used herein, the term "mammal" includes any mammal. Typical mammal includes but not limited to cattle, horse, sheep, pig, cat, dog, mouse, rat, rabbit, Guinea pig, monkey, human and so on, human is the most preferable.

In one embodiment, "treat" or "treating" refers to an improvement, prevention or reversion of a disease or a condition or at least one distinguished symptom thereof. In another embodiment, "treat" or "treating" refers to an improvement, prevention or reversion of at least one of measurable body parameters of a disease or a condition which is being treated, which may not been distinguished in a mammal. However, in another embodiment, "treat" or "treating" refers to slowing the development of a disease or a condition, or refers to stabilizing in body, such as a recognizable symptom, or refers to stabilizing in physiology, such as body parameters, or refers to both. In another embodiment, treat" or "treating" refers to slowing the initiation of a disease or a condition.

In certain embodiments, the claimed compound is administered for prevention. As used herein, "prevent" or "preventing" refers to lowering a risk of having a disease or a condition. In a preferred embodiment, administering an indicated compound to a subject for a preventive purpose, such as the subject having a tendency to catch or having a family history of cancer or autoimmune diseases.

In the present invention, abbr. "Abs" refers to the absolute configuration of the chiral carbon atom contained in the compound is unknown, indicating S-configuration or R-configuration.

In the present invention, 0.1% DEA refers to that DEA volume accounts for 0.1% volume of the mixture solution containing DEA, for example, in Hexane-0.1% DEA, 0.1% DEA refers to that DEA volume accounts for 0.1% total volume of Hexane and DEA. Additionally, the definition of 0.1% $NH_4OH$ is the same as that of 0.1% DEA.

In the present invention, room temperature refers to ambient temperature, generally refers to 10-30° C.

Without departing from the common knowledge in the art, the optimized embodiments can be obtained by optionally combining the preferred conditions above.

The reagents and raw materials are commercially available.

The positive effects achieved by the present invention lie in that:
the present invention provides a condensed ring derivative which is totally distinguished from the prior art, the preparation method, the intermediate, the pharmaceutical composition and the use thereof. The condensed ring derivative of the present invention has distinct inhibitory effects against URAT1, which can relieve or treat hyperuricemia etc. and related diseases.

DETAILED DESCRIPTION OF THE PREFERRED EMBODIMENT

The structure of the compound is determined by NMR or MS, NMR is obtained by Bruker Avance-500 apparatus, $d_6$-DMSO, $CDCl_3$ and $CD_3OD$ etc. as a solvent, TMS as an interior label. MS is obtained by LC-MS Agilent Technologies 6110, ESI as an ion source.

Microwave reaction is conducted in Explorer full automatic microwave irradiation equipment supplied by CEM, US Corporation, magnetron frequency is 2450 MHz, continuous microwave output power is 300 W.

HPLC is Gilson 281, the preparative column is Xbridge, 21.2×250 mm $C_{18}$, 10 μm.

Process I for separating enantiomers: the apparatus is Gilson 281, the preparative column is r,r-Whelk-O1 (20×250 mm, 5 μm); process II: the apparatus is SFC-80 (Thar, Waters), the preparative column is AD 30×250 mm, 5 μm (Decial).

Embodiment 1

4-(4-cyanophenyl)isoquinoline-6-carboxylic Acid (Compound 1)

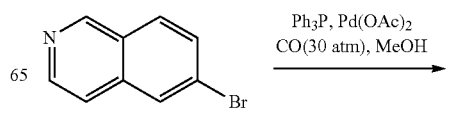

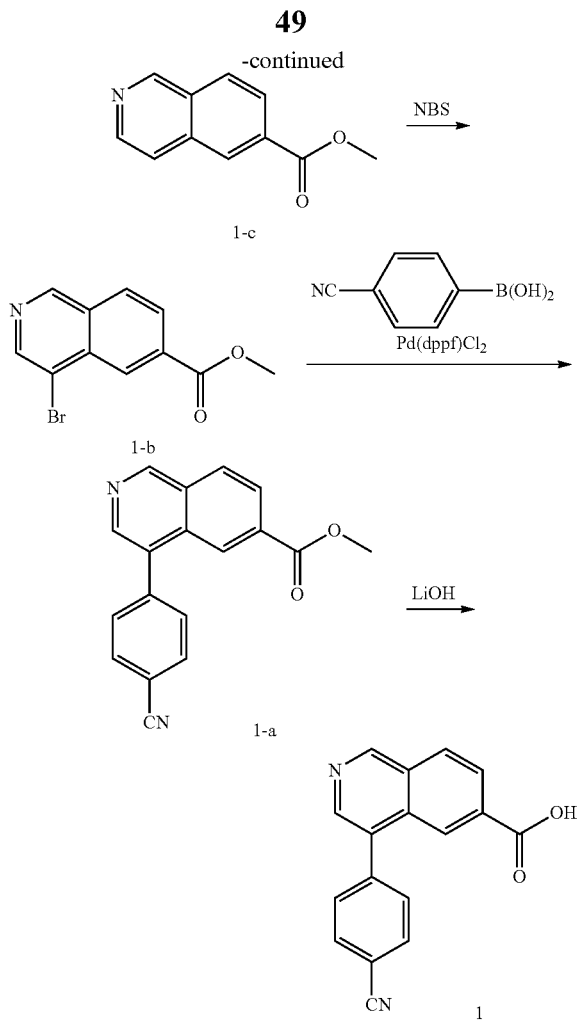

Synthesis of Compound 1-c

Under CO atmosphere (30 atm), 6-bromoisoquinoline (10.0 g, 48 mmol), sodium acetate (5.0 g, 61 mmol), triphenylphosphine (3.8 g, 14 mmol) and palladium acetate (2.8 g, 12 mmol) were dissolved in DMF (40 mL) and methanol (40 mL), the mixture was reacted at 100° C. for 24 hrs. The mixture was then cooled to room temperature, evaporated to remove methanol, the residue was filtered through celite, the filtrate cake was washed with EA (200 mL). The filtrate was washed in turn with water (100 mL×3) and saturated brine (100 mL), dried over anhydrous sodium sulfate, filtered, concentrated under reduced pressure. The residue was purified with silica column chromatography (PE:EA=10:1) to give white solid 1-c (7 g, yield: 78%). LC-MS (ESI): m/z=188 [M+H]$^+$.

Synthesis of Compound 1-b

Compound 1-c (1.88 g, 10 mmol) and N-bromosuccinimide (2.7 g, 15 mmol) were dissolved in acetic acid (40 mL), the mixture was cooled to room temperature after reacting at 80° C. for 24 hrs. Part of acetic acid was removed under reduced pressure, the residue was filtered through celite, the filtrate cake was washed with DCM (200 mL). The filtrate was in turn washed with saturated sodium sulfite solution (200 mL), dried over anhydrous sodium sulfate, filtered, evaporated under reduced pressure. The residue was purified with silica column chromatography (PE:EA=50:1) to give colorless solid 1-b (2.5 g, yield 94%). LC-MS (ESI): m/z=266 [M+H]$^+$.

Synthesis of Compound 1-a

Under N$_2$ atmosphere, compound 1-b (133 mg, 0.5 mmol), 4-cyanophenylboronic acid (75 mg, 0.5 mmol) and sodium carbonate (60 mg, 0.6 mmol) were suspended in a mixed solution of dioxane (4 mL) and water (1 mL), [1,1'-bis(diphenylphosphine)ferrocene]palladium dichloride (25 mg, 0.03 mmol) was added. The mixture was stirred at 80° C. for 3 hrs, then cooled to room temperature. The mixture was filtered through celite, the filtrate cake was washed with EA (50 mL). The filtrate was in turn washed with water (20 mL×3) and saturated brine (10 mL), dried over anhydrous sodium sulfate, filtered, evaporated under reduced pressure. The residue was purified by silica column chromatography (PE:EA=1:1) to give compound 1-a (126 mg, yield 83%). LC-MS (ESI): m/z=289 [M+H]$^+$.

Synthesis of Compound 1

At room temperature, LiOH (42 mg, 1.0 mmol) was added to a solution of compound 1-a (120 mg, 0.42 mmol) in a mixed solution of methanol (1 mL), THF (4 mL) and water (1 mL). The mixture was stirred at room temperature for 1 h, followed by adding 2M HCl aqueous solution (1 mL) and water (20 mL), solid was precipitated and filtered out. The solid was washed with water (10 mL), dried under vacuum to give white solid 1 (91 mg, yield 79%). LC-MS (ESI): m/z=295 [M+H]$^+$.

$^1$H-NMR (400 MHz, DMSO-d6) δ: 13.55 (s, 1H), 9.53 (s, 1H), 8.60 (s, 1H), 8.34 (m, 2H), 8.21 (m, 1H), 8.10 (d, J=8.0 Hz, 1H), 7.82 (d, J=8.0 Hz, 1H) ppm.

Embodiment 2

3-[4-(4-Cyanophenyl)isoquinolin-6-yl]propionic Acid (Compound 2)

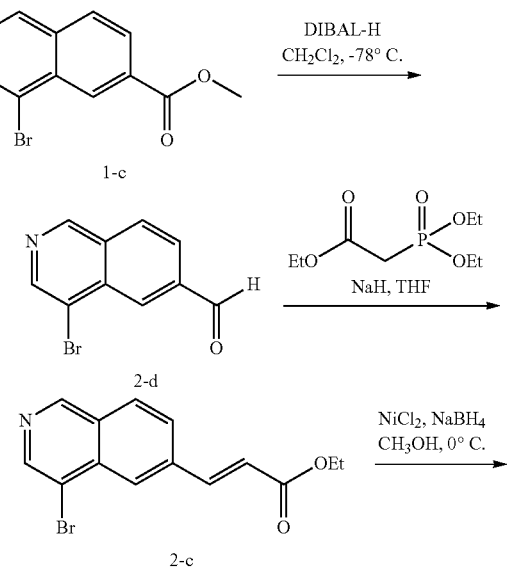

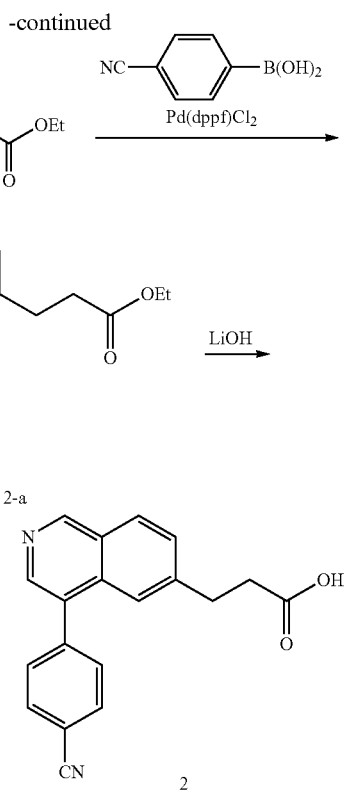

Synthesis of Compound 2-d

A solution of compound 1-c (1.33 g, 5 mmol) in DCM (50 mL) was cooled to −78° C., 1.0M diisobutylaluminum hydride in DCM (20 mL, 20 mmol) was slowly added dropwise, the mixture was further stirred for 1 h. The mixture was warmed to room temperature, saturated aqueous solution of NH$_4$Cl (300 mL) was added, organic phase was separated, aqueous phase was extracted with DCM (50 mL×3). The organic phases were combined, dried over anhydrous sodium sulfate, filtered, evaporated under reduced pressure. The residue was purified with silica column chromatography (PE:EA=3:1) to give light yellow solid 2-d (900 mg, yield 76%). LC-MS (ESI): m/z=236 [M+H]$^+$.

Synthesis of Compound 2-c

At 0° C., triethyl phosphonoacetate (1.4 mL, 5 mmol) and sodium hydride (240 mg, 6 mmol) were added into a solution of compound 2-d (470 mg, 2 mmol) in THF (10 mL), the mixture was further stirred for 1 h. The mixture was warmed to room temperature, followed by adding saturated aqueous solution of NH$_4$Cl (300 mL), extracted with EA (50 mL×3). The organic phases were combined, washed in turn with water (10 mL×3) and saturated brine (10 mL), dried over anhydrous sodium sulfate, filtered, evaporated under reduced pressure. The residue was purified with silica column chromatography (PE:EA=5:1) to give light yellow solid 2-c (380 mg, yield 62%). LC-MS (ESI): m/z=306 [M+H]$^+$.

Synthesis of Compound 2-b

At 0° C., NaBH$_4$ (40 mg, 1 mmol) was added slowly into a solution of compound 2-c (310 mg, 1 mmol) and NiCl$_2$ (13 mg, 0.1 mmol) in methanol (5 mL), the mixture was further stirred for 3 hrs. The mixture was warmed to room temperature, followed by adding saturated aqueous solution of NH$_4$Cl (30 mL), being extracted with EA (10 mL×3). The organic phases were combined, washed in turn with water (5 mL×3) and saturated brine (5 mL), dried over anhydrous sodium sulfate, filtered, evaporated under reduced pressure. The residue was purified with silica column chromatography (PE:EA=4:1) to give light yellow solid 2-b (280 mg, yield 91%). LC-MS (ESI): m/z=308 [M+H]$^+$.

Synthesis of Compound 2-a

Under N$_2$ atmosphere, compound 2-b (155 mg, 0.5 mmol), 4-cyanophenylboronic acid (75 mg, 0.5 mmol) and sodium carbonate (106 mg, 1 mmol) were suspended in a mixture of dioxane (4 mL) and water (1 mL), [1,1'-bis(diphenylphosphine)ferrocene]palladium dichloride (40 mg, 0.05 mmol) was added. The mixture was stirred at 80° C. for 3 hrs, then cooled to room temperature. The mixture was filtered through celite, the filtrate cake was washed with EA (50 mL). The filtrate was in turn washed with water (20 mL×3) and saturated brine (10 mL), dried over anhydrous magnesium sulfate, filtered, evaporated under reduced pressure. The residue was purified with silica column chromatography (PE:EA=1:1) to give compound 2-a (100 mg, yield 61%). LC-MS (ESI): m/z=331 [M+H]$^+$.

Synthesis of Compound 2

At room temperature, LiOH (42 mg, 1.0 mmol) was added to a mixed solution of compound 2-a (100 mg, 0.3 mmol) in methanol (1 mL), THF (4 mL) and water (1 mL), the mixture was further stirred for 1 h, 2M HCl aqueous solution (1 mL) and water (20 mL) were added, solid was precipitated and filtered out. The solid was washed with water (10 mL), dried under vacuum to give white solid 2 (61 mg, yield 67%). LC-MS (ESI): m/z=303 [M+H]$^+$.

$^1$H-NMR (400 MHz, DMSO-d6) δ: 12.18 (s, 1H), 9.34 (s, 1H), 8.44 (s, 1H), 8.18 (d, J=8.0 Hz, 1H), 8.04 (d, J=8.0 Hz, 2H), 7.77 (d, J=8.0 Hz, 2H), 7.68 (d, J=8.0 Hz, 1H), 2.99 (t, J=8.0 Hz, 2H), 2.59 (t, J=8.0 Hz, 1H) ppm.

Embodiment 3

2-[4-(4-Cyanonaphthalen-1-yl)isoquinolin-6-yl]acetic Acid (Compound 3)

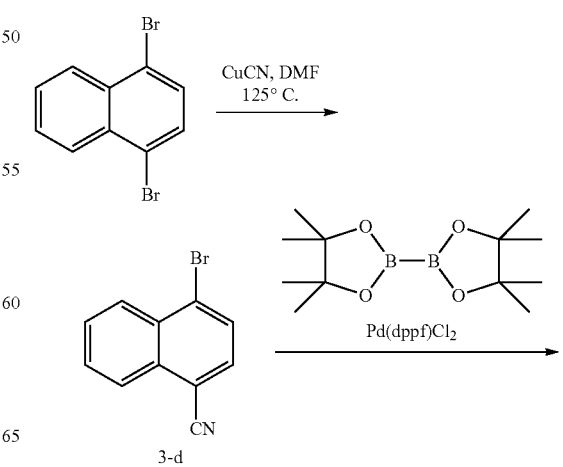

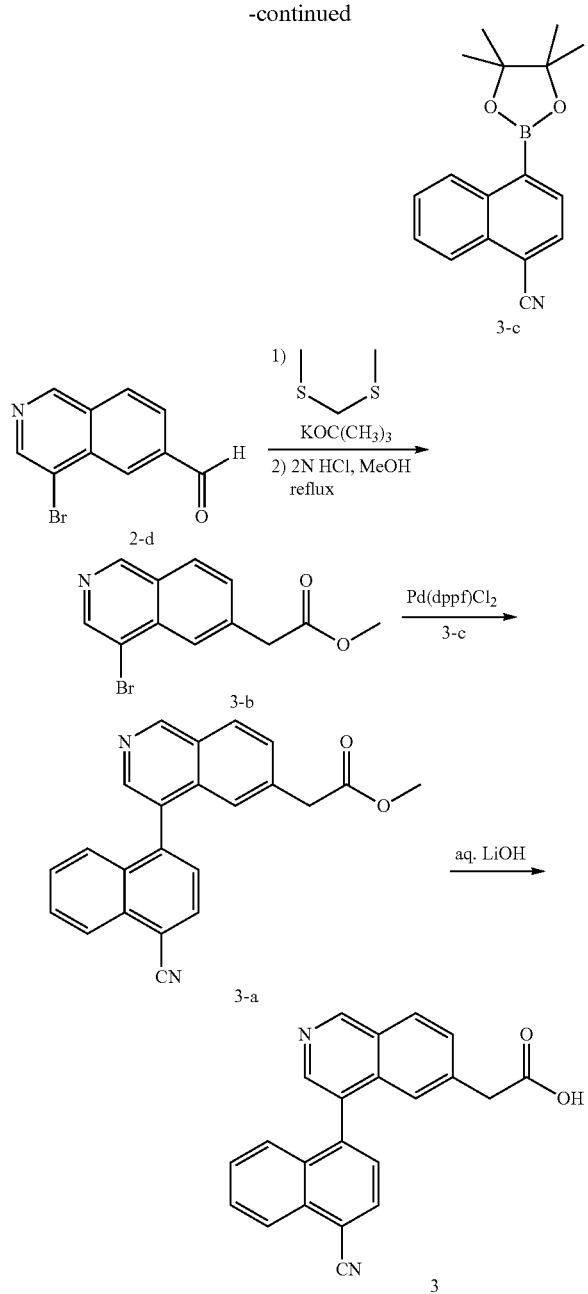

Synthesis of Compound 3-d

CuCN (5.0 g, 56.3 mmol) was added to a solution of 1,4-dibromonaphthalene (20 g, 70.4 mmol) in DMF (250 mL), the mixture was reacted for 16 hrs at 125° C., evaporated under reduced pressure. Aqueous ammonia (200 mL) and EA (200 mL) were added to the residue, the mixture was stirred for 1 h and organic phase was separated. The organic phase was in turn washed with water (100 mL×3) and saturated brine (100 mL), dried over anhydrous magnesium sulfate, filtered, evaporated under reduced pressure. The residue was purified with silica chromatography (PE:EA=10:1) to give compound 3-d (5.1 g, yield 31%). LC-MS (ESI): m/z=232 [M+H]$^+$.

Synthesis of Compound 3-c

Under $N_2$ atmosphere, bis(pinacolato)diboron (8.4 g, 33 mmol), potassium acetate (6.5 g, 66 mmol) and [1,1'-bis(diphenylphosphine)ferrocene]palladium dichloride (1.2 g, 1.76 mmol) were respectively added to a solution of compound 3-d (5.1 g, 22 mmol) in dioxane (150 mL), the mixture was stirred at 80° C. for 6 hrs. The mixture was evaporated under reduced pressure, the residue was filtered through celite, the filtrate cake was washed with dioxane (50 mL), the filtrate was evaporated under reduced pressure. The residue was purified with silica column chromatography (PE:EA=10:1) to give compound 3-c (6 g, yield 97%). LC-MS (ESI): m/z=280 [M+H]$^+$.

Synthesis of Compound 3-b

At 0° C., under $N_2$ atmosphere, potassium tert-butanolate (71 mg, 0.63 mmol) was added to a solution of methyl (methylthiomethyl)sulfoxide (78 mg, 0.63 mmol) in anhydrous THF (5 mL). The mixture was stirred for 30 mins, followed by adding compound 2-d (100 mg, 0.42 mmol), stirred for 1 h at room temperature, then evaporated under reduced pressure. 2M HCl in methanol (5 mL) was added to the residue, the mixture was refluxed for 3 hrs, then concentrated under reduced pressure. The residue was purified with silica column chromatography (PE:EA=5:1) to give compound 3-b (70 mg, yield 60%). LC-MS (ESI): m/z=281 [M+H]$^+$.

Synthesis of Compound 3-a

Under $N_2$ atmosphere, compound 3-c (40 mg, 0.14 mmol), sodium carbonate (46 mg, 0.43 mmol) and [1,1'-bis(diphenylphosphine)ferrocene]palladium dichloride (30 mg, 0.036 mmol) were respectively added to a mixed solution of compound 3-b (40 mg, 0.14 mmol) in ethylene glycol dimethyl ether (150 mL) and water (1 mL). The mixture was stirred at 75° C. for 16 hrs, and then concentrated under reduced pressure. The residue was purified by silica column chromatography (PE:EA=2:1) to give compound 3-a (27 mg, yield 53%). LC-MS (ESI): m/z=353 [M+H]$^+$.

Synthesis of Compound 3

At room temperature, 1M LiOH aqueous solution (1.0 mL) was added to a mixed solution of compound 3-a (27 mg, 0.076 mmol) in methanol (5 mL) and THF (5 mL), the mixture was stirred for 16 hrs, and evaporated under reduced pressure. The residue was dissolved with water (6 mL), adjusted to pH=3 with 1M citric acid aqueous solution, solid was precipitated and filtered out. The solid was washed with water (5 mL), dried under vacuum to give white solid 3 (20 mg, yield 77%). LC-MS (ESI): m/z=339 [M+H]$^+$.

$^1$H-NMR (400 MHz, DMSO-d6) δ: 12.34 (s, br., 1H), 9.47 (s, 1H), 8.45 (s, 1H), 8.35 (d, J=8.0 Hz, 1H), 8.27 (d, J=8.0 Hz, 1H), 8.24 (d, J=8.0 Hz, 1H), 7.85 (t, J=8.0 Hz, 1H), 7.73 (d, J=8.0 Hz, 2H), 7.64 (d, J=8.0 Hz, 1H), 7.59 (t, J=8.0 Hz, 1H), 7.41 (d, J=8.0 Hz, 1H), 7.14 (s, 1H), 3.63 (s, 2H) ppm.

Embodiment 4

2{[4-(4-Cyanophenyl)isoquinolin-6-yl]thio-2-methylpropionic Acid (Compound 4)

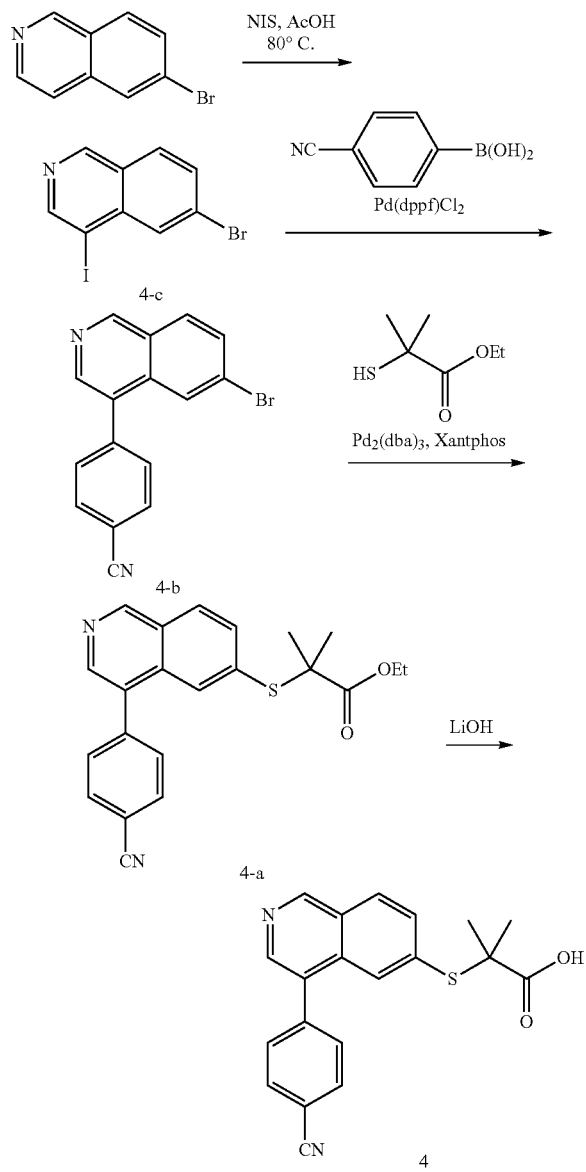

Synthesis of Compound 4-c

6-Bromoisoquinoline (10.4 g, 50 mmol) and N-iodosuccinimide (13.5 g, 60 mmol) were dissolved in acetic acid (100 mL), the mixture was reacted for 8 hrs at 80° C. The mixture was cooled to room temperature, followed by concentrating under reduced pressure to remove half of acetic acid, the residue was filtered through celite, the filtrate cake was washed with DCM (200 mL), the organic phase was in turn washed with saturated sodium sulfite solution (200 mL) and water (100 mL), dried over anhydrous magnesium sulfate, filtered, concentrated under reduced pressure. The residue was purified with silica column chromatography (PE:EA=5:1) to give compound 4-c (11.6 g, yield 70%). LC-MS (ESI): m/z=334 [M+H]$^+$.

Synthesis of Compound 4-b

Under $N_2$ atmosphere, compound 4-c (2.33 g, 10 mmol), 4-cyanobenzene boronic acid (1.5 g, 10 mmol) and sodium carbonate (2.12 g, 20 mmol) were suspended in dioxane (40 mL) and water (10 mL), [1,1'-bis(diphenylphosphine)ferrocene]palladium dichloride (0.55 g, 1 mmol) was added. The mixture was stirred at 80° C. for 3 hrs, and then cooled to room temperature. The mixture was filtered through celite, the filtrate cake was washed with EA (50 mL). The filtrate was in turn washed with water (100 mL×3) and saturated brine (100 mL), dried over magnesium sulfate, filtered, concentrated under reduced pressure. The residue was purified by silica column chromatography (PE:EA=3:1) to give compound 4-b (1.6 g, yield 52%). LC-MS (ESI): m/z=309 [M+H]$^+$.

Synthesis of Compound 4-a

Under $N_2$ atmosphere, tris(dibenzylidene indene acetone)dipalladium (0.29 g, 0.5 mmol) and 4,5-bis(diphenylphosphine)-9,9-dimethyloxacanthracene (0.46 mg, 0.5 mmol) were added to a solution of compound 4-b (1.5 g, 5 mmol), ethyl 2-methyl-2-mercaptopropionate (0.75 g, 5 mmol) and diisopropylethylamine (1.29 g, 1 mmol) in dioxane (8 mL), the mixture was reacted in microwave at 110° C. for 30 mins. The mixture was cooled to room temperature, concentrated under reduced pressure to remove dioxane. The residue was filtered through celite, the filtrate cake was washed with EA (200 mL). The filtrate was in turn washed with water (100 mL×3) and saturated brine (100 mL), dried over anhydrous magnesium sulfate, filtered, concentrated under reduced pressure. The residue was purified by silica column chromatography (PE:EA=3:1) to give compound 4-a (1.39 g, yield 74%). LC-MS (ESI): m/z=377 [M+H]$^+$.

Synthesis of Compound 4

At room temperature, LiOH (0.178 g, 0.74 mmol) was added to a mixed solution of compound 4-a (1.39 g, 0.37 mmol) in methanol (5 mL), THF (20 mL) and water (5 mL), the mixture was stirred at room temperature for 1 h, 2M HCl aqueous solution (2 mL) and water (20 mL) were added, solid was precipitated and filtered out. The solid was washed with water (10 mL), dried under vacuum to give white solid 4 (1.1 g, yield 85%). LC-MS (ESI): m/z=349 [M+H]$^+$.
$^1$H-NMR (400 MHz, DMSO-d6) δ: 12.78 (s, 1H), 9.41 (s, 1H), 8.53 (s, 1H), 8.23 (d, J=8.0 Hz, 1H), 8.06 (d, J=8.0 Hz, 2H), 7.73 (m, 4H), 1.44 (s, 6H) ppm.

Embodiment 5

2{[4-(4-Cyanonaphthalen)isoquinolin-6-yl]thio}-2-methylpropionic acid (Compound 5)

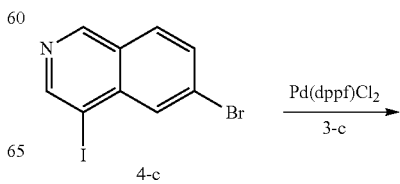

-continued

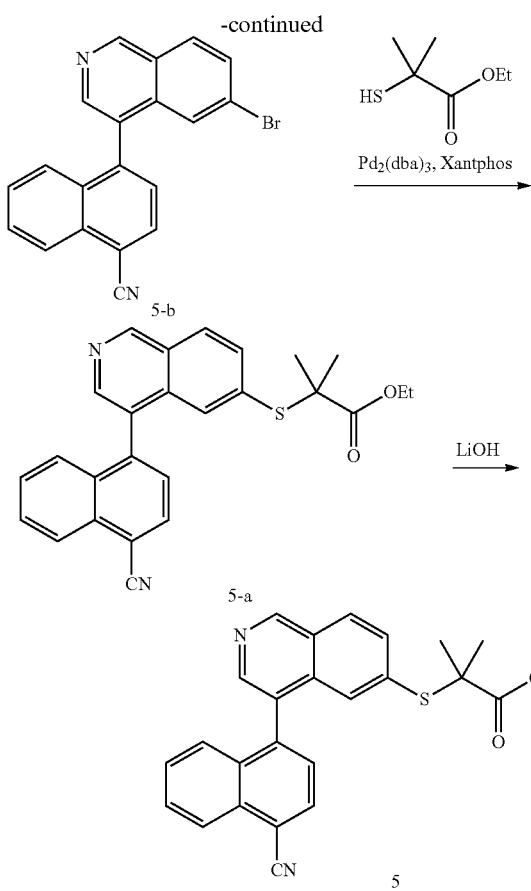

Synthesis of Compound 5-b

Under N₂ atmosphere, compound 4-c (0.66 g, 2 mmol), compound 3-c (0.56 g, 2 mmol) and sodium carbonate (0.42 g, 0.4 mmol) were suspended in dioxane (4 mL) and water (1 mL), [1,1'-bis(diphenylphosphine)ferrocene]palladium dichloride (0.12 g, 0.2 mmol) was added. The mixture was stirred at 80° C. for 3 hrs, and then cooled to room temperature, filtered through celite, washed with EA (20 mL). The filtrate was in turn washed with water (10 mL×3) and saturated brine (10 mL), dried over anhydrous magnesium sulfate, filtered, concentrated under reduced pressure. The residue was purified by silica column chromatography (PE:EA=3:1) to give compound 5-b (0.46 g, yield 64%). LC-MS (ESI): m/z=359 [M+H]⁺.

Synthesis of Compound 5-a

Under N₂ atmosphere, tris(dibenzylidene indene acetone) dipalladium (0.06 g, 0.1 mmol) and 4,5-bis(diphenylphosphine)-9,9-dimethyloxacanthracene (0.1 g, 0.1 mmol) were added to a solution of compound 5-b (0.36 g, 1 mmol), ethyl 2-methyl-2-mercaptopropionate (0.15 g, 1 mmol) and diisopropylethylamine (0.26 g, 2 mmol) in dioxane (8 mL), the mixture was reacted in a microwave at 110° C. for 30 mins. The mixture was cooled to room temperature, and then concentrated under reduced pressure to remove dioxane, the residue was filtered through celite, the filtrate cake was washed with EA (50 mL). The filtrate was in turn washed with water (50 mL×3) and saturated brine (50 mL), dried over anhydrous magnesium sulfate, filtered, concentrated under reduced pressure. The residue was purified by silica column chromatography (PE:EA=3:1) to give compound 5-a (0.37 g, yield 87%). LC-MS (ESI): m/z=427 [M+H]⁺.

Synthesis of Compound 5

At room temperature, LiOH (42 mg, 1 mmol) was added to a mixed solution of compound 5-a (370 mg, 0.86 mmol) in methanol (1 mL), THF (4 mL) and water (1 mL), the mixture was stirred for 1 h, and then 2M HCl aqueous solution (2 mL) and water (20 mL) were added, solid was precipitated and filtered out. The solid was washed with water (10 mL), dried under vacuum to give white solid 5 (280 mg, yield 82%). LC-MS (ESI): m/z=399 [M+H]⁺.

¹H-NMR (400 MHz, DMSO-d6) δ: 12.67 (s, 1H), 9.51 (s, 1H), 8.57 (s, 1H), 8.35 (d, J=7.6 Hz, 1H), 8.27 (m, 2H), 7.85 (t, J=7.6 Hz, 1H), 7.75 (d, J=7.6 Hz, 1H), 7.66 (d, J=8.0 Hz, 1H), 7.60 (t, J=8.0 Hz, 2H), 7.41 (d, J=8.0 Hz, 1H), 7.26 (s, 1H), 1.27 (s, 3H), 1.24 (s, 3H) ppm.

Embodiment 6

2{[4-(4-Cyanophenyl)isoquinolin-6-yl]oxy}-2-methylpropionic Acid (Compound 6)

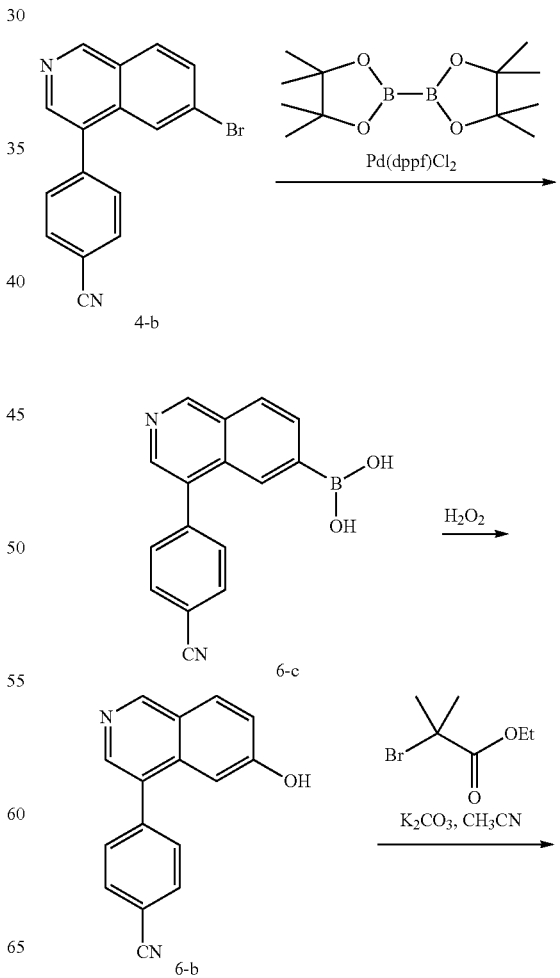

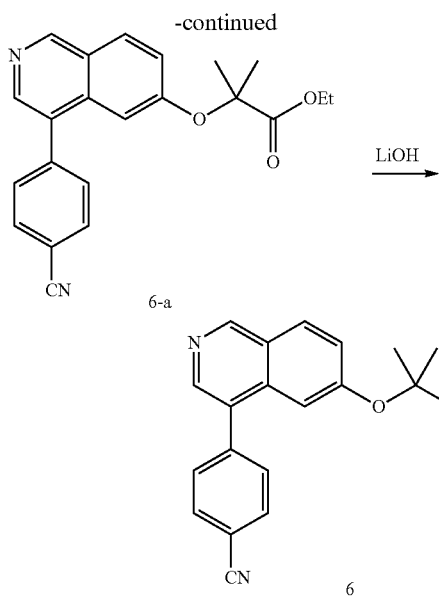

(PE:EA=3:1) to give yellow liquid 6-a (56 mg, yield 52%). LC-MS (ESI): m/z=361 [M+H]⁺.

Synthesis of Compound 6

At room temperature, LiOH (42 mg, 1 mmol) was added to a mixed solution of compound 6-a (56 mg, 0.156 mmol) in methanol (1 mL), THF (2 mL) and water (1 mL), the mixture was stirred for 1 h, followed by adding 2M HCl aqueous solution (2 mL) and water (1 mL), solid was precipitated and filtered. The solid was washed with water (5 mL), dried under vacuum to give white solid 6 (32 mg, yield 62%). LC-MS (ESI): m/z=333 [M+H]⁺.

¹H-NMR (400 MHz, DMSO-d6) δ: 13.27 (s, 1H), 9.24 (s, 1H), 8.39 (s, 1H), 8.16 (d, J=8.0 Hz, 1H), 8.02 (d, J=8.0 Hz, 1H), 7.72 (d, J=8.0 Hz, 2H), 7.30 (d, J=8.0 Hz, 2H), 7.26 (s, 1H), 6.94 (s, 1H), 1.55 (s, 6H) ppm.

Embodiment 7

Compound 7A

Compound 7B

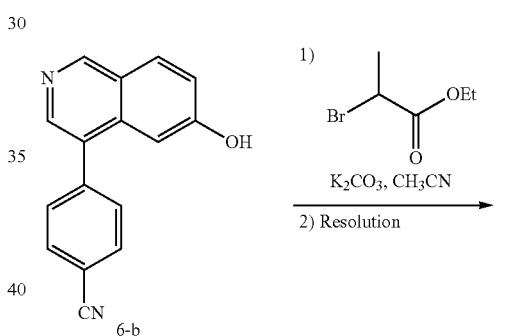

Synthesis of Compound 6-c

Under N₂ atmosphere, bis(pinacolato)diboron (3.1 g, 12 mmol), potassium acetate (2.0 g, 20 mmol) and [1,1'-bis(diphenylphosphine)ferrocene]palladium dichloride (0.56 g, 1 mmol) were respectively added to a solution of compound 4-b (3.1 g, 10 mmol) in dioxane (15 mL), the mixture was stirred at 80° C. for 8 hrs. The mixture was cooled to room temperature, filtered through celite, the filtrate cake was washed with EA (50 mL). The filtrate was in turn washed with water (50 mL×3) and saturated brine (50 mL), dried over anhydrous magnesium sulfate, filtered, concentrated under reduced pressure. The residue was purified with silica column chromatography (PE:EA=1:1) to give white solid 6-c (1.76 g, yield 63%). LC-MS (ESI): m/z=275 [M+H]⁺.

Synthesis of Compound 6-b

At 0° C., 30% H₂O₂ solution (2 mL) was added to a solution of compound 6-c (1.1 g, 4 mmol) in THF (20 mL), the mixture was stirred for 4 hrs before water (100 mL) was added. The mixture was extracted with EA (100 mL×3), the combined organic phases were washed in turn with water (50 mL×3) and saturated brine (50 mL), dried over anhydrous magnesium sulfate, filtered, concentrated under reduced pressure. The residue was purified by silica column chromatography (PE:EA=1:1) to give white solid 6-b (0.5 g, yield 50%). LC-MS (ESI): m/z=247 [M+H]⁺.

Synthesis of Compound 6-a

Under N₂ atmosphere, ethyl 2-bromoisobutyrate (190 mg, 1 mmol) and potassium carbonate (138 mg, 1 mmol) were added to a solution of compound 6-b (75 mg, 0.3 mmol) in acetonitrile (4 mL), the mixture was reacted for 3 hrs at 80° C. The mixture was cooled to room temperature, concentrated under reduced pressure. The residue was filtered through celite, the filtrate cake was washed with EA (50 mL). The filtrate was in turn washed with water (8 mL×3) and saturated brine (10 mL), dried over anhydrous magnesium sulfate, filtered, concentrated under reduced pressure. The residue was purified by silica column chromatography

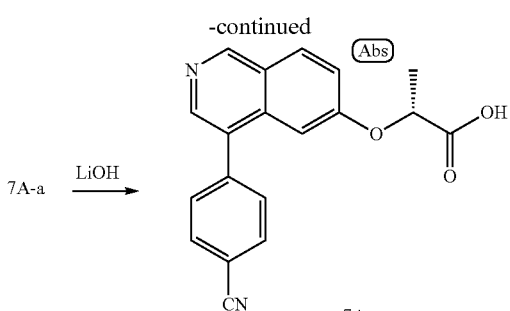

7A-a $\xrightarrow{\text{LiOH}}$

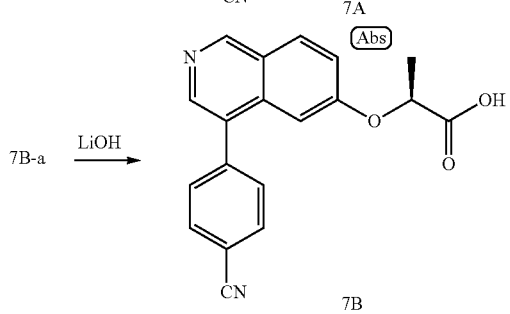

7B-a $\xrightarrow{\text{LiOH}}$

Synthesis of Compound 7A-a and 7B-a

Under N₂ atmosphere, ethyl 2-bromopropionate (540 mg, 3 mmol) and potassium carbonate (560 mg, 4 mmol) were added to a solution of compound 6-b (500 mg, 2 mmol) in acetonitrile (20 mL), the mixture was reacted for 6 hrs at 80° C. The mixture was cooled to room temperature, concentrated under reduced pressure, the residue was filtered through celite, the filtrate cake was washed with EA (200 mL). The filtrate was washed with water (50 mL×3) and saturated brine (50 mL), dried over anhydrous magnesium sulfate, filtered, concentrated under reduced pressure. The residue was purified by silica column chromatography (PE:EA=3:1) to give yellow liquid, followed by separating with enantiomeric chromatographic column (process I, mobile phase: Hexane:EtOH:DEA=70:30:0.1) to give enantiomer 7A-a which is obtained firstly (80 mg, yield 11.5%; LC-MS (ESI): m/z=347 [M+H]⁺) (T_r=9.0 min) and enantiomer 7B-a which is obtained later (90 mg, yield 13%; LC-MS (ESI): m/z=347 [M+H]⁺) (T_r=11.0 min). The absolute configuration of 7A-a and 7B-a is unknown.

Synthesis of Compound 7A

At room temperature, LiOH (42 mg, 1 mmol) was added to a mixed solution of compound 7A-a (70 mg, 0.2 mmol) in methanol (1 mL), THF (2 mL) and water (1 mL), the mixture was stirred for 1 h, followed by adding 2M HCl aqueous solution (2 mL) and water (2 mL), solid was precipitated and filtered out. The solid was washed with water (5 mL), dried under vacuum to give white solid 7A (51 mg, yield 80%). LC-MS (ESI): m/z=319 [M+H]⁺.

¹H-NMR (400 MHz, DMSO-d6) δ: 13.15 (s, 1H), 9.24 (s, 1H), 8.40 (s, 1H), 8.19 (d, J=8.0 Hz, 1H), 8.01 (d, J=8.0 Hz, 1H), 7.73 (d, J=8.0 Hz, 2H), 7.40 (d, J=8.0 Hz, 2H), 7.26 (s, 1H), 6.94 (s, 1H), 4.89 (m, 1H), 1.53 (d, J=8.0 Hz, 3H) ppm.

Synthesis of Compound 7B

At room temperature, LiOH (42 mg, 1 mmol) was added to a mixed solution of compound 7B-a (70 mg, 0.2 mmol) in methanol (1 mL), THF (2 mL) and water (1 mL), the mixture was stirred for 1 h, followed by adding 2M HCl aqueous solution (2 mL) and water (2 mL), solid was precipitated and filtered out. The solid was washed with water (5 mL), dried under vacuum to give white solid 7B (46 mg, yield 72%). LC-MS (ESI): m/z=319 [M+H]⁺.

¹H-NMR (400 MHz, DMSO-d6) δ: 13.15 (s, 1H), 9.24 (s, 1H), 8.40 (s, 1H), 8.19 (d, J=8.0 Hz, 1H), 8.01 (d, J=8.0 Hz, 1H), 7.73 (d, J=8.0 Hz, 2H), 7.40 (d, J=8.0 Hz, 2H), 7.26 (s, 1H), 6.94 (s, 1H), 4.89 (m, 1H), 1.53 (d, J=8.0 Hz, 3H) ppm.

Embodiment 8

2{[4-(4-Cyano-2-fluorophenyl)isoquinolin-6-yl]thio}-2-methylpropionic Acid (Compound 8)

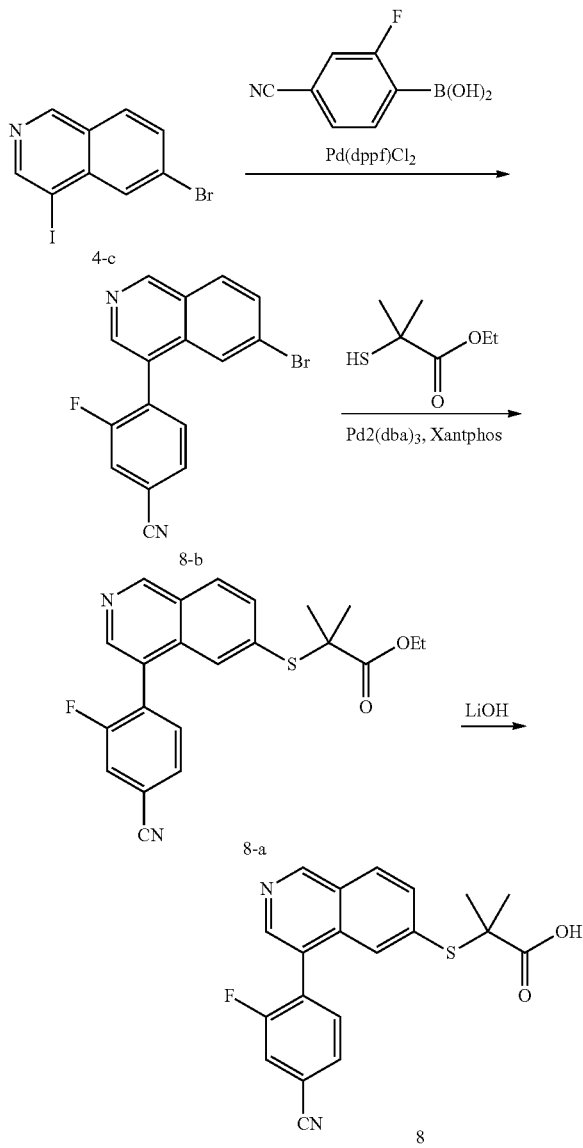

Synthesis of Compound 8-b

Under N₂ atmosphere, compound 4-c (330 mg, 1 mmol), 2-fluoro-4-cyanophenylboronic acid (165 mg, 1 mmol) and sodium carbonate (212 mg, 0.2 mmol) were suspended in a mixed solution of dioxane (4 mL) and water (1 mL), [1,1'-bis(diphenylphosphine)ferrocene]palladium dichloride (56 mg, 0.1 mmol) was added. The mixture was stirred at 80° C. for 3 hrs, cooled to room temperature, filtered through celite, the filtrate cake was washed with EA (20 mL). The filtrate was in turn washed with water (10 mL×3) and saturated brine (10 mL), dried over anhydrous magnesium sulfate, filtered, concentrated under reduced pressure. The residue was purified by silica column chromatography (PE: EA=3:1) to give compound 8-b (63 mg, yield 19%). LC-MS (ESI): m/z=387 [M+H]+.

Synthesis of Compound 8-a

Under $N_2$ atmosphere, tris(dibenzylidene indene acetone) dipalladium (12 mg, 0.02 mmol) and 4,5-bis(diphenylphosphine)-9,9-dimethyloxacanthracene (20 mg, 0.02 mmol) were added to a solution of compound 8-b (63 mg, 0.2 mmol), ethyl 2-methyl-2-mercaptopropionate (30 mg, 0.2 mmol) and diisopropylethylamine (52 mg, 0.4 mmol) in dioxane (8 mL), the mixture was reacted in a microwave at 110° C. for 30 mins. The mixture was cooled to room temperature, followed by evaporating dioxane under reduced pressure, the residue was filtered through celite, the filtrate cake was washed with EA (50 mL). The filtrate was in turn washed with water (10 mL×3) and saturated brine (10 mL), dried over anhydrous magnesium sulfate, filtered, concentrated under reduced pressure. The residue was purified by silica column chromatography (PE:EA=3:1) to give compound 8-a (72 mg, yield 91.3%). LC-MS (ESI): m/z=395 [M+H]+.

Synthesis of Compound 8

At room temperature, LiOH (42 mg, 1 mmol) was added to a mixed solution of compound 8-a (72 mg, 0.18 mmol) in methanol (1 mL), THF (2 mL) and water (1 mL). The mixture was stirred for 1 h, followed by adding 2M HCl aqueous solution (2 mL) and water (2 mL), solid was precipitated and filtered out. The solid was washed with water (5 mL), dried under vacuum to give white solid 8 (16 mg, yield 24%). LC-MS (ESI): m/z=367 [M+H]+.
$^1$H-NMR (400 MHz, DMSO-d6) δ: 12.8 (s, 1H), 9.44 (s, 1H), 8.54 (s, 1H), 8.23 (d, J=7.6 Hz, 1H), 8.10 (d, J=7.6 Hz, 1H), 7.92 (d, J=7.6 Hz, 1H), 7.78 (t, J=7.6 Hz, 1H), 7.70 (d, J=7.6 Hz, 1H), 7.59 (s, 1H), 1.44 (s, 6H) ppm.

Embodiment 9

2{[4-(4-Cyanonaphthalen-1-yl)-8-fluoroisoquinolin-6-yl]thio}-2-methylpropionic Acid (Compound 9)

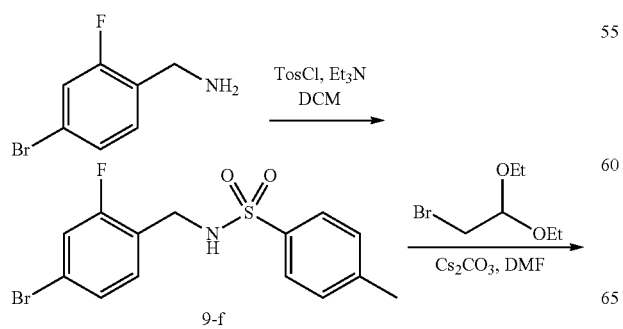

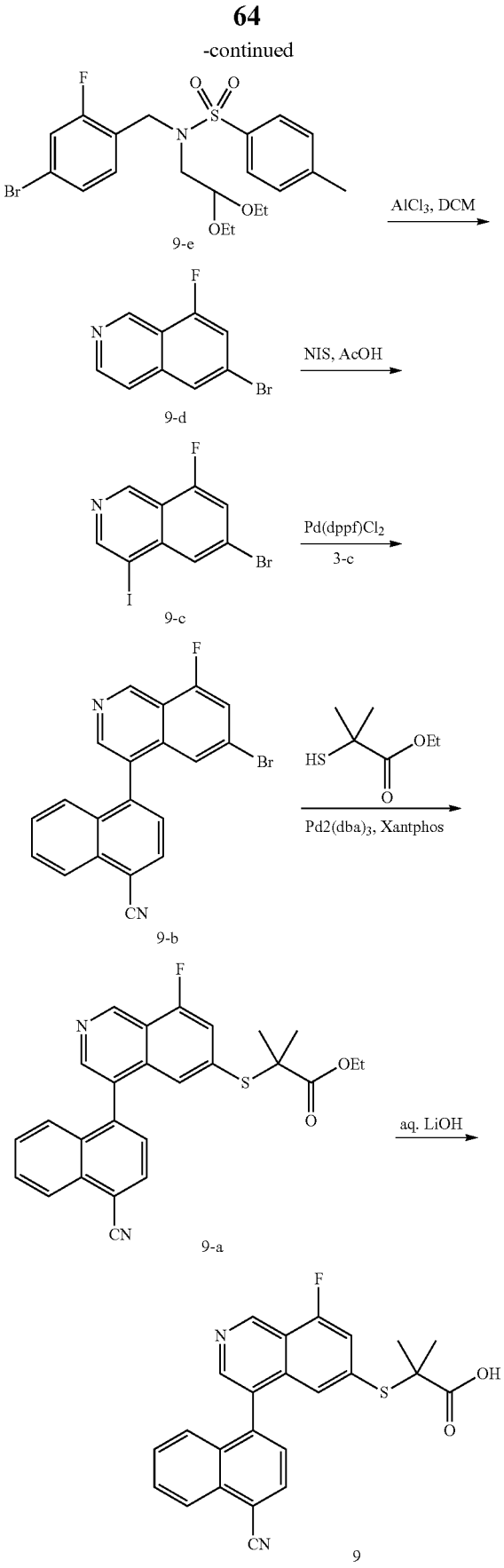

Synthesis of Compound 9-f

At 0° C., p-toluenesulfonyl chloride (4.00 g, 21 mmol) was added in portion to a solution of 5-bromo-2-fluorobenzylamine (4.08 g, 20 mmol) and triethylamine (4.04 g, 40 mmol) in DCM (60 mL). The mixture was reacted at 0° C. for 30 mins, followed by removing the ice bath, further reacting at room temperature for 16 hrs, then being concentrated under reduced pressure. The residue was purified by silica column chromatography (PE:EA=5:1) to give compound 9-f (5.30 g, yield 74%). LC-MS (ESI): m/z=358 [M+H]$^+$.

Synthesis of Compound 9-e

At room temperature, 2-bromo-1,1-diethoxyethane (3.0 g, 15 mmol), cesium carbonate (6.5 g, 20 mmol) were added to a solution of compound 9-f (3.57 g, 10 mmol) in DMF (15 mL). The mixture was reacted for 16 hrs at 80° C., concentrated under reduced pressure. The residue was purified by column chromatography (PE:EA=8:1) to give compound 9-e (3.80 g, 80%).

Synthesis of Compound 9-d

At −5° C., compound 9-e (1.50 mg, 3.18 mmol) was added to a mixture of AlCl$_3$ (2.0 g, 15 mmol) in DCM (20 mL). The mixture was reacted for 16 hrs at room temperature, followed by adding 2M HCl aqueous solution (20 mL), extracted with DCM (30 mL×3). The organic phases were combined, washed in turn with water (10 mL×3) and saturated brine (20 mL), dried over anhydrous magnesium sulfate, filtered, concentrated under reduced pressure. The residue was purified by silica column chromatography (PE:EA=7:1) to give compound 9-d (220 mg, yield 31%). LC-MS (ESI): m/z=226 [M+H]$^+$.

Synthesis of Compound 9-c

Compound 9-d (200 mg, 0.89 mmol) and N-iodosuccinimide (300 mg, 1.33 mmol) were dissolved in acetic acid (10 mL) and trifluoroacetic acid (2 mL), the mixture was reacted for 6 hrs at 80° C. The mixture was cooled to room temperature, concentrated under reduced pressure to remove the solvent. The residue was purified by silica column chromatography (PE:EA=8:1) to give compound 9-c (200 mg, yield 64%). LC-MS (ESI): m/z=352 [M+H]$^+$.

Synthesis of Compound 9-b

Under N$_2$ atmosphere, compound 9-c (144 mg, 0.4 mmol), compound 3-c (111 mg, 0.4 mmol) and sodium carbonate (170 mg, 1.6 mmol) were suspended in ethylene glycol dimethyl ether (10 mL) and water (1 mL), [1,1'-bis(diphenylphosphine)ferrocene]palladium dichloride (43 mg, 0.05 mmol) was added. The mixture was reacted for 4 hrs at 50° C., cooled to room temperature, concentrated under reduced pressure. The residue was purified by silica column chromatography (PE:EA=3:1) to give compound 9-b (100 mg, yield 66%). LC-MS (ESI): m/z=377 [M+H]$^+$.

Synthesis of Compound 9-a

Under N$_2$ atmosphere, tris(dibenzylidene indene acetone) dipalladium (30 mg, 0.033 mmol) and 4,5-bis(diphenylphosphine))-9,9-dimethyloxacanthracene (38 mg, 0.066 mmol) were added to a solution of compound 9-b (110 mg, 0.29 mmol), ethyl 2-methyl-2-mercaptopropionate (64 mg, 0.44 mmol) and diisopropylethylamine (187 mg, 1.45 mmol) in dioxane (10 mL). The mixture was reacted for 5 hrs at 100° C., followed by cooling to room temperature, concentrating under reduced pressure to remove dioxane. The residue was purified by silica column chromatography (PE:EA=4:1) to give compound 9-a (120 mg, yield 93%). LC-MS (ESI): m/z=445 [M+H]$^+$.

Synthesis of Compound 9

At room temperature, 1M LiOH aqueous solution (2.0 mL) was added to a mixed solution of compound 9-a (100 mg, 0.22 mmol) in methanol (8 mL) and THF (8 mL). The mixture was stirred at room temperature for 16 hrs, followed by being concentrated under reduced pressure. The residue was dissolved with water (10 mL), adjusted to pH=3 with 1M citric acid aqueous solution, solid was precipitated and filtered out. The solid was washed with water (10 mL), dried under vacuum to give white solid 9 (70 mg, yield 76%). LC-MS (ESI): m/z=417 [M+H]$^+$.

$^1$H-NMR (400 MHz, DMSO-d6) δ: 12.79 (s, br., 1H), 9.61 (s, 1H), 8.68 (s, 1H), 8.35 (d, J=8.0 Hz, 1H), 8.28 (d, J=8.0 Hz, 1H), 7.86 (d, J=7.2 Hz, 1H), 7.75 (d, J=8.0 Hz, 1H), 7.60 (t, J=8.0 Hz, 1H), 7.51 (d, J=10.4 Hz, 1H), 7.42 (d, J=11.2 Hz, 1H), 7.07 (s, 1H), 1.29 (s, 3H), 1.22 (s, 3H) ppm.

Embodiment 10

2{[4-(5-Cyanonaphthalen-1-yl)isoquinolin-6-yl]thio}-2-methylpropionic Acid (Compound 10)

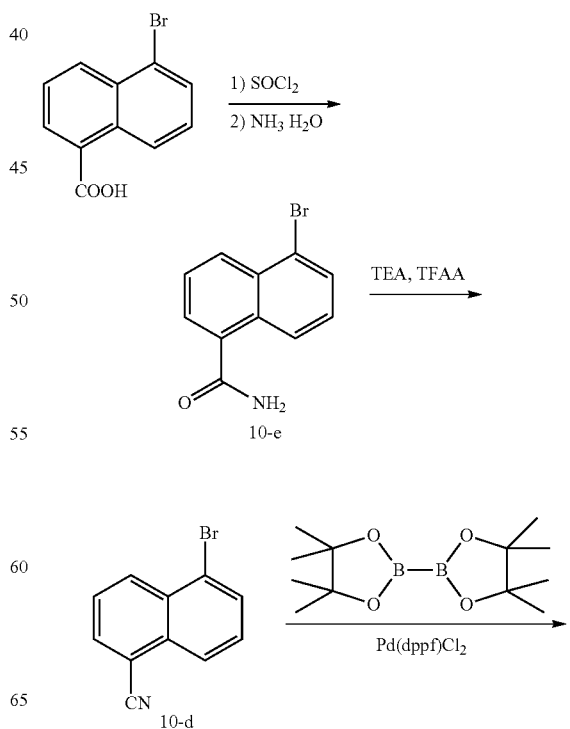

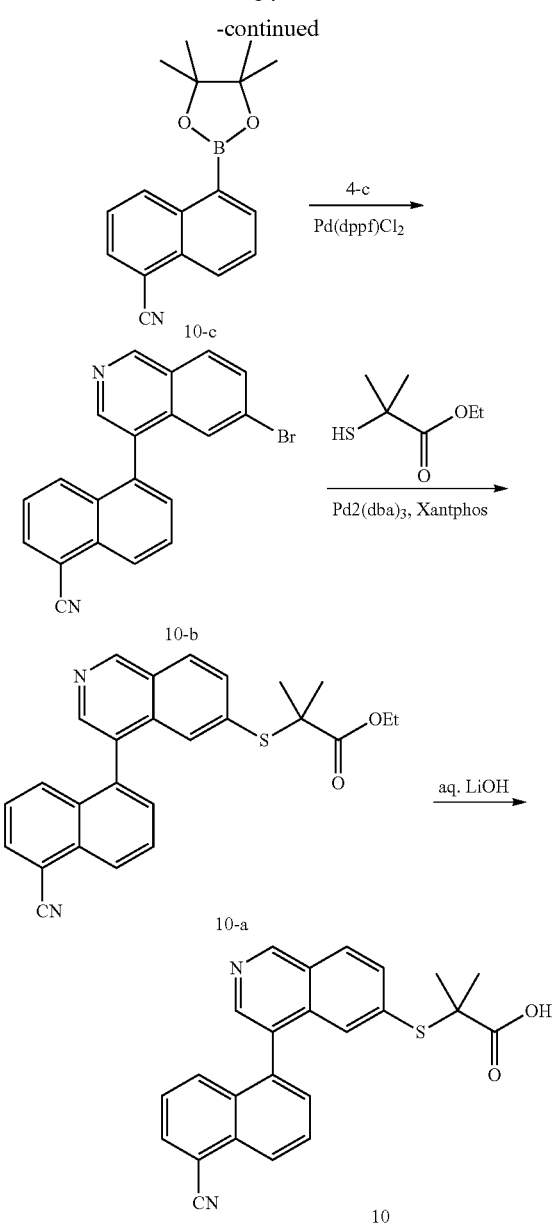

Synthesis of Compound 10-e

5-Bromo-1-naphthoic acid (980 mg, 3.92 mmol) was added to thionyl chloride (5 mL). The mixture was stirred at 85° C. for 2 hrs, concentrated under reduced pressure. The residue was dissolved in anhydrous THF (10 mL), the solution was added dropwise into 25%-28% aqueous ammonia (20 mL) at 0. The mixture was warmed to room temperature and further stirred for 2 hrs, followed by being extracted with EA (60 mL×3). The organic phases were combined, dried over anhydrous sodium sulfate, filtered, and concentrated under reduced pressure to give white solid 10-e (950 mg, yield 97%). The product was used directly for the next step without further purification. LC-MS (ESI): m/z=250 [M+H]$^+$.

Synthesis of Compound 10-d

At 0° C., trifluoroacetic anhydride (3.2 g, 15.1 mmol) was added dropwise to a solution of compound 10-e (0.94 g, 3.78 mmol) and triethylamine (1.53 g, 15.1 mmol) in THF (8 mL). The mixture was slowly warmed to room temperature and further reacted for 3 hrs, and then concentrated under reduced pressure. The residue was purified by silica column chromatography (PE:EA=10:1) to give compound 10-d (0.85 g, yield 97%). LC-MS (ESI): m/z=232 [M+H]$^+$.

Synthesis of Compound 10-c

Under $N_2$ atmosphere, bis(pinacolato)diboron (1.32 g, 5.2 mmol), potassium acetate (1.0 g, 10.38 mmol) and [1,1'-bis(diphenylphosphine)ferrocene]palladium dichloride (0.253 g, 0.346 mmol) were added respectively to a solution of compound 10-d (0.8 g, 3.46 mmol) in dioxane (15 mL). The mixture was stirred at 80° C. for 6 hrs, concentrated under reduced pressure. The residue was purified by silica column chromatography (PE:EA=10:1) to give compound 10-c (0.85 g, yield 88%). LC-MS (ESI): m/z=280 [M+H]$^+$.

Synthesis of Compound 10-b

Under $N_2$ atmosphere, compound 10-c (200 mg, 0.72 mmol), compound 4-c (200 mg, 0.6 mmol) and sodium carbonate (130 mg, 1.2 mmol) were suspended in dioxane (20 mL) and water (2 mL), [1,1'-bis(diphenylphosphine)ferrocene]palladium dichloride (50 mg, 0.06 mmol) was added. The mixture was reacted for 2 hrs at 80° C., cooled to room temperature, filtered through celite, the filtrate cake was washed with EA (20 mL), the filtrate was concentrated under reduced pressure. The residue was purified by silica column chromatography (PE:EA=3:1) to give compound 10-b (50 mg, yield 81%). LC-MS (ESI): m/z=359 [M+H]$^+$.

Synthesis of Compound 10-a

Under $N_2$ atmosphere, tris(dibenzylidene indene acetone) dipalladium (16 mg, 0.015 mmol) and 4,5-bis(bis(diphenylphosphine)-9,9-dimethyloxacanthracene (17 mg, 0.03 mmol) were added to a solution of compound 10-b (53 mg, 0.15 mmol), ethyl 2-methyl-2-mercaptopropionate (28 mg, 0.19 mmol) and diisopropylethylamine (38 mg, 0.29 mmol) in dioxane (5 mL). The mixture was reacted for 6 hrs at 100° C., cooled to room temperature, followed by being concentrated under reduced pressure to remove dioxane. The residue was purified by silica column chromatography (PE:EA=2:1) to give compound 10-a (45 mg, yield 71%). LC-MS (ESI): m/z=427 [M+H]$^+$.

Synthesis of Compound 10

At room temperature, 1M NaOH aqueous solution (2.5 mL) was added to a solution of compound 10-a (59 mg, 0.14 mmol) in methanol (5 mL), the mixture was stirred for 5 hrs, followed by adding 1M HCl aqueous solution to adjust pH=6, being concentrated under reduced pressure to remove methanol, solid was precipitated and filtered out. The solid was washed with water (5 mL), dried under vacuum to give white solid 10 (43 mg, yield 78%). LC-MS (ESI): m/z=399 [M+H]$^+$.

$^1$H-NMR (400 MHz, DMSO-d6) δ: 12.63 (s, 1H), 9.50 (s, 1H), 8.56 (s, 1H), 8.28 (m, 3H), 7.99 (m, 1H), 7.78 (d, J=6.3 Hz, 1H), 7.61 (m, 3H), 7.26 (s, 1H), 1.29 (s, 3H), 1.23 (s, 3H) ppm.

Embodiment 11

2-{[4-(8-Cyano-2,3-dihydro-1,4-benzodioxan-5-yl)isoquinolin-6-yl]thio}-2-methylpropionic Acid (Compound 11)

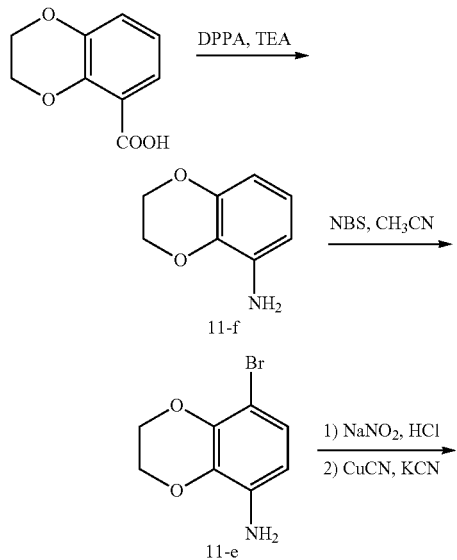

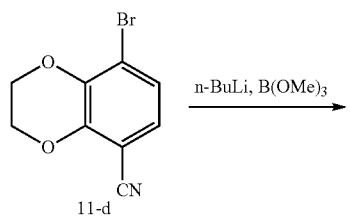

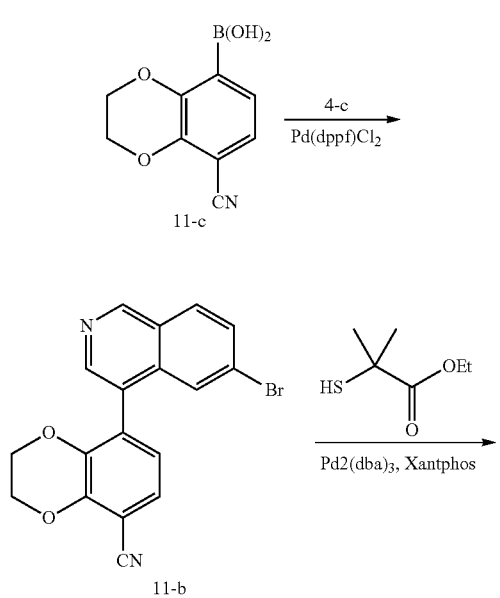

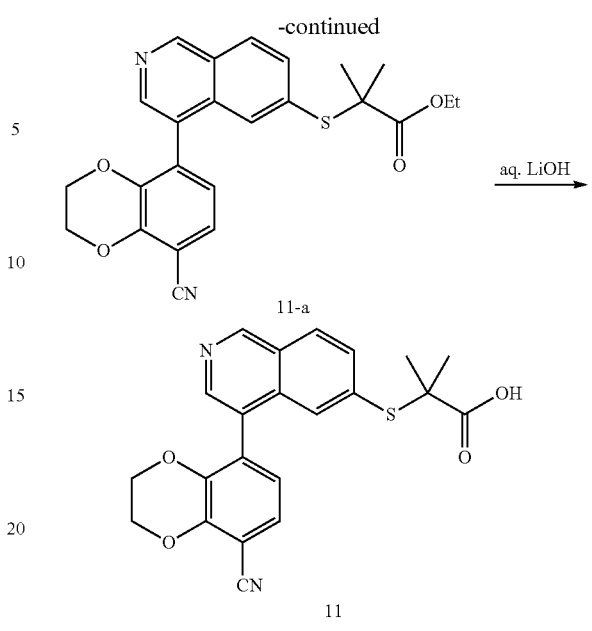

Synthesis of Compound 11-f

At room temperature, diphenyl phosphoryl azide (8.02 g, 29 mmol) and triethyl amine (4.2 g, 42 mmol) were added to a solution of 2,3-dihydro-1,4-benzodioxane-5-carboxylic acid (5.0 g, 28 mmol) in anhydrous THF (110 mL). The mixture was stirred for 2 hrs, followed by adding water (30 mL), heating to 70° C. and further reacting for 3 hrs, then cooling to room temperature, being extracted with EA (100 mL×3). The organic phases were combined, dried over anhydrous sodium sulfate, filtered, and concentrated under reduced pressure. The residue was purified by silica column chromatography (PE:EA=5:1) to give compound 11-f (1.58 g, yield 37%). LC-MS (ESI): m/z=152 [M+H]$^+$.

Synthesis of Compound 11-e

At 0° C., a solution of N-bromosuccinimide (1.73 g, 9.73 mmol) in acetonitrile (5 mL) was added to a solution of compound 11-f (1.4 g, 9.27 mmol) in acetonitrile (35 mL). The mixture was warmed to room temperature and reacted for 3 hrs, evaporated under reduced pressure to remove the solvent. The residue was purified by silica column chromatography (PE:EA=10:1 to 5:1) to give compound 11-e (1.63 g, yield 77%). LC-MS (ESI): m/z=230 [M+H]$^+$.

Synthesis of Compound 11-d

At 0° C., sodium nitrite (0.5 g, 7.2 mmol) was slowly added to a suspension of compound 11-e (1.5 g, 6.55 mmol) in 3M HCl aqueous solution (12 mL), reacted for 30 mins, sodium bicarbonate solid was added to adjust the reaction mixture to pH=7. The mixture was heated to 60° C., a solution of CuCN (0.7 g, 7.86 mmol) and KCN (1.06 g, 16.37 mmol) in water (20 mL) was added dropwise, and further stirred for 30 mins. The reaction solution was cooled to room temperature, extracted with DCM (60 mL×3). The organic phases were combined, dried over anhydrous sodium sulfate, filtered, and concentrated under reduced pressure. The residue was purified by silica column chromatography (PE:EA=10:1) to give compound 11-d (1.2 g, yield 77%). LC-MS (ESI): m/z=240 [M+H]⁺.

Synthesis of Compound 11-c

At −78° C., a solution of 2.5M n-butyl lithium in n-hexane (1.7 mL, 4.2 mmol) was added dropwise to a solution of compound 11-d (910 mg, 3.8 mmol) in anhydrous THF (20 mL), the mixture was stirred for 1 h, followed by adding trimethyl borate (594 mg, 5.7 mmol) to the reaction solution. The reaction solution was slowly warmed to room temperature, further stirred for 16 hrs, saturated NaCl aq. solution (20 mL) was added. Organic phase was separated, the aqueous phase was extracted with EA (60 mL×3). The combined organic phases were dried over anhydrous sodium sulfate, filtered, concentrated under reduced pressure to give yellow solid 11-c (700 mg, yield 90%). The product was directly used for the next step without further purification. LC-MS (ESI): m/z=206 [M+H]⁺.

Synthesis of Compound 11-b

Under N₂ atmosphere, compound 11-c (130 mg, 0.63 mmol), compound 4-c (200 mg, 0.6 mmol) and cesium carbonate (390 mg, 1.2 mmol) were suspended to a mixture of dioxane (10 mL) and water (1 mL), [1,1'-bis(diphenylphosphine)ferrocene]palladium dichloride (43 mg, 0.06 mmol) was added. The mixture was reacted for 10 hrs at 80° C., cooled to room temperature, filtered through celite, the filtrate cake was washed with EA (20 mL), the filtrate was concentrated under reduced pressure. The residue was purified by silica preparative plate chromatography (PE:EA=3:1) to give compound 11-b (146 mg, yield 66%). LC-MS (ESI): m/z=367 [M+H]⁺.

Synthesis of Compound 11-a

Under N₂ atmosphere, tris(dibenzylidene indene acetone) dipalladium (36 mg, 0.04 mmol) and 4,5-bis(diphenylphosphine)9,9-dimethyloxacanthracene (46 mg, 0.08 mmol) were added to a solution of compound 11-b (146 mg, 0.52 mmol), ethyl 2-methyl-2-mercaptopropionate (77 mg, 0.52 mmol) and diisopropylethylamine (103 mg, 0.8 mmol) in dioxane (8 mL). The mixture was stirred for 6 hrs at 100° C., cooled to room temperature, concentrated under reduced pressure to remove dioxane. The residue was purified by silica preparative plate chromatography (PE:EA=1:2) to give compound 11-a (147 mg, yield 85%). LC-MS (ESI): m/z=435 [M+H]⁺.

Synthesis of Compound 11

At room temperature, 1M NaOH aq. solution (2.5 mL) was added to a solution of compound 11-a (146 mg, 0.34 mmol) in methanol (5 mL), the mixture was stirred for 5 hrs. The mixture was adjusted to pH=6 with 1M HCl aq. solution, concentrated under reduced pressure to remove methanol, solid was precipitated and filtered out. The solid was washed with water (5 mL), dried under vacuum to give white solid 11 (95 mg, yield 69%). LC-MS (ESI): m/z=407 [M+H]⁺.
¹H-NMR (400 MHz, DMSO-d6) δ: 12.79 (s, 1H), 9.36 (s, 1H), 8.56 (s, 1H), 8.42 (s, 1H), 8.17 (d, J=8.0 Hz, 1H), 7.63 (m, 2H), 7.46 (d, J=8.0 Hz, 1H), 7.04 (d, J=8.0 Hz, 1H), 4.47 (m, 2H), 4.23 (m, 2H), 1.47 (s, 3H), 1.44 (s, 3H) ppm.

Embodiment 12

2-{[4-(4-Cyano-7-fluoronaphthalen-1-yl)isoquinolin-6-yl]thio}-2-methyl propionic Acid (Compound 12)

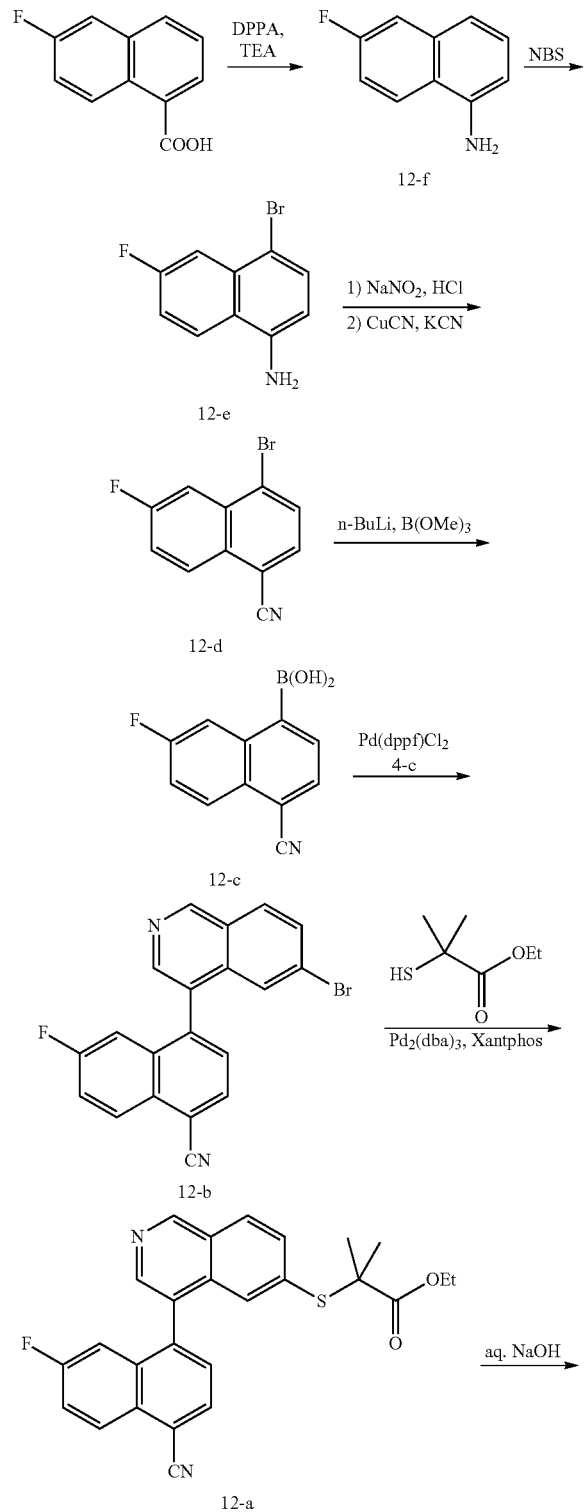

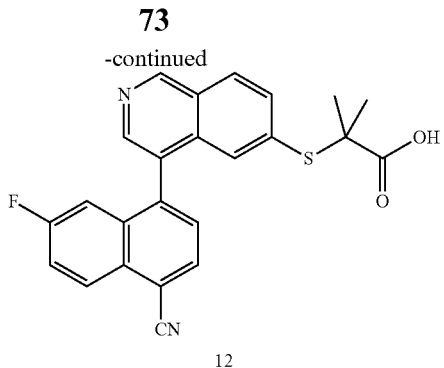

12

Synthesis of Compound 12-f

At room temperature, diphenyl phosphoryl azide (7.6 g, 27.6 mmol) and triethyl amine (4.0 g, 54 mmol) were added to a solution of 6-fluoronaphthalene-1-carboxylic acid (5.0 g, 26.3 mmol) in anhydrous THF (60 mL). The mixture was stirred for 2 hrs, followed by adding water (30 mL), heating to 70° C. and further stirring for 3 hrs. The reaction solution was cooled to room temperature, extracted with EA (150 mL×3). The organic phases were combined, dried over anhydrous sodium sulfate, filtered, and concentrated under reduced pressure. The residue was purified by silica column chromatography (PE:EA=15:1) to give compound 12-f (1.0 g, yield 16%). LC-MS (ESI): m/z=162 [M+H]$^+$.

Synthesis of Compound 12-e

At 0° C., a solution of N-bromosuccinimide (1.55 g, 8.7 mmol) in DCM (5 mL) was added dropwise to a solution of compound 12-f (1.4 g, 8.7 mmol) in DCM (50 mL). The reaction solution was stirred for 30 mins, concentrated under reduced pressure to remove the solvent. The residue was purified by silica column chromatography (PE:EA=15:1) to give compound 12-e (1.45 g, yield 70%). LC-MS (ESI): m/z=240 [M+H]$^+$.

Synthesis of Compound 12-d

At 0° C., sodium nitrite (0.5 g, 7.2 mmol) was slowly added to a suspension of compound 12-e (800 mg, 3.3 mmol) in 3M HCl aqueous solution (12 mL), the mixture was reacted for 30 mins, sodium bicarbonate solid was added to adjust the reaction solution to pH=7. At 60° C., the mixture was added to a solution of CuCN (357 mg, 4.0 mmol) and KCN (536 mg, 8.25 mmol) in water (20 mL), the mixture was further reacted for 30 mins. The reaction solution was cooled to room temperature, extracted with DCM (60 mL×3). The organic phases were combined, dried over anhydrous sodium sulfate, filtered, and concentrated under reduced pressure. The residue was purified by silica column chromatography (PE:EA=5:1) to give compound 12-d (420 mg, yield 50%). LC-MS (ESI): m/z=250 [M+H]$^+$.

Synthesis of Compound 12-c

At −78° C., a solution of 2.5M n-butyl lithium in n-hexane (0.5 mL, 1.17 mmol) was added dropwise to a solution of compound 12-d (226 mg, 0.9 mmol) in anhydrous THF (10 mL). The mixture was stirred for 1 h, followed by adding trimethyl borate (142 mg, 1.36 mmol) dropwise, then slowly warming to room temperature, and further stirring for 16 hrs, 1M HCl aqueous solution (5 mL) was added. The organic phase was separated, the aqueous phase was extracted with EA (30 mL×3). The organic phases were combined, dried over anhydrous sodium sulfate, filtered, and concentrated under reduced pressure to give yellow solid 12-c (200 mg, yield 100%). The product was directly used for the next step without further purification. LC-MS (ESI): m/z=216 [M+H]$^+$.

Synthesis of Compound 12-b

Under N$_2$ atmosphere, compound 12-c (120 mg, 0.93 mmol), compound 4-c (223 mg, 1.11 mmol) and cesium carbonate (363 mg, 1.11 mmol) were suspended in a mixture of dioxane (8 mL) and water (0.8 mL), [1,1'-bis(diphenylphosphine)ferrocene]palladium dichloride (41 mg, 0.056 mmol) was added. The mixture was reacted for 5 hrs at 80° C., cooled to room temperature, filtered through celite, the filtrate cake was washed with EA (20 mL). The filtrate was concentrated under reduced pressure, the residue was purified by silica preparative plate chromatography (PE:EA=1:1) to give compound 12-b (90 mg, yield 43%). LC-MS (ESI): m/z=377 [M+H]$^+$.

Synthesis of Compound 12-a

Under N$_2$ atmosphere, tris(dibenzylidene indene acetone) dipalladium (22 mg, 0.02 mmol) and 4,5-bis(diphenylphosphine)-9,9-dimethyloxacanthracene (28 mg, 0.05 mmol) were added to a solution of compound 12-b (90 mg, 0.24 mmol), ethyl 2-methyl-2-mercaptopropionate (46 mg, 0.3 mmol) and diisopropylethylamine (62 mg, 0.48 mmol) in dioxane (8 mL). The mixture was stirred for 6 hrs at 100° C., cooled to room temperature, concentrated under reduced pressure to remove dioxane. The residue was purified by silica preparative plate chromatography (PE:EA=1:1) to give compound 12-a (100 mg, yield 94%). LC-MS (ESI): m/z=445 [M+H]$^+$.

Synthesis of Compound 12

At room temperature, 1M NaOH aq. solution (2.5 mL) was added to a solution of compound 12-a (100 mg, 0.22 mmol) in methanol (5 mL), the mixture was stirred for 10 hrs. The mixture was adjusted to pH=6 with 1M HCl aq. solution, concentrated under reduced pressure to remove methanol, solid was precipitated and filtered out. The solid was washed with water (5 mL), dried under vacuum to give white solid 12 (70 mg, yield 75%). LC-MS (ESI): m/z=417 [M+H]$^+$.

$^1$H-NMR (400 MHz, DMSO-d6) δ: 12.69 (s, 1H), 9.51 (s, 1H), 8.68 (s, 1H), 8.47 (d, J=8.5 Hz, 1H), 8.29 (m, 2H), 8.12 (m, 1H), 7.83 (m, 2H), 7.73 (d, J=8.5 Hz, 1H), 7.61 (s, 1H), 1.41 (s, 3H), 1.40 (s, 3H) ppm.

Embodiment 13

3-[4-(4-Cyanophenyl)isoquinolin-6-yl]butyric Acid (Compound 13)

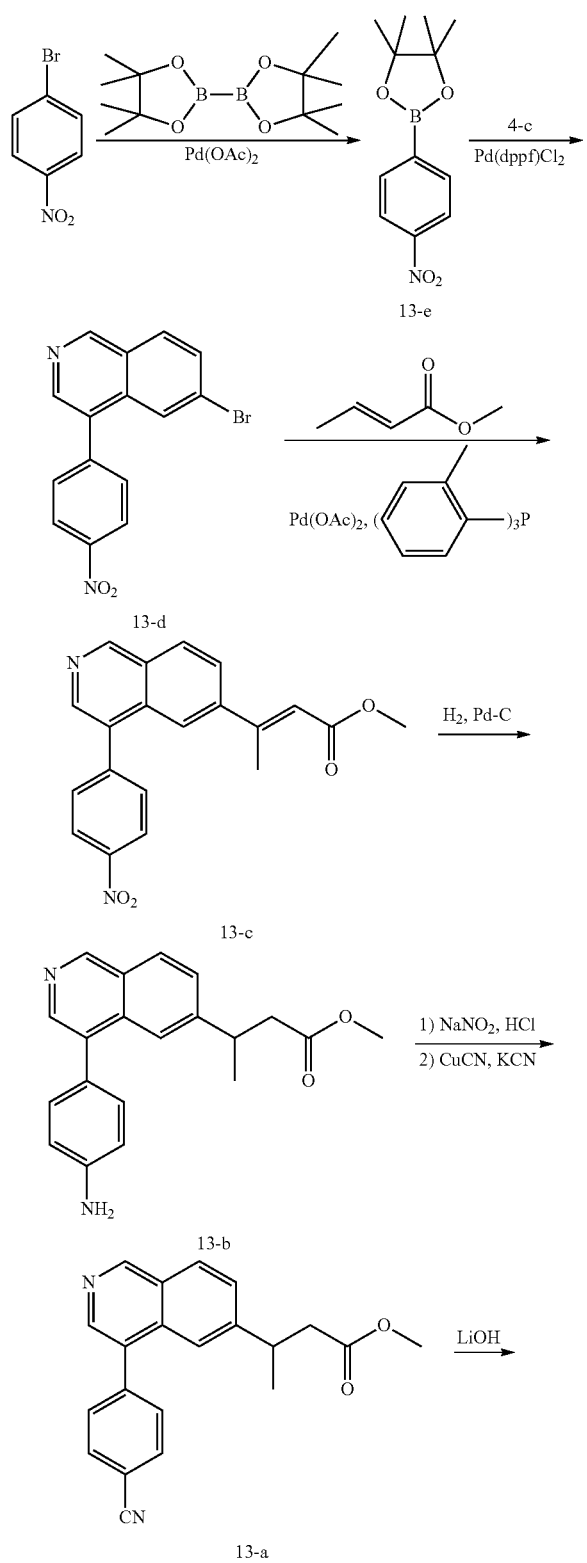

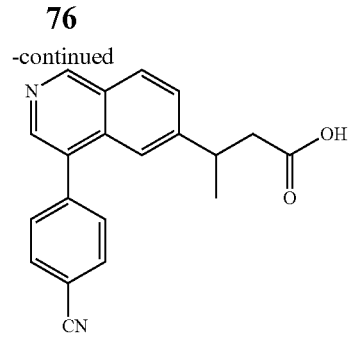

Synthesis of Compound 13-e

Under $N_2$ atmosphere, bis(pinacolato)diboron (4.53 g, 17.82 mmol), potassium acetate (4.37 g, 44.55 mmol) and palladium acetate (0.17 g, 0.74 mmol) were added respectively to a solution of 1-bromo-4-nitrobenzene (3.0 g, 14.85 mmol) in DMF (10 mL). The mixture was stirred at 80° C. for 2 hrs, followed by adding water (20 mL) and EA (20 mL), the organic phase was in turn washed with water (10 mL×3) and saturated brine (10 mL), dried over anhydrous magnesium sulfate, filtered, concentrated under reduced pressure. The residue was purified by silica column chromatography (PE:EA=10:1) to give compound 13-e (2 g, yield 54%). LC-MS (ESI): m/z=250 [M+H]$^+$.

Synthesis of Compound 13-d

Under $N_2$ atmosphere, compound 4-c (1.0 g, 3 mmol), compound 13-e (0.82 g, 3.3 mmol) and sodium carbonate (0.95 g, 8.98 mmol) were suspended in DMF (10 mL) and water (5 mL), [1,1'-bis(diphenylphosphine)ferrocene]palladium dichloride (0.245 g, 0.3 mmol) was added. The mixture was stirred at 80° C. for 2 hrs, cooled to room temperature, followed by adding water (15 mL), being extracted with EA (30 mL×3). The organic phase was in turn washed with water (20 mL×3) and saturated brine (20 mL), dried over anhydrous magnesium sulfate, filtered, concentrated under reduced pressure. The residue was purified by silica column chromatography (PE:EA=2:1) to give compound 13-d (0.9 g, yield 90%). LC-MS (ESI): m/z=329 [M+H]$^+$.

Synthesis of Compound 13-c

Under $N_2$ atmosphere, methyl crotonate (0.29 mL, 2.7 mmol), palladium acetate (41 mg, 0.18 mmol), tri-o-methylphenylphosphine (111 mg, 0.36 mmol) and triethyl amine (0.5 mL, 3.6 mmol) were added to a solution of compound 13-d (600 mg, 1.8 mmol) in DMF (5 mL). The mixture was stirred for 16 hrs at 80° C., cooled to room temperature, followed by adding water (15 mL) and being extracted with EA (30 mL×3). The organic phase was washed with water (20 mL×3) and saturated brine (20 mL), dried over anhydrous magnesium sulfate, filtered, concentrated under reduced pressure. The residue was purified by silica column chromatography (PE:EA=1:1) to give compound 13-c (360 mg, yield 57%). LC-MS (ESI): m/z=349 [M+H]$^+$.

Synthesis of Compound 13-b

Under $H_2$ atmosphere (1 atm.), Pd-C (100 mg) was added to a solution of compound 13-c (180 mg, 0.51 mmol) in ethanol (20 mL). The mixture was stirred for 16 hrs at room temperature, filtered, concentrated under reduced pressure. The residue was purified by silica chromatography (PE:EA=1:1) to give compound 13-b (360 mg, yield 57%). LC-MS (ESI): m/z=321 [M+H]$^+$.

Synthesis of Compound 13-a

At 0° C., sodium nitrite (14.2 mg, 0.2 mmol) was slowly added to a suspension of compound 13-b (60 mg, 0.18 mmol) in concentrated HCl aqueous solution (1 mL), the mixture was stirred for 30 mins, sodium bicarbonate solid was added to adjust the reaction solution to pH=7. The mixture was heated to 60° C., then was added to a solution of CuCN (20.1 mg, 0.22 mmol) and KCN (30.5 mg, 0.46 mmol) in water (3 mL), further reacted for 30 mins. The reaction solution was cooled to room temperature, extracted with DCM (20 mL×3). The organic phases were combined, dried over anhydrous sodium sulfate, filtered, and concentrated under reduced pressure. The residue was purified by silica column chromatography (PE:EA=5:1) to give compound 13-a (30 mg, yield 48%). LC-MS (ESI): m/z=331 [M+H]$^+$.

Synthesis of Compound 13

At room temperature, LiOH (50 mg, 2 mmol) was added to a mixed solution of compound 13-a (30 mg, 0.09 mmol) in methanol (2 mL), THF (2 mL) and water (4 mL). The mixture was stirred for 2 hrs, followed by being adjusted to pH=7 with 2M HCl aq. solution and then extracted with EA (10 mL×3). The organic phases were combined, washed in turn with water (10 mL×3) and saturated brine (10 mL), dried over anhydrous magnesium sulfate, filtered, concentrated under reduced pressure to give compound 13 (10 mg, yield 35%). LC-MS (ESI): m/z=317 [M+H]$^+$.

$^1$H-NMR (400 MHz, DMSO-d6) δ: 12.10 (s, 1H), 9.34 (s, 1H), 8.44 (s, 1H), 8.20 (d, J=8.8 Hz, 1H), 8.05 (d, J=8.0 Hz, 2H), 7.77 (d, J=8.0 Hz, 2H), 7.74 (d, J=8.8 Hz, 2H), 7.62 (s, 1H), 3.30 (m, 1H), 2.57 (d, J=7.6 Hz, 2H), 1.26 (d, J=8.8 Hz, 3H) ppm.

Embodiment 14

(2E)-3-[4-(4-Cyanonaphthalen-1-yl)isoquinolin-6-yl]acrylic Acid (Compound 14)

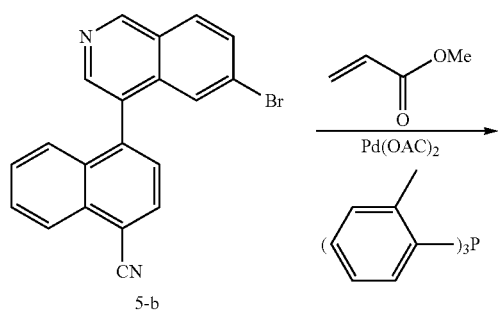

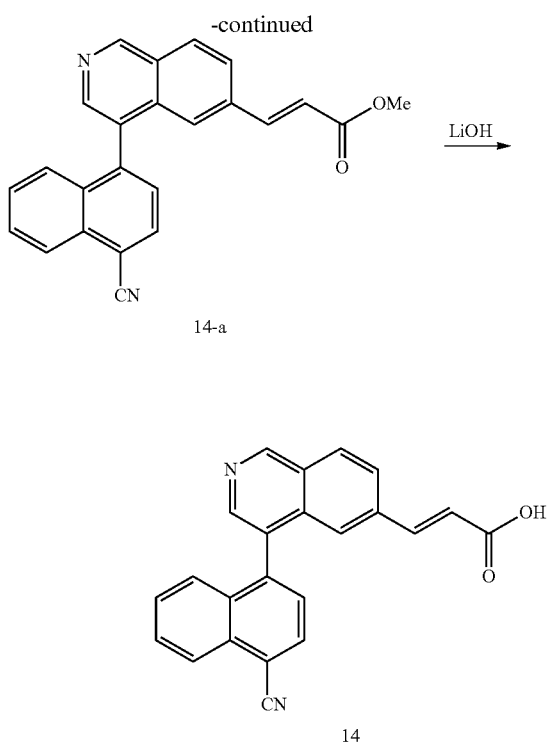

Synthesis of Compound 14-a

Under N$_2$ atmosphere, methyl acrylate (0.189 mL, 2.09 mmol), palladium acetate (31.2 mg, 0.14 mmol), tri-o-methylphenylphosphine (85 mg, 0.27 mmol) and triethyl amine (0.39 mL, 2.78 mmol) were added to a solution of compound 5-b (500 mg, 1.39 mmol) in DMF (5 mL). The mixture was stirred at 80° C. for 16 hrs, cooled to room temperature, followed by adding water (15 mL), being extracted with EA (30 mL×3). The organic phases were combined, washed in turn with water (20 mL×3) and saturated brine (20 mL), dried over anhydrous magnesium sulfate, filtered, and concentrated under reduced pressure. The residue was purified with silica column chromatography (PE:EA=1:1) to give compound 14-a (400 mg, yield 79%). LC-MS (ESI): m/z=379 [M+H]$^+$.

Synthesis of Compound 14

At room temperature, LiOH (52.6 mg, 2.19 mmol) was added to a mixed solution of compound 14-a (80 mg, 0.22 mmol) in methanol (2 mL), THF (2 mL) and water (4 mL). The mixture was stirred for 2 hrs, adjusted to pH=7 with 2M HCl aq. solution, extracted with EA (20 mL×3). The organic phases were combined, washed in turn with water (10 mL×3) and saturated brine (10 mL), dried over anhydrous magnesium sulfate, filtered, concentrated under reduced pressure to give compound 14 (68 mg, yield 88%). LC-MS (ESI): m/z=351 [M+H]$^+$.

$^1$H-NMR (400 MHz, DMSO-d6) δ: 12.60 (s, 1H), 9.51 (s, 1H), 8.55 (s, 1H), 8.24 (m, 3H), 8.13 (d, J=8.4 Hz, 1H), 7.85 (t, J=7.6 Hz, 1H), 7.75 (d, J=7.6 Hz, 1H), 7.51 (m, 4H), 6.61 (d, J=15.6 Hz, 1H) ppm.

Embodiment 15

3-[4-(4-Cyanonaphthalen-1-yl)isoquinolin-6-yl]butyric Acid (Compound 15)

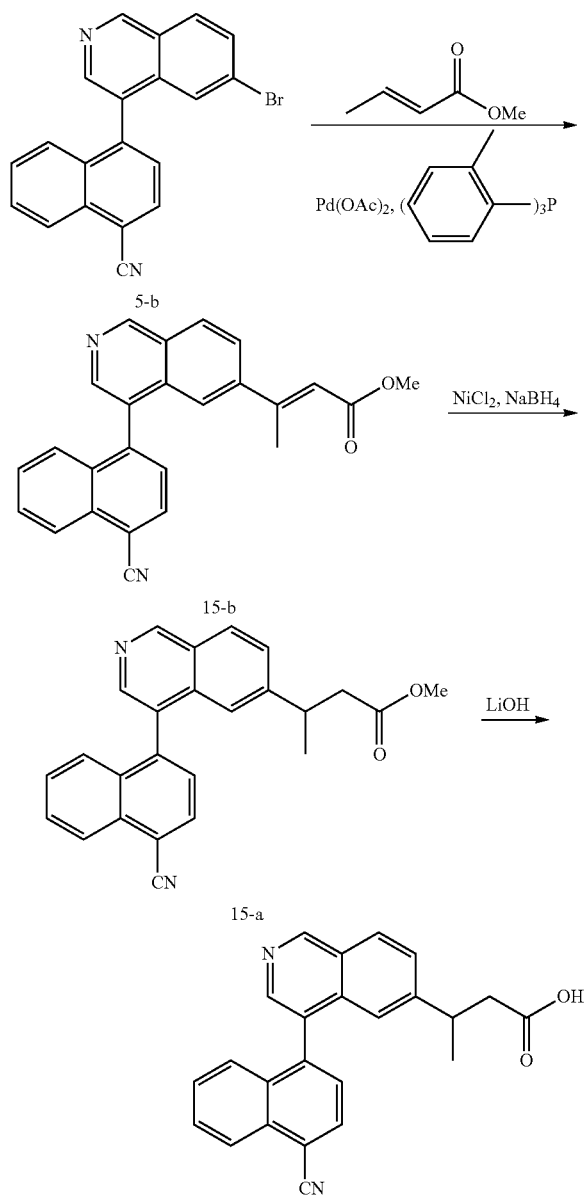

Synthesis of Compound 15-b

Under $N_2$ atmosphere, methyl crotonate (72 mg, 0.56 mmol), palladium acetate (12.5 mg, 0.05 mmol), tri-o-methylphenylphosphine (34 mg, 0.11 mmol) and triethyl amine (0.15 mL, 1.11 mmol) were added to a solution of compound 5-b (200 mg, 0.56 mmol) in DMF (5 mL). The mixture was stirred at 80° C. for 16 hrs, cooled to room temperature, followed by adding water (10 mL), being extracted with EA (20 mL×3). The organic phases were combined, washed in turn with water (10 mL×3) and saturated brine (10 mL), dried over anhydrous magnesium sulfate, filtered, and concentrated under reduced pressure. The residue was purified by silica column chromatography (PE:EA=1:1) to give compound 15-b (120 mg, yield 59%). LC-MS (ESI): m/z=379 [M+H]$^+$.

Synthesis of Compound 15-a

At 0° C., NaBH$_4$ (120 mg, 3.17 mmol) was slowly added to a solution of compound 15-b (120 mg, 0.31 mmol) and NiCl$_2$ (102 mg, 0.79 mmol) in methanol (150 mL). The mixture was stirred at 0° C. for 4.5 hrs, warmed to room temperature, and concentrated under reduced pressure, followed by adding water (20 mL) to the residue, being extracted with EA (50 mL×3). The organic phases were combined, washed in turn with water (50 mL×3) and saturated brine (50 mL), dried over anhydrous sodium sulfate, filtered, and concentrated under reduced pressure. The residue was purified with silica column chromatography (PE:EA=2:1) to give compound 15-a (45 mg, yield 37%). LC-MS (ESI): m/z=381 [M+H]$^+$.

Synthesis of Compound 15

At room temperature, LiOH (28.3 mg, 1.18 mmol) was added to a mixed solution of compound 15-a (45 mg, 0.11 mmol) in methanol (2 mL), THF (2 mL) and water (4 mL). The mixture was stirred for 2 hrs, and then adjusted to pH=7 with 2M HCl aq. solution, extracted with EA (20 mL×3). The organic phases were combined, washed in turn with water (10 mL×3) and saturated brine (10 mL), dried over anhydrous magnesium sulfate, filtered, concentrated under reduced pressure to give compound 15 (18 mg, yield 42%). LC-MS (ESI): m/z=367 [M+H]$^+$.

$^1$H-NMR (400 MHz, CD$_3$OD) δ: 9.25 (s, 1H), 8.31 (s, 1H), 8.25 (d, J=8.4 Hz, 1H), 8.12 (d, J=4.4 Hz, 1H), 8.09 (d, J=7.2 Hz, 1H), 7.70 (t, J=7.2 Hz, 1H), 7.59 (m, 2H), 7.44 (m, 1H), 7.35 (t, J=8.8 Hz, 1H), 7.04 (d, J=10 Hz, 1H), 3.12 (m, 1H), 2.36 (m, 1H), 1.07 (m, 3H) ppm.

Embodiment 16

3-[4-(4-Cyanonaphthalen-1-yl)isoquinolin-6-yl]-2-methyl propionic acid (Compound 16)

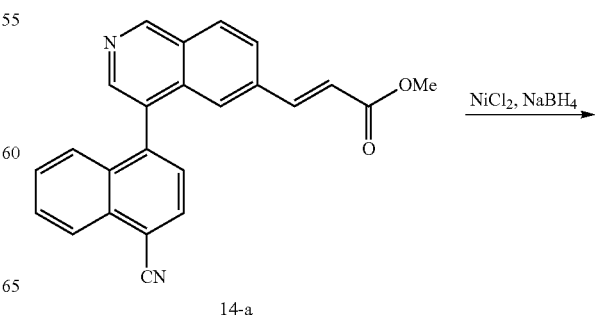

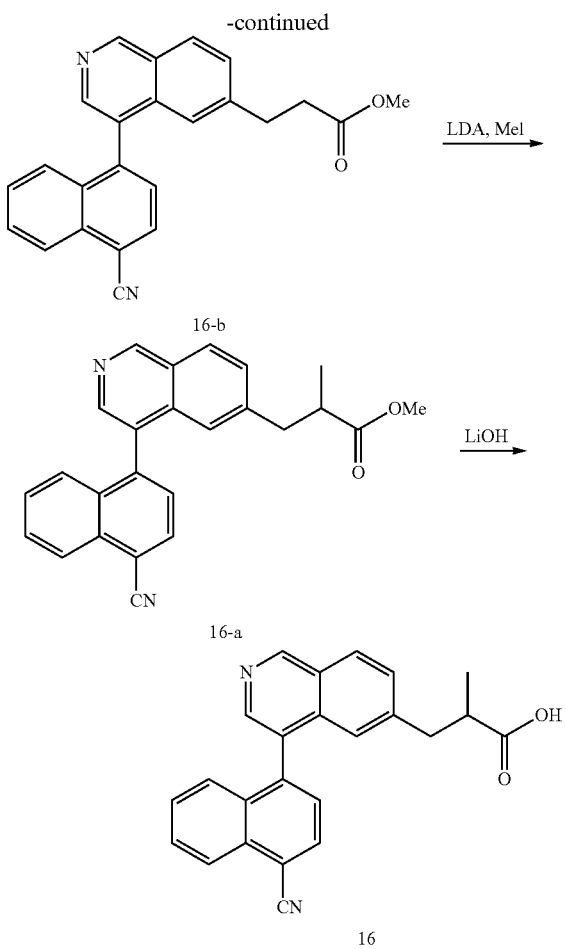

Synthesis of Compound 16-b

At 0° C., NaBH₄ (145 mg, 3.84 mmol) was slowly added to a solution of compound 14-a (350 mg, 0.96 mmol) and NiCl₂ (62.2 mg, 0.48 mmol) in methanol (150 mL). The mixture was stirred at 0° C. for 4.5 hrs, warmed to room temperature, and concentrated under reduced pressure, followed by adding water (20 mL) to the residue, being extracted with EA (50 mL×3). The organic phases were combined, washed in turn with water (50 mL×3) and saturated brine (50 mL), dried over anhydrous sodium sulfate, filtered, and concentrated under reduced pressure. The residue was purified with silica column chromatography (PE:EA=2:1) to give compound 16-b (200 mg, yield 57%). LC-MS (ESI): m/z=367 [M+H]⁺.

Synthesis of Compound 16-a

Under N₂ atmosphere, at −78° C., a solution of 2.5M n-butyl lithium in n-hexane (0.87 mL, 2.18 mmol) was added dropwise in a solution of diisopropylamine (0.11 mL, 2.18 mmol) in anhydrous THF (10 mL). The mixture was stirred for 30 mins, a solution of compound 16-b (200 mg, 0.55 mmol) in anhydrous THF (5 mL) was added dropwise, and the mixture was further stirred for 30 mins, a solution of CH₃I (139.5 mg, 0.98 mmol) in anhydrous THF (5 mL) was added dropwise, the mixture was slowly warmed to room temperature and further stirred for 2 hrs, saturated NH₄Cl aq. solution (10 mL) was added, the mixture was extracted with EA (20 mL×3). The organic phases were combined, dried over anhydrous sodium sulfate, filtered, and concentrated under reduced pressure. The residue was purified by silica column chromatography (PE:EA=2:1) to give compound 16-a (20 mg, yield 19%). LC-MS (ESI): m/z=381 [M+H]⁺.

Synthesis of Compound 16

At room temperature, LiOH (25 mg, 1.05 mmol) was added to a mixed solution of compound 16-a (20 mg, 0.05 mmol) in methanol (2 mL), THF (2 mL) and water (4 mL). The mixture was stirred for 2 hrs, adjusted to pH=7 with 2M HCl aq. solution, extracted with EA (20 mL×3). The organic phases were combined, washed in turn with water (10 mL×3) and saturated brine (10 mL), dried over anhydrous magnesium sulfate, filtered, concentrated under reduced pressure to give compound 16 (10 mg, yield 52%). LC-MS (ESI): m/z=367 [M+H]⁺.

¹H-NMR (400 MHz, CD₃OD) δ: 9.37 (s, 1H), 8.42 (d, J=2.4 Hz, 1H), 8.36 (d, J=8.4 Hz, 1H), 8.21 (m, 2H), 7.81 (t, J=7.6 Hz, 1H), 7.69 (d, J=7.6 Hz, 1H), 7.66 (d, J=8.4 Hz, 1H), 7.50 (m, 2H), 7.13 (d, J=7.6 Hz, 1H), 2.97 (m, 1H), 2.65 (m, 2H), 1.02 (m, 3H) ppm.

Embodiment 17

3-[4-(4-Cyanonaphthalen-1-yl)isoquinolin-6-yl]-2,2-dimethyl propionic Acid (Compound 17)

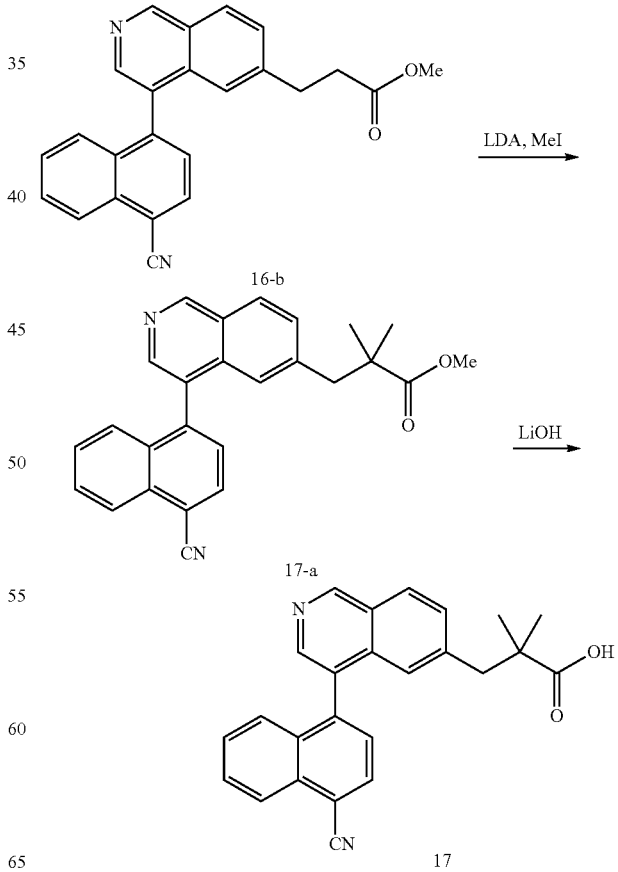

Synthesis of Compound 17-a

Under $N_2$ atmosphere, at −78° C., a solution of 2.5M n-butyl lithium in n-hexane (0.87 mL, 2.18 mmol) was slowly added to a solution of diisopropylamine (0.11 mL, 2.18 mmol) in anhydrous THF (10 mL) dropwise. The mixture was stirred for 30 mins, followed by adding a solution of compound 16-b (200 mg, 0.55 mmol) in anhydrous THF (5 mL) dropwise, further stirred for 30 mins, followed by adding a solution of $CH_3I$ (139.5 mg, 0.98 mmol) in anhydrous THF (5 mL). The mixture was slowly warmed to room temperature, further stirred for 2 hrs, followed by adding saturated $NH_4Cl$ aq. solution (10 mL) and being extracted with EA (20 mL×3). The organic phases were combined, dried over anhydrous sodium sulfate, filtered, and concentrated under reduced pressure. The residue was purified by silica column chromatography (PE:EA=2:1) to give compound 17-a (20 mg, yield 18.5%). LC-MS (ESI): m/z=395 [M+H]⁺.

Synthesis of Compound 17

At room temperature, LiOH (24 mg, 1.01 mmol) was added to a mixed solution of compound 17-a (20 mg, 0.05 mmol) in methanol (2 mL), THF (2 mL) and water (4 mL). The mixture was stirred for 2 hrs, followed by adding 2M HCl aq. solution to adjust pH=7, and then extracted with EA (20 mL×3). The organic phases were combined, washed in turn with water (10 mL×3) and saturated brine (10 mL), dried over magnesium sulfate, filtered, concentrated under reduced pressure to give compound 17 (5 mg, yield 26%). LC-MS (ESI): m/z=381 [M+H]⁺.

¹H-NMR (400 MHz, $CD_3OD$) δ: 9.37 (s, 1H), 8.42 (s, 1H), 8.37 (d, J=8.8 Hz, 1H), 8.21 (d, J=7.6 Hz, 1H), 7.81 (m, 1H), 7.55 (m, 5H), 7.11 (s, 1H), 2.97 (m, 1H), 2.89 (m, 2H), 1.02 (s, 3H), 0.97 (s, 3H) ppm.

Embodiment 18

2-{[8-(4-Cyanophenyl)isoquinolin-2-yl]thio}-2-methyl propionic Acid (Compound 18)

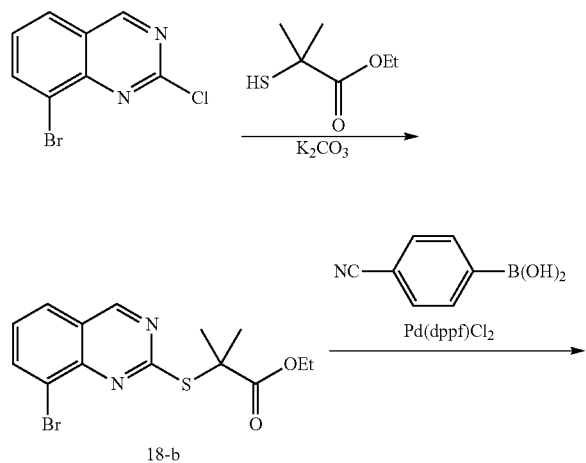
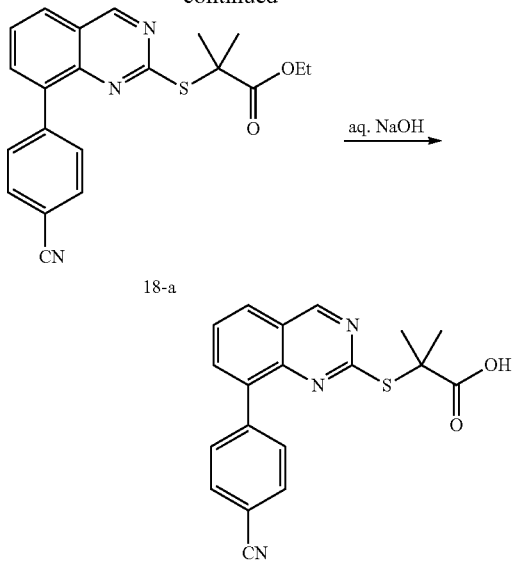

Synthesis of Compound 18-b

8-Bromo-2-chloroquinazoline (110 mg, 0.45 mmol) was added to a suspension of ethyl 2-methyl-2-mercaptopropionate (80 mg, 0.54 mmol), potassium carbonate (124 mg, 0.9 mmol) in DMF (3 mL). The mixture was stirred for 3 hrs at 130° C., cooled to room temperature, followed by adding water (20 mL), being extracted with EA (30 mL×3). The organic phases were combined, washed in turn with water (20 mL×3) and saturated brine (20 mL), dried over anhydrous sodium sulfate, filtered, and concentrated under reduced pressure. The residue was purified by silica column chromatography (PE:EA=6:1) to give colorless oil 18-b (108 mg, yield 67.5%). LC-MS (ESI): m/z=355 [M+H]⁺.

Synthesis of Compound 18-a

Under $N_2$ atmosphere, compound 18-b (108 mg, 0.3 mmol), 4-cyanophenyl boronic acid (54 mg, 0.36 mmol) and cesium carbonate (196 mg, 0.6 mmol) were suspended in dioxane (10 mL) and water (1 mL), [1,1'-bis(diphenylphosphine)ferrocene]palladium dichloride (40 mg, 0.05 mmol) was added. The mixture was stirred at 90° C. for 16 hrs, followed by cooling to room temperature, being concentrated under reduced pressure. The residue was purified by silica column chromatography (PE:EA=5:1) to give colorless oil 18-a (83 mg, yield 72%). LC-MS (ESI): m/z=378 [M+H]⁺.

Synthesis of Compound 18

At room temperature, 1M NaOH aq. solution (2.0 mL) was added to a solution of compound 18-a (83 mg, 0.22 mmol) in methanol (5 mL). The mixture was stirred for 2 hrs, followed by adding 1M HCl aq. solution to adjust pH=5-6, being extracted with EA (20 mL×3). The organic phases were combined, dried over anhydrous sodium sulfate, filtered, and concentrated under reduced pressure. The residue was purified by HPLC (mobile phase: 10 mM $NH_4HCO_3$ aq. solution:acetonitrile=25%-55%) to give yellow solid 18 (7 mg, yield 9%). LC-MS (ESI): m/z=350 [M+H]⁺.

$^1$H-NMR (400 MHz, CD$_3$OD) δ: 9.31 (s, 1H), 8.07 (dd, J=8.0 Hz, 1.6 Hz, 1H), 7.98 (dd, J=7.6 Hz, 2.4 Hz, 1H), 7.84 (d, J=7.6 Hz, 2H), 7.77 (d, J=7.6 Hz, 2H), 7.71 (dd, J=7.8 Hz, 3.6 Hz, 1H), 1.68 (s, 6H) ppm.

Embodiment 19

{[4-(4-Cyanophenyl)isoquinolin-6-yl](methyl)carbamoyl}formic Acid (Compound 19)

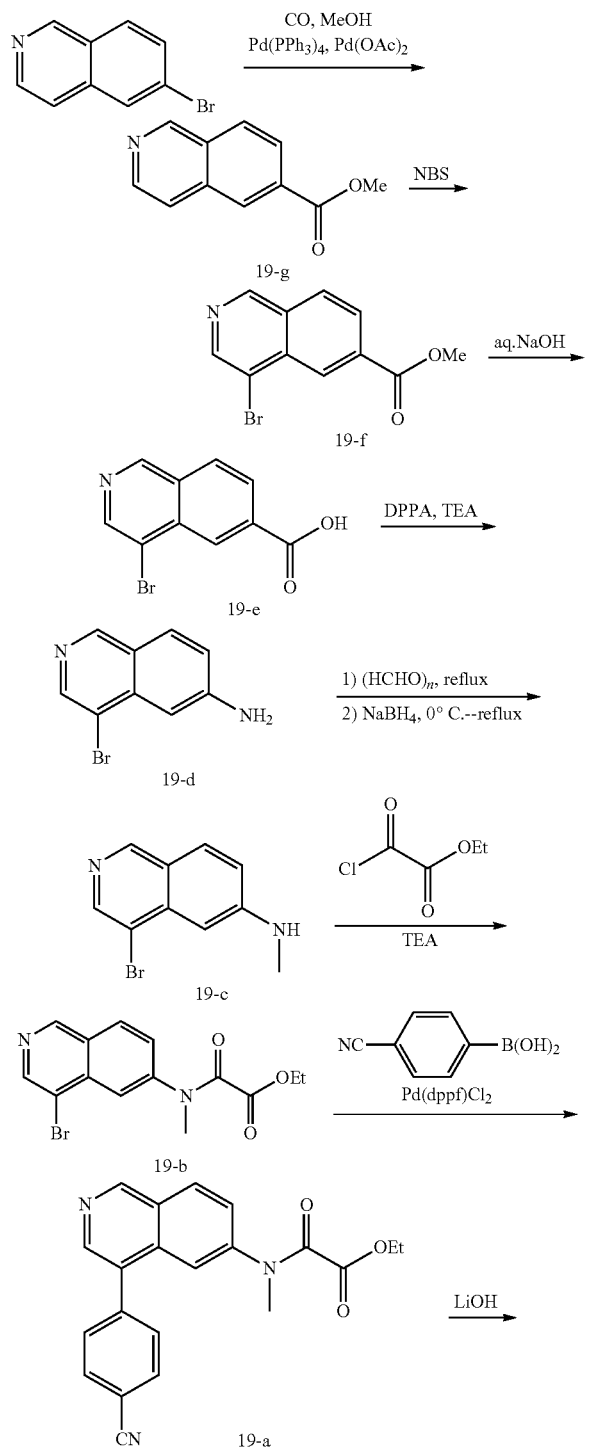

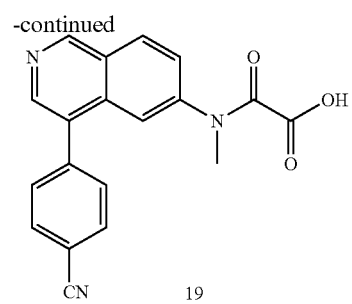

Synthesis of Compound 19-g

Under CO atmosphere (10 atm.), a mixture of 6-bromoisoquinoline (5.0 g, 24 mmol), sodium acetate (2.56 g, 31 mmol), tetrakis(triphenylphosphine)palladium (2.77 g, 2.4 mmol), palladium acetate (1.1 g, 4.8 mmol), DMF (50 mL) and DCM (50 mL) was heated to 100° C., stirred for 16 hrs and then cooled to room temperature, concentrated under reduced pressure to remove methanol. Water (100 mL) was added to the residue, EA (200 mL×2) was used for extract. The organic phases were combined, washed in turn with water (100 mL×3) and saturated brine (100 mL), dried over anhydrous sodium sulfate, filtered, and concentrated under reduced pressure. The residue was purified by silica column chromatography (PE:EA=5:1) to give white solid 19-g (4.34 g, yield 96%). LC-MS (ESI): m/z=188 [M+H]$^+$.

Synthesis of Compound 19-f

N-Bromosuccinimide (6.19 g, 34.8 mmol), compound 19-g (4.34 g, 23.2 mmol) and acetic acid (25 mL) were added to 80° C. and stirred for 16 hrs, the mixture was cooled to room temperature, concentrated under reduced pressure. Saturated sodium bicarbonate solution was added to the residue (30 mL), the mixture was extracted with EA (50 mL×2). The organic phases were combined, dried over anhydrous sodium sulfate, filtered, and concentrated under reduced pressure. The residue was purified by silica chromatography (PE:EA=5:1) to give compound 19-f (3.59 g, yield 58%). LC-MS (ESI): m/z=268 [M+H]$^+$.

Synthesis of Compound 19-e

At room temperature, 2M NaOH aq. solution (10 mL) was added to a solution of compound 19-f (3.59 g, 13.5 mmol) in methanol (30 mL). The mixture was stirred for 16 hrs, followed by adding 1M HCl aq. solution to adjust pH=5-6, solid was precipitated and filtered out. The solid was washed with water (10 mL), dried under vacuum to give yellow solid 19-e (3.29 g, yield 96.8%). LC-MS (ESI): m/z=254 [M+H]$^+$.

Synthesis of Compound 19-d

At room temperature, diphenyl phosphoryl azide (5.2 g, 25.2 mmol) and triethyl amine (2.5 g, 25.2 mmol) were added to a solution of compound 19-e (3.17 g, 12.6 mmol) in anhydrous THF (30 mL). The mixture was stirred for 3 hrs, followed by adding water (10 mL), refluxing for 12 hrs, then cooling to room temperature, being concentrated under reduced pressure. The residue was purified by silica column chromatography (PE:EA=1:1) to give yellow solid 19-g (0.2 g, yield 7%). LC-MS (ESI): m/z=225 [M+H]$^+$.

Synthesis of Compound 19-c

Sodium methoxide (218 mg, 4.03 mmol) and polyformaldehyde (121 mg, 4.03 mmol) were added to a solution of compound 19-d (180 mg, 0.81 mmol) in methanol (6 mL). The mixture was refluxed for 1.5 hrs, cooled to 0° C., NaBH$_4$ (185 mg, 4.86 mmol) was added in portions. The mixture was refluxed again for 1.5 hrs, then cooled to room temperature, saturated NaHCO$_3$ (30 mL) was added, the mixture was extracted with DCM (20 mL×3). The organic phases were combined, dried over anhydrous sodium sulfate, filtered, concentrated under reduced pressure to give yellow solid 19-c (175 mg, yield 91.6%), the product was directly used for the next step without further purification. LC-MS (ESI): m/z=237 [M+H]$^+$.

Synthesis of Compound 19-b

At room temperature, ethyl oxalyl monochloride (151 mg, 1.11 mmol) was added to a solution of compound 19-c (175 mg, 0.74 mmol) and triethyl amine (150 mg, 1.48 mmol) in DCM (10 mL). The mixture was stirred for 1 h, followed by adding water (10 mL), being extracted with DCM (20 mL×3). The organic phases were combined, dried over anhydrous sodium sulfate, filtered, concentrated under reduced pressure to give yellow oil 19-b (249 mg, yield 99%), the product was directly used for the next step without further purification. LC-MS (ESI): m/z=339 [M+H]$^+$.

Synthesis of Compound 19-a

Under N$_2$ atmosphere, compound 19-b (249 mg, 0.74 mmol), 4-cyanophenylboronic acid (163 mg, 1.11 mmol) and sodium carbonate (157 mg, 1.48 mmol) were suspended in dioxane (15 mL) and water (2 mL), [1,1'-bis(diphenylphosphine)ferrocene]palladium dichloride (54 mg, 0.07 mmol) was added. The mixture was stirred at 90° C. for 12 hrs, followed by cooling to room temperature, being concentrated under reduced pressure. The residue was purified by silica column chromatography (PE:EA=3:1-1:1) to give compound 19-a (90 mg, yield 34%). LC-MS (ESI): m/z=360 [M+H]$^+$.

Synthesis of Compound 19

At room temperature, LiOH (2.0 mL) was added to a solution of compound 19-a (90 mg, 0.25 mmol) in methanol (5 mL), THF (3 mL) and water (1 mL). The reaction solution was stirred for 2 hrs, and then concentrated under reduced pressure. The residue was adjusted to pH=5-6 with 1M HCl aq. solution, then extracted with EA (20 mL×3). The organic phases were combined, dried over anhydrous sodium sulfate, filtered, concentrated under reduce pressure. The residue underwent HPLC preparation (mobile phase: 10 mM NH$_4$HCO$_3$ aq. solution:acetonitrile=25%-55%) to give white solid 19 (5 mg, yield 7%). LC-MS (ESI): m/z=332 [M+H]$^+$.

$^1$H-NMR (400 MHz, CD$_3$OD) δ: 9.34 (s, 1H), 8.47 (s, 1H), 8.31 (d, J=8.6 Hz, 1H), 7.96 (d, J=8.6 Hz, 1H), 7.80 (m, 4H), 3.39 (s, 3H) ppm.

Embodiment 20

{[4-(4-Cyanonaphthalen-1-yl)isoquinolin-6-yl](methyl)carbamoyl}formic Acid (Compound 20)

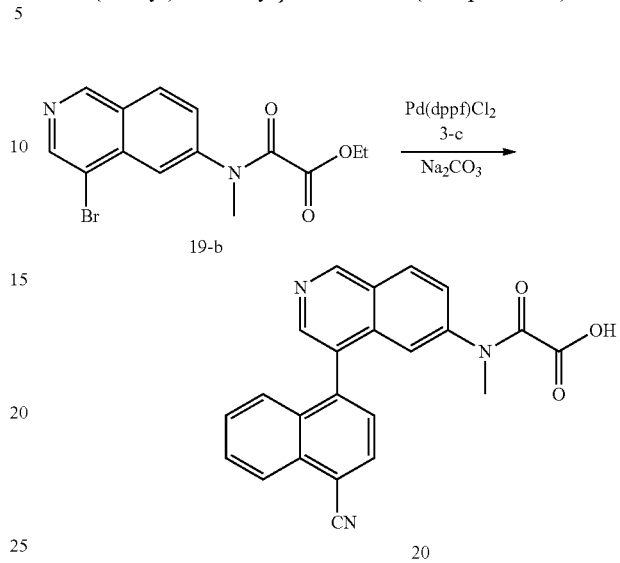

Synthesis of Compound 20

Under N$_2$ atmosphere, compound 19-b (260 mg, 0.77 mmol), compound 3-c (258 mg, 0.93 mmol) and sodium carbonate (163 mg, 1.54 mmol) were suspended in dioxane (8 mL) and water (1 mL), [1,1'-bis(diphenylphosphine)ferrocene]palladium dichloride (56 mg, 0.07 mmol) was added. The mixture was stirred at 90° C. for 12 hrs, followed by cooling to room temperature, being concentrated under reduced pressure. The residue underwent HPLC preparation (mobile phase: 10 mM NH$_4$HCO$_3$ aq. solution:acetonitrile=25%-45%) to give yellow solid 20 (40 mg, yield 13.6%). LC-MS (ESI): m/z=382 [M+H]$^+$.

$^1$H-NMR (400 MHz, CD$_3$OD) δ: 9.42 (s, 1H), 8.47 (s, 1H), 8.33 (d, J=8.7 Hz, 2H), 8.20 (d, J=7.3 Hz, 1H), 7.79 (dd, J=8.6 Hz, 4.8 Hz, 1H), 7.71 (d, J=7.3 Hz, 1H), 7.56 (m, 2H), 7.33 (d, J=1.4 Hz, 2H), 3.24 (s, 3H) ppm.

Embodiment 21

2-{[4-(4-Cyanonaphthalen-1-yl)isoquinolin-6-yl]thio}propionic Acid (Compound 21)

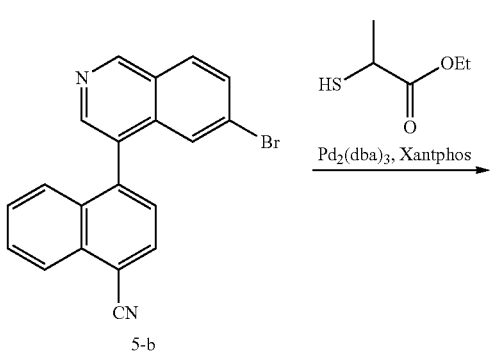

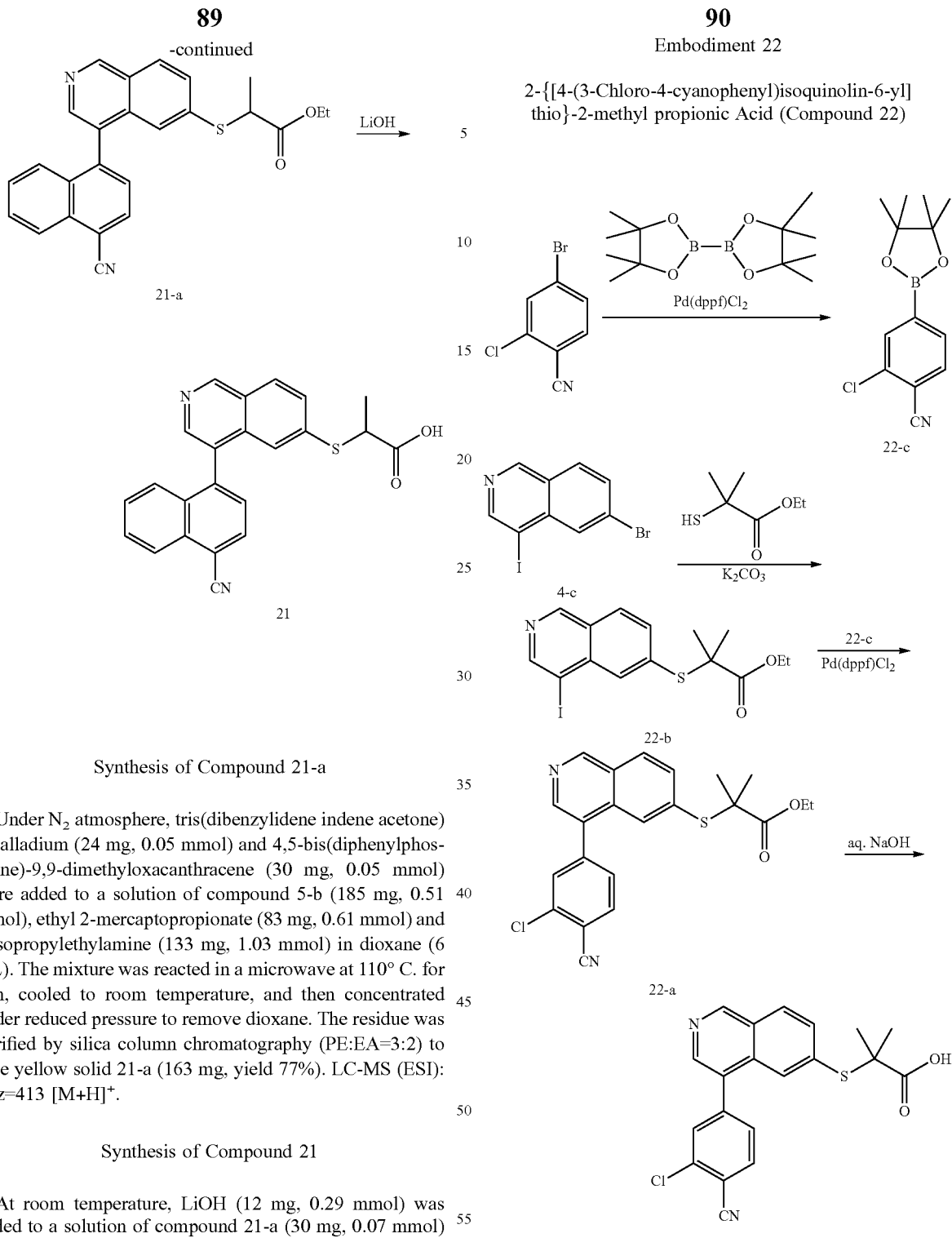

Synthesis of Compound 21-a

Under N$_2$ atmosphere, tris(dibenzylidene indene acetone) dipalladium (24 mg, 0.05 mmol) and 4,5-bis(diphenylphosphine)-9,9-dimethyloxacanthracene (30 mg, 0.05 mmol) were added to a solution of compound 5-b (185 mg, 0.51 mmol), ethyl 2-mercaptopropionate (83 mg, 0.61 mmol) and diisopropylethylamine (133 mg, 1.03 mmol) in dioxane (6 mL). The mixture was reacted in a microwave at 110° C. for 1 h, cooled to room temperature, and then concentrated under reduced pressure to remove dioxane. The residue was purified by silica column chromatography (PE:EA=3:2) to give yellow solid 21-a (163 mg, yield 77%). LC-MS (ESI): m/z=413 [M+H]$^+$.

Synthesis of Compound 21

At room temperature, LiOH (12 mg, 0.29 mmol) was added to a solution of compound 21-a (30 mg, 0.07 mmol) in methanol (1 mL), THF (4 mL) and water (1 mL). The mixture was stirred for 1 h, followed by adding 1M HCl aq. solution to adjust pH=5-6, the mixture was extracted with EA (15 mL×2). The organic phases were combined, dried over anhydrous sodium sulfate, filtered, concentrated under reduced pressure to give white solid 21 (16 mg, yield 57%). LC-MS (ESI): m/z=385 [M+H]$^+$.

$^1$H-NMR (400 MHz, DMSO-d6) δ: 9.43 (s, 1H), 8.50 (s, 1H), 8.27 (m, 3H), 7.85 (s, 1H), 7.72 (dd, J=11.7 Hz, 7.5 Hz, 2H), 7.59 (d, J=7.2 Hz, 1H), 7.45 (d, J=9.0 Hz, 1H), 7.15 (d, J=10.1 Hz, 1H), 1.35 (s, 1H), 1.24 (m, 3H) ppm.

Embodiment 22

2-{[4-(3-Chloro-4-cyanophenyl)isoquinolin-6-yl]thio}-2-methyl propionic Acid (Compound 22)

Synthesis of Compound 22-c

Under N$_2$ atmosphere, bis(pinacolato)diboron (391 mg, 1.54 mmol), potassium acetate (412 mg, 4.2 mmol) and [1,1'-bis(diphenylphosphine)ferrocene]palladium dichloride (102 mg, 0.14 mmol) were respectively added to a solution of 2-chloro-4-bromobenzonitrile (300 mg, 1.4 mmol) in dioxane (15 mL). The mixture was stirred at 115° C. for 12 hrs, cooled to room temperature, filtered through celite, washed with EA (50 mL). The filtrate was evaporated under reduced pressure to give compound 22-c (620 mg, yield 100%). The product was directly used for the next step without further purification. LC-MS (ESI): m/z=182 [M+H]+.

Synthesis of Compound 22-b

Compound 4-c (80 mg, 0.24 mmol) was added to a suspension of ethyl 2-methyl-2-mercaptopropionate (71 mg, 0.48 mmol) and potassium carbonate (100 mg, 0.72 mmol) in DMF (2 mL). The mixture was stirred at 130° C. for 2 hrs, cooled to room temperature, followed by adding water (20 mL), being extracted with EA (20 mL×3). The organic phases were combined, washed in turn with water (20 mL×3) and saturated brine (20 mL), dried over anhydrous sodium sulfate, filtered and concentrated under reduced pressure. The residue was purified with silica preparative plate (PE:EA=3:1) to give yellow oil 22-b (75 mg, yield 78%). LC-MS (ESI): m/z=402 [M+H]+.

Synthesis of Compound 22-a

Under N₂ atmosphere, compound 22-b (60 mg, 0.15 mmol), compound 22-c (120 mg, 0.23 mmol) and cesium carbonate (98 mg, 0.3 mmol) were suspended in dioxane (3 mL) and water (0.3 mL), [1,1'-bis(diphenylphosphine)ferrocene]palladium dichloride (11 mg, 0.02 mmol) was added. The mixture was stirred at 100° C. for 12 hrs, cooled to room temperature, followed by adding water (10 mL), being extracted with EA (10 mL×3). The organic phases were combined, washed in turn with water (10 mL×3) and saturated brine (10 mL), dried over anhydrous sodium sulfate, filtered, and concentrated under reduced pressure. The residue was purified with silica preparative plate (DCM:methanol=20:1) to give brown solid 22-a (43 mg, yield 70%).

Synthesis of Compound 22

At room temperature, 1M NaOH aq. solution (1 mL) was added to a solution of compound 22-a (43 mg, 0.1 mmol) in methanol (1 mL) and THF (1 mL). The mixture was stirred for 4 hrs, followed by evaporating under reduced pressure to remove methanol. The residue was adjusted to pH=5-6 with 1M HCl aq. solution, followed by being extracted with DCM (10 mL×3). The organic phases were combined, dried over anhydrous sodium sulfate, filtered, and concentrated under reduced pressure. The residue was purified by silica preparative plate (DCM:methanol=10:1) to give yellow solid 22 (21 mg, yield 53%). LC-MS (ESI): m/z=383 [M+H]+.

¹H-NMR (400 MHz, CDCl₃) δ: 9.21 (s, 1H), 8.38 (s, 1H), 7.98 (d, J=8.4 Hz, 1H), 7.95 (s, 2H), 7.78 (d, J=8.8 Hz, 1H), 7.73 (d, J=8.0 Hz, 1H), 7.63 (s, 1H), 7.50 (d, J=8.0 Hz, 1H), 1.61 (s, 6H) ppm.

Embodiment 23

2-{[4-(2-Chloro-4-cyanophenyl)isoquinolin-6-yl]thio}-2-methyl propionic Acid (Compound 23)

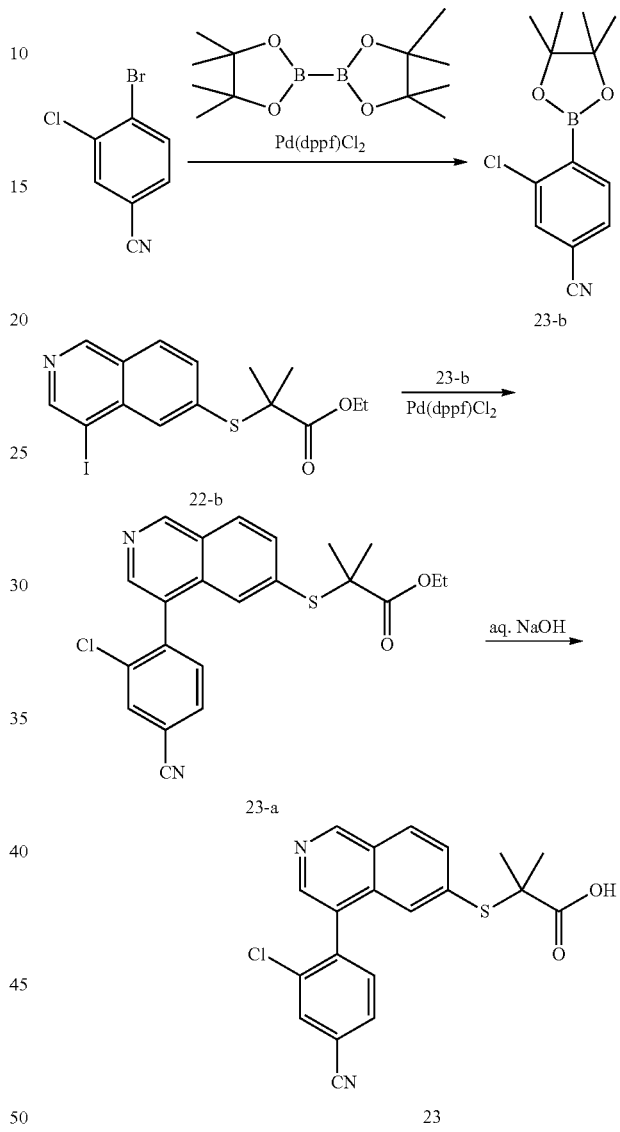

Synthesis of Compound 23-b

Under N₂ atmosphere, bis(pinacolato)diboron (391 mg, 1.54 mmol), potassium acetate (412 mg, 4.5 mmol) and [1,1'-bis(diphenylphosphine)ferrocene]palladium dichloride (102 mg, 0.14 mmol) were respectively added to a solution of 2-chloro-4-bromobenzonitrile (300 mg, 1.4 mmol) in dioxane (15 mL). The mixture was stirred at 80° C. for 12 hrs, cooled to room temperature, filtered through celite, washed with EA (50 mL). The filtrate was evaporated under reduced pressure, and the residue was purified by silica preparative plate to give white solid 23-b (73 mg, yield 20%).

$^1$H-NMR (400 MHz, CDCl$_3$) δ: 7.78 (d, J=7.6 Hz, 1H), 7.62 (d, J=1.2 Hz, 1H), 7.52 (dd, J=7.6 Hz, 1.2 Hz, 1H), 1.37 (s, 12H) ppm.

Synthesis of Compound 23-a

Under N$_2$ atmosphere, compound 22-b (100 mg, 0.15 mmol), compound 23-b (73 mg, 0.27 mmol) and cesium carbonate (163 mg, 0.5 mmol) were suspended in dioxane (3 mL) and water (0.3 mL), [1,1'-bis(diphenylphosphine)ferrocene]palladium dichloride (19 mg, 0.03 mmol) was added. The mixture was stirred at 100° C. for 12 hrs, cooled to room temperature, followed by adding water (10 mL), being extracted with EA (10 mL×3). The organic phases were combined, washed in turn with water (10 mL×3) and saturated brine (10 mL), dried over anhydrous sodium sulfate, filtered, and concentrated under reduced pressure. The residue was purified by silica preparative plate (DCM:methanol=20:1) to give white solid 23-a (72 mg, yield 71%). LC-MS (ESI): m/z=411 [M+H]$^+$.

Synthesis of Compound 23

At room temperature, 1M NaOH aq. solution (1 mL) was added to a solution of compound 23-a (72 mg, 0.18 mmol) in methanol (1 mL) and THF (1 mL). The mixture was stirred for 2 hrs, followed by evaporating under reduced pressure to remove methanol. The residue was adjusted to pH=5-6 with 1M HCl aq. solution, followed by being extracted with DCM (10 mL×3). The organic phases were combined, dried over anhydrous sodium sulfate, filtered, and concentrated under reduced pressure. The residue was purified with silica preparative plate (DCM:methanol=10:1) to give white solid 23 (31 mg, yield 46%). LC-MS (ESI): m/z=383 [M+H]$^+$.

$^1$H-NMR (400 MHz, DMSO-d6) δ: 9.42 (s, 1H), 8.44 (s, 1H), 8.31 (d, J=1.6 Hz, 1H), 8.21 (d, J=8.4 Hz, 1H), 8.03 (dd, J=8.0 Hz, 1.2 Hz, 1H), 7.73 (d, J=8.0 Hz, 1H), 7.39 (s, 1H), 1.42 (s, 3H), 1.41 (s, 3H) ppm.

Embodiment 24

1-{[4-(4-cyanonaphthalen-1-yl)isoquinolin-6-yl]thio}cyclobutane-1-carboxylic Acid (Compound 24)

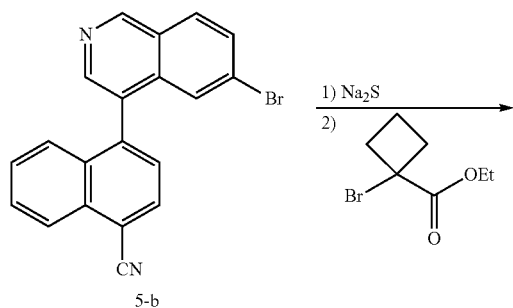

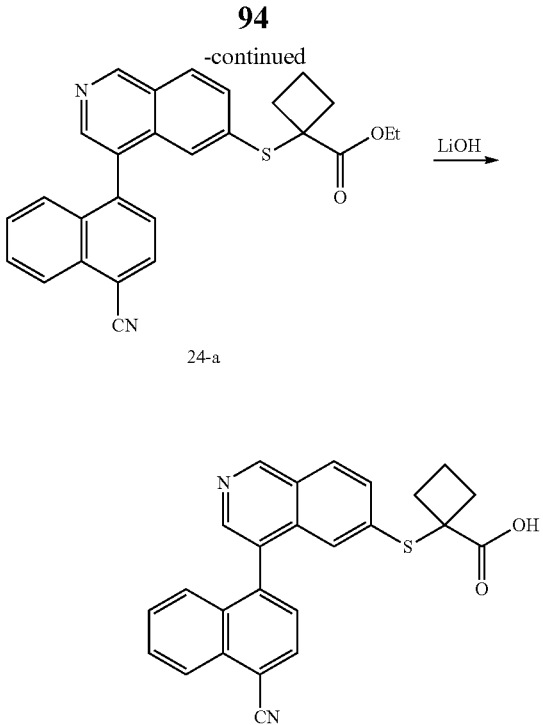

Synthesis of Compound 24-a

Na$_2$S.9H$_2$O (182 mg, 0.75 mmol) was added to a solution of compound 5-b (180 mg, 0.5 mmol) in DMF (2 mL). The mixture was reacted in a microwave at 130° C. for 1 h, cooled to room temperature, 1-bromo-cyclobutanoic acid ethyl ester (155 mg, 0.75 mmol) was added, the mixture was stirred at 50° C. for 2 hrs. The mixture was cooled to room temperature, followed by adding ice water (20 mL), being extracted with EA (50 mL). The organic phases were combined, dried over anhydrous sodium sulfate, filtered, and concentrated under reduced pressure. The residue was purified by silica preparative plate (PE:EA=1:1) to give white solid 24-a (89 mg, yield 40%). LC-MS (ESI): m/z=439 [M+H]$^+$.

Synthesis of Compound 24

At room temperature, LiOH.H$_2$O (26 mg, 0.61 mmol) was added to a mixed solution of compound 24-a (89 mg, 0.20 mmol) in methanol (1 mL), THF (1 mL) and water (1 mL). The mixture was stirred for 4 hrs, concentrated under reduced pressure, followed by adding water (10 mL) and EA (20 mL). The aqueous phase was adjusted to pH=5-6 with 0.5M HCl aq. solution, solid turned out, the mixture was further stirred for 30 mins and filtered. The solid was washed with water (10 mL), dried under vacuum to give white solid 24 (65 mg, yield 78%). LC-MS (ESI): m/z=411 [M+H]$^+$.

$^1$H-NMR (400 MHz, DMSO-d6) δ: 12.69 (s, 1H), 9.41 (s, 1H), 8.52 (s, 1H), 8.33 (d, J=8.0 Hz, 1H), 8.31 (d, J=8.0 Hz, 1H), 8.19 (d, J=8.0 Hz, 1H), 7.83 (m, 1H), 7.69 (d, J=8.0 Hz, 1H), 7.57 (m, 1H), 7.51 (d, J=8.0 Hz, 1H), 7.39 (d, J=8.0 Hz, 1H), 2.51 (m, 1H), 2.01 (m, 3H), 1.71 (m, 2H) ppm.

Embodiment 25

3-{3-[(2, 6-dichlorophenyl)methyl]-1-methylimidazole[1,5-a]pyridine-6-yl}propionic Acid (Compound 25)

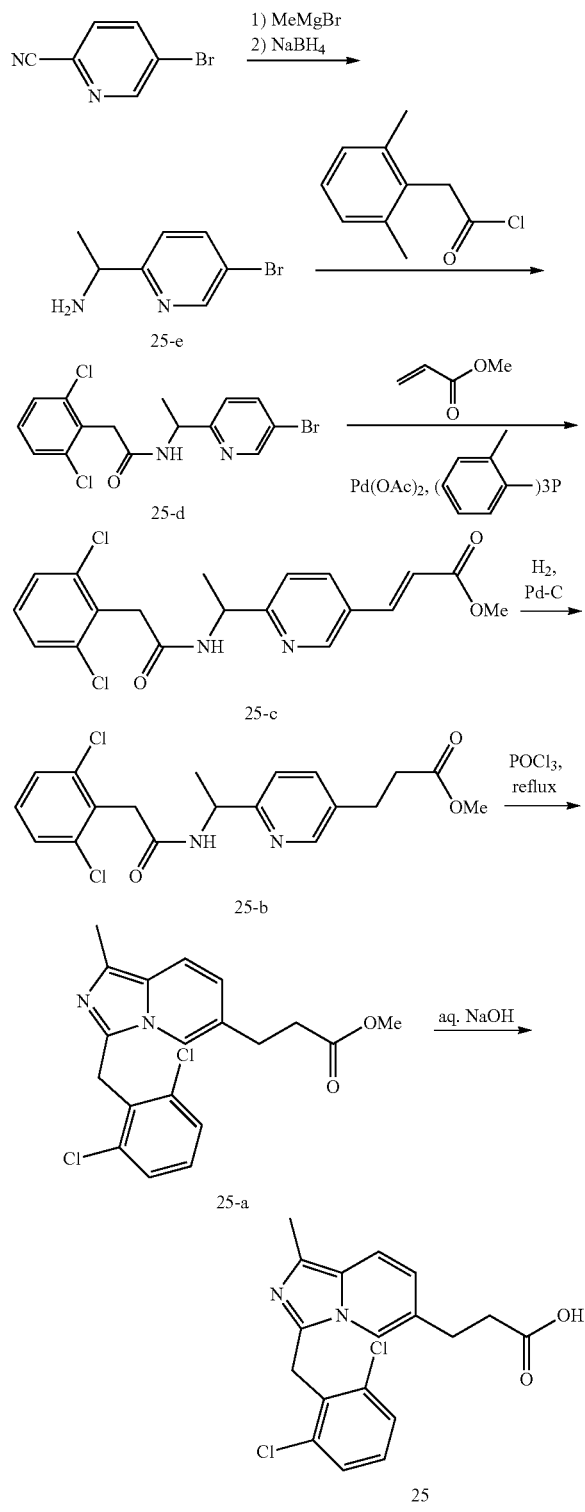

Synthesis of Compound 25-e

At 0° C., a solution of 3M methyl magnesium bromide in THF (2.09 mL, 6.28 mmol) was added into a solution of 5-bromo-2-cyanopyridine (1.0 g, 5.46 mmol) in anhydrous THF (10 mL). The mixture was warmed to room temperature slowly, further stirred for 30 mins, and followed by adding methanol (20 mL), adding $NaBH_4$ (410 mg, 10.93 mmol) in portions. The mixture was further stirred for 10 hrs, followed by adding water (10 mL) and 2M NaOH aq. solution (10 mL) in turn, being extracted with EA (50 mL×3). The organic phases were combined, washed in turn with water (20 mL×3) and saturated brine (20 mL), dried over anhydrous sodium sulfate, filtered, and concentrated under reduced pressure. The residue was purified by silica preparative plate (PE:EA=1:1) to give white solid 25-e (1.0 g, yield 91%). LC-MS (ESI): m/z=201 $[M+H]^+$.

Synthesis of Compound 25-d

At room temperature, oxalyl chloride (0.69 g, 5.47 mmol) and DMF (0.1 mL) were added to a solution of 2,6-dichlorophenylacetic acid (1.02 g, 4.97 mmol) in DCM (10 mL), the mixture was stirred for 2 hrs and concentrated under reduced pressure. The residue was dissolved in DCM (10 mL) again, at 0° C., the above solution was slowly added to a solution of compound 25-e (1.0 g, 4.97 mmol) and triethyl amine (1.39 mL, 9.95 mmol) in DCM (10 mL). The mixture was warmed to room temperature and further stirred for 2 hrs, followed by adding water (20 mL), and being extracted with DCM (50 mL×3). The organic phases were combined, washed in turn with water (20 mL×3) and saturated brine (20 mL), dried over anhydrous sodium sulfate, filtered, and concentrated under reduced pressure. The residue was purified (PE:EA=5:1) to give light yellow solid 25-d (0.9 g, yield 46%). LC-MS (ESI): m/z=387 $[M+H]^+$.

Synthesis of Compound 25-c

Under $N_2$ atmosphere, methyl acrylate (0.186 mL, 2.06 mmol), palladium acetate (23.1 mg, 0.1 mmol), tris(o-methylphenyl)phosphine (62.7 mg, 0.2 mmol) and triethyl amine (0.28 mL, 2 mmol) were added to a solution of compound 25-d (400 mg, 1.03 mmol) in DMF (5 mL). The mixture was reacted in a microwave at 120° C. for 10 mins, cooled to room temperature, followed by adding water (15 mL), being extracted with EA (30 mL×3). The organic phase was washed in turn with water (20 mL×3) and saturated brine (20 mL), dried over anhydrous magnesium sulfate, filtered, and concentrated under reduced pressure. The residue was purified by silica column chromatography (PE:EA=1:1) to give compound 25-c (400 mg, yield 98%). LC-MS (ESI): m/z=393 $[M+H]^+$.

Synthesis of Compound 25-b

Under $H_2$ atmosphere (1 atm.), the Pd-C (50 mg) was added to a solution of compound 25-c (400 mg, 1.02 mmol) in ethanol (10 mL). The mixture was stirred for 12 hrs, filtered, and concentrated under reduced pressure to give compound 25-b (350 mg, yield 87%). The product was used directly for the next step without further purification. LC-MS (ESI): m/z=393 $[M+H]^+$.

Synthesis of Compound 25-a

Compound 25-b (350 mg, 0.89 mmol) was dissolved in phosphorus oxychloride (8 mL), stirred at 110° C. for 5 hrs.

The mixture was cooled to room temperature, added to ice water (20 mL), followed by adding sodium carbonate solid to adjust pH=8, and then extracted with EA (30 mL×3). The organic phases were in turn washed with water (20 mL) and saturated brine (20 mL), dried over anhydrous magnesium sulfate, filtered, and concentrated under reduced pressure. The residue was purified by silica column chromatography (PE:EA=2:1) to give yellow oil 25-a (150 mg, yield 45%). LC-MS (ESI): m/z=377 [M+H]$^+$.

Synthesis of Compound 25

At room temperature, 20% NaOH aq. solution (2 mL) was added to a solution of compound 25-a (120 mg, 0.32 mmol) in methanol (2 mL). The reaction solution was stirred for 2 hrs, concentrated under reduced pressure to remove methanol, 6M HCl aq. solution was added to adjust pH=7, solid was precipitated and filtered out. The solid was washed with water (10 mL), dried under vacuum to give white solid 25 (65 mg, yield 56%). LC-MS (ESI): m/z=363 [M+H]$^+$.

$^1$H-NMR (400 MHz, CD$_3$OD) δ: 7.91 (s, 1H), 7.30-7.46 (m, 4H), 6.67 (d, J=9.6 Hz, 1H), 4.60 (s, 2H), 2.89 (t, J=7.6 Hz, 1H), 2.67 (t, J=7.6 Hz, 2H), 2.38 (s, 3H) ppm.

Embodiment 26

2-({1-[(2,6-dichlorophenyl)methyl]-3-methyl-1H-indazol-6-yl}thio)-2-methyl propionic Acid (Compound 26)

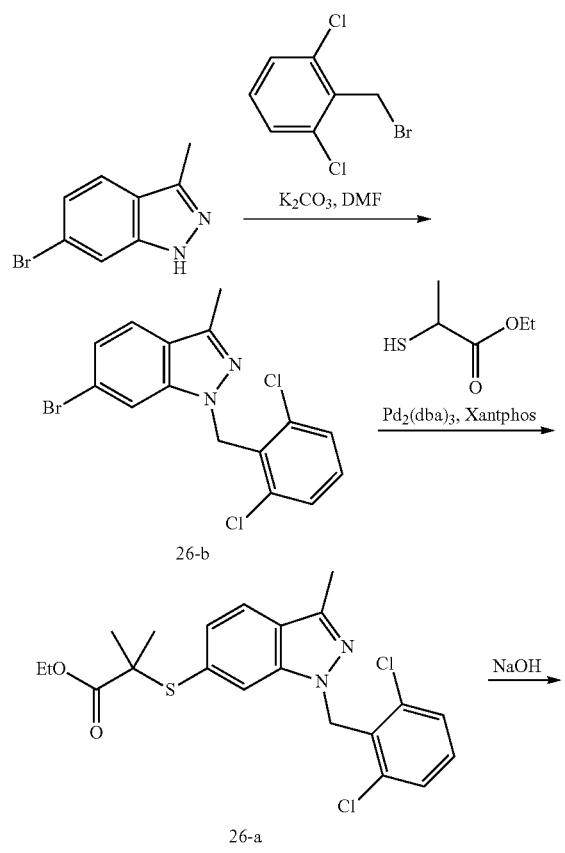

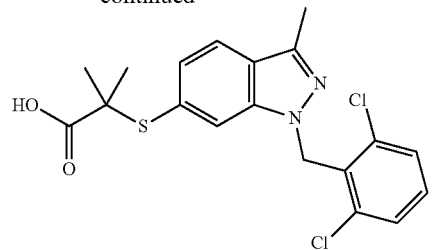

26

Synthesis of Compound 26-b

At room temperature, potassium carbonate (490 mg, 3.55 mmol) was added to a solution of 6-bromo-3-methyl-1H-indazole (500 mg, 2.37 mmol) and 2,6-dichlorobenzyl bromide (680 mg, 2.84 mmol) in DMF (5 mL). The mixture was stirred for 12 hrs, followed by adding water (10 mL), being extracted with EA (20 mL×3). The organic phases were combined, washed in turn with water (10 mL) and saturated brine (10 mL), dried over magnesium sulfate, filtered, and concentrated under reduced pressure. The residue was purified by silica column chromatography (PE:EA=10:1) to give yellow oil 26-b (400 mg, yield 45%). LC-MS (ESI): m/z=369 [M+H]$^+$.

Synthesis of Compound 26-a

Under N$_2$ atmosphere, tris(dibenzylidene indene acetone) dipalladium (25.5 mg, 0.02 mmol), 4,5-bis(diphenylphosphine)-9,9-dimethyloxacanthracene (31 mg, 0.05 mmol) and CuI (5.1 mg, 0.02 mmol) were added to a solution of compound 26-b (100 mg, 0.27 mmol), ethyl 2-methyl-2-mercaptopropionate (0.04 mL, 0.27 mmol) and diisopropylethylamine (0.14 mL, 0.81 mmol) in dioxane (2 mL). The mixture was reacted in a microwave at 125° C. for 1 h, cooled to room temperature, concentrated under reduced pressure to remove dioxane. The residue was purified by silica preparative plate chromatography (PE:EA=1:1) to give compound 26-a (80 mg, yield 67%). LC-MS (ESI): m/z=437 [M+H]$^+$.

Synthesis of Compound 26

At room temperature, NaOH (72 mg, 1.8 mmol) was added to a mixed solution of compound 26-a (80 mg, 0.18 mmol) in methanol (2 mL), THF (2 mL) and water (2 mL). The mixture was stirred for 2 hrs, adjusted to pH=7 by 2M HCl aq. solution, extracted with EA (20 mL×3). The organic phases were washed in turn with water (10 mL) and saturated brine (10 mL), dried over anhydrous magnesium sulfate, filtered, and concentrated under reduced pressure to give compound 26 (20 mg, yield 27%). LC-MS (ESI): m/z=409 [M+H]$^+$.

$^1$H-NMR (400 MHz, CD$_3$OD) δ: 7.60 (s, 1H), 7.52 (d, J=8.0 Hz, 1H), 7.34 (m, 2H), 7.24 (m, 1H), 7.13 (d, J=8.0 Hz, 1H), 5.64 (s, 1H), 2.37 (s, 3H), 1.35 (s, 6H) ppm.

Embodiment 27

2-{[5-(4-Cyanophenyl)imidazo[1,2-a]pyridin-6-yl]thio}-2-methyl propionic Acid (Compound 27)

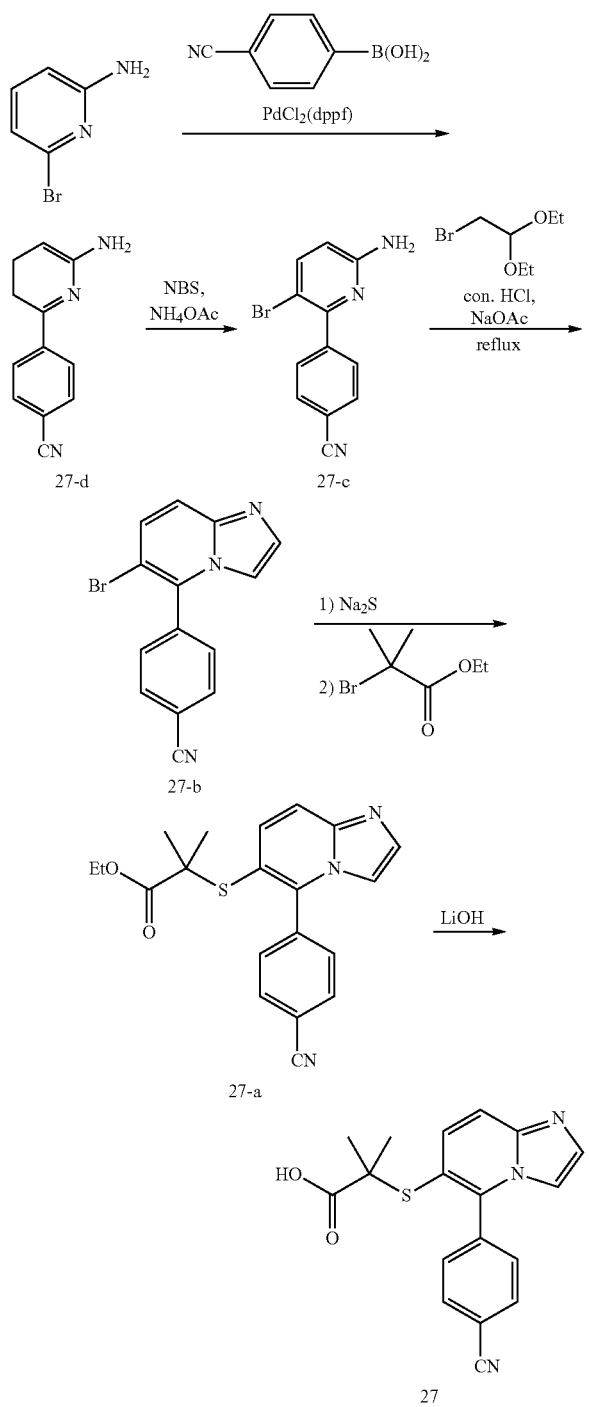

Synthesis of Compound 27-d

Under $N_2$ atmosphere, 2-amino-6-bromopyridine (500 mg, 2.89 mmol), 4-cyanophenylboronic acid (510 mg, 3.47 mmol) and sodium carbonate (920 mg, 8.67 mmol) were suspended in DMF (10 mL) and water (5 mL), [1,1'-bis(diphenylphosphine)ferrocene]palladium dichloride (240 mg, 0.29 mmol) was added. The mixture was stirred at 80° C. for 2 hrs, cooled to room temperature, followed by adding water (15 mL), being extracted with EA (30 mL×3). The organic phase was washed in turn with water (20 mL) and saturated brine (20 mL), dried over anhydrous magnesium sulfate, filtered, and concentrated under reduced pressure. The residue was purified by silica column chromatography (PE:EA=2:1) to give compound 27-d (400 mg, yield 71%). LC-MS (ESI): m/z=196 [M+H]+.

Synthesis of Compound 27-c

At 0° C., N-bromosuccinimide (360 mg, 2.05 mmol) was added to a solution of compound 27-d (400 mg, 2.05 mmol) and ammonium acetate (160 mg, 2.05 mmol) in $CH_3CN$ (10 mL). The reaction solution was warmed to room temperature and stirred for 12 hrs, and concentrated under reduced pressure to remove solvent. The residue was purified by silica column chromatography (PE:EA=2:1) to give compound 27-c (500 mg, yield 89%). LC-MS (ESI): m/z=274 [M+H]+.

Synthesis of Compound 27-b

A solution of sodium acetate (42 mg, 0.78 mmol) and 2-bromo-1,1-diethoxyethane (0.28 mL, 1.8 mmol) in conc. HCl aqueous solution (0.1 mL) and water (0.6 mL) was heated to 110° C. and refluxed for 10 mins. The reaction solution was cooled to 60° C., the solution was added to a solution of compound 27-b (250 mg, 0.91 mmol) and sodium acetate (83 mg, 1.55 mmol) in 60% ethanol aqueous solution (10 mL). The mixture was heated to 100° C. and refluxed for 2.5 hrs, cooled to room temperature, and concentrated under reduced pressure. The residue was added to ice water (5 mL), adjusted to pH=7 with saturated sodium bicarbonate solution, extracted with EA (30 mL×3). The organic phase was washed in turn with water (20 mL) and saturated brine (20 mL), dried over anhydrous magnesium sulfate, filtered, and concentrated under reduced pressure. The residue was purified with silica column chromatography (PE:EA=1:1) to give compound 27-b (150 mg, yield 55%). LC-MS (ESI): m/z=298 [M+H]+.

Synthesis of Compound 27-a $Na_2S \cdot 9H_2O$ (182 mg, 0.75 mmol) was added to a solution of compound 27-b (180 mg, 0.5 mmol) in N-methyl pyrrolidone (2 mL). The reaction solution was reacted in a microwave at 150° C. for 1 h, cooled to room temperature, followed by adding ethyl 2-bromo-2-methylpropionate (100 mg, 0.67 mmol) and potassium carbonate (90 mg, 0.67 mmol). The mixture was stirred at 50° C. for 2 hrs, cooled to room temperature, followed by adding water (5 mL), being extracted with EA (10 mL). The organic phase was washed in turn with water (10 mL) and saturated brine (10 mL), dried over anhydrous magnesium sulfate, filtered, and concentrated under reduced pressure. The residue was purified by silica column chromatography (PE:EA=1:1) to give compound 27-a (10 mg, yield 8%). LC-MS (ESI): m/z=366 [M+H]+.

Synthesis of Compound 27

At room temperature, LiOH (13.1 mg, 0.55 mmol) was added to a solution of compound 27-a (10 mg, 0.02 mmol)

in methanol (2 mL), THF (2 mL) and water (4 mL). The mixture was stirred for 2 hrs, adjusted to pH=7 with 2M HCl aq. solution, extracted with EA (20 mL×3). The organic phase was in turn washed with water (10 mL) and saturated brine (10 mL), dried over anhydrous magnesium sulfate, filtered, and concentrated under reduced pressure to give compound 27 (5 mg, yield 54%). LC-MS (ESI): m/z=338 [M+H]$^+$.

$^1$H-NMR (400 MHz, CD$_3$OD) δ: 7.97 (d, J=8.0 Hz, 1H), 7.59-7.70 (m, 5H), 7.26 (s, 1H), 1.38 (s, 6H) ppm.

Embodiment 28

2-{[3-(4-Cyanophenyl)-[1,2,4]triazo[4,3-a]pyridin-6-yl]thio}-2-methyl propionic Acid (Compound 28)

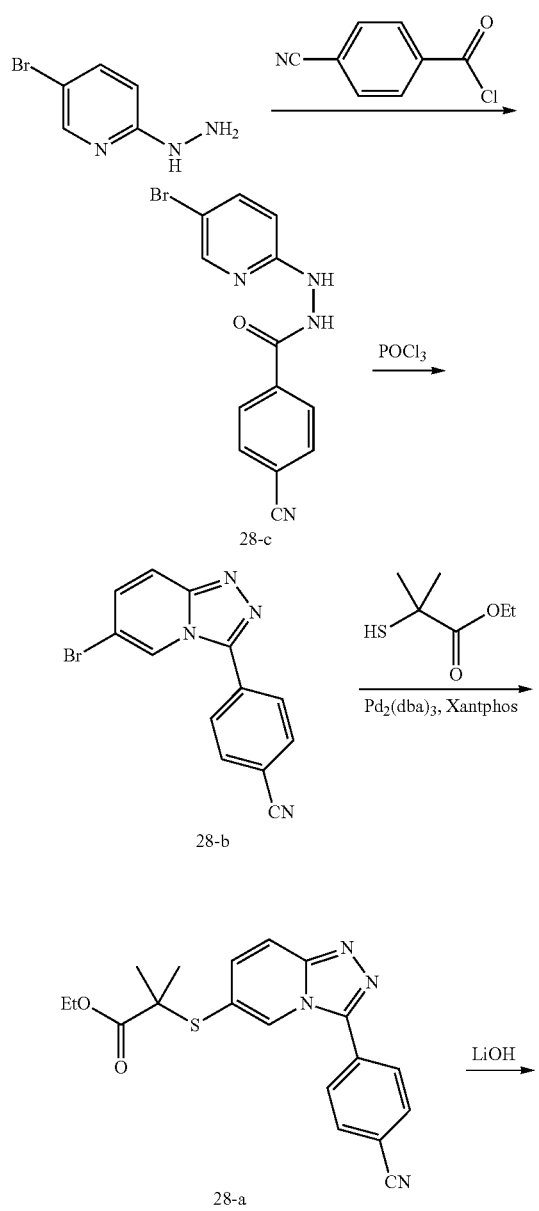

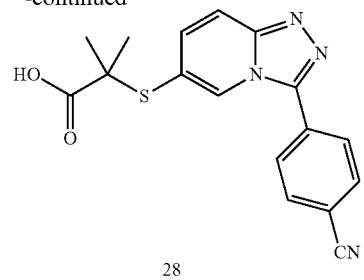

28

Synthesis of Compound 28-c

At room temperature, a mixture of 2-hydrazino-5-bromopyridine (1.0 g, 5.3 mmol), 4-cyanobenzoyl chloride (0.97 g, 5.85 mmol), triethyl amine (0.64 g, 0.88 mmol) and DCM (15 mL) was stirred for 12 hrs, and filtered. The solid was washed with DCM (5 mL), dried under vacuum to give yellow solid 28-c (1.13 g, yield 67%). The product was used directly for the next step without further purification. LC-MS (ESI): m/z=319 [M+H]$^+$.

Synthesis of Compound 28-b

Compound 28-c (1.03 g, 3.25 mmol) was added to POCl$_3$ (10 mL). The mixture was stirred at 100° C. for 12 hrs, cooled to room temperature, and concentrated under reduced pressure. Saturated NaHCO$_3$ aq. solution was added to the residue to adjust pH=7, the mixture was extracted with EA (50 mL×2). The organic phase was in turn washed with water (30 mL) and saturated NaHCO$_3$ aq. solution (30 mL), dried over anhydrous sodium sulfate, filtered and concentrated under reduced pressure to give compound 28-b (0.85 g, yield 80%). The product was used directly for the next step without further purification. LC-MS (ESI): m/z=301 [M+H]$^+$.

Synthesis of Compound 28-a

Under N$_2$ atmosphere, tris(dibenzylidene indene acetone) dipalladium (54 mg, 0.05 mmol) and 4,5-bis(diphenylphosphine)-9,9-dimethyloxacanthracene (68 mg, 0.11 mmol) were added to a solution of compound 28-b (350 mg, 1.17 mmol), ethyl 2-methyl-2-mercaptopropionate (208 mg, 1.4 mmol) and diisopropylethylamine (302 mg, 2.34 mmol) in dioxane (10 mL). The mixture was reacted in a microwave at 110° C. for 1 h, cooled to room temperature, concentrated under reduced pressure to remove dioxane. The residue was purified by silica preparative plate chromatography (PE:EA=3:1-1:1) to give compound 28-a (268 mg, yield 55%). LC-MS (ESI): m/z=367 [M+H]$^+$.

Synthesis of Compound 28

At room temperature, LiOH (51 mg, 1.22 mmol) was added to a solution of compound 28-a (223 mg, 0.61 mmol) in methanol (2 mL), THF (6 mL) and water (2 mL). The mixture was stirred for 3 hrs, concentrated under reduced pressure, followed by adding water (10 mL), being extracted with EA (30 mL×2), the aqueous phase was adjusted to pH=5-6 with 2M HCl aq. solution and extracted with EA (30 mL×2). The organic phases were combined, washed in turn with water (10 mL) and saturated brine (10 mL), dried over anhydrous sodium sulfate, filtered and concentrated under reduced pressure. The residue was recrystallized in EA (15 mL) and PE (10 mL) to give yellow solid 28 (108 mg, yield 52%). LC-MS (ESI): m/z=339 [M+H]+.

1H-NMR (400 MHz, DMSO-d6) δ: 12.92 (s, 1H), 8.56 (s, 1H), 8.12 (m, 4H), 7.92 (d, J=9.8 Hz, 1H), 7.45 (d, J=9.4 Hz, 1H), 1.44 (s, 6H) ppm.

Embodiment 29

7-(4-Cyanonaphthalen-1-yl)thieno[3,2-c]pyridin-2-formic Acid (Compound 29)

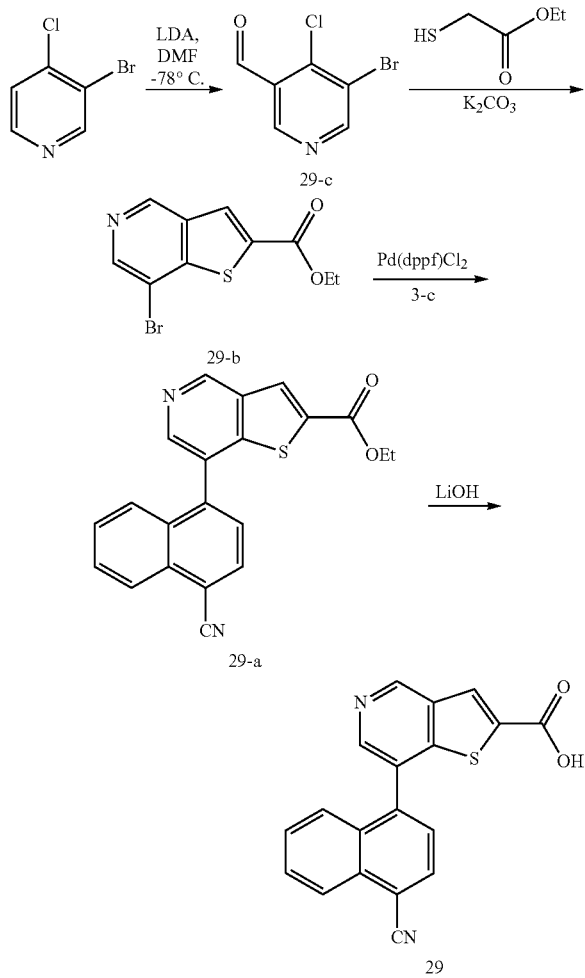

Synthesis of Compound 29-c

Under N2 atmosphere, at −78° C., a solution of 2.5M n-butyl lithium in n-hexane (24 mL, 60 mmol) was slowly added to a solution of diisopropylamine (6.1 g, 60 mmol) in anhydrous THF (100 mL). The mixture was stirred for 15 mins, followed by adding a solution of 3-bromo-4-chloro-pyridine (9.6 g, 50 mmol) in anhydrous THF (100 mL), further stirred for 1 h, followed by adding anhydrous DMF (10 mL) and stirred for 30 mins. The mixture was slowly warmed to room temperature, followed by adding saturated NH4Cl aq. solution (300 mL), the mixture was extracted with EA (300 mL×3). The organic phases were combined, washed in turn with water (100 mL) and saturated brine (100 mL), dried over anhydrous sodium sulfate, filtered and concentrated under reduced pressure. The residue was purified by silica preparative plate chromatography (PE:EA=2:1-1:1) to give light yellow solid 29-c (5.9 g, yield 54%).

1H-NMR (400 MHz, CDCl3) δ: 10.44 (s, 1H), 8.80 (s, 1H), 7.67 (s, 1H) ppm.

Synthesis of Compound 29-b

Ethyl mercaptoacetate (2.4 g, 20 mmol) and potassium carbonate (3.0 g, 24 mmol) were added to a solution of compound 29-c (4.4 g, 20 mmol) in DMF (40 mL). The mixture was heated to 45° C. and stirred for 12 hrs, cooled to room temperature, followed by adding ice water (200 mL), solid was precipitated and filtered out. The solid was washed with water (100 mL×3) and dried under vacuum to give white solid 29-b (5.1 g, yield 89.5%). The product was used directly for the next step without further purification. LC-MS (ESI): m/z=286 [M+H]+.

Synthesis of Compound 29-a

Under N2 atmosphere, compound 29-b (285 mg, 1 mmol), compound 3-c (279 mg, 1 mmol) and sodium carbonate (212 mg, 2 mmol) were suspended in dioxane (6 mL) and water (2 mL), [1,1'-bis(diphenylphosphine)ferrocene]palladium dichloride (73 mg, 0.1 mmol) was added. The mixture was stirred at 80° C. for 3 hrs, cooled to room temperature and concentrated under reduced pressure. The residue was purified by silica preparative plate (PE:EA=2:1) to give compound 29-a (190 mg, yield 53%). LC-MS (ESI): m/z=359 [M+H]+.

Synthesis of Compound 29

At room temperature, LiOH (41 mg, 1 mmol) was added to a solution of compound 29-a (190 mg, 0.53 mmol) in methanol (3 mL), THF (3 mL) and water (3 mL). The mixture was stirred for 1 h, adjusted to pH=5-6 with 2M HCl aq. solution, solid was precipitated and filtered out. The solid was washed with water (10 mL), dried under vacuum to give light yellow solid 29 (130 mg, yield 74%). LC-MS (ESI): m/z=331 [M+H]+.

1H-NMR (400 MHz, DMSO-d6) δ: 9.42 (s, 1H), 8.64 (s, 1H), 8.40 (s, 1H), 8.35 (d, J=8.0 Hz, 1H), 8.29 (d, J=8.0 Hz, 1H), 7.90 (m, 2H), 7.66 (s, 2H) ppm.

Embodiment 30

3-[7-(4-Cyanonaphthalen-1-yl)thieno[3,2-c]pyridin-2-yl]propionic acid (Compound 30)

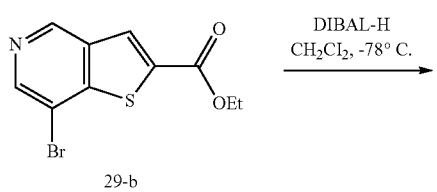

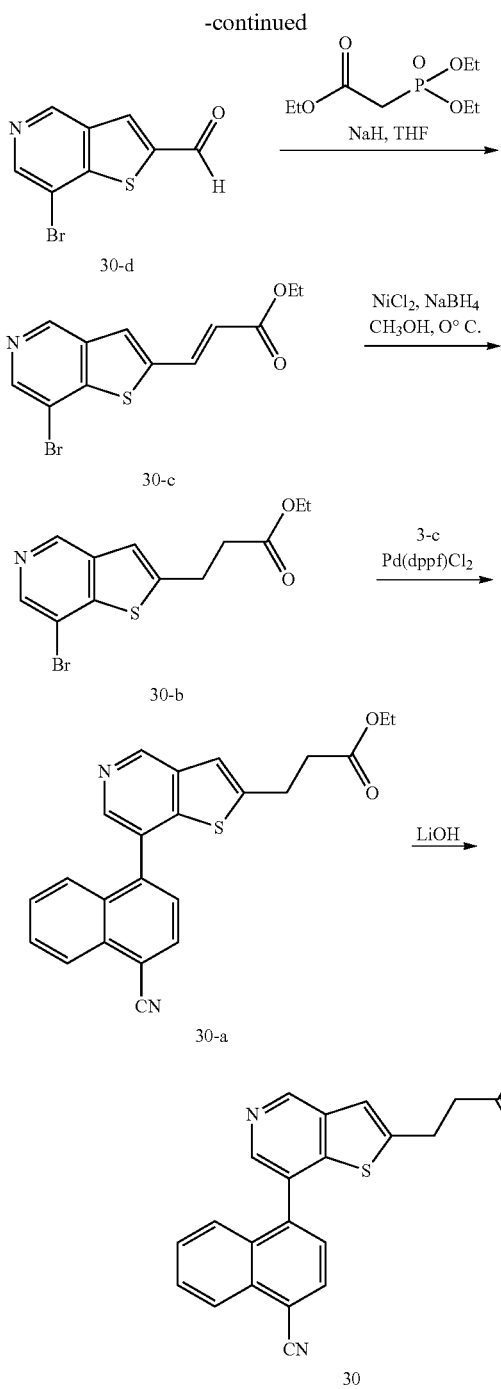

Synthesis of Compound 30-d

At −78° C., a solution of 1.0M diisobutylaluminum hydride in DCM (58 mL, 58 mmol) was slowly added to a solution of compound 29-b (5.7 g, 20 mmol) in DCM (50 mL). The mixture was stirred for 1 h, warmed to room temperature, followed by adding saturated NH$_4$Cl aq. solution (300 mL). The organic phase was separated, the aqueous phase was extracted with DCM (50 mL×3). The organic phases were combined, washed in turn with water (50 mL) and saturated brine (50 mL), dried over anhydrous sodium sulfate, filtered and concentrated under reduced pressure. The residue was purified by silica column chromatography (PE:EA=3:1) to give light yellow solid 30-d (4 g, yield 83%). LC-MS (ESI): m/z=242 [M+H]$^+$.

Synthesis of Compound 30-c

At 0° C., triethyl phosphonoacetate (2.82 mL, 10 mmol) and sodium hydride (0.48 g, 12 mmol) were respectively added to a solution of compound 30-d (2.42 g, 10 mmol) in THF (50 mL). The mixture was further stirred for 1 h, warmed to room temperature, followed by adding saturated NH$_4$Cl aq. solution (300 mL), the mixture was extracted with EA (50 mL×3). The organic phases were combined, washed in turn with water (30 mL×3) and saturated brine (30 mL), dried over anhydrous sodium sulfate, filtered, and concentrated under reduced pressure. The residue was purified by silica column chromatography (PE:EA=5:1) to give light yellow solid 30-c (2 g, yield 64%). LC-MS (ESI): m/z=312 [M+H]$^+$.

Synthesis of Compound 30-b

At 0° C., NaBH$_4$ (0.25 g, 6.4 mmol) was slowly added to a solution of compound 30-c (2.0 g, 6.4 mmol) and NiCl (0.82 g, 6.4 mmol) in methanol (50 mL). The mixture was stirred for 3 hrs, warmed to room temperature, followed by adding NH$_4$Cl aq. solution (300 mL), the mixture was extracted with EA (100 mL×3). The organic phases were combined, washed in turn with water (50 mL×3) and saturated brine (50 mL), dried over anhydrous sodium sulfate, filtered and concentrated under reduced pressure. The residue was purified by silica column chromatography (PE:EA=4:1) to give light yellow solid 30-b (1.6 g, yield 80%). LC-MS (ESI): m/z=314 [M+H]$^+$.

Synthesis of Compound 30-a

Under N$_2$ atmosphere, compound 30-b (155 mg, 0.5 mmol), compound 3-c (140 mg, 0.5 mmol) and sodium carbonate (106 mg, 1 mmol) were suspended in dioxane (4 mL) and water (1 mL), [1,1′-bis(diphenylphosphine)ferrocene]palladium dichloride (40 mg, 0.05 mmol) was added. The mixture was stirred at 80° C. for 3 hrs, cooled to room temperature and concentrated under reduced pressure. The residue was filtered through celite, the filtrate cake was washed with EA (30 mL). The filtrate was washed in turn with water (10 mL×3) and saturated brine (10 mL), dried over anhydrous sodium sulfate, filtered and concentrated under reduced pressure. The residue was purified by silica column chromatography (PE:EA=1:1) to give compound 30-b (120 mg, yield 62%). LC-MS (ESI): m/z=387 [M+H]$^+$.

Synthesis of Compound 30

At room temperature, LiOH (42 mg, 1 mmol) was added to a solution of compound 30-a (120 mg, 0.31 mmol) in methanol (1 mL), THF (4 mL) and water (1 mL). The mixture was stirred for 1 h, adjusted to pH=5-6 by 2M HCl aq. solution, solid was precipitated and filtered out. The solid was washed with water (10 mL), dried under vacuum to give white solid 30 (93 mg, yield 84%). LC-MS (ESI): m/z=359 [M+H]$^+$.

$^1$H-NMR (400 MHz, DMSO-d6) δ: 9.15 (s, 1H), 8.42 (s, 1H), 8.32 (d, J=8.0 Hz, 1H), 8.27 (d, J=8.0 Hz, 1H), 7.90 (m, 1H), 7.81 (m, 1H), 7.68 (m, 2H), 3.10 (t, J=8.0 Hz, 2H), 3.07 (d, J=8.0 Hz, 2H) ppm.

Embodiment 31

2-[7-(4-Cyanonaphthalen-1-yl)thieno[3,2-c]pyridin-2-yl]acetic Acid (Compound 31)

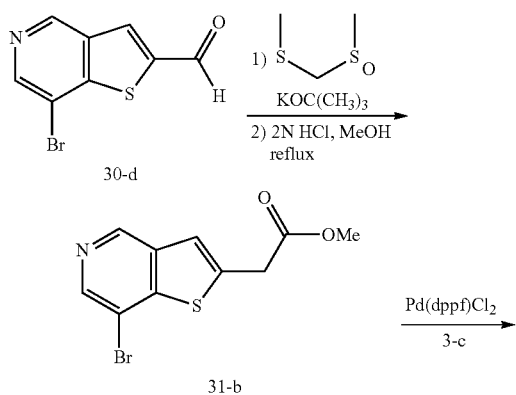

Synthesis of Compound 31-a

Under N₂ atmosphere, compound 31-b (87 mg, 0.3 mmol), compound 3-c (84 mg, 0.3 mmol) and sodium carbonate (60 mg, 0.6 mmol) were suspended in dioxane (4 mL) and water (1 mL), [1,1'-bis(diphenylphosphine)ferrocene]palladium dichloride (25 mg, 0.03 mmol) was added. The mixture was stirred at 80° C. for 3 hrs, cooled to room temperature and concentrated under reduced pressure. The residue was filtered through celite, the filtrate cake was washed with EA (30 mL). The filtrate was washed in turn with water (20 mL×3) and saturated brine (10 mL), dried over anhydrous magnesium sulfate, filtered and concentrated under reduced pressure. The residue was purified by silica column chromatography (PE:EA=1:1) to give compound 31-a (76 mg, yield 71%). LC-MS (ESI): m/z=359 [M+H]⁺.

Synthesis of Compound 31

At room temperature, LiOH (42 mg, 1 mmol) was added to a solution of compound 31-a (120 mg, 0.31 mmol) in methanol (1 mL), THF (4 mL) and water (1 mL). The mixture was stirred for 1 h, followed by adding 2M HCl aq. solution to adjust pH=5-6, solid was precipitated and filtered out. The solid was washed with water (10 mL), dried under vacuum to give white solid 31 (44 mg, yield 64%). LC-MS (ESI): m/z=345 [M+H]⁺.

$^1$H-NMR (400 MHz, DMSO-d6) δ: 9.30 (s, 1H), 8.55 (s, 1H), 8.36 (d, J=7.6 Hz, 1H), 8.29 (d, J=7.6 Hz, 1H), 7.90 (m, 2H), 7.72 (m, 3H), 4.04 (s, 2H) ppm.

Embodiment 32

2-[7-(4-Cyanophenyl)thieno[3,2-c]pyridin-2-yl]acetic Acid (Compound 32)

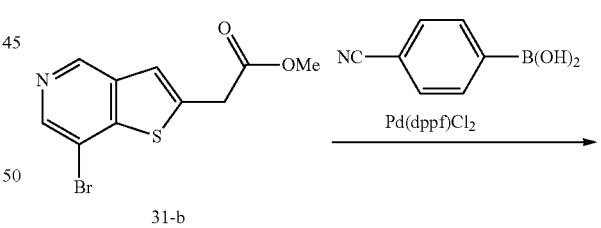

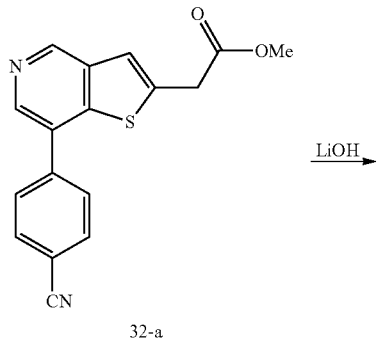

Synthesis of Compound 31-b

NaOH (40 mg, 1 mmol) was added to a solution of methyl(methylthiomethyl)sulfoxide (18 mg, 1.5 mmol) and compound 30-d (240 mg, 1 mmol) in THF (6 mL). The mixture was heated to 80° C. and stirred for 4 hrs, cooled to room temperature, concentrated under reduced pressure to remove the solvent. The residue was added to a solution of 2M HCl in methanol (10 mL), refluxed for 1 h, concentrated under reduced pressure. The residue was added to saturated NaHCO₃ aq. solution (10 mL), extracted with EA (10 mL×3). The organic phases were combined, washed in turn with water (10 mL×3) and saturated brine (10 mL), dried over anhydrous sodium sulfate, filtered and concentrated under reduced pressure. The residue was purified by silica column chromatography (PE:EA=4:1) to give compound 31-b (0.15 g, yield 88%). LC-MS (ESI): m/z=285 [M+H]⁺.

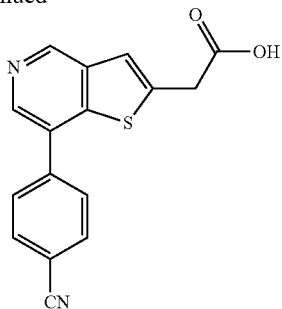

32

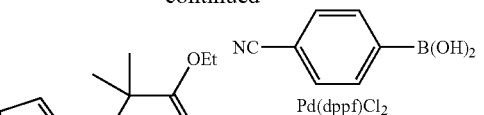

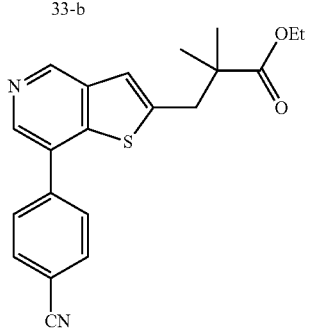

33-a

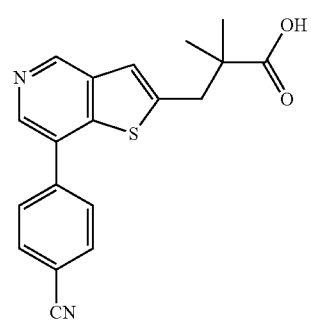

33

Synthesis of Compound 32-a

Under $N_2$ atmosphere, compound 31-b (140 mg, 0.5 mmol), 4-cyanophenyl boronic acid (75 mg, 0.5 mmol) and sodium carbonate (60 mg, 0.6 mmol) were suspended in dioxane (4 mL) and water (10 mL), [1,1'-bis(diphenylphosphine)ferrocene]palladium dichloride (25 mg, 0.03 mmol) was added. The mixture was stirred at 80° C. for 3 hrs, cooled to room temperature and concentrated under reduced pressure. The residue was filtered through celite, the filtrate cake was washed with EA (30 mL). The filtrate was in turn washed with water (20 mL×3) and saturated brine (10 mL), dried over anhydrous magnesium sulfate, filtered, concentrated under reduced pressure. The residue was purified by silica column chromatography (PE:EA=1:1) to give compound 32-b (86 mg, yield 56%). LC-MS (ESI): m/z=309 [M+H]$^+$.

Synthesis of Compound 32

At room temperature, LiOH (42 mg, 1 mmol) was added to a solution of compound 32-a (86 mg, 0.28 mmol) in methanol (1 mL), THF (4 mL) and water (1 mL). The mixture was stirred for 1 h, followed by adding 2M HCl aq. solution (2 mL), solid was precipitated and filtered out. The solid was washed with water (10 mL), dried under vacuum to give white solid 32 (28 mg, yield 34%). LC-MS (ESI): m/z=295 [M+H]$^+$.

$^1$H-NMR (400 MHz, DMSO-d6) δ: 12.87 (s, 1H), 9.11 (s, 1H), 8.64 (s, 1H), 8.06 (d, J=7.6 Hz, 1H), 7.91 (d, J=7.6 Hz, 1H), 7.57 (s, 1H), 4.06 (s, 2H) ppm.

Embodiment 33

3-[7-(4-Cyanophenyl)thieno[3,2-c]pyridin-2-yl]-2,2-dimethylpropionic Acid (Compound 33)

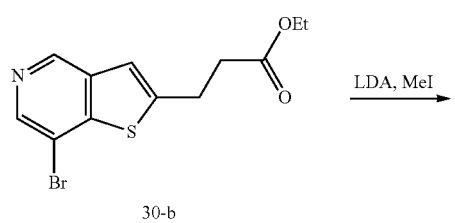

30-b

Synthesis of Compound 33-b

Under $N_2$ atmosphere, at −78° C., a solution of 2.5M n-butyl lithium in n-hexane (2.0 mL, 5 mmol) was slowly added to a solution of diisopropylamine (505 mg, 5 mmol) in anhydrous THF (10 mL). The mixture was stirred for 15 mins, added dropwise to a solution of compound 30-b (630 mg, 2 mmol) in anhydrous THF (10 mL), stirred for 2 hrs, followed by adding CH$_3$I (720 mg, 5 mmol) and the mixture was further stirred for 3 hrs. The mixture was slowly warmed to room temperature, then added to saturated NH$_4$Cl aq. solution (30 mL), extracted with EA (30 mL×3). The organic phases were combined, washed in turn with water (10 mL) and saturated brine (10 mL), dried over anhydrous sodium sulfate, filtered and concentrated under reduced pressure. The residue was purified by silica preparative plate chromatography (PE:EA=2:1-1:1) to give light yellow liquid 33-b (310 mg, yield 45%).

Synthesis of Compound 33-a

Under $N_2$ atmosphere, compound 33-b (310 mg, 0.91 mmol), 4-cyanophenyl boronic acid (140 mg, 0.91 mmol) and sodium carbonate (212 mg, 2 mmol) were suspended in dioxane (4 mL) and water (1 mL), [1,1'-bis(diphenylphosphine)ferrocene]palladium dichloride (40 mg, 0.05 mmol) was added. The mixture was stirred at 80° C. for 3 hrs, and then cooled to room temperature, concentrated under reduced pressure to remove the solvent. The residue was filtered through celite, the filtrate cake was washed with EA (30 mL). The filtrate was in turn washed with water (20 mL×3) and saturated brine (10 mL), dried over anhydrous magnesium sulfate, filtered, concentrated under reduced pressure. The residue was purified by silica column chromatography (PE:EA=1:1) to give yellow liquid 33-a (76 mg, yield 23%). LC-MS (ESI): m/z=365 [M+H]$^+$.

Synthesis of Compound 33

At room temperature, LiOH (42 mg, 1 mmol) was added to a solution of compound 33-a (73 mg, 0.19 mmol) in methanol (1 mL), THF (4 mL) and water (1 mL). The mixture was stirred for 1 h, followed by adding 2M HCl aq. solution (2 mL) and water (1 mL), solid was precipitated and filtered out. The solid was washed with water (5 mL), dried under vacuum to give white solid 33 (39 mg, yield 61%). LC-MS (ESI): m/z=337 [M+H]$^+$.

$^1$H-NMR (400 MHz, CD$_3$OD) δ: 9.34 (s, 1H), 8.64 (s, 1H), 8.02 (s, 4H), 7.71 (s, 1H), 7.57 (s, 1H), 3.34 (s, 2H), 1.26 (s, 6H) ppm.

Embodiment 34

3-[7-(4-Cyanonaphthalen-1-yl)thieno[3,2-c]pyridin-2-yl]-2,2-dimethylpropionic Acid (Compound 34)

Synthesis of Compound 34-a

Under N$_2$ atmosphere, compound 33-b (230 mg, 0.7 mmol), compound 3-c (280 mg, 0.5 mmol) and sodium carbonate (150 mg, 1.4 mmol) were suspended in dioxane (4 mL) and water (1 mL), [1,1'-bis(diphenylphosphine)ferrocene]palladium dichloride (40 mg, 0.05 mmol) was added. The mixture was stirred at 80° C. for 3 hrs, cooled to room temperature and concentrated under reduced pressure. The residue was filtered through celite, the filtrate cake was washed with EA (30 mL). The filtrate was in turn washed with water (20 mL×3) and saturated brine (10 mL), dried over anhydrous magnesium sulfate, filtered, concentrated under reduced pressure. The residue was prepared by HPLC (mobile phase: 10 mM NH$_4$HCO$_3$ aq. solution:acetonitrile=35%-45%) to give compound 34-a (53 mg, yield 18%). LC-MS (ESI): m/z=401 [M+H]$^+$.

Synthesis of Compound 34

At room temperature, LiOH (42 mg, 1 mmol) was added to a solution of compound 34-a (41 mg, 0.1 mmol) in methanol (1 mL), THF (4 mL) and water (1 mL). The mixture was stirred for 1 h, followed by adding 2M HCl aq. solution (2 mL) and water (1 mL), solid was precipitated and filtered out. The solid was washed with water (5 mL), dried under vacuum to give white solid 34 (16 mg, yield 41%). LC-MS (ESI): m/z=387 [M+H]$^+$.

$^1$H-NMR (400 MHz, DMSO-d6) δ: 12.41 (s, 1H), 9.19 (s, 1H), 8.43 (s, 1H), 8.32 (d, J=7.6 Hz, 1H), 8.27 (d, J=7.6 Hz, 1H), 7.88 (m, 2H), 7.65 (m, 2H), 7.47 (s, 1H), 3.14 (s, 2H), 1.12 (s, 6H) ppm.

Embodiment 35

3-{7-[(2,6-Dichlorophenyl)methyl]-1-benzothiophene-2-yl}propionic Acid (Compound 35)

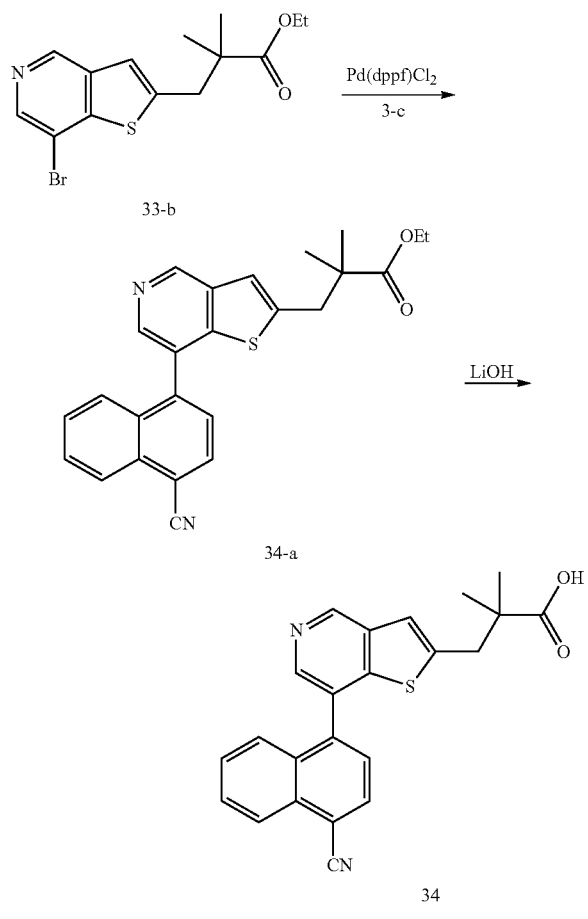

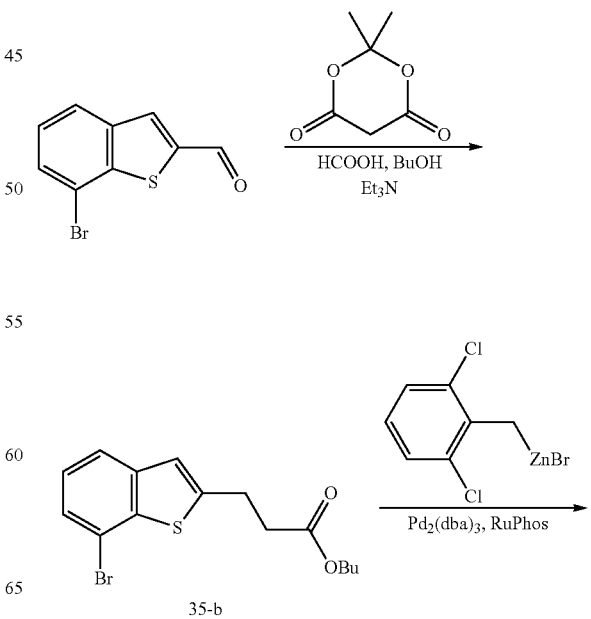

113

-continued

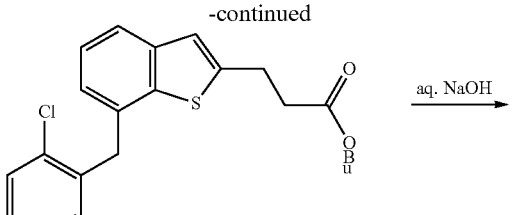

35-a

Synthesis of Compound 35-b

At 0° C., triethyl amine (3.6 mL) was slowly added to a mixture of n-butanol (10 mL) and formic acid (1 mL). The mixture was stirred for 10 mins, followed by adding 7-bromo-1-benzothiophene-2-carbaldehyde (241 mg, 1 mmol) and 2,2-dimethyl-1,3-dioxane-4,6-dione (216 mg, 1.5 mmol). The mixture was heated to reflux for 8 hrs, cooled to room temperature and concentrated under reduced pressure. The residue was purified by silica column chromatography (PE:EA=15:1) to give compound 35-b (200 mg, yield 59%). LC-MS (ESI): m/z=341 [M+H]$^+$.

Synthesis of Compound 35-a

Under N$_2$ atmosphere, tris(dibenzylidene indene acetone) dipalladium (54 mg, 0.05 mmol) and 4,5-bis(diphenylphosphine)-9,9-dimethyloxacanthracene (94 mg, 0.02 mmol) and a solution of 0.4M 2,6-dichlorobenzyl zinc bromide in THF solution (2.5 mL, 1 mmol) were added to a solution of compound 35-b (170 mg, 0.5 mmol) in anhydrous THF (10 mL). The mixture was reacted at 60° C. for 16 hrs, cooled to room temperature, concentrated under reduced pressure. The residue was purified by silica column chromatography (PE:EA=10:1) to give compound 35-a (170 mg, yield 80%). LC-MS (ESI): m/z=421 [M+H]$^+$.

Synthesis of Compound 35

At room temperature, 1.0M NaOH aq. solution (3 mL) was added to a solution of compound 35-a (84 mg, 0.2 mmol) in methanol (4 mL) and THF (8 mL). The mixture was stirred for 16 hrs, and concentrated under reduced pressure. The residue was adjusted to pH=3 with 1M HCl aq. solution, solid was precipitated and filtered out. The solid was washed with water (5 mL), dried under vacuum to give white solid 35 (60 mg, yield 82%). LC-MS (ESI): m/z=365 [M+H]$^+$.

$^1$H-NMR (400 MHz, DMSO-d6) δ: 12.35 (s, br. 1H), 7.61 (d, J=8.0 Hz, 1H), 7.58 (d, J=8.0 Hz, 2H), 7.42 (t, J=8.0 Hz, 1H), 7.25 (s, 1H), 7.21 (t, J=8.0 Hz, 1H), 6.47 (d, J=7.2 Hz, 1H), 4.35 (s, 2H), 3.16 (t, J=7.2 Hz, 2H), 2.71 (t, J=7.2 Hz, 2H) ppm.

114

Embodiment 36

3-{4-[(2,6-Dichlorophenyl)methyl]-1-benzothiophene-2-yl}propionic Acid (Compound 36)

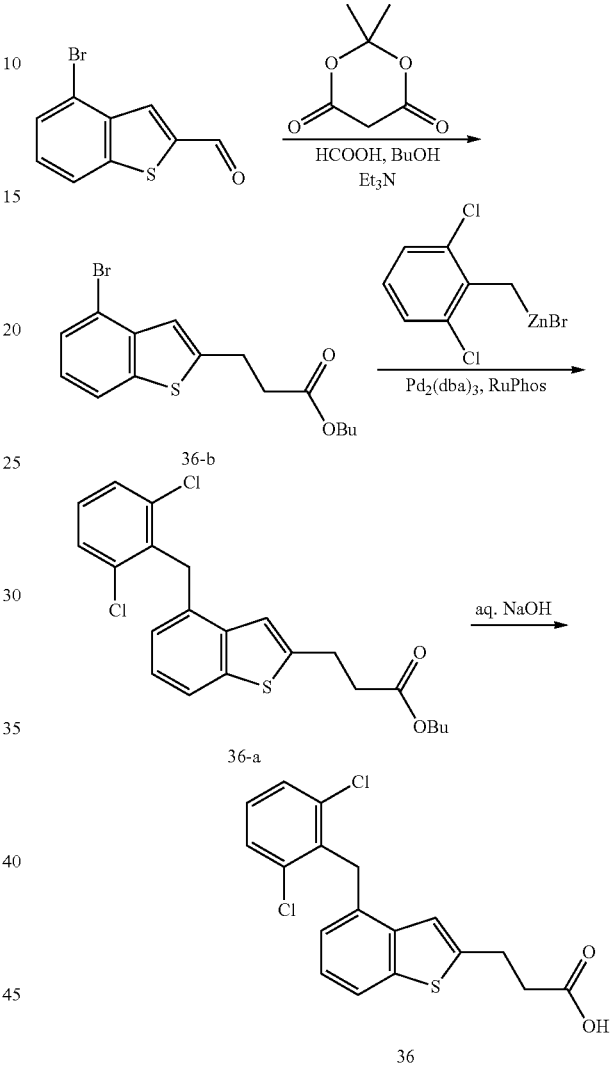

Synthesis of Compound 36-b

At 0° C., triethyl amine (3.6 mL) was slowly added to a mixture of n-butanol (10 mL) and formic acid (1 mL). The mixture was stirred for 10 mins, followed by adding 4-bromo-1-benzothiophene-2-carbaldehyde (241 mg, 1 mmol) and 2,2-dimethyl-1,3-dioxane-4,6-dione (216 mg, 1.5 mmol). The mixture was heated to reflux for 8 hrs, cooled to room temperature, concentrated under reduced pressure. The residue was purified by silica column chromatography (PE:EA=15:1) to give compound 36-b (221 mg, yield 65%). LC-MS (ESI): m/z=341 [M+H]$^+$.

Synthesis of Compound 36-a

Under N$_2$ atmosphere, tris(dibenzylidene indene acetone) dipalladium (47 mg, 0.05 mmol) and 2-dicyclohexylphospho-2',6'-diisopropoxy-1,1'-biphenyl (94 mg, 0.02 mmol) and a solution of 0.4M 2,6-dichlorobenzyl zinc bromide in THF solution (2.5 mL, 1 mmol) were added to a solution of compound 36-b (170 mg, 0.5 mmol) in anhydrous THF (10 mL). The mixture was reacted at 60° C. for 16 hrs, cooled to room temperature, concentrated under reduced pressure. The residue was purified by silica column chromatography (PE:EA=10:1) to give compound 36-a (180 mg, yield 86%). LC-MS (ESI): m/z=421 [M+H]$^+$.

Synthesis of Compound 36

At room temperature, a solution of 1.0M NaOH aq. solution (3 mL) was added to a solution of compound 36-a (84 mg, 0.2 mmol) in methanol (4 mL) and THF (8 mL). The mixture was stirred for 16 hrs, and concentrated under reduced pressure. The residue was adjusted to pH=3 with 1M HCl aq. solution, solid was precipitated and filtered out. The solid was washed with water (5 mL), dried under vacuum to give white solid 36 (70 mg, yield 95%). LC-MS (ESI): m/z=365 [M+H]$^+$.

$^1$H-NMR (400 MHz, DMSO-d6) δ: 12.30 (s, br. 1H), 7.73 (d, J=8.0 Hz, 1H), 7.57 (d, J=8.0 Hz, 2H), 7.51 (s, 1H), 7.41 (t, J=8.0 Hz, 1H), 7.13 (t, J=8.0 Hz, 1H), 6.41 (d, J=7.2 Hz, 1H), 4.54 (s, 2H), 3.18 (t, J=7.2 Hz, 2H), 2.72 (t, J=7.2 Hz, 2H) ppm.

Embodiment 37

3-[4-[(4-Cyanonaphthalen-1-yl)thieno[2,3-c]pyridine-2-yl]propionic acid (Compound 37)

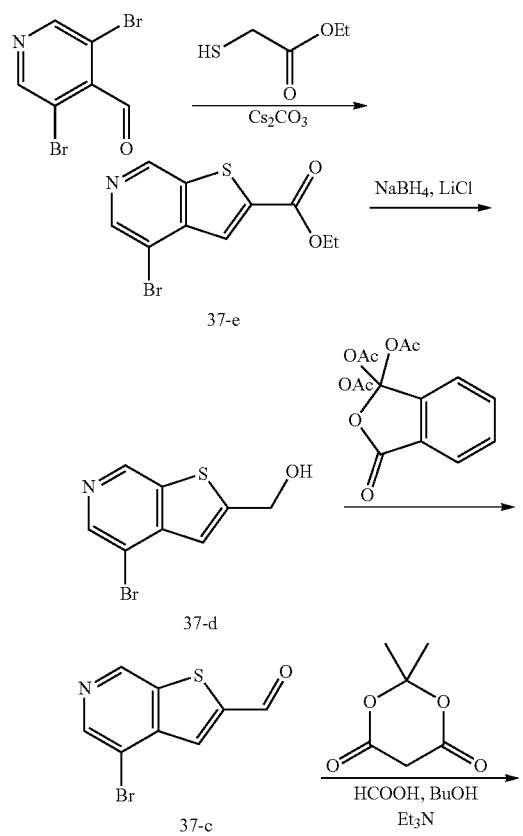

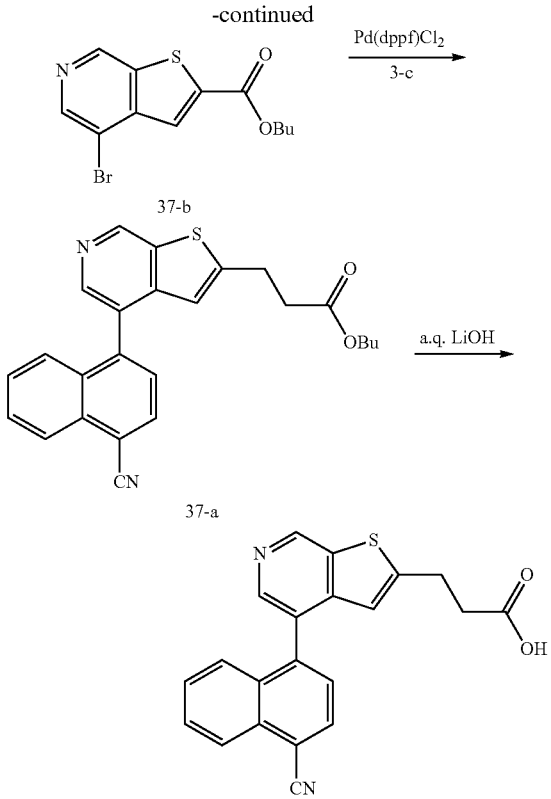

Synthesis of Compound 37-e

Ethyl mercaptoacetate (1.81 g, 15.1 mmol) and cesium carbonate (6.0 g, 18.6 mmol) were added to a solution of 3,5-dibromo-4-pyridinecarboxaldehyde (4.0 g, 15.1 mmol) in THF (100 mL). The mixture was stirred at 60° C. for 3 hrs, cooled to room temperature, concentrated under reduced pressure. The residue was purified by silica column chromatography (PE:EA=15:1) to give compound 37-e (3.7 g, yield 85%). LC-MS (ESI): m/z=286 [M+H]$^+$.

Synthesis of Compound 37-d

At 0° C., NaBH$_4$ (530 mg, 13.9 mmol) was added into a solution of compound 37-e (1.0 g, 3.48 mmol), LiCl (590 mg, 13.9 mmol) in THF (40 mL) and methanol (20 mL). The mixture was warmed to room temperature and stirred for 4 hrs, concentrated under reduced pressure. Water (40 mL) and DCM (40 mL) were added to the residue, the organic phase was separated, aqueous phase was extracted with DCM (20 mL×3). The organic phases were combined, washed in turn with water (20 mL×3) and saturated brine (10 mL), dried over anhydrous sodium sulfate, filtered and concentrated under reduced pressure to give compound 37-d (750 mg, yield 89%). The product was used directly for the next step without further purification. LC-MS (ESI): m/z=244 [M+H]$^+$.

Synthesis of Compound 37-c

At 0° C., (1,1,1-triacetoxy)-1,1-dihydro-1,2-benzoiodooxol-3(1H)-one (1.39 g, 3.27 mmol) was added to a solution of compound 37-d (750 mg, 2.18 mmol) in DCM (30 mL). The reaction solution was warmed to room temperature and further stirred for 2 hrs, followed by adding saturated sodium bicarbonate aq. solution (10 mL) and saturated sodium thiosulfate aq. solution (10 mL). The mixture was stirred for 10 mins, organic phase was separated. The organic phase was in turn washed with water (20 mL×3) and saturated brine (20 mL), dried over anhydrous magnesium sulfate, filtered, concentrated under reduced pressure. The residue was purified by silica column chromatography (PE:EA=10:1) to give compound 37-c (680 mg, yield 91%). LC-MS (ESI): m/z=342 [M+H]$^+$.

Synthesis of Compound 37-b

At 0° C., triethyl amine (3.6 mL) was slowly added to a mixture of n-butanol (10 mL) and formic acid (1 mL). The mixture was stirred for 10 mins, followed by adding compound 37-c (300 mg, 1.24 mmol) and 2,2-dimethyl-1,3-dioxane-4,6-dione (300 mg, 2.08 mmol), refluxing for 8 hrs. The mixture was cooled to room temperature, concentrated under reduced pressure. The residue was purified by silica column chromatography (PE:EA=12:1) to give compound 37-b (280 mg, yield 66%). LC-MS (ESI): m/z=342 [M+H]$^+$.

Synthesis of Compound 37-a

Under N$_2$ atmosphere, compound 37-b (120 mg, 0.35 mmol), compound 3-c (110 mg, 0.39 mmol) and sodium carbonate (150 mg, 1.4 mmol) were suspended in ethylene glycol dimethyl ether (10 mL) and water (1 mL), [1,1'-bis (diphenylphosphine)ferrocene]palladium dichloride (40 mg, 0.05 mmol) was added. The mixture was stirred at 75° C. for 16 hrs, cooled to room temperature, and concentrated under reduced pressure. The residue was purified by silica column chromatography (PE:EA=8:1) to give compound 37-a (90 mg, yield 62%). LC-MS (ESI): m/z=415 [M+H]$^+$.

Synthesis of Compound 37

At room temperature, a solution of 1.0M LiOH aq. solution (2 mL) was added to a solution of compound 37-a (100 mg, 0.25 mmol) in methanol (10 mL) and THF (10 mL). The mixture was stirred for 16 hrs, concentrated under reduced pressure. The residue was dissolved in water (10 mL), adjusted to pH=3 with 1M citric acid aq. solution, solid was precipitated and filtered out. The solid was washed with water (5 mL), dried under vacuum to give white solid 37 (50 mg, yield 55%). LC-MS (ESI): m/z=359 [M+H]$^+$.

$^1$H-NMR (400 MHz, DMSO-d6) δ: 12.30 (s, br. 1H), 9.30 (s, 1H), 8.44 (s, 1H), 8.32 (d, J=8.0 Hz, 1H), 8.26 (d, J=8.0 Hz, 1H), 7.87 (t, J=8.8 Hz, 1H), 7.73 (d, J=7.2 Hz, 1H), 7.68 (t, J=7.2 Hz, 1H), 7.57 (d, J=8.8 Hz, 1H), 6.74 (s, 1H), 3.10 (t, J=7.2 Hz, 2H), 2.59 (t, J=7.2 Hz, 2H) ppm.

Embodiment 38

3-[4-(4-Cyanonaphthalen-1-yl)-1-benzothiophen-2-yl]-2,2-dimethyl propionic Acid (Compound 38)

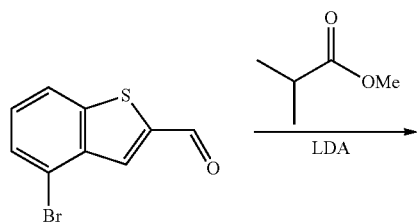

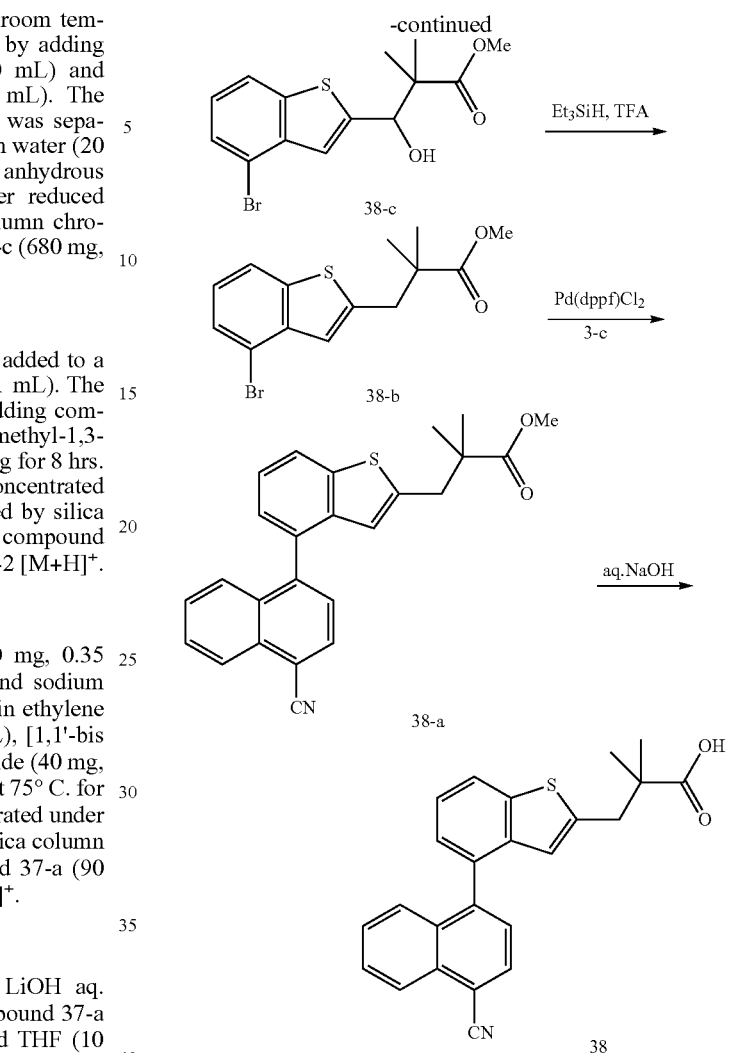

Synthesis of Compound 38-c

At −78° C., a solution of 1M lithium diisopropylamide in THF (3 mL, 3 mmol) was added slowly to a solution of methyl isobutyrate (714 mg, 7.1 mmol) in anhydrous THF (5 mL). The mixture was stirred for 1 h, followed by adding 4-bromo-1-benzothiophene-2-carbaldehyde (500 mg, 2.38 mmol). The mixture was slowly warmed to room temperature, followed by adding NH$_4$Cl aq. solution (20 mL), being extracted with EA (30 mL×3). The organic phases were combined, dried over anhydrous sodium sulfate, filtered and concentrated under reduced pressure. The residue was purified by silica column chromatography (PE:EA=10:1) to give compound 38-c (700 mg, yield 86%). LC-MS (ESI): m/z=365 [M+Na]$^+$.

Synthesis of Compound 38-b

At 0° C., trifluoroacetic acid (2 mL) was added to a solution of compound 38-c (170 mg, 0.5 mmol) and triethylsilane (392 mg, 4 mmol) in DCM (10 mL). The mixture was warmed to room temperature and further stirred for 16 hrs, and then concentrated under reduced pressure. DCM (30 mL) was added to the residue. The mixture was in turn washed with saturated sodium bicarbonate solution (10 mL)

and saturated brine (10 mL), dried over anhydrous sodium sulfate, filtered, concentrated under reduced pressure. The residue was purified by silica column chromatography (PE:EA=10:1) to give compound 38-b (150 mg, yield 92%). LC-MS (ESI): m/z=349 [M+Na]$^+$.

Synthesis of Compound 38-a

Under $N_2$ atmosphere, compound 38-b (150 mg, 0.46 mmol), compound 3-c (150 mg, 0.54 mmol) and sodium carbonate (300 mg, 2.8 mmol) were suspended in ethylene glycol dimethyl ether (12 mL) and water (1 mL), [1,1'-bis(diphenylphosphine)ferrocene]palladium dichloride (50 mg, 0.06 mmol) was added. The mixture was stirred at 75° C. for 16 hrs, cooled to room temperature, concentrated under reduced pressure. The residue was purified by column chromatography (PE:EA=4:1) to give compound 38-a (105 mg, yield 57%). LC-MS (ESI): m/z=400 [M+H]$^+$.

Synthesis of Compound 38

At room temperature, 1.0M LiOH aq. solution (2.5 mL) was added to a solution of compound 38-a (100 mg, 0.25 mmol) in methanol (10 mL) and THF (10 mL). The mixture was stirred for 16 hrs, concentrated under reduced pressure. Water (10 mL) was added to the residue. The mixture was adjusted to pH=3 with 1M citric acid aq. solution, solid was precipitated and filtered out. The solid was washed with water (5 mL), dried under vacuum to give white solid 37 (80 mg, yield 83%). LC-MS (ESI): m/z=408 [M+Na]$^+$.

$^1$H-NMR (400 MHz, DMSO-d6) δ: 12.37 (s, br. 1H), 8.29 (d, J=8.0 Hz, 1H), 8.24 (d, J=8.0 Hz, 1H), 8.06 (d, J=8.0 Hz, 1H), 7.85 (t, J=8.0 Hz, 1H), 7.67 (d, J=8.0 Hz, 1H), 7.58-7.62 (m, 2H), 7.49 (t, J=7.2 Hz, 2H), 7.36 (d, J=7.2 Hz, 1H), 2.99 (s, 2H), 1.06 (s, 6H) ppm.

Embodiment 39

3-[4-(4-Cyanonaphthalen-1-yl)-1-benzothiophen-2-yl]-2,2-difluoro-3-hydroxyl propionic Acid (Compound 39)

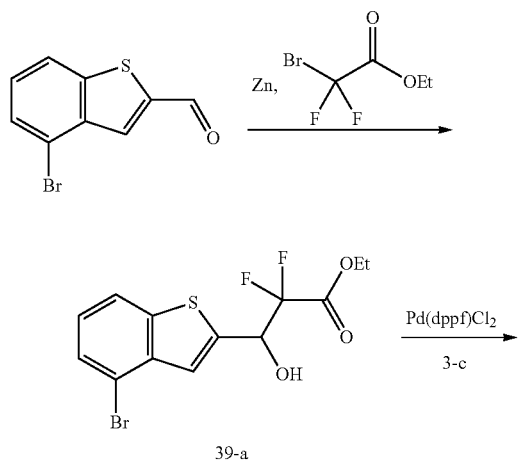

39-a

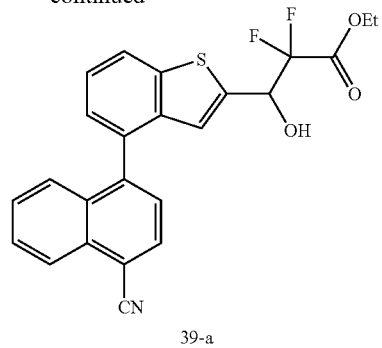

39-a

Synthesis of Compound 39-a

Under $N_2$ atmosphere, Zn powder (130 mg, 2 mmol) was added to a solution of 4-bromo-1-benzothiophene-2-carbaldehyde (500 mg, 2.38 mmol) and ethyl difluorobromoacetate (808 mg, 4 mmol) in anhydrous THF (10 mL). The mixture was heated to 45° C. and further stirred for 16 hrs, cooled to room temperature, followed by adding saturated NH$_4$Cl aq. solution (20 mL), being extracted with EA (30 mL×3). The organic phases were combined, dried over anhydrous sodium sulfate, filtered, and concentrated under reduced pressure. The residue was purified by silica column chromatography (PE:EA=10:1) to give compound 39-a (253 mg, yield 71%). LC-MS (ESI): m/z=388 [M+Na]$^+$.

Synthesis of Compound 39

Under $N_2$ atmosphere, compound 39-a (190 mg, 0.5 mmol), compound 3-c (140 mg, 0.5 mmol) and sodium carbonate (106 mg, 1 mmol) were suspended in ethylene glycol dimethyl ether (20 mL) and water (2 mL), [1,1'-bis(diphenylphosphine)ferrocene]palladium dichloride (50 mg, 0.06 mmol) was added. The mixture was stirred at 75° C. for 16 hrs, cooled to room temperature, concentrated under reduced pressure. Water (20 mL) was added to the residue, the mixture was extracted with EA (30 mL×3). The aqueous phase was adjusted to pH=3 with 1M HCl aqueous solution, solid was precipitated and filtered out. The solid was washed with water (5 mL), dried under vacuum to give white solid 39 (120 mg, yield 58%). LC-MS (ESI): m/z=432 [M+Na]$^+$.

$^1$H-NMR (400 MHz, DMSO-d6) δ: 8.30 (d, J=7.2 Hz, 1H), 8.25 (d, J=8.0 Hz, 1H), 8.14 (d, J=8.0 Hz, 1H), 7.85 (t, J=7.0 Hz, 1H), 7.65-7.68 (m, 1H), 7.60-7.63 (m, 1H), 7.55 (t, J=8.0 Hz, 2H), 7.39-7.42 (m, 1H), 6.82 (d, J=16.8 Hz, 1H), 5.23-5.30 (m, 1H) ppm.

Embodiment 40

3-{4-[(2,6-Dichlorophenyl)methyl]-1-benzothiophen-2-yl]-2,2-dimethyl propionic Acid (Compound 40)

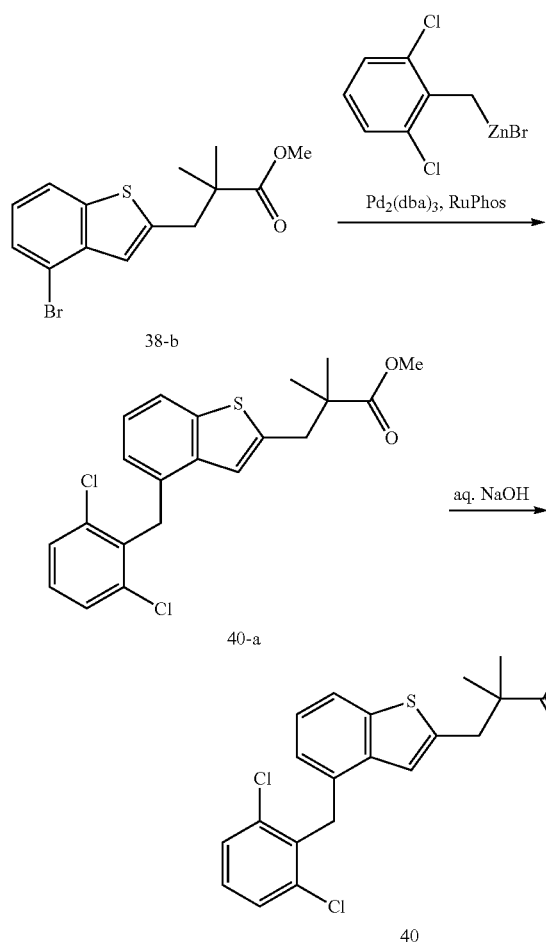

Synthesis of Compound 40-a

Under N₂ atmosphere, tris(dibenzylidene indene acetone) dipalladium (47 mg, 0.05 mmol) and 2-dicyclohexylphospho-2',6'-diisopropoxy-1,1'-biphenyl (94 mg, 0.02 mmol) and a solution of 0.4M 2,6-dichlorobenzyl zinc bromide in THF solution (2.5 mL, 1 mmol) were added to a solution of compound 38-b (130 mg, 0.4 mmol) in anhydrous THF (10 mL). The mixture was reacted at 60° C. for 16 hrs, cooled to room temperature, concentrated under reduced pressure. The residue was purified by silica column chromatography (PE:EA=8:1) to give compound 40-a (150 mg, yield 72%). LC-MS (ESI): m/z=407 [M+H]⁺.

Synthesis of Compound 40

At room temperature, 1.0M NaOH aq. solution (1 mL) was added to a solution of compound 40-a (84 mg, 0.2 mmol) in methanol (5 mL) and THF (5 mL). The mixture was stirred for 16 hrs, concentrated under reduced pressure. Water (10 mL) was added to the residue, 1M HCl aq. solution was added to adjust pH=3, solid was precipitated and filtered out. The solid was washed with water (5 mL), dried under vacuum to give white solid 40 (40 mg, yield 50%). LC-MS (ESI): m/z=393 [M+H]⁺.

¹H-NMR (400 MHz, DMSO-d6) δ: 12.49 (s, br. 1H), 7.73 (d, J=8.0 Hz, 1H), 7.56 (d, J=8.0 Hz, 1H), 7.45 (s, 1H), 7.41 (t, J=8.0 Hz, 2H), 6.45 (d, J=10.4 Hz, 1H), 4.54 (s, 2H), 3.16 (s, 3H), 1.20 (s, 6H) ppm.

Embodiment 41

3-[4-(4-Cyanonaphthalen-1-yl)thieno[2,3-c]pyridin-2-yl]-3-hydroxyl butyric Acid (Compound 41)

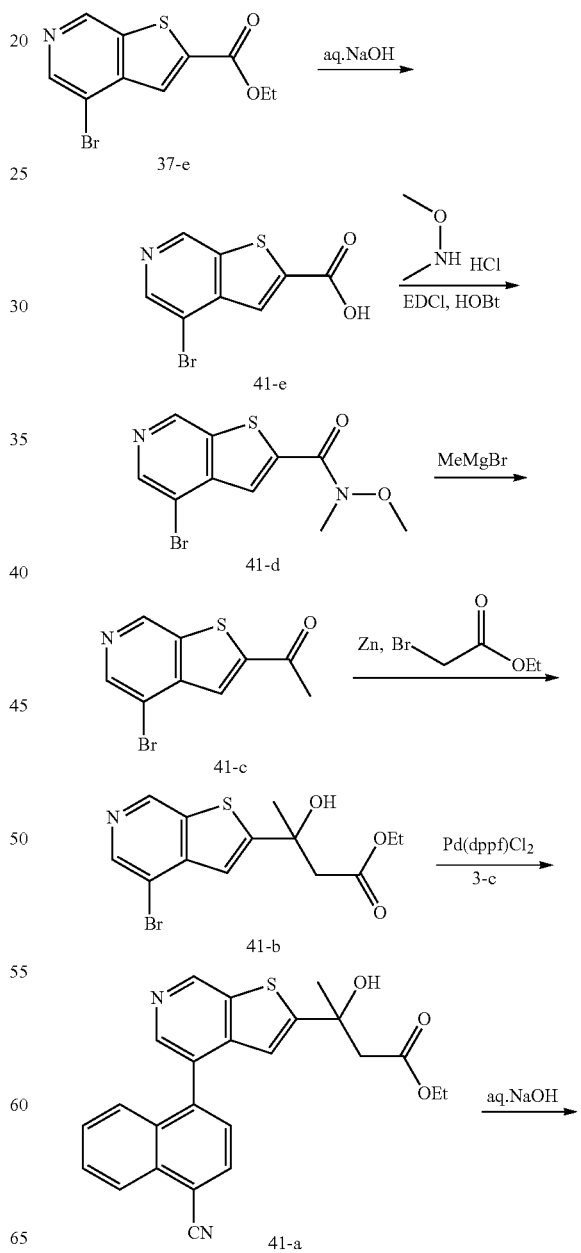

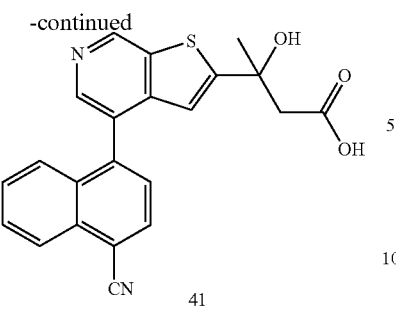

41

Synthesis of Compound 41-e

At room temperature, 7.0M NaOH aq. solution (2 mL) was added to a solution of compound 37-e (1.0 g, 3.5 mmol) in methanol (4 mL) and THF (10 mL). The mixture was stirred for 2 hrs, concentrated under reduced pressure. Water (30 mL) was added to the residue, 1M citric acid aq. solution was added to adjust pH=3, solid was precipitated and filtered out. The solid was washed with water (5 mL), dried under vacuum to give compound 41-e (740 mg, yield 82%).

Synthesis of Compound 41-d

At room temperature, N,O-dimethylhydroxylamine hydrochloride (546 mg, 5.6 mmol), 1-(3-dimethylaminopropyl)-3-ethylcarbodiimide hydrochloride (1.08 g, 5.6 mmol), 1-hydroxybenzotriazole (378 mg, 2.8 mmol) and triethyl amine (1.13 g, 11.2 mmol) were added to a solution of compound 41-e (720 mg, 2.8 mmol) in DMF (10 mL) and DCM (30 mL). The mixture was stirred for 24 hrs, concentrated under reduced pressure. The residue was purified by silica column chromatography (PE:EA=3:1) to give compound 41-d (740 mg, yield 82%). LC-MS (ESI): m/z=301 [M+H]$^+$.

Synthesis of Compound 41-c

At −78° C., 3M methyl magnesium bromide in ether (1 mL, 3 mmol) was added to a solution of compound 41-d (604 mg, 2 mmol) in anhydrous THF (20 mL). The mixture was slowly warmed to room temperature and further stirred for 20 mins, followed by adding saturated NH$_4$Cl aq. solution (5 mL), water (20 mL) and EA (30 mL) in turn. The organic phase was separated, the aqueous phase was extracted with EA (20 mL×2). The organic phases were combined, concentrated under reduced pressure. The residue was purified by silica column chromatography (PE:EA=8:1) to give compound 41-c (740 mg, yield 82%). LC-MS (ESI): m/z=256 [M+H]$^+$.

Synthesis of Compound 41-b

Under N$_2$ atmosphere, Zn powder (65 mg, 1 mmol) was added to a solution of compound 41-c (257 mg, 1 mmol) and ethyl bromoacetate (217 mg, 1.3 mmol) in anhydrous THF (10 mL). The mixture was heated to 50° C. and further stirred for 16 hrs, cooled to room temperature, followed by adding saturated NH$_4$Cl aq. solution (5 mL) and water (20 mL) in turn. The mixture was extracted with EA (30 mL×3). The organic phases were combined, dried over anhydrous sodium sulfate, filtered, and concentrated under reduced pressure. The residue was purified by silica column chromatography (PE:EA=4:1) to give compound 41-b (281 mg, yield 82%). LC-MS (ESI): m/z=344 [M+H]$^+$.

Synthesis of Compound 41-a

Under N$_2$ atmosphere, compound 41-b (137 mg, 1 mmol), compound 3-c (140 mg, 0.5 mmol) and sodium carbonate (106 mg, 1 mmol) were suspended in ethylene glycol dimethyl ether (15 mL) and water (1 mL), [1,1'-bis(diphenylphosphine)ferrocene]palladium dichloride (50 mg, 0.06 mmol) was added. The mixture was stirred at 75° C. for 16 hrs, cooled to room temperature, concentrated under reduced pressure. The residue was purified by silica column chromatography (PE:EA=3:1) to give compound 41-a (160 mg, yield 96%). LC-MS (ESI): m/z=417 [M+H]$^+$.

Synthesis of Compound 41

At room temperature, 1.0M LiOH aq. solution (5 mL) was added to a solution of compound 41-a (42 mg, 0.1 mmol) in methanol (5 mL) and THF (5 mL). The mixture was stirred for 16 hrs, concentrated under reduced pressure. Water (10 mL) was added to the residue, 1M citric acid aq. solution was added to adjust pH=3, solid was precipitated and filtered out. The solid was washed with water (5 mL), dried under vacuum to give white solid 41 (30 mg, yield 77%). LC-MS (ESI): m/z=389 [M+H]$^+$.

$^1$H-NMR (400 MHz, DMSO-d6) δ: 12.08 (s, br. 1H), 9.31 (s, 1H), 8.44 (s, 1H), 8.32 (d, J=7.2 Hz, 1H), 8.27 (d, J=8.0 Hz, 1H), 7.87 (t, J=8.0 Hz, 1H), 7.73 (t, J=7.2 Hz, 1H), 7.62-7.67 (m, 1H), 7.59 (d, J=8.0 Hz, 1H), 6.79 (d, J=10.0 Hz, 1H), 2.65-2.76 (m, 2H), 1.56 (d, J=6.0 Hz, 3H) ppm.

Embodiment 42

3-[4-(4-Cyanonaphthalen-1-yl)thieno[2,3-c]pyridin-2-yl] butyric Acid (Compound 42)

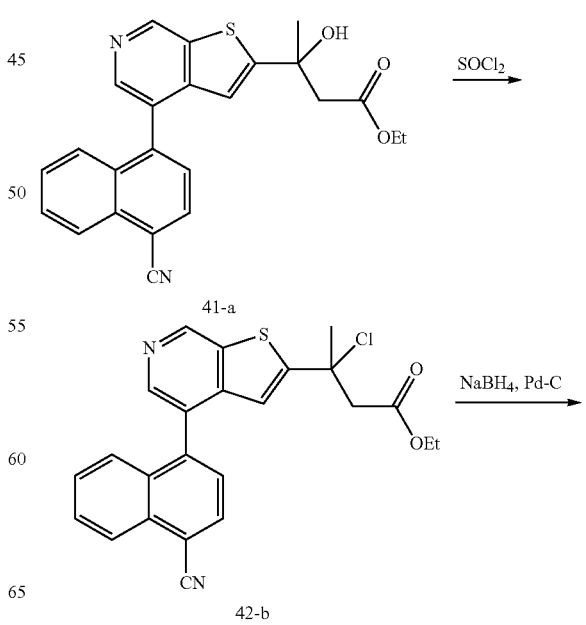

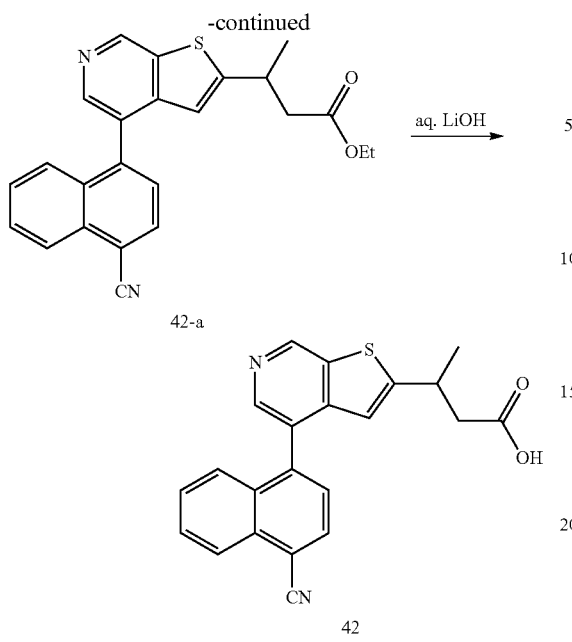

42-a

42

Synthesis of Compound 42-b

At 20° C., thionyl chloride (2 mL) was added to a solution of compound 41-a (160 mg, 0.4 mmol) in DCM (10 mL). The mixture was stirred for 16 hrs, concentrated under reduced pressure to give compound 42-b. The product was used directly for the next step without further purification.

Synthesis of Compound 42-a

At 0° C., NaBH$_4$ (114 mg, 3 mmol) was added to a solution of compound 42-b, 10% Pd-C (30 mg) and ethanol (10 mL) in portions. The mixture was warmed to room temperature and stirred for 16 hrs, filtered through celite. Water (10 mL) was added to the filtrate, the mixture was extracted with DCM (10 mL×3). The organic phases were combined, dried over anhydrous sodium sulfate, filtered, and concentrated under reduced pressure. The residue was purified by silica column chromatography (PE:EA=10:1) to give compound 42-a (62 mg, yield 42%). LC-MS (ESI): m/z=401 [M+H]$^+$.

Synthesis of Compound 42

At room temperature, 1M LiOH aq. solution (5 mL) was added to a solution of compound 42-a (40 mg, 0.1 mmol) in methanol (5 mL) and THF (5 mL). The mixture was stirred for 16 hrs, and concentrated under reduced pressure. Water (10 mL) was added to the residue, 1M citric acid aq. solution was added to adjust pH=3, solid was precipitated and filtered out. The solid was washed with water (5 mL), dried under vacuum to give white solid 42 (20 mg, yield 53%). LC-MS (ESI): m/z=373 [M+H]$^+$.

$^1$H-NMR (400 MHz, CDCl$_3$) δ: 9.12 (s, 1H), 8.43 (s, 1H), 8.36 (d, J=8.8 Hz, 1H), 8.01 (t, J=8.0 Hz, 1H), 7.69-7.74 (m, 1H), 7.61 (d, J=8.8 Hz, 1H), 7.47-7.55 (m, 2H), 6.67 (d, J=4.4 Hz, 1H), 3.59-3.64 (m, 1H), 2.58-2.74 (m, 2H), 1.24 (d, J=9.0 Hz, 3H) ppm.

Embodiment 43

Compound 43A

Compound 43B

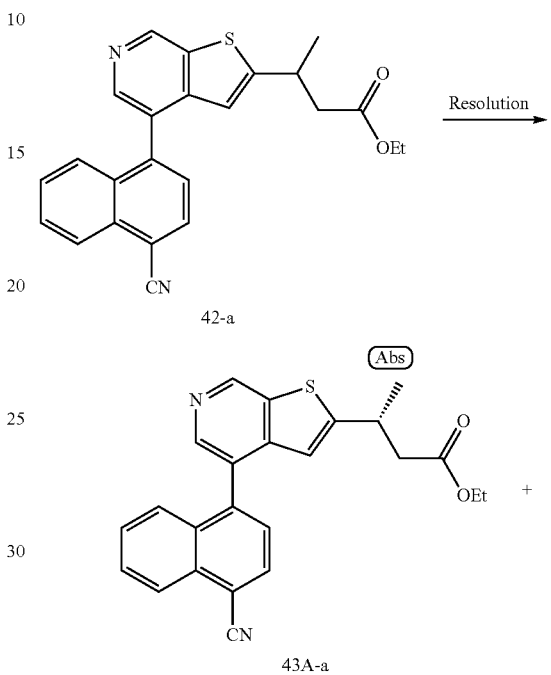

42-a

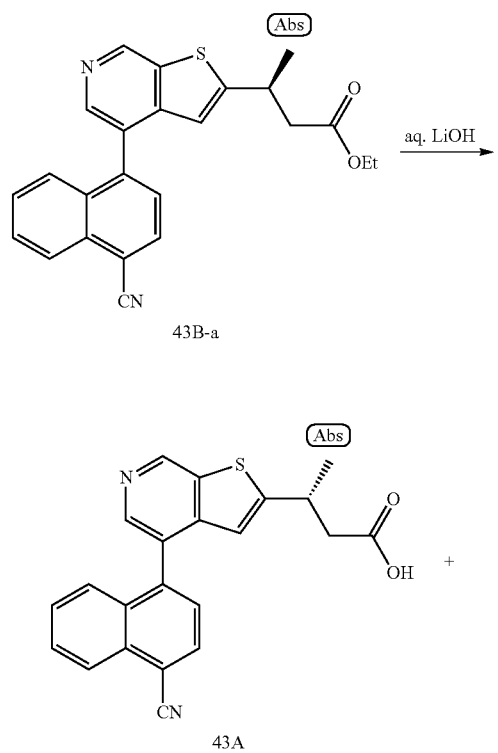

43A-a 43B-a

43A

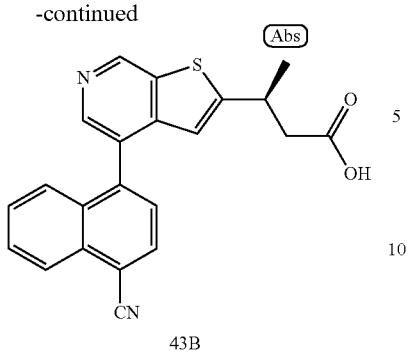

43B

Synthesis of Compound 43A

Compound 42-a (170 mg) underwent enantiomeric chromatographic column (process II, mobile phase: n-Hexane (0.1% DEA):EtOH (0.1% DEA)=80:20), compound 43A-a (59 mg) ($T_r$=18.0 min) was eluted firstly and compound 43B-a (46 mg) ($T_r$=20.0 min) was eluted later, the absolute configuration of 43A-a and 43B-a remains unknown. At room temperature, 1M LiOH aq. solution (2.5 mL) was added to a solution of 43A-a (59 mg, 0.14 mmol) in methanol (5 mL). The mixture was stirred for 4 hrs, concentrated under reduced pressure to remove the solvent. Water (10 mL) was added to the residue, 1M citric acid aq. solution was added to adjust pH=6, solid was precipitated and filtered out. The solid was washed with water (5 mL), dried under vacuum to give white solid 43A (38 mg, yield 69%). LC-MS (ESI): m/z=373 [M+H]$^+$.

$^1$H-NMR (400 MHz, DMSO-d6) δ: 12.20 (s, 1H), 9.31 (s, 1H), 8.43 (s, 1H), 8.45 (s, 1H), 8.30 (dd, J=20.3 Hz, 7.9 Hz, 1H), 7.87 (t, J=7.4 Hz, 1H), 7.81-7.52 (m, 3H), 6.67 (d, J=5.7 Hz, 1H), 3.50 (dd, J=13.4 Hz, 6.4 Hz, 1H), 2.57 (dd, J=9.7 Hz, 6.30 Hz, 1H), 1.28 (d, J=9.0 Hz, 3H) ppm.

Synthesis of Compound 43B

At room temperature, 1M LiOH aq. solution (2.5 mL) was added to a solution of 43B-a (46 mg, 0.11 mmol) in methanol (5 mL). The mixture was stirred for 4 hrs, concentrated under reduced pressure to remove the solvent. Water (10 mL) was added to the residue, 1M citric acid aq. solution was added to adjust pH=6, solid was precipitated and filtered out. The solid was washed with water (5 mL), dried under vacuum to give white solid 43B (25 mg, yield 58%). LC-MS (ESI): m/z=373 [M+H]$^+$.

$^1$H-NMR (400 MHz, CD$_3$OD) δ: 9.19 (s, 1H), 8.47-8.28 (m, 2H), 8.18 (d, J=7.4 Hz, 1H), 7.93-7.78 (m, 1H), 7.70 (d, J=7.4 Hz, 1H), 7.63 (t, J=3.7 Hz, 1H), 6.75 (d, J=8.6 Hz, 1H), 3.61 (dd, J=13.6 Hz, 6.9 Hz, 1H), 2.73-2.56 (m, 2H), 1.40 (d, J=9.0 Hz, 3H) ppm.

Embodiment 44

Compound 44A

Compound 44B

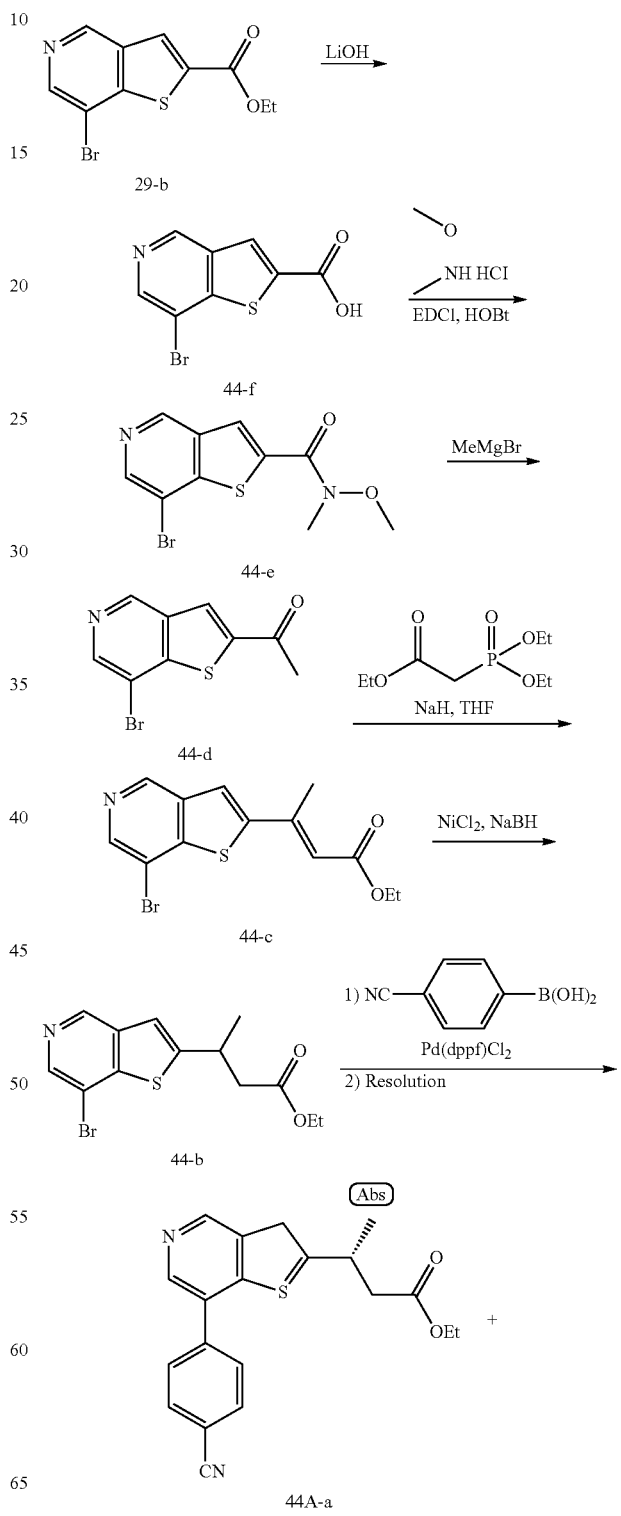

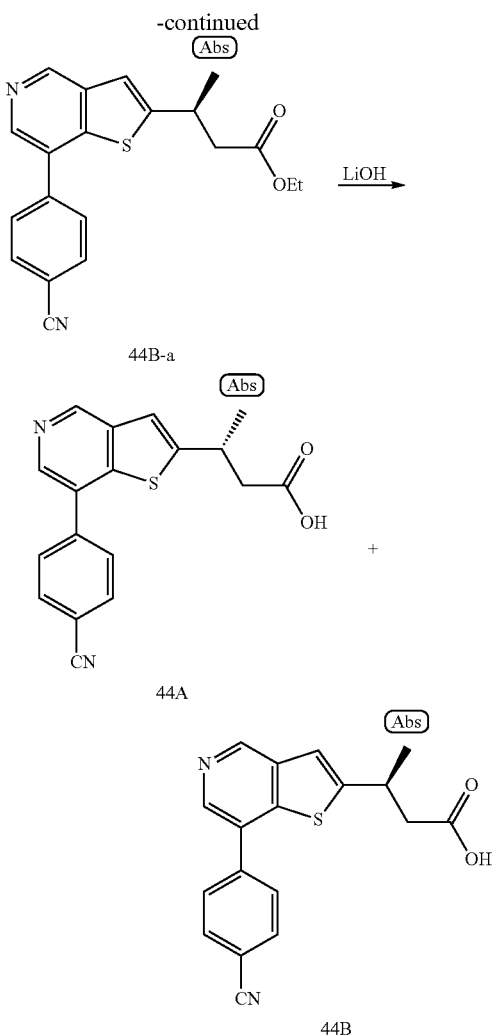

Synthesis of Compound 44-f

At room temperature, LiOH (1.68 g, 40 mmol) was added to a solution of compound 29-b (5.7 g, 20 mmol) in methanol (10 mL), THF (40 mL) and water (10 mL). The mixture was stirred for 1 h, followed by adding 2M HCl (20 mL) and water (20 mL), solid was precipitated and filtered out. The solid was washed with water (50 mL), dried under vacuum to give compound 44-f (4.5 g, yield 100%). LC-MS (ESI): m/z=258 [M+H]$^+$.

Synthesis of Compound 44-e

At room temperature, N,O-dimethylhydroxylamine hydrochloride (1.6 g, 3 mmol), 1-(3-dimethylaminopropyl)-3-ethylcarbodiimide hydrochloride (5.6 g, 3 mmol), 1-hydroxybenzotriazole (4.04 g, 3 mmol) and diisopropylethylamine (3.9 g, 3 mmol) were added to a solution of compound 44-f (4.9 g, 3 mmol) in DCM (100 mL). The mixture was stirred for 8 hrs, followed by adding 2M HCl (50 mL) and water (20 mL), being extracted with DCM (80 mL×3). The organic phases were combined, dried over anhydrous magnesium sulfate, filtered and concentrated under reduced pressure. The residue was purified by silica column chromatography (PE:EA=1:1) to give compound 44-e (6 g, yield 100%). LC-MS (ESI): m/z=301 [M+H]$^+$.

Synthesis of Compound 44-d

At −78° C., a solution of 1.5M methyl magnesium bromide in ether (20 mL, 30 mmol) was added dropwise to a solution of compound 44-e (6.0 g, 20 mmol) in anhydrous THF (100 mL). The mixture was slowly warmed to room temperature and further stirred for 20 mins, saturated NH$_4$Cl aq. solution (30 mL) was added, the mixture was extracted with EA (30 mL×3). The organic phases were combined, concentrated under reduced pressure. The residue was purified by silica column chromatography (PE:EA=2:1-1:1) to give compound 44-d (4.8 g, yield 94%). LC-MS (ESI): m/z=256 [M+H]$^+$.

Synthesis of Compound 44-c

At 0° C., triethyl phosphonoacetate (5.6 mL, 20 mmol) and sodium hydride (1.6 g, 20 mmol) were added to a solution of compound 44-d (4.8 g, 18.9 mmol) in THF (100 mL) respectively. The mixture was stirred for 1 h, warmed to room temperature, followed by adding NH$_4$Cl aq. solution (100 mL), being extracted with EA (100 mL×3). The organic phases were combined, washed in turn with water (100 mL×3) and saturated brine (100 mL), dried over anhydrous sodium sulfate, filtered and concentrated under reduced pressure. The residue was purified by silica column chromatography (PE:EA=5:1) to give light yellow solid 44-c (5.2 g, yield 89%). LC-MS (ESI): m/z=326 [M+H]$^+$.

Synthesis of Compound 44-b

At 0° C., NaBH$_4$ (0.38 g, 10 mmol) was added into a solution of compound 44-c (5.2 g, 16 mmol) and NiCl$_2$ (1.3 g, 10 mmol) in methanol (50 mL). The mixture was stirred for 3 hrs, warmed to room temperature, followed by adding saturated NH$_4$Cl aqueous solution (100 mL), being extracted with EA (10 mL×3). The organic phases were combined, washed in turn with water (50 mL×3) and saturated brine (50 mL), dried over anhydride sodium sulfate, filtered, and evaporated under reduced pressure. The residue was purified with silica column chromatography (PE:EA=4:1) to give light yellow solid 44-b (2.24 g, yield 43%). LC-MS (ESI): m/z=328 [M+H]$^+$.

Synthesis of Compound 44A-a and 44B-a

Under N$_2$ atmosphere, compound 44-b (327 mg, 1 mmol), 4-cyanophenyl boronic acid (150 mg, 1 mmol) and sodium carbonate (212 mg, 2 mmol) were suspended in dioxane (8 mL) and water (2 mL), [1,1'-bis(diphenylphosphine)ferrocene]palladium dichloride (60 mg, 0.1 mmol) was added. The mixture was stirred at 80° C. for 3 hrs, and then cooled to room temperature, filtered through celite, the filtrate cake was washed with EA (50 mL). The filtrate was in turn washed with water (20 mL×3) and saturated brine (10 mL), dried over anhydrous magnesium sulfate, filtered, concentrated under reduced pressure. The residue was purified by silica column chromatography (PE:EA=1:1) to give racemic compound, followed by separating by enantiomeric chromatographic column (process I, mobile phase: Hexane: EtOH:DEA=70:30:0.1), compound 44A-a (80 mg, yield 22.8%; LC-MS (ESI): m/z=351[M+H]$^+$) (T$_r$=6.0 min) was diluted firstly and compound 44B-a (90 mg, yield 25.6%;

LC-MS (ESI): m/z=351 [M+H]$^+$) (T$_r$=7.0 min) was diluted later. Absolute configuration of 44A-a and 44B-a remains unknown.

Synthesis of Compound 44A

At room temperature, LiOH (42 mg, 1 mmol) was added to a solution of compound 44A-a (70 mg, 0.2 mmol) in methanol (1 mL), THF (2 mL) and water (1 mL). The mixture was stirred for 1 h, followed by adding 1M HCl aq. solution (1 mL) and water (2 mL), solid was precipitated and filtered out. The solid was washed with water (5 mL), dried under vacuum to give compound 44A (53 mg, yield 82%). LC-MS (ESI): m/z=323 [M+H]$^+$.

$^1$H-NMR (400 MHz, DMSO-d6) δ: 12.30 (s, 1H), 9.07 (s, 1H), 8.52 (s, 1H), 8.06 (d, J=8.0 Hz, 2H), 7.97 (d, J=8.0 Hz, 2H), 7.51 (s, 1H), 3.58 (m, 1H), 2.66 (t, J=8.0 Hz, 2H), 1.37 (d, J=8.0 Hz, 3H) ppm.

Synthesis of Compound 44B

At room temperature, LiOH (42 mg, 1 mmol) was added to a solution of compound 44B-a (70 mg, 0.2 mmol) in methanol (1 mL), THF (2 mL) and water (1 mL). The mixture was stirred for 1 h, followed by adding 1M HCl aq. solution (1 mL) and water (2 mL), solid was precipitated and filtered out. The solid was washed with water (5 mL), dried under vacuum to give compound 44B (39 mg, yield 60.6%). LC-MS (ESI): m/z=323 [M+H]$^+$.

$^1$H-NMR (400 MHz, DMSO-d6) δ: 12.30 (s, 1H), 9.07 (s, 1H), 8.52 (s, 1H), 8.06 (d, J=8.0 Hz, 2H), 7.97 (d, J=8.0 Hz, 2H), 7.51 (s, 1H), 3.58 (m, 1H), 2.66 (t, J=8.0 Hz, 2H), 1.37 (d, J=8.0 Hz, 3H) ppm.

Embodiment 45

Compound 45A

Compound 45B

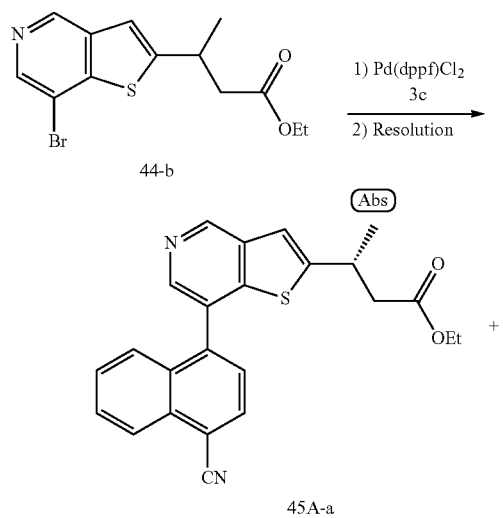

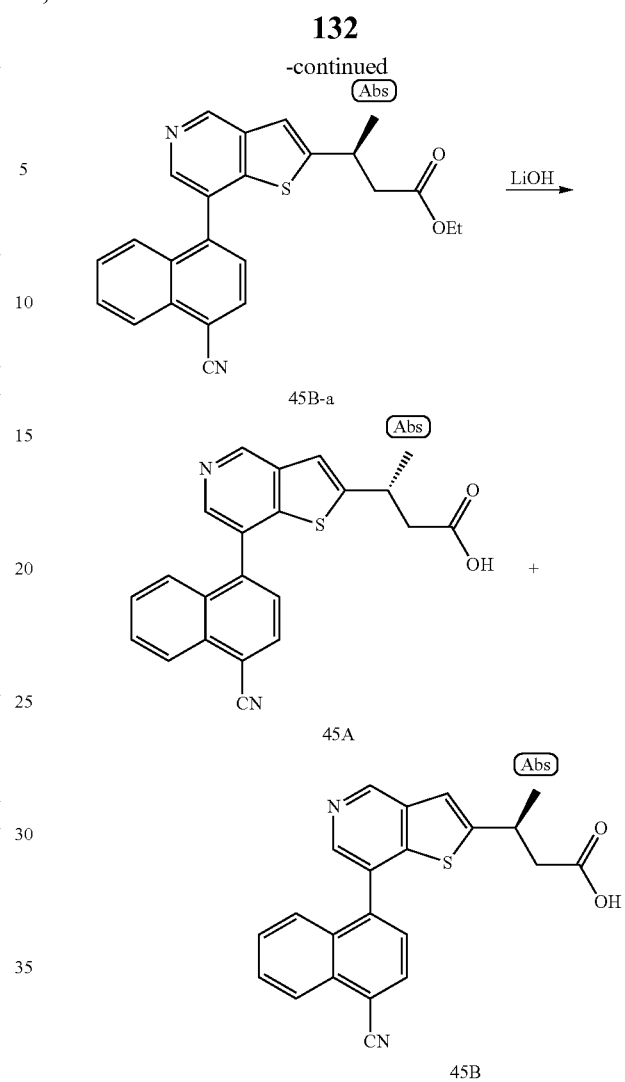

Synthesis of Compound 45A-a and 45B-a

Under N$_2$ atmosphere, compound 44-b (800 mg, 2.5 mmol), compound 3-c (750 mg, 2.5 mmol) and sodium carbonate (510 mg, 5 mmol) were suspended in dioxane (8 mL) and water (2 mL), [1,1'-bis(diphenylphosphine)ferrocene]palladium dichloride (140 mg, 0.25 mmol) was added. The mixture was stirred for 3 hrs at 80° C., cooled to room temperature, filtered through celite, the filtrate cake was washed with EA (50 mL). The filtrate was washed in turn with water (20 mL×3) and saturated brine (10 mL), dried over anhydrous magnesium sulfate, filtered, and concentrated under reduced pressure. The residue was purified by silica column chromatography (PE:EA=1:1) to give racemic compound, followed by separating by enantiomeric chromatographic column (process II, mobile phase: CO$_2$:Methanol (0.1% NH$_4$OH)=65:35), compound 45A-a was diluted firstly (260 mg, yield 26%; LC-MS (ESI): m/z=401 [M+H]$^+$) (T$_r$=8.5 min), and compound 45B-a (230 mg, yield 23%; LC-MS (ESI): m/z=401 [M+H]$^+$) (T$_r$=10.5 min) was diluted later. Absolute configuration of 45A-a and 45B-a remains unknown.

Synthesis of Compound 45A

At room temperature, LiOH (42 mg, 1 mmol) was added to a solution of compound 45A-a (80 mg, 0.2 mmol) in methanol (1 mL), THF (2 mL) and water (1 mL). The mixture was stirred for 1 h, followed by adding 1M HCl aq. solution (1 mL) and water (2 mL), solid was precipitated and filtered out. The solid was washed with water (5 mL), dried under vacuum to give compound 45A (61 mg, yield 82%). [a]$^{25}_D$=+26.248 (c=1.1018 MeOH), LC-MS (ESI): m/z=373 [M+H]$^+$.

$^1$H-NMR (400 MHz, DMSO-d6) δ: 12.27 (s, 1H), 9.17 (s, 1H), 8.43 (s, 1H), 8.33 (d, J=7.2 Hz, 1H), 8.27 (d, J=8.4 Hz, 1H), 7.90 (dd, J=7.2 Hz, 5.6 Hz, 1H), 7.83 (d, J=7.2 Hz, 1H), 7.68 (dd, J=6.8 Hz, 6.0 Hz, 1H), 7.64 (d, J=8.4 Hz, 1H), 7.52 (s, 1H), 3.50 (m, 1H), 2.60 (m, 2H), 1.31 (dd, J=7.6 Hz, 6.8 Hz, 3H) ppm.

Synthesis of Compound 45B

At room temperature, LiOH (42 mg, 1 mmol) was added to a solution of compound 45B-a (80 mg, 0.2 mmol) in methanol (1 mL), THF (2 mL) and water (1 mL). The mixture was stirred for 1 h, followed by adding 1M HCl aq. solution (1 mL) and water (2 mL), solid was precipitated and filtered out. The solid was washed with water (5 mL), dried under vacuum to give compound 45B (56 mg, yield 75%). [a]$^{25}_D$=−25.594 (c=1.002 MeOH), LC-MS (ESI): m/z=373 [M+H]$^+$.

$^1$H-NMR (400 MHz, DMSO-d6) δ: 12.27 (s, 1H), 9.17 (s, 1H), 8.43 (s, 1H), 8.33 (d, J=7.2 Hz, 1H), 8.27 (d, J=8.4 Hz, 1H), 7.90 (dd, J=7.2 Hz, 5.6 Hz, 1H), 7.83 (d, J=7.2 Hz, 1H), 7.68 (dd, J=6.8 Hz, 6.0 Hz, 1H), 7.64 (d, J=8.4 Hz, 1H), 7.52 (s, 1H), 3.50 (m, 1H), 2.60 (m, 2H), 1.31 (dd, J=7.6 Hz, 6.8 Hz, 3H) ppm.

Embodiment 46

Compound 46A

Compound 46B

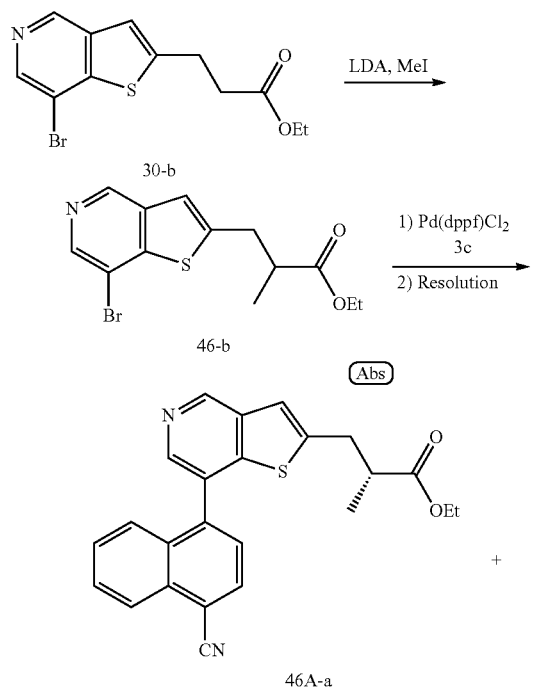

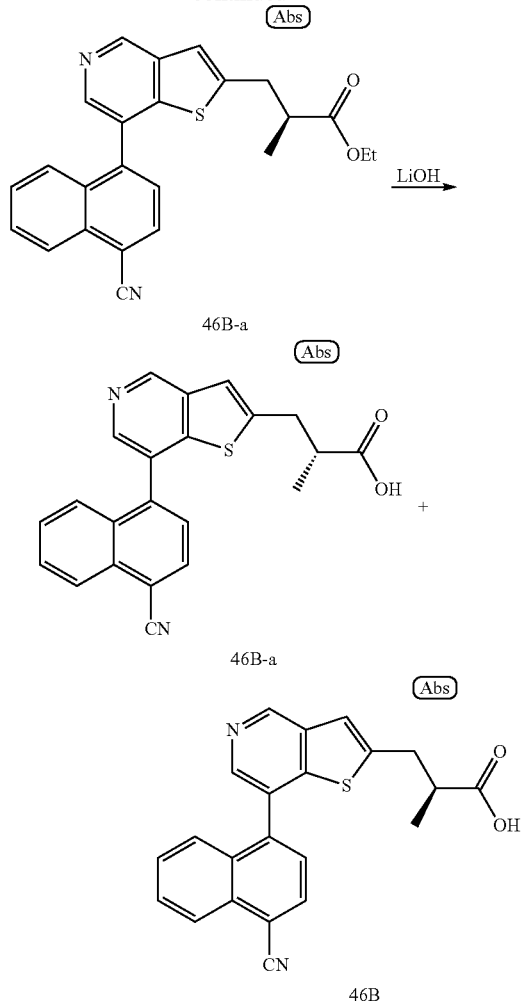

Synthesis of Compound 46-b

Under N2 atmosphere, at −78° C., 2.5M n-butyl lithium in n-hexane (2.0 mL, 5 mmol) was slowly added to a solution of diisopropylamine (505 mg, 5 mmol) in anhydrous THF (10 mL) dropwise. The mixture was stirred for 15 mins, followed by adding a solution of compound 30-b (630 mg, 2 mmol) in anhydrous THF (10 mL) dropwise, the mixture was stirred for 2 hrs, followed by adding CH$_3$I (720 mg, 5 mmol) and the mixture was further stirred for 3 hrs. The mixture was slowly warmed to room temperature, followed by adding saturated NH$_4$Cl aq. solution (30 mL), being extracted with EA (30 mL×3). The organic phases were combined, washed in turn with water (10 mL) and saturated brine (10 mL), dried over anhydrous sodium sulfate, filtered, and concentrated under reduced pressure. The residue was purified by silica preparative plate chromatography (PE:EA=2:1-1:1) to give compound 46-b (170 mg, yield 26%). LC-MS (ESI): m/z=328 [M+H]$^+$.

Synthesis of Compound 46A-a and 46B-a

Under N$_2$ atmosphere, compound 46-b (170 mg, 0.52 mmol), compound 3-c (145 mg, 0.52 mmol) and sodium carbonate (120 mg, 1.13 mmol) were suspended in dioxane (4 mL) and water (1 mL), [1,1'-bis(diphenylphosphine)ferrocene]palladium dichloride (43 mg, 0.05 mmol) was added. The mixture was stirred at 80° C. for 3 hrs, cooled to room temperature, concentrated under reduced pressure. The residue was filtered through celite, the filtrate cake was washed with EA (30 mL). The filtrate was washed in turn with water (20 mL×3) and saturated brine (10 mL), dried over anhydrous magnesium sulfate, filtered, concentrated under reduced pressure. The residue was purified by silica column chromatography (PE:EA=1:1) to give racemic compound, followed by separating by enantiomeric chromatographic column (process I, mobile phase: Hexane:EtOH:DEA=80:20:0.1), compound 46A-a was eluted firstly (66 mg, yield 31%; LC-MS (ESI): m/z=401 [M+H]$^+$) ($T_r$=14.0 min) and compound 46B-a was eluted later (61 mg, yield 29%; LC-MS (ESI): m/z=401 [M+H]$^+$) ($T_r$=18.0 min). Absolute configuration of 46A-a and 46B-a remains unknown.

Synthesis of Compound 46A

At room temperature, LiOH (42 mg, 1 mmol) was added to a solution of compound 46A-a (60 mg, 0.15 mmol) in methanol (1 mL), THF (4 mL) and water (1 mL). The mixture was stirred for 1 h, followed by adding 1M HCl aq. solution (1 mL) and water (10 mL), solid was precipitated and filtered out. The solid was washed with water (5 mL), dried under vacuum to give compound 46A (26 mg, yield 46%). LC-MS (ESI): m/z=373 [M+H]$^+$.

$^1$H-NMR (400 MHz, DMSO-d6) δ: 12.31 (s, 1H), 9.17 (s, 1H), 8.44 (s, 1H), 8.33 (d, J=8.0 Hz, 1H), 8.27 (d, J=8.0 Hz, 1H), 7.88 (m, 2H), 7.66 (m, 2H), 7.49 (s, 1H), 3.16 (m, 1H), 3.02 (m, 1H), 2.68 (m, 1H), 1.23 (d, J=6.8 Hz, 1H) ppm.

Synthesis of Compound 46B

At room temperature, LiOH (42 mg, 1 mmol) was added to a solution of compound 46B-a (60 mg, 0.15 mmol) in methanol (1 mL), THF (4 mL) and water (1 mL). The mixture was stirred for 1 h, followed by adding 1M HCl aq. solution (1 mL) and water (10 mL), solid was precipitated and filtered out. The solid was washed with water (5 mL), dried under vacuum to give compound 46B (26 mg, yield 46%). LC-MS (ESI): m/z=373 [M+H]$^+$.

$^1$H-NMR (400 MHz, DMSO-d$_6$) δ: 12.31 (s, 1H), 9.17 (s, 1H), 8.44 (s, 1H), 8.33 (d, J=8.0 Hz, 1H), 8.27 (d, J=8.0 Hz, 1H), 7.88 (m, 2H), 7.66 (m, 2H), 7.49 (s, 1H), 3.16 (m, 1H), 3.02 (m, 1H), 2.68 (m, 1H), 1.23 (d, J=6.8 Hz, 1H) ppm.

Embodiment 47

3-[4-(4-Cyanonaphthalen-1-yl)thieno[2,3-c]pyridin-2-yl]-2,2-dimethyl propionic Acid (Compound 47)

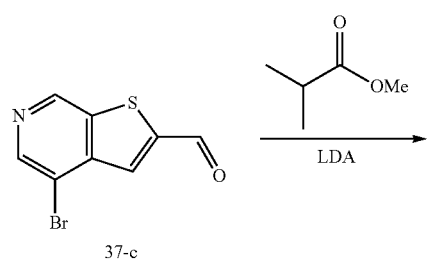

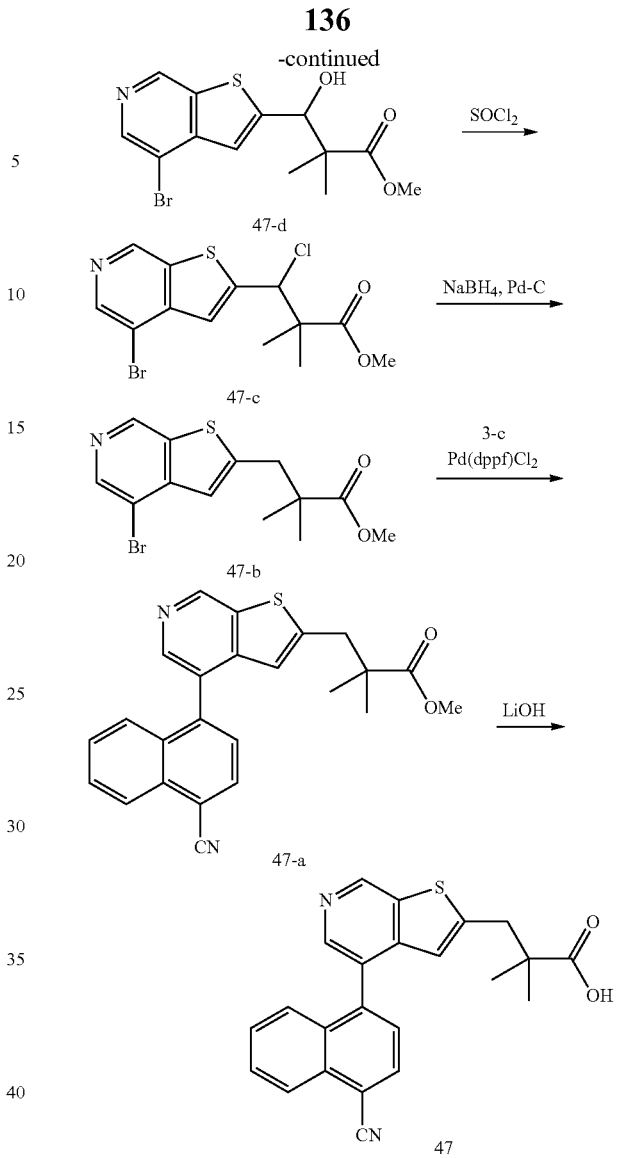

Synthesis of Compound 47-d

At −78° C., 1M Lithium diisopropylamide in THF (3 mL, 3 mmol) was slowly added to a solution of methyl isobutyrate (306 mg, 3 mmol) in anhydrous THF (4 mL). The mixture was stirred for 1 h, followed by adding compound 37-c (242 mg, 1 mmol), the mixture was further stirred for 1 h. The mixture was slowly warmed to room temperature, followed by adding saturated NaHCO$_3$ aq. solution (20 mL), being extracted with EA (20 mL×3). The organic phases were combined, dried over anhydrous sodium sulfate, filtered, and concentrated under reduced pressure to give compound 47-d (425 mg). The product was used directly for the next step without further purification. LC-MS (ESI): m/z=344 [M+H]$^+$.

Synthesis of Compound 47-c

Thionyl chloride (6 mL) was added to a solution of compound 47-d (425 mg) in DCM (10 mL). The mixture was heated to 40° C., stirred for 16 hrs and concentrated under reduced pressure to remove the solvent. Water (15 mL) was added to the residue, the mixture was extracted with EA (15 mL×3). The organic phases were combined, dried over anhydrous sodium sulfate, filtered and concentrated under reduced pressure to give compound 47-c (487 mg). The product was used directly for the next step without further purification. LC-MS (ESI): m/z=364 [M+H]⁺.

Synthesis of Compound 47-b

At room temperature, NaBH₄ (204 mg, 5.37 mmol) was added to a mixture of compound 47-c (487 mg), 10% Pd-C (50 mg) and ethanol (20 mL) in portions, the mixture was stirred for 16 hrs. The mixture was filtered through celite, the filtrate cake was washed with ethanol (10 mL×3). The filtrate was concentrated under reduced pressure. The residue was purified by silica column chromatography (PE: EA=5:1) to give compound 47-b (135 mg, yield 31%). LC-MS (ESI): m/z=328 [M+H]⁺.

Synthesis of Compound 47-a

Under N₂ atmosphere, compound 47-b (135 mg, 0.41 mmol), compound 3-c (121 mg, 0.43 mmol) and sodium sulfate (106 mg, 1 mmol) were suspended in dioxane (8 mL) and water (1 mL), [1,1'-bis(diphenylphosphine)ferrocene] palladium dichloride (30 mg, 0.04 mmol) was added. The mixture was stirred at 90° C. for 16 hrs, cooled to room temperature, and concentrated under reduced pressure. The residue was purified by silica column chromatography (PE: EA=3:1) to give compound 47-a (130 mg, yield 79%). LC-MS (ESI): m/z=401 [M+H]⁺.

Synthesis of Compound 47

At room temperature, LiOH (55 mg, 1.3 mmol) was added to a solution of compound 47-a (130 mg, 0.32 mmol) in methanol (1 mL), THF (5 mL) and water (1 mL). The mixture was stirred for 1 h, followed by adding 1M HCl aq. solution to adjust pH=5-6, being extracted with EA (15 mL×3). The organic phases were combined, dried over anhydrous sodium sulfate, filtered, and concentrated under reduced pressure. The residue was prepared by HPLC (mobile phase: 10 mM NH₄HCO₃ aq. solution:acetonitrile=35%-45%) to give white solid 47 (13 mg, yield 10.5%). LC-MS (ESI): m/z=387 [M+H]⁺.

¹H-NMR (400 MHz, CD₃OD) δ: 9.22 (s, 1H), 8.39 (s, 1H), 8.22 (d, J=8.1 Hz, 1H), 8.10-8.01 (m, 1H), 7.71 (dd, J=7.9 Hz, 3.7 Hz, 1H), 7.60 (d, J=7.1 Hz, 1H), 7.50 (s, 2H), 6.68 (s, 1H), 3.13-3.02 (m, 2H), 1.19 (s, 3H), 1.18 (s, 3H) ppm.

Embodiment 48

3-[4-(4-Cyanophenyl)thieno[2,3-c]pyridin-2-yl]-2,2-dimethyl propionic Acid (Compound 48)

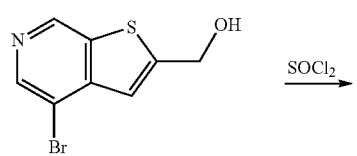

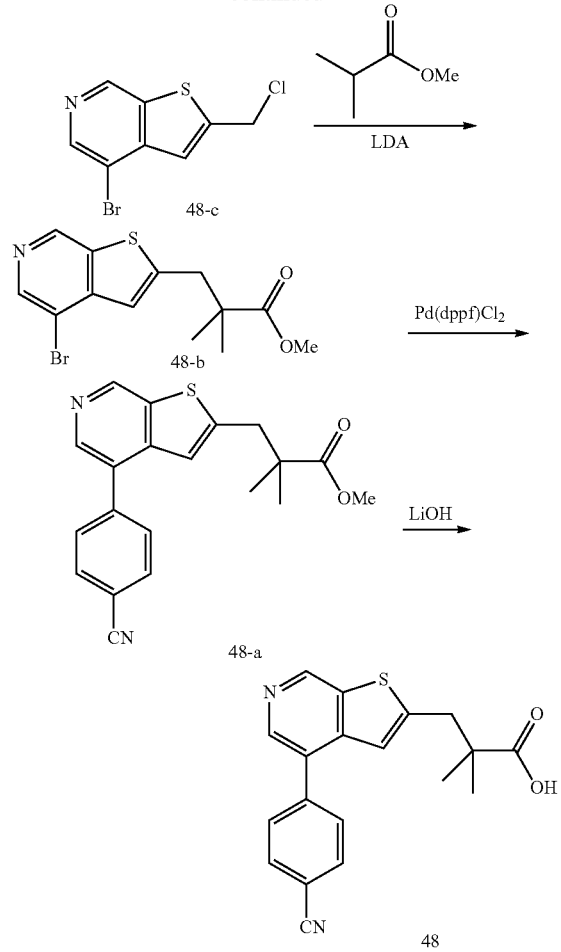

Synthesis of Compound 48-c

Thionyl chloride (5 mL) was added to a solution of compound 37-d (200 mg, 0.82 mmol) in DCM (10 mL). The mixture was heated to 30° C., stirred for 16 hrs, and concentrated under reduced pressure to give compound 48-c (236 mg). The product was used directly for the next step without further purification. LC-MS (ESI): m/z=264 [M+H]⁺.

Synthesis of Compound 48-b

Under N₂ atmosphere, at −78° C., a solution of 2.5M n-butyl lithium in n-hexane (1.37 mL, 3.43 mmol) was slowly added to a solution of diisopropylamine (347 mg, 3.43 mmol) in anhydrous THF (10 mL). The mixture was warmed to 0° C. and further stirred for 1 h, then cooled again to −78° C., methyl isobutyrate (350 mg, 3.43 mmol) was added, the mixture was stirred for 1 h, followed by adding compound 48-c (180 mg, 0.69 mmol) and further stirred for 1 h. The mixture was slowly warmed to room temperature, stirred for 2 hrs, followed by adding saturated NH₄Cl aq. solution (20 mL), being extracted with EA (50 mL×2). The organic phases were combined, dried over anhydrous sodium sulfate, filtered, and concentrated under reduced pressure. The residue was purified by silica column chromatography (PE:EA=3:1) to give compound 48-b (280 mg, yield 97%). LC-MS (ESI): m/z=329 [M+H]⁺.

Synthesis of Compound 48-a

Under N₂ atmosphere, compound 48-b (280 mg, 0.85 mmol), 4-cyanophenylboronic acid (138 mg, 0.94 mmol) and sodium sulfate (180 mg, 1.7 mmol) were suspended in dioxane (15 mL) and water (2 mL), [1,1'-bis(diphenylphosphine)ferrocene]palladium dichloride (62 mg, 0.08 mmol) was added. The mixture was added at 90° C. for 16 hrs, cooled to room temperature, concentrated under reduced pressure. The residue was purified by silica column chromatography (PE:EA=3:1) to give compound 48-a (135 mg, yield 45%). LC-MS (ESI): m/z=351 [M+H]⁺.

Synthesis of Compound 48

At room temperature, LiOH (65 mg, 1.54 mmol) was added to a solution of compound 48-a (135 mg, 0.38 mmol) in methanol (1 mL), THF (5 mL) and water (1 mL). The mixture was stirred for 6 hrs, 1M HCl aq. solution was added to adjust pH=5-6, and concentrated under reduced pressure. The residue was adjusted to pH=7-8 with 2M NaOH aq. solution, and then extracted with EA (10 mL) to remove the impurities. The aqueous phase was adjusted to pH=5-6 with 1M HCl aq. solution, extracted with EA (15 mL×2). The organic phases were combined, dried over anhydrous sodium sulfate, filtered, and concentrated under reduced pressure to give yellow solid 48 (75 mg, yield 58%). LC-MS (ESI): m/z=337 [M+H]⁺.
¹H-NMR (400 MHz, DMSO-d6) δ: 12.52 (s, 1H), 9.21 (s, 1H), 8.48 (s, 1H), 8.03 (d, J=8.2 Hz, 2H), 7.84 (d, J=8.2 Hz, 2H), 7.30 (s, 1H), 3.21 (s, 2H), 1.16 (s, 6H) ppm.

Embodiment 49

2-[4-(4-Cyanonaphthalen-1-yl)isoquinolin-6-yl]-2-methyl propionic acid (Compound 49)

Synthetic Route

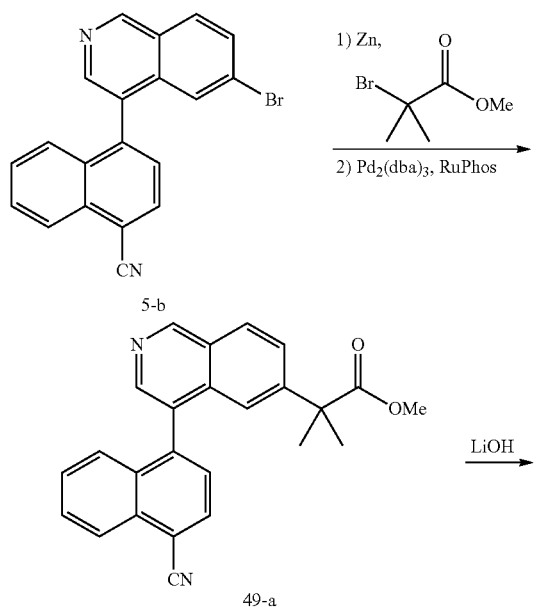

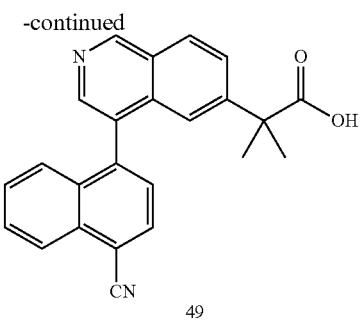

Synthesis of Compound 49-a

Under N₂ atmosphere, trimethylchlorosilane (11 mg, 0.1 mmol) was added dropwise to a solution of Zn powder (130 mg, 2 mmol) and THF (4 mL). The mixture was stirred for 15 mins at room temperature, heated to 40° C., followed by adding a solution of methyl 2-bromoisobutyrate (181 mg, 1 mmol) in THF (2 mL). The mixture was further stirred at 40° C. for 30 mins, added to a mixture of compound 5-b (90 mg, 0.25 mmol), LiCl (11 mg, 0.25 mmol), tris(dibenzylidene indene acetone)dipalladium (23 mg, 0.025 mmol), 2-dicyclohexylphospho-2',6'-diisopropoxy-1,1'-biphenyl (12 mg, 0.025 mmol) and THF (4 mL). The mixture was heated to 80° C. and further stirred for 1 h, and then cooled to room temperature, and concentrated under reduced pressure to remove the solvent. The residue was dissolved in DCM (50 mL), washed in turn with water (20 mL×3) and saturated brine (10 mL), dried over anhydrous sodium sulfate, filtered, concentrated under reduced pressure. The residue was purified by silica preparative plate chromatography (DCM:methanol=20:1) to give compound 49-a (40 mg, yield 42%). LC-MS (ESI): m/z=381 [M+H]⁺.

Synthesis of Compound 49

At room temperature, LiOH (22 mg, 0.5 mmol) was added to a solution of compound 49-a (40 mg, 0.1 mmol) in methanol (1 mL) and THF (3 mL). The mixture was stirred for 16 hrs, evaporated to remove the solvent, followed by adding water (5 mL), being extracted with EA (10 mL×3). 1M HCl aq. solution was added to the aqueous phase to adjust pH=5-6, extracted with EA (15 mL×3), the organic phases were combined, dried over anhydrous sodium sulfate, filtered and concentrated under reduced pressure. The residue was prepared by HPLC (mobile phase: water (0.05% trifluoroacetic acid):nitrile=25%-40%) to give compound 49 (15 mg, yield 39%). LC-MS (ESI): m/z=367 [M+H]⁺.
¹H-NMR (400 MHz, CDCl₃) δ: 9.39 (s, 1H), 8.50 (s, 1H), 8.36 (d, J=8.4 Hz, 1H), 8.13 (d, J=8.4 Hz, 1H), 7.77 (d, J=8.4 Hz, 1H), 7.72-7.67 (m, 1H), 7.58 (d, J=7.2 Hz, 1H), 7.48-7.46 (m, 2H), 7.34 (s, 1H), 1.45 (s, 6H) ppm.

Embodiment 50

2-{[4-(4-Cyanonaphthalen-1-yl)phthalazin-6-yl]thio}-2-methyl propionic Acid (Compound 50)

Synthetic Route

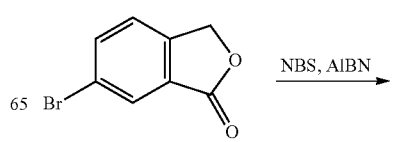

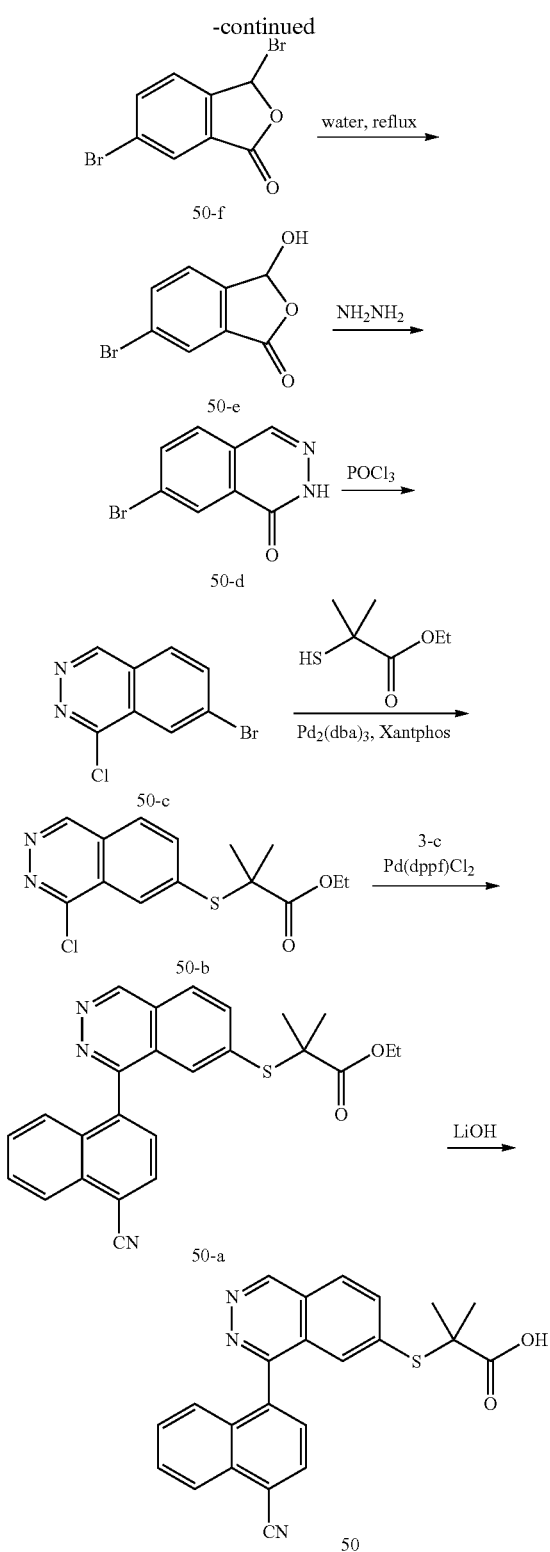

Synthesis of Compound 50-f

6-Bromo-phthalide (2.30 g, 10.9 mmol) was added to a solution of N-bromosuccinimide (2.1 g, 11.8 mmol), azobisisobutyronitrile (0.1 g, 0.06 mmol) in 1,2-dichloroethane (60 mL). The mixture was heated to reflux for 2 hrs, cooled to room temperature, and concentrated under reduced pressure. The residue was washed with water (10 mL×3) to give compound 50-f. The product was used directly for the next step without further purification.

Synthesis of Compound 50-e

A mixture of compound 50-f and water (40 mL) was heated to reflux for 2 hrs, cooled to room temperature, white solid was precipitated and filtered out. Solid was washed with water (20 mL×3), dried under vacuum to give compound 50-e (1.6 g, yield 64%). The product was used directly for the next step without further purification.

Synthesis of Compound 50-d

85% Hydrazine hydrate (2 mL) was added to a solution of compound 50-e (1.60 g, 7 mmol) in isopropyl alcohol (40 mL). The mixture was heated to reflux for 2 hrs, cooled to room temperature, white solid was precipitated and filtered out. The solid was washed with water (20 mL×3), dried under vacuum to give compound 50-d (1.2 g, yield 76%). The product was used directly for the next step without further purification.

Synthesis of Compound 50-c

A mixture of compound 50-d (600 mg, 2.67 mmol) and POCl$_3$ (8 mL) was heated to reflux for 1.5 h, cooled to room temperature and concentrated under reduced pressure. The residue was dissolved in DCM (40 mL), washed in turn with saturated sodium bicarbonate (40 mL) and saturated brine (10 mL), dried over anhydrous sodium sulfate, filtered and concentrated under reduced pressure. The residue was purified by silica column chromatography (PE:EA=3:1) to give compound 50-c (500 mg, yield 75%). LC-MS (ESI): m/z=243 [M+H]$^+$.

Synthesis of Compound 50-b

Under N$_2$ atmosphere, tris(dibenzylidene indene acetone) dipalladium (30 mg, 0.03 mmol) and 4,5-bis(diphenylphosphine)-9,9-dimethyloxacanthracene (38 mg, 0.06 mmol) were added to a solution of compound 50-c (131 mg, 0.5 mmol), ethyl 2-methyl-2-mercaptopropionate (73 mg, 0.5 mmol) and diisopropylethylamine (193 mg, 1.5 mmol) in dioxane (10 mL). The mixture was stirred at 100° C. for 16 hrs, cooled to room temperature, concentrated under reduced pressure. The residue was purified by silica column chromatography (PE:EA=3:1) to give compound 50-b (120 mg, yield 77%). LC-MS (ESI): m/z=311 [M+H]$^+$.

Synthesis of Compound 50-a

Under N$_2$ atmosphere, compound 50-b (120 mg, 0.38 mmol), compound 3-c (111 mg, 0.4 mmol) and sodium carbonate (170 mg, 2.8 mmol) were suspended in ethylene glycol dimethyl ether (10 mL) and water (1 mL), [1,1'-bis(diphenylphosphine)ferrocene]palladium dichloride (43 mg, 0.05 mmol) was added. The mixture was stirred at 80° C. for 4 hrs, cooled to room temperature and concentrated under reduced pressure. The residue was purified by silica column chromatography (PE:EA=2:1) to give compound 50-a (96 mg, yield 60%). LC-MS (ESI): m/z=428 [M+H]$^+$.

Synthesis of Compound 50

At room temperature, 1M LiOH aq. solution (3.0 mL) was added to a solution of compound 50-a (86 mg, 0.2 mmol) in methanol (4 mL) and THF (8 mL). The mixture was stirred for 16 hrs and concentrated under reduced pressure. The residue was dissolved in water (10 mL), adjusted to pH=3 with 1M HCl aq. solution, solid was precipitated and filtered out. The solid was washed with water (5 mL), dried under vacuum to give white solid 50 (60 mg, yield 75%). LC-MS (ESI): m/z=400 [M+H]+.

1H-NMR (400 MHz, DMSO-d6) δ: 12.77 (s, br. 1H), 9.87 (s, 1H), 8.39 (d, J=8.0 Hz, 1H), 8.30 (d, J=8.0 Hz, 2H), 7.98-8.00 (m, 1H), 7.85-7.90 (m, 2H), 7.62 (t, J=8.0 Hz, 1H), 7.47 (d, J=8.8 Hz, 1H), 7.42 (s, 1H), 1.32 (s, 3H), 1.26 (s, 3H) ppm.

Embodiment 51

3-[4-(4-Cyanophenyl)isoquinolin-6-yl]-2,2-dimethyl propionic Acid (Compound 51)

Synthetic Route

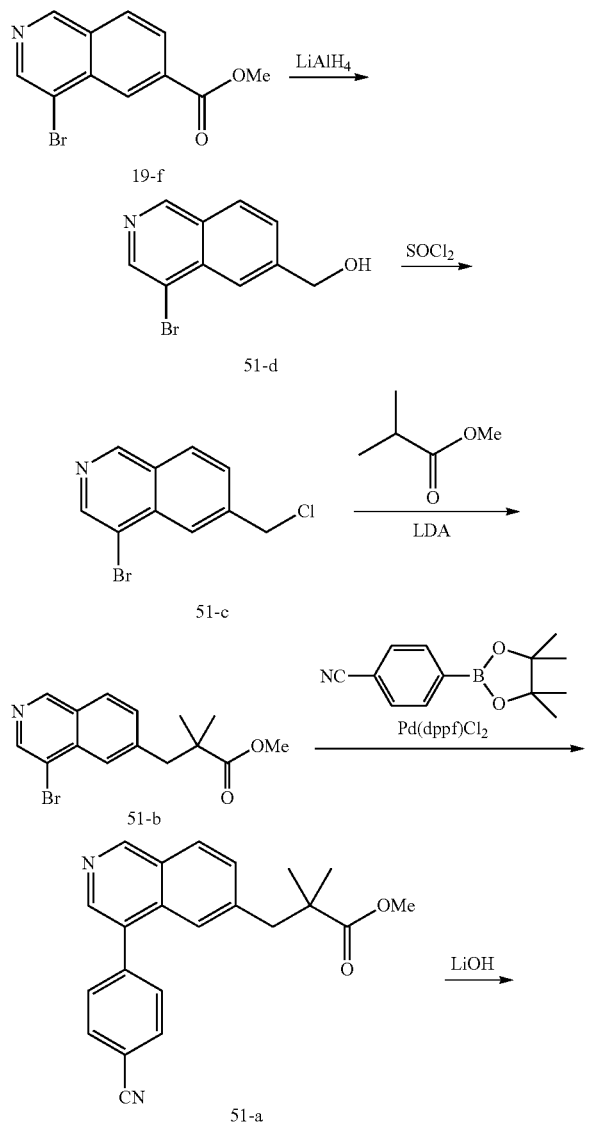

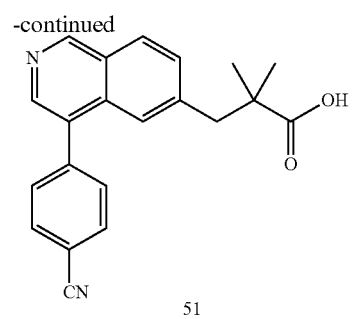

Synthesis of Compound 51-d

At 0° C., lithium aluminum hydride (214 mg, 5.64 mmol) was suspended in anhydrous THF (100 mL), a solution of compound 19-f (1.5 g, 5.64 mmol) in THF (10 mL) was slowly added. The mixture was stirred for 10 mins, Na2SO4.10H2O (2.0 g) was added in portions, then the mixture was warmed to room temperature and further stirred for 30 mins. The mixture was filtered, the filtrate cake was washed with EA (20 mL). The filtrate was concentrated under reduced pressure, the residue was purified by silica column chromatography (PE:EA=3:1) to give compound 51-d (600 mg, yield 44%). LC-MS (ESI): m/z=238 [M+H]+.

Synthesis of Compound 51-c

Thionyl chloride (1.84 mL) was added to a solution of compound 51-d (600 mg, 2.52 mmol) in DCM (25 mL). The mixture was heated to 30° C., stirred for 16 hrs and concentrated under reduced pressure to give compound 51-c (720 mg). The product was used directly for the next step without further purification. LC-MS (ESI): m/z=256 [M+H]+.

Synthesis of Compound 51-b

Under N2 atmosphere, at −78° C., a solution of 2.5M n-butyl lithium in n-hexane (2.05 mL, 5.1 mmol) was added to a solution of diisopropylamine (0.72 mL, 5.1 mmol) in anhydrous THF (20 mL). The mixture was warmed to room temperature, stirred for 1 h, cooled again to −78° C. The mixture was added to methyl isobutyrate (0.59 mL, 5.1 mmol), stirred for 1 h, followed by adding compound 51-c (300 mg, 1.02 mmol) and further stirred for 1 h. The mixture was slowly warmed to room temperature, stirred for 2 hrs, followed by adding saturated NH4Cl aq. solution (20 mL), being extracted with EA (50 mL×2). The organic phases were combined, dried over anhydrous sodium sulfate, filtered and concentrated under reduced pressure. The residue was purified by silica column chromatography (PE:EA=3:1) to give yellow oil 51-b (300 mg, yield 91%). LC-MS (ESI): m/z=322 [M+H]+.

Synthesis of Compound 51-a

Under N2 atmosphere, compound 51-b (300 mg, 0.93 mmol), 4-cyanophenylboronic acid (215 mg, 0.93 mmol) and sodium carbonate (296 mg, 2.79 mmol) were suspended in DMF (10 mL) and water (5 mL), [1,1'-bis(diphenylphosphine)ferrocene]palladium dichloride (76 mg, 0.09 mmol) was added. The mixture was stirred at 80° C. for 16 hrs, cooled to room temperature, and concentrated under reduced pressure. The residue was purified by silica column chromatography (PE:EA=3:1-2:1) to give compound 51-a (250 mg, yield 78%). LC-MS (ESI): m/z=345 [M+H]+.

Synthesis of Compound 51

At room temperature, LiOH (152 mg, 3.6 mmol) was added to a solution of compound 51-a (250 mg, 0.72 mmol) in methanol (1 mL), THF (5 mL) and water (2 mL). The mixture was stirred for 6 hrs, 1M HCl aq. solution was added to adjust pH=5-6, the mixture was concentrated under reduced pressure, extracted with EA (20 mL×3). The organic phases were combined, dried over anhydrous sodium sulfate, filtered, and concentrated under reduced pressure. The residue was prepared by HPLC (mobile phase: water (0.01% $NH_3$+10 mm $NH_4HCO_3$):nitrile=45%-75%) to give compound 51 (33 mg, yield 14%). LC-MS (ESI): m/z=331 $[M+H]^+$.

$^1$H-NMR (400 MHz, $CDCl_3$) δ: 9.19 (s, 1H), 8.36 (s, 1H), 7.94 (m, 1H), 7.51-7.65 (m, 6H), 3.06 (s, 2H), 1.27 (s, 6H) ppm.

Embodiment 52

3-[7-(4-Cyanonaphthalen-1-yl)thieno[3,2-c]pyridine-2-yl]-butyric Acid (Compound 52)

Synthetic Route

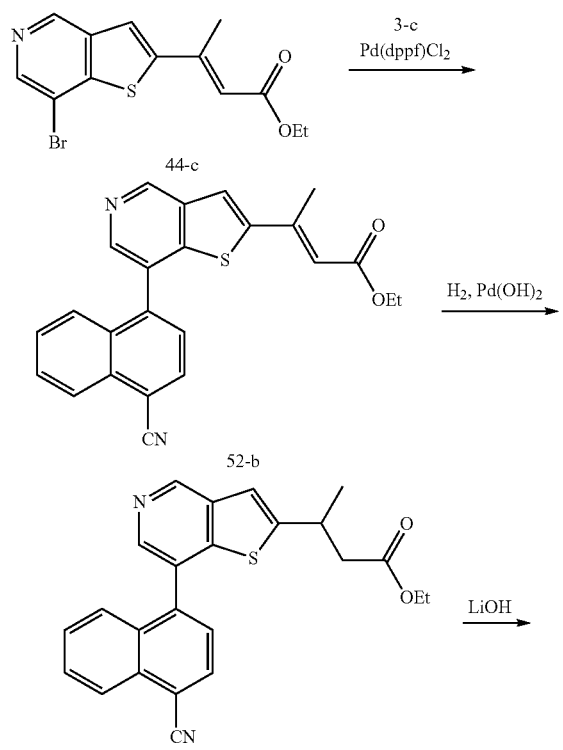

Synthesis of Compound 52-b

Under $N_2$ atmosphere, compound 44-c (9.0 g, 27.6 mmol), compound 3-c (15.4 g, 55.2 mmol) and sodium carbonate (5.85 g, 55.2 mmol) were suspended in dioxane (240 mL) and water (40 mL), [1,1'-bis(diphenylphosphine)ferrocene]palladium dichloride (1.0 g, 1.38 mmol) was added. The mixture was stirred at 80° C. for 16 hrs, cooled to room temperature, and concentrated under reduced pressure. The residue was purified by silica column chromatography (PE:EA=10:1) to give yellow solid 52-b (9.1 g, yield 82.8%). LC-MS (ESI): m/z=399 $[M+H]^+$.

Synthesis of Compound 52-a

Under $H_2$ (1 atm.) atmosphere, palladium hydroxide (3.0 g) was added to a solution of compound 52-b (9.1 g, 22.8 mmol) in THF (100 mL) and methanol (280 mL). The mixture was stirred for 16 hrs, filtered, and concentrated under reduced pressure. The residue was purified by silica column chromatography (PE:EA=1:1) to give yellow oil 52-a (8.0 g, yield 87.5%). LC-MS (ESI): m/z=401 $[M+H]^+$.

Synthesis of Compound 52

At room temperature, LiOH (1.51 g, 36 mmol) was added to a solution of compound 52-a (8.0 g, 20 mmol) in methanol (15 mL), THF (30 mL) and water (5 mL). The mixture was stirred for 8 hrs, followed by adding 1M HCl aq. solution to adjust pH=5-6, solid was precipitated and filtered out. The solid was washed with water (20 mL×3), dried under vacuum to give white solid 52 (6.18 g, yield 83%). LC-MS (ESI): m/z=373 $[M+H]^+$.

$^1$H-NMR (400 MHz, DMSO-d6) δ: 12.27 (s, 1H), 9.17 (s, 1H), 8.43 (s, 1H), 8.33 (d, J=7.2 Hz, 1H), 8.27 (d, J=8.4 Hz, 1H), 7.90 (dd, J=7.2 Hz, 5.6 Hz, 1H), 7.83 (d, J=7.2 Hz, 1H), 7.68 (dd, J=6.8 Hz, 6.0 Hz, 1H), 7.64 (d, J=8.4 Hz, 1H), 7.52 (s, 1H), 3.50 (m, 1H), 2.60 (m, 2H), 1.31 (dd, J=7.6 Hz, 6.8 Hz, 3H) ppm.

Embodiment 53

Compound 53A

Synthetic Route

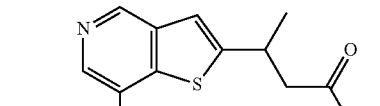

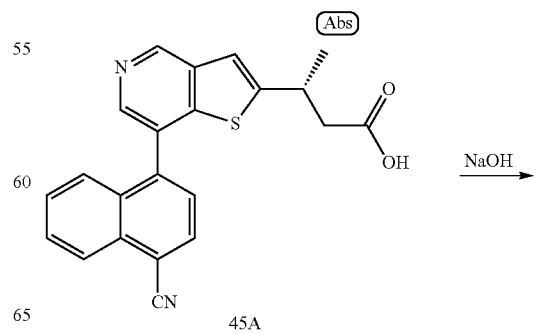

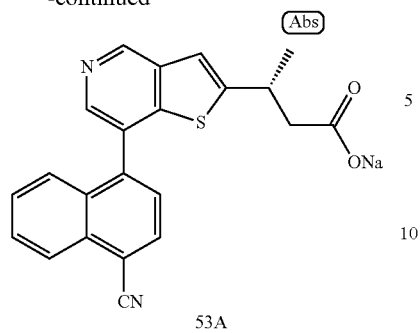

53A

Synthesis of Compound 53A

At room temperature, NaOH (8 mg, 0.02 mmol) was added to a solution of compound 45A (74 mg, 0.02 mmol) in water (1 mL). The mixture was stirred for 2 hrs, freeze-dried to give white solid 53A (79 mg, yield 100%). LC-MS (ESI): m/z=373 [M-Na+2H]$^+$.

$^1$H-NMR (400 MHz, DMSO-d6) δ: 9.11 (s, 1H), 8.38 (s, 1H), 8.32 (d, J=7.2 Hz, 1H), 8.27 (d, J=8.0 Hz, 1H), 7.88 (t, J=6.4 Hz, 1H), 7.82 (d, J=7.2 Hz, 1H), 7.65 (m, 2H), 7.42 (s, 1H), 3.47 (m, 1H), 2.23 (m, 1H), 2.11 (m, 1H), 1.25 (dd, J=7.2 Hz, 6.8 Hz, 3H) ppm.

Embodiment 54

3-[4-(4-Cyanonaphthalen-1-yl)thieno[3,2-c]pyridine-2-yl]-2,2-bis(triadecylmethyl)propionic Acid (Compound 54)

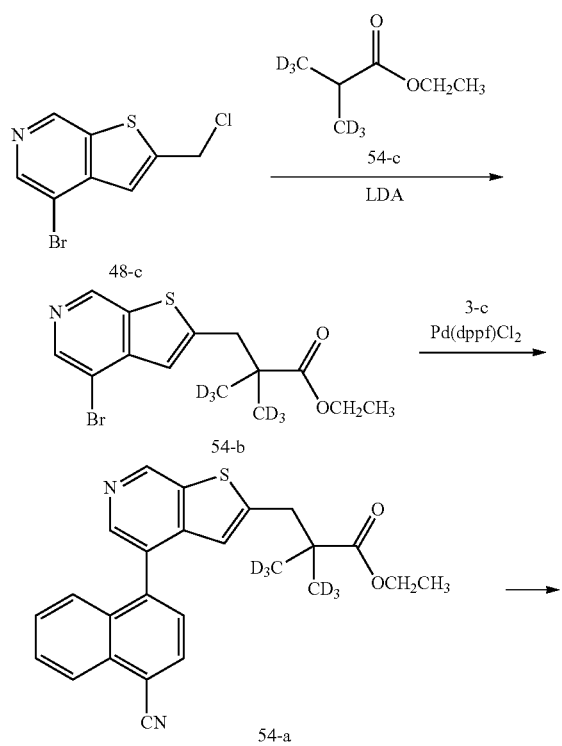

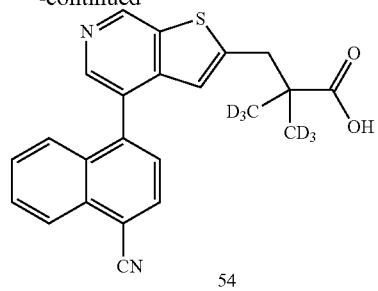

54

Synthesis of Compound 54-b

According to the process for preparing compound 48-b, compound 54-b (1000 mg, 46%) was prepared by using commercially available compound 54-c. LC-MS (ESI): m/z=349 [M+H]$^+$.

According to the process for preparing compound 47-a, compound 54-a (500 mg, 72%) was prepared by using compound 54-b. LC-MS (ESI): m/z=421 [M+H]$^+$.

Synthesis of Compound 54

According to the process for preparing compound 47, white solid compound 54 (63 mg, 32%) was prepared by compound 47-a. LC-MS (ESI): m/z=394 [M+H]$^+$. $^1$H-NMR (400 MHz, DMSO-d6) δ: 12.46 (s, 1H), 9.30 (s, 1H), 8.45 (s, 1H), 8.32 (d, J=8 Hz, 1H), 8.26 (d, J=8 Hz, 1H), 7.89 (d, J=8 Hz, 1H), 7.74 (d, J=8 Hz, 1H), 7.65 (m, 1H), 7.59 (m, 1H), 6.67 (s, 1H), 3.09 (s, 2H) ppm Effect Example Biological Assessment Example 1: The Inhibitory Activity Against URAT1 of the Compound of the Present Invention Human embryonic kidney cells (HEK293) was incubated in DMEM tissue culture medium, at 37° C., under 5% $CO_2$ and 95% air atmosphere. TransIT-293 transfection agent (MIRUS BIO, Cat. No. MIR2706) and model URAT1 were used to construct transfected HEK293 cells. Transfected HEK293/hURAT1 cells were used to the test for $^{14}$C-uric acid transport activity.

HEK293/hURAT1 cells were seeded in a 96-well plate (BD, Cat. No. 356461) fully coating with poly-D-lysine at a density of 6×10$^4$ cells per well. Cells were incubated at 37° C. for at least 12 hrs in the calorstat, and then washed with pre-heated washing buffer (125 mM sodium gluconate, 10 mM HEPES pH=7.4) at an amount of 200 μL per well to wash out the culture medium. The uric acid [8-14C] (ARC, Cat. No. ARC0513-250UCI) containing or not containing the compound was added to 50 μL HBSS buffer which was free of chloric ion each well (HBSS buffer: 125 mM sodium gluconate, 4.8 mM potassium gluconate, 1.3 mM calcium gluconate, 1.2 mM potassium dihydrogen phosphate, 1.2 mM magnesium sulfate, 5.6 mM glucose, 25 mM HEPES pH=7.4) to make the specific concentration of the uric acid 1 μCi per well. The incubating solution was removed after 10 mins incubation, followed by adding 100 μL cold washing buffer, after washing with this buffer for 3 times, the buffer was completely removed from the well. 50 μL Lysis buffer (0.1 mM NaOH) was added to each well, and transferred to a 96-well plate (PERKIN ELMER, Cat. No.

6005040) containing scintillation fluid after 5 mins, and counted by MicroBeta Trilux (PerkinElmer) to give IC$_{50}$ value eventually.

The inhibitory activity of the compound of the present invention against hURAT1 was tested according to the assessment above, the results were listed below (Table 1):

TABLE 1

IC$_{50}$ value of partial compounds of the present invention against hURAT1

| Compound | IC$_{50}$ (μM) | Compound | IC$_{50}$ (μM) |
|---|---|---|---|
| Verinurad (RDEA3170) | 0.113 | 30 | 0.087 |
| 1 | 2.534 | 31 | 3.418 |
| 2 | 0.161 | 32 | 5.405 |
| 3 | 0.327 | 33 | 0.042 |
| 4 | 0.015 | 34 | 0.139 |
| 5 | 0.008 | 35 | 2.408 |
| 6 | 0.214 | 36 | 0.542 |
| 7A | 5.524 | 37 | 0.035 |
| 7B | 2.687 | 38 | 0.209 |
| 8 | 0.057 | 40 | 3.467 |
| 9 | 0.127 | 41 | 0.934 |
| 10 | 0.019 | 42 | 0.024 |
| 11 | 0.062 | 43A | 0.011 |
| 12 | 0.071 | 43B | 0.037 |
| 13 | 0.189 | 44A | 0.038 |
| 14 | 0.385 | 44B | 1.858 |
| 15 | 0.024 | 45A | 0.580 |
| 16 | 0.015 | 45B | 0.010 |
| 17 | 0.012 | 46A | 0.148 |
| 21 | 0.100 | 46B | 0.051 |
| 22 | 0.055 | 47 | 0.018 |
| 23 | 0.018 | 48 | 0.012 |
| 24 | 0.018 | 49 | 0.116 |
| 25 | 0.289 | 50 | 0.971 |
| 26 | 0.119 | 51 | 0.019 |
| 27 | 1.731 | 52 | 0.037 |
| 29 | 2.858 | / | / |

Compound Verinurad (RDEA3170, CAS No.:1352792-74-5) was a known hURAT1 inhibitor having a structure shown as below:

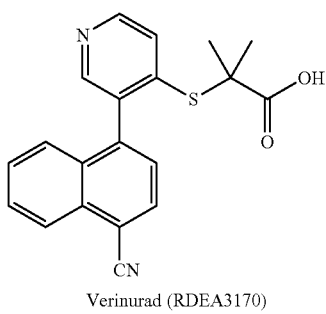 [SMILES: CC(C)(Sc1ccncc1-c1ccc(C#N)c2ccccc12)C(=O)O]

Verinurad (RDEA3170)

What can be concluded from Table 1 was that compounds of the present invention are of significantly inhibitory effects against hURAT1.

It is to be understood that the foregoing description of two preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A condensed ring derivative having a structure of formula II, a tautomer, a mesomer, a racemate, an enantiomer, a diastereoisomer, or a pharmaceutically acceptable salt, a metabolite, a metabolic precursor or a pro-drug thereof,

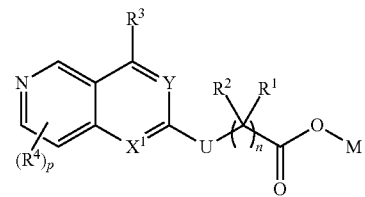

M is H, D or a pharmaceutically acceptable cation;
U is

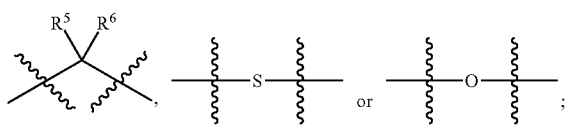

$X^1$ is CH or N,
Y is

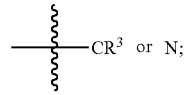

each of $R^1$ and $R^2$ is independently H, D, a halogen, CN, an alkyl, an alkoxy, a cycloalkyl, an alkenyl, an alkynyl or a heterocycloalkyl; or, $R^1$, $R^2$ together with the carbon atom attached form a cycloalkyl or a heterocyclic group; the alkyl, the alkoxy, the cycloalkyl, the alkenyl, the alkynyl, the heterocycloalkyl, the cycloalkyl formed by $R^1$, $R^2$ and the carbon atom attached, or the heteroalkyl formed by $R^1$, $R^2$ and the carbon atom attached can further be substituted by a substituent selected from the group consisting of D, a halogen, CN, an alkyl, an alkoxy, a cycloalkyl, an alkenyl, an alkynyl, a heterocycloalkyl or an aryl;

$R^3$ is H, D, a halogen, an alkyl, an alkoxy, an aryl, a heteroaryl, a heterocycloalkyl or an amino; wherein the alkyl, the alkoxy, the aryl, the heteroaryl, the heterocycloalkyl or the amino can be further substituted by a substituent selected from the group consisting of D, a halogen, CN, an alkyl, an aryl, an aryl substituted by halogen, a benzyl, a benzyl which is substituted by halogen in the phenyl, a benzoyl or a benzoyl which is substituted by halogen in the phenyl; when the substituents are more than one, the substituents are the same or different;

$R^4$ is D, CN, NH$_2$, an alkyl, an alkoxy, a cycloalkyl, an alkenyl, an alkynyl, a heterocycloalkyl, an aryl or a heteroaryl; wherein NH$_2$, the cycloalkyl, the alkenyl, the alkynyl, the heterocyclic group, the aryl or the heteroaryl can further be substituted by a substituent selected from the group consisting of D, a halogen, CN, an alkyl, an alkoxy, a cycloalkyl, an alkenyl, an alkynyl, a heterocycloalkyl, an aryl, an aryl substituted by a halogen and/or CN, a heteroaryl or a heteroaryl substituted by CN; the alkyl or the alkoxy is substituted by a substituent selected from the group consisting of D, a halogen, CN, an alkyl, an alkoxy, a cycloalkyl, an alkenyl, an alkynyl, a heterocycloalkyl, an aryl, an aryl substituted by a halogen and/or CN, a heteroaryl or a heteroaryl substituted by CN;

each of $R^5$ and $R^6$ is independently H, D, OH, a halogen, CN, an alkyl, an alkoxy, a cycloalkyl, an alkenyl, an alkynyl or a heterocycloalkyl; or $R^5$, $R^6$ together with the carbon atom attached form a cycloalkyl or a heterocyclic group; the alkyl, the alkoxy, the cycloalkyl, the alkenyl, the alkynyl, the heterocycloalkyl, the cycloalkyl formed by $R^5$, $R^6$ together with the carbon atom attached or the heterocyclic group formed by $R^5$, $R^6$ together with the carbon atom attached can further be substituted by a substituent selected from the group consisting of D, halogen, CN, an alkyl, an alkoxy, a cycloalkyl, an alkenyl, an alkynyl, a heterocycloalkyl or an aryl;

n is 0, 1 or 2; and p is 1, 2, or 3.

2. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1, wherein, M is H or a pharmaceutically acceptable cation;

each of $R^1$ and $R^2$ is independently H, D or an alkyl; or $R^1$ and $R^2$, together with the carbon atom attached form a cycloalkyl;

$R^3$ is H, a halogen, an alkyl or an aryl;

$R^4$ is H, a halogen, an alkyl, an aryl or a heteroaryl;

each of $R^5$ and $R^6$ is independently H, OH, a halogen or an alkyl; and p is 1.

3. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1, wherein, M is Na ion, K ion or Ca ion;

or, each of $R^1$ and $R^2$ is independently F, Cl, Br or I, $C_{1-4}$ alkyl, $C_{1-4}$ alkoxy, $C_{3-6}$ cycloalkyl, $C_{2-4}$ alkenyl, $C_{2-4}$ alkynyl, or a $C_{2-10}$ heterocycloalkyl having 1-2 heteroatom(s) selected from O, S or N;

or, $R^1$ and $R^2$ together with the carbon atom attached form a $C_{3-6}$ cycloalkyl;

or, $R^1$ and $R^2$ together with the carbon atom attached form a $C_{2-5}$ heterocyclic group having 1-2 heteroatom(s) selected from O or S;

or, $R^3$ is F, Cl, Br or I, $C_{1-4}$ alkyl, $C_{1-4}$ alkoxy, $C_{6-10}$ aryl, or a $C_{2-5}$ heteroaryl having 1-3 heteroatom(s) selected from N, or a $C_{2-10}$ heterocycloalkyl having 1-3 heteroatom(s) selected from N, O or S;

or, $R^4$ is F, Cl, Br or I, a $C_{1-4}$ alkyl, a $C_{1-4}$ alkoxy, a $C_{3-6}$ cycloalkyl, a $C_{2-4}$ alkenyl, a $C_{2-4}$ alkynyl, or a $C_{2-10}$ heterocycloalkyl having 1-3 heteroatom(s) selected from N, O or S, or a $C_{6-10}$ aryl, or a $C_{2-10}$ heteroaryl having 1-2 heteroatom(s) selected from O;

or, each of $R^5$ and $R^6$ is independently F, Cl, Br or I, a $C_{1-4}$ alkyl, $C_{1-4}$ alkoxy, a $C_{3-6}$ cycloalkyl, a $C_{2-4}$ alkenyl, a $C_{2-4}$ alkynyl, or a $C_{2-10}$ heterocycloalkyl having 1-2 heteroatom(s) selected from O, S or N, or $R^5$ and $R^6$ together with the carbon atom form a $C_{3-6}$ cycloalkyl, or $R^5$, $R^6$ together with the carbon atom attached form a $C_{2-10}$ heterocycloalkyl having 1-2 heteroatom(s) selected from O or S.

4. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1, wherein, the cycloalkyl formed by $R^1$ and $R^2$ together with the carbon atom attached, the heterocyclic group formed by $R^1$, $R^2$ together with the carbon atom attached, is substituted by a substituent select from the group consisting of F, Cl, Br, I, a $C_{1-4}$ alkyl, a $C_{1-4}$ alkoxy, a $C_{3-6}$ cycloalkyl, a $C_{2-4}$ alkenyl, a $C_{2-4}$ alkynyl, a $C_{6-10}$ aryl, a $C_{2-10}$ heterocycloalkyl having 1-2 heteroatom(s) selected from O, S or N;

or, the cycloalkyl formed by $R^5$, $R^6$ together with the carbon atom attached or the heterocyclic group formed by $R^5$, $R^6$ together with the carbon atom attached is substituted by a substituent selected from the group consisting of F, Cl, Br, I, a $C_{1-4}$ alkyl, a $C_{1-4}$ alkoxy, a $C_{3-6}$ cycloalkyl, a $C_{2-4}$ alkenyl, a $C_{2-4}$ alkynyl, a $C_{6-10}$ aryl, a $C_{2-10}$ heterocycloalkyl having 1-2 heteroatom(s) selected from O, S or N;

or, the alkyl, the alkoxy, the aryl, the heteroaryl, the heterocycloalkyl or the amino defined in $R^3$ is substituted by a substituent selected from the group consisting of F, Cl, Br, I, a $C_{1-4}$ alkyl, a $C_{6-10}$ aryl, 2,6-dichlorophenyl, 2,6-dichlorobenzyl and 2,6-dichlorobenzoyl;

or, $NH_2$, OH, the alkyl, the alkoxy, the cycloalkyl, the alkenyl, the alkynyl, the heterocycloalkyl, the aryl or the heteroaryl defined in $R^4$ is substituted by a substituent selected from the group consisting of F, Cl, Br, I, a $C_{1-4}$ alkyl, a $C_{1-4}$ alkoxy, a $C_{3-6}$ cycloalkyl, a $C_{2-4}$ alkenyl, a $C_{2-4}$ alkynyl, a $C_{6-10}$ aryl, a $C_{2-10}$ heterocycloalkyl having 1-2 heteroatom(s) selected from O, S or N,

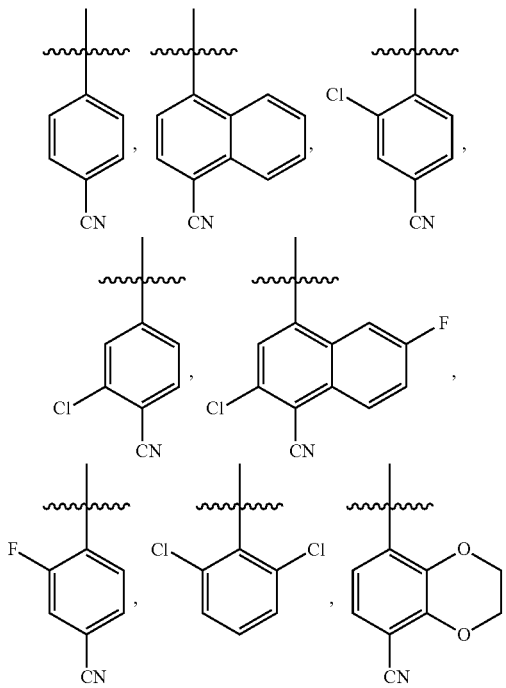

and a $C_{2-10}$ heteroaryl having 1-2 heteroatom(s) selected from O.

5. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 3, wherein, each of $R^1$ and $R^2$ is independently methyl, ethyl, n-propyl, iso-propyl, n-butyl, iso-butyl or tert-butyl;

or, $R^1$ and $R^2$ together with the carbon atom attached form a cyclobutyl;

or, $R^3$ is methyl, ethyl, n-propyl, iso-propyl, n-butyl, iso-butyl, tert-butyl, a phenyl, a pyridyl or

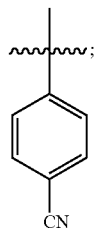
;

or, $R^4$ is a phenyl, a naphthyl,

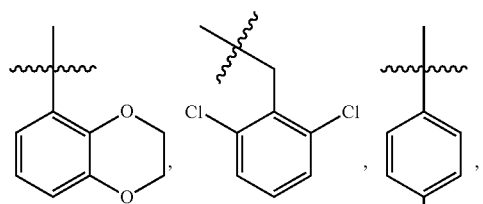

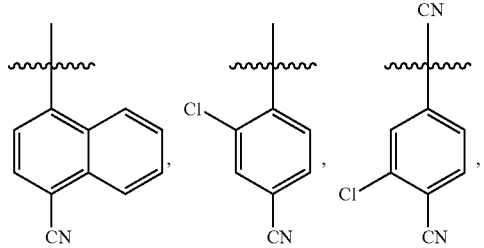

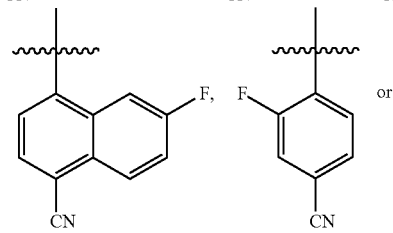

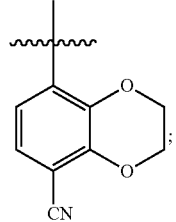
;

or, each of $R^5$ and $R^6$ is independently methyl, ethyl, n-propyl, iso-propyl, n-butyl, iso-butyl or tert-butyl.

6. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1, wherein, the compound having a structure of formula II has a structure of formula II-1:

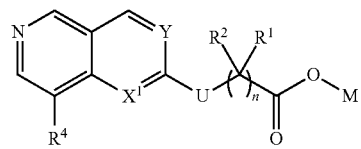

II-1 in the formula II-1, the definitions of $X^1$, Y, $R^1$, $R^2$, $R^4$, U, M and n refer to those in claim 1.

7. The condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 6, wherein, in the compound of general formula II-1, each of $R^1$ and $R^2$ is independently H, methyl, ethyl, n-propyl, iso-propyl, n-butyl, iso-butyl or tert-butyl; or $R^1$, $R^2$ together with the carbon atom attached form a cyclobutyl;

M is H;

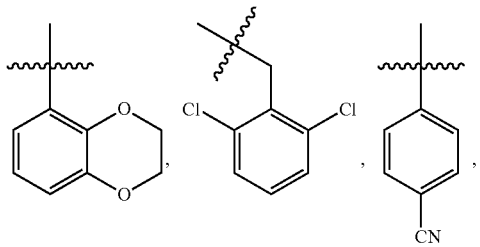

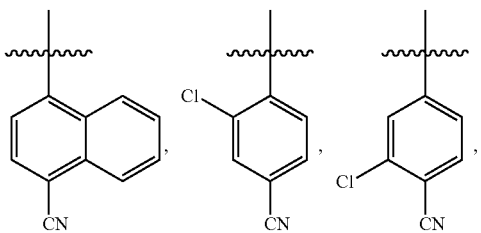

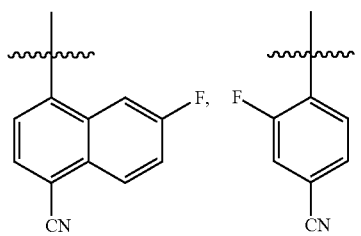

-continued

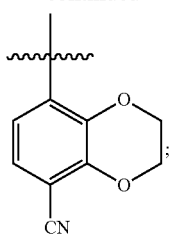

$R^4$ is a phenyl, a naphthyl,
U is

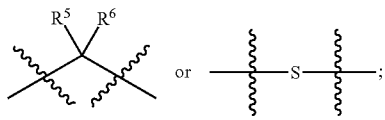

each of $R^5$ and $R^6$ is independently H, methyl, ethyl, n-propyl, iso-propyl, n-butyl, iso-butyl or tert-butyl;
n is 1;
or, in the compound of formula II-1, where U is

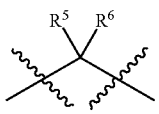

and $R^5$ and $R^6$ are H, $R^1$ and $R^2$ are not H at the same time.

8. A condensed ring derivative, the tautomer, the mesomer, the racemate, the enantiomer, the diastereoisomer, or the pharmaceutically acceptable salt, the metabolite, the metabolic precursor or the pro-drug thereof, of the structures selected from

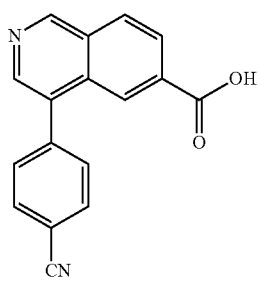

1

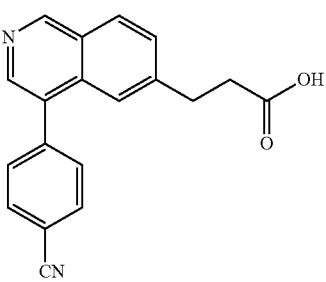

2

-continued

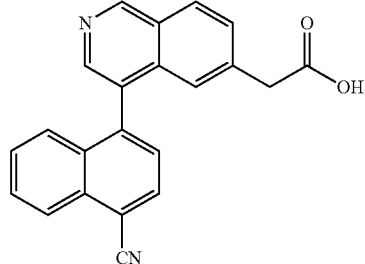

3

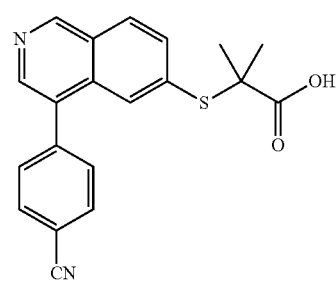

4

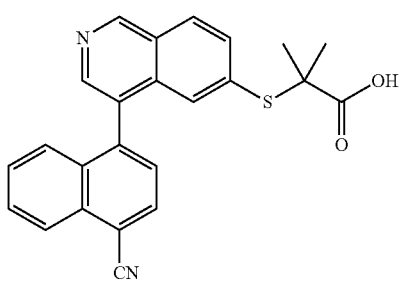

5

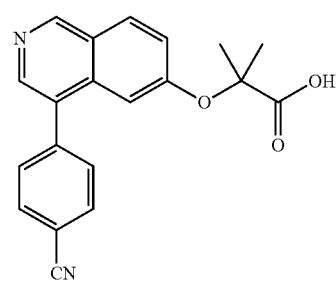

6

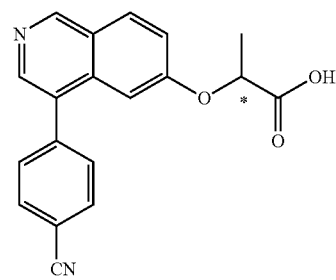

7

8
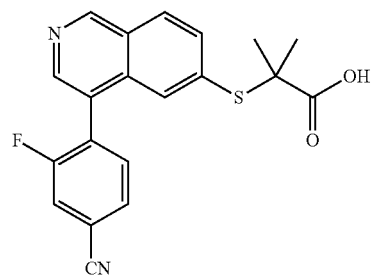
9
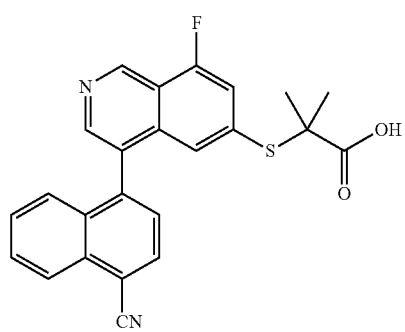
10
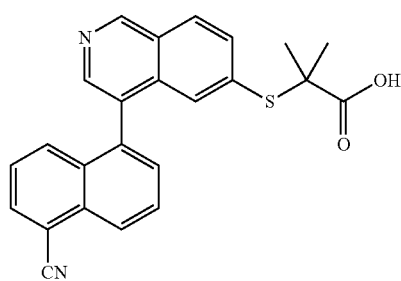
11
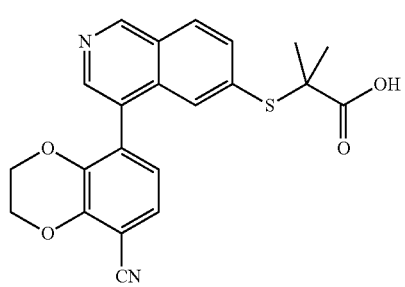
12
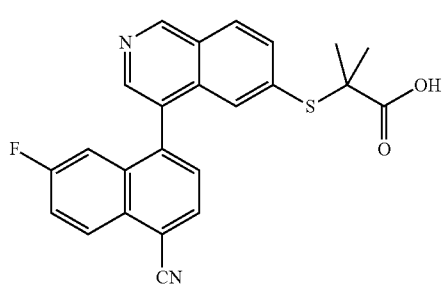
13
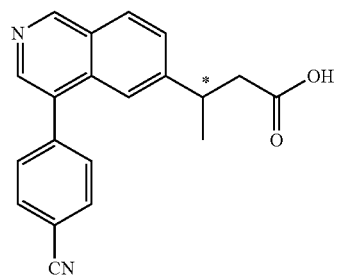
14
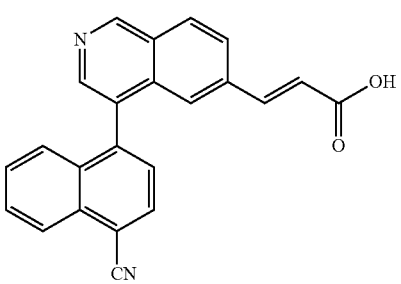
15
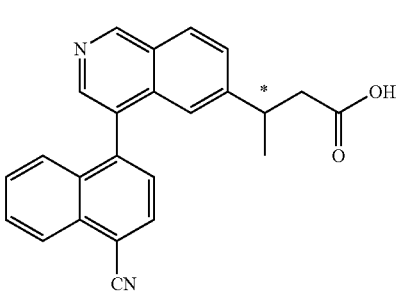
16
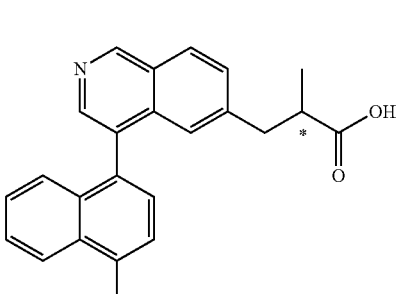
17
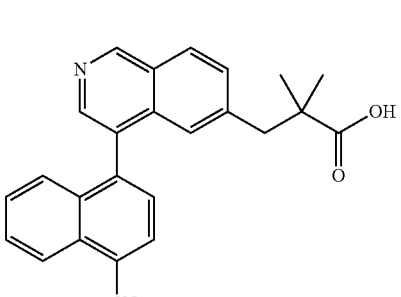

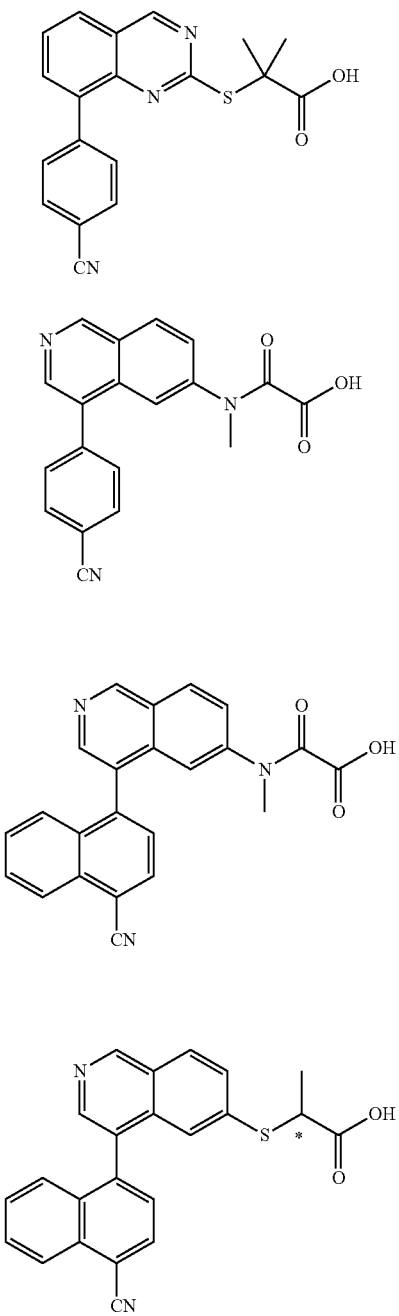

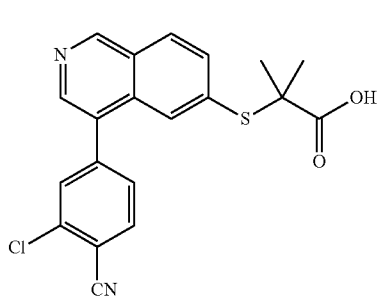

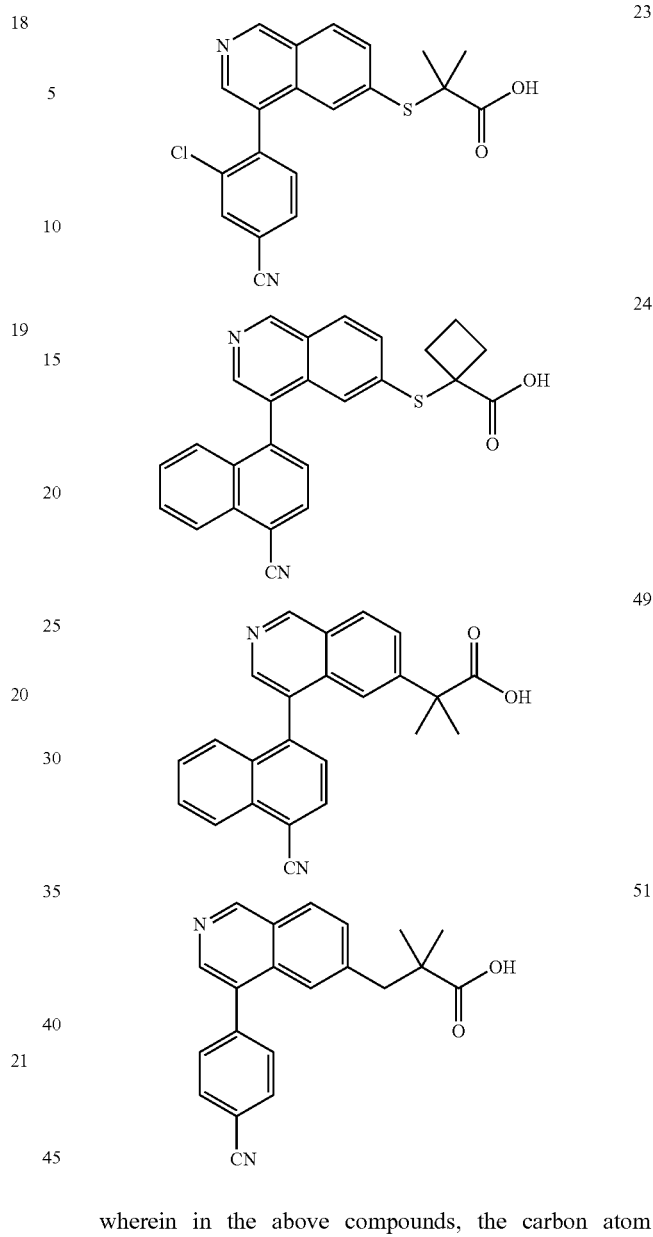

wherein in the above compounds, the carbon atom marked with * refers to a chiral carbon atom or a non-chiral carbon atom, when it is a chiral carbon atom, it is of S-configuration or R-configuration, when it is a non-chiral carbon atom, it refers to racemate.

9. The compound of formula II a:

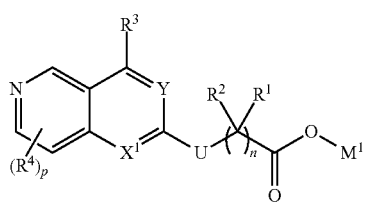

wherein $M^1$ is an alkyl;
in the compound of formula II-a, $X^1$ is CH or N; Y is CH or Y; the definitions of $R^1$, $R^2$, $R^3$, $R^4$, U, n and p refers to those in claim 1.

10. The compound of formula II-a according to claim 9, wherein, the compound of formula II-a has a structure of formula II-a-1:
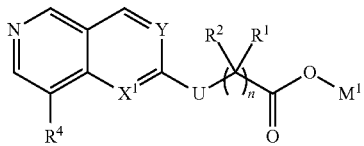
II-a-1
wherein, the definitions of $R^1$, $R^2$, $R^4$, U, $M^1$ and n refer to those in claim 9.
11. The compound of formula II-a according to claim 9, wherein, the compound is selected from the group consisting of
1-a
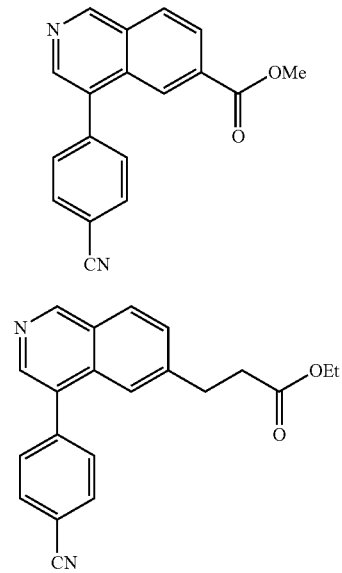
2-a
3-a
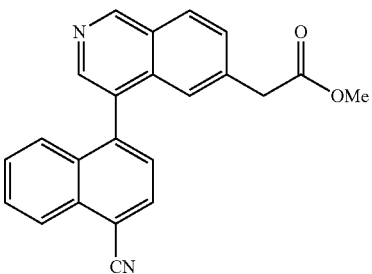
4-a
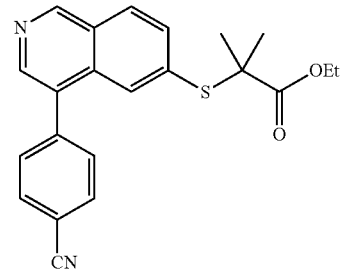
-continued
5-a
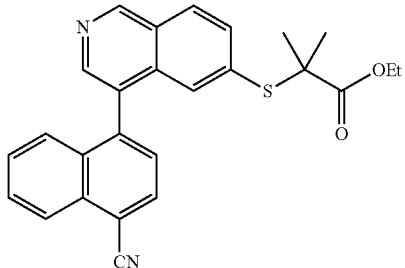
6-a
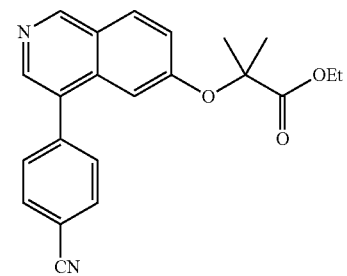
7-a
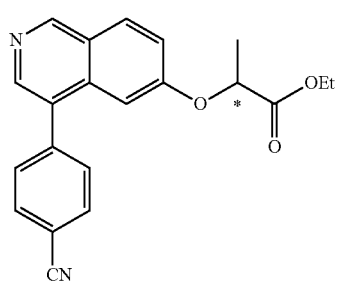
8-a
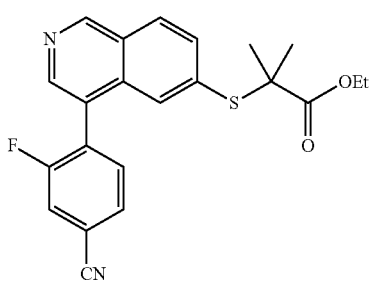
9-a
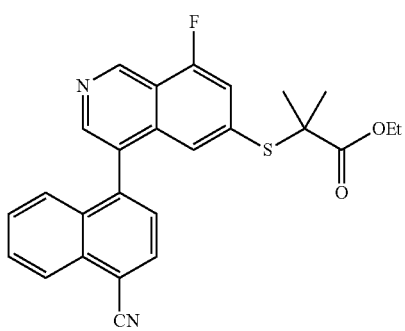

10-a
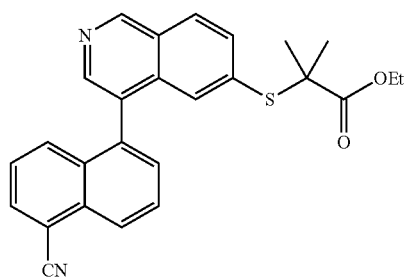
11-a
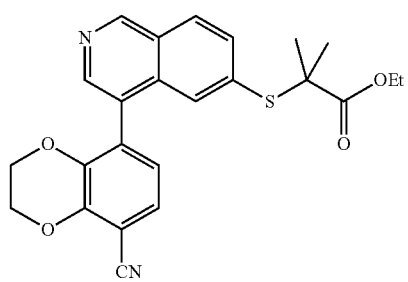
12-a
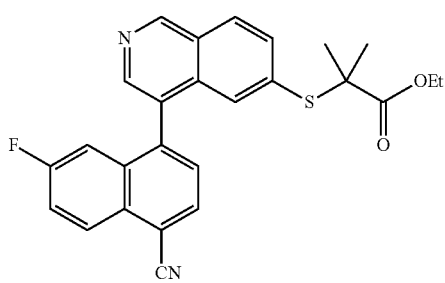
13-a
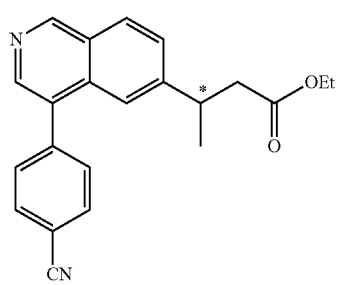
14-a
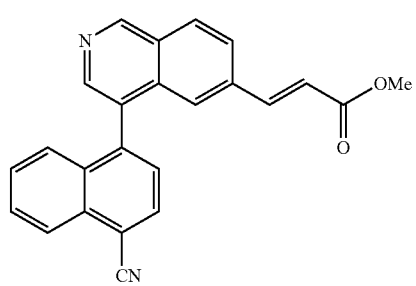
15-a
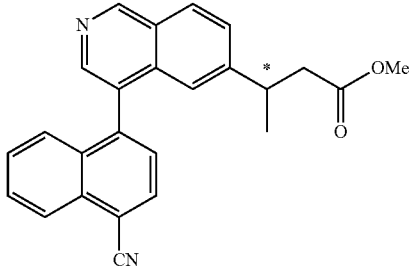
16-a
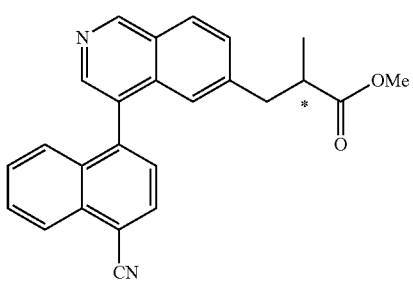
17-a
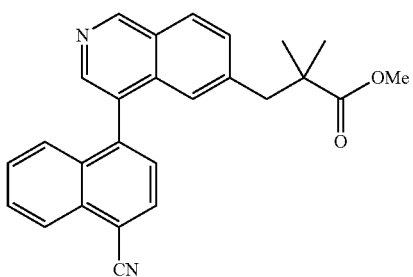
18-a
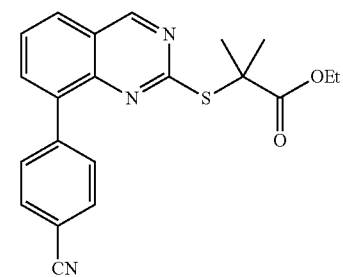
19-a
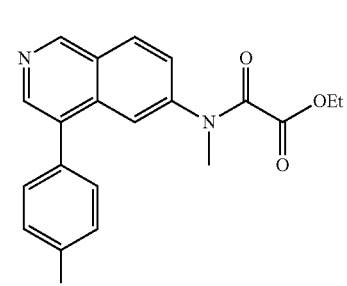

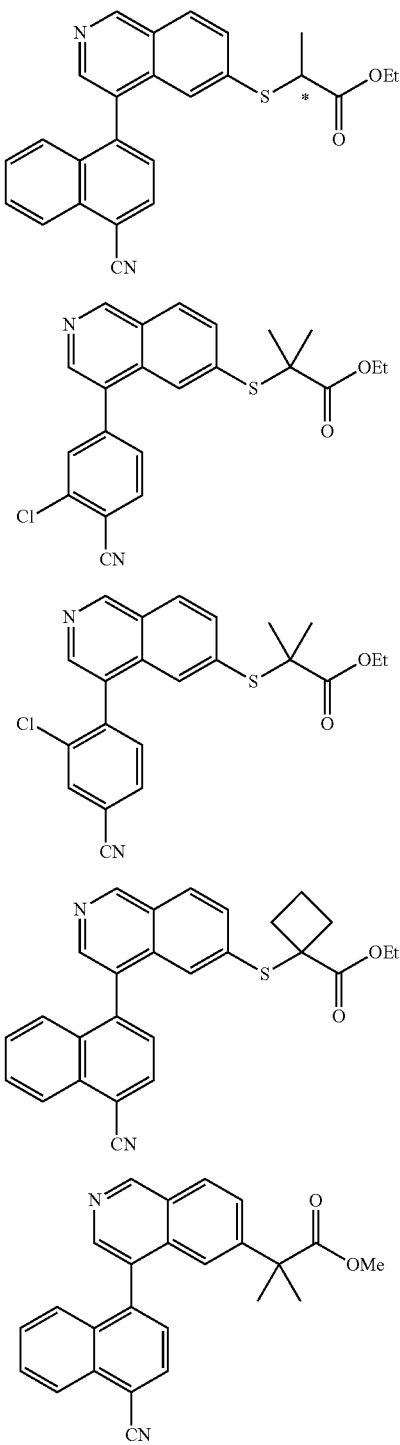

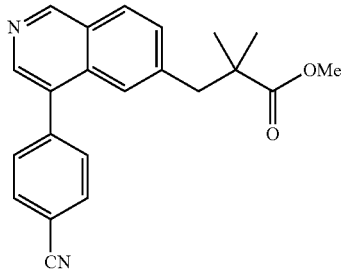

in the above compounds, the carbon atom marked with * is a chiral carbon atom or a non-chiral carbon atom, when it is a chiral carbon atom, it is of S-configuration or R-configuration, when it is a non-chiral carbon atom, it refers to racemate.

12. A pharmaceutical composition, comprising a pharmaceutically effective amount of the condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1, and one or more than one pharmaceutically acceptable carrier and/or diluent.

13. The pharmaceutical composition according to claim 12, wherein, the composition further contains other uric acid-lowering drugs; the uric acid-lowering drugs is selected from the group consisting of uric acid transporter 1 inhibitor, xanthine oxidase inhibitor, xanthine oxidoreductase and xanthine dehydrogenase inhibitor, or purine alcohol and/or Febuxostat.

14. A medicament for preventing and/or treating hyperuricemia, gout, hypertension, diabetes, hypertriglyceridemia, metabolic syndrome, coronary heart disease or kidney damage manufactured from the condensed ring derivative having a structure of formula II, the tautomer, the mesomer, the racemate, the enantiomer, the diastereoisomer, or the pharmaceutically acceptable salt, the metabolite, the metabolic precursor or the pro-drug thereof according to claim 1.

15. A method for treating hyperuricemia or the disease related to hyperuricemia comprising: administrating to the subject the condensed ring derivative having a structure of formula II, the tautomer, the mesomere, the racemate, the enantiomer, the diastereoisomer, or the pharmaceutically acceptable salt, the metabiolite, the metabolic precursor or the pro-drug thereof according to claim 1.

16. The method according to claim 15 wherein the disease related to hyperuricemia is selected from the group consisting of gout, hypertension, diabetes, hypertriglyceridemia, metabolic syndrome, coronary heart disease and kidney damage.

* * * * *